United States Patent
Sagehashi et al.

(10) Patent No.: US 10,023,674 B2
(45) Date of Patent: Jul. 17, 2018

(54) MONOMER, POLYMER, RESIST COMPOSITION, AND PATTERNING PROCESS

(71) Applicant: Shin-Etsu Chemical Co., Ltd., Tokyo (JP)

(72) Inventors: Masayoshi Sagehashi, Joetsu (JP); Masahiro Fukushima, Joetsu (JP); Koji Hasegawa, Joetsu (JP); Teppei Adachi, Joetsu (JP); Kazuhiro Katayama, Joetsu (JP); Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/426,227

(22) Filed: Feb. 7, 2017

(65) Prior Publication Data
US 2017/0226252 A1    Aug. 10, 2017

(30) Foreign Application Priority Data

Feb. 10, 2016    (JP) .................................. 2016-023878

(51) Int. Cl.
*G03F 7/004*    (2006.01)
*C08F 222/20*   (2006.01)
(Continued)

(52) U.S. Cl.
CPC .......... *C08F 222/20* (2013.01); *C07C 69/675* (2013.01); *C07C 381/12* (2013.01);
(Continued)

(58) Field of Classification Search
CPC ...... G03F 7/004; G03F 7/0045; G03F 7/0046; G03F 7/0397; G03F 7/2041; G03F 7/325;
(Continued)

(56) References Cited

U.S. PATENT DOCUMENTS 6,800,423 B2    10/2004    Yokoyama et al.
7,300,739 B2    11/2007    Allen et al.
(Continued)

FOREIGN PATENT DOCUMENTS

EP    2 466 379 A1    6/2012
JP    2003-195502 A   7/2003
(Continued)

OTHER PUBLICATIONS

European Search Report dated Jul. 5, 2017, issued in counterpart European Patent Application No. 17154786.2. (7 pages).
(Continued)

*Primary Examiner* — Amanda C Walke
(74) *Attorney, Agent, or Firm* — Westerman, Hattori, Daniels & Adrian, LLP

(57) ABSTRACT

A monomer having a substituent group capable of polarity switch under the action of acid is provided. A useful polymer is obtained by polymerizing the monomer. A resist composition comprising the polymer has improved development properties and is processed to form a negative pattern having high resolution and etch resistance which is insoluble in alkaline developer.

11 Claims, 8 Drawing Sheets

(51) Int. Cl.
*C07C 69/675* (2006.01)
*C08F 220/28* (2006.01)
*G03F 7/038* (2006.01)
*G03F 7/16* (2006.01)
*G03F 7/20* (2006.01)
*G03F 7/38* (2006.01)
*G03F 7/32* (2006.01)
*C08F 220/24* (2006.01)
*C07C 381/12* (2006.01)
*C08F 220/18* (2006.01)
*C08F 220/30* (2006.01)

(52) U.S. Cl.
CPC .......... *C08F 220/18* (2013.01); *C08F 220/24* (2013.01); *C08F 220/28* (2013.01); *C08F 220/30* (2013.01); *G03F 7/0045* (2013.01); *G03F 7/038* (2013.01); *G03F 7/162* (2013.01); *G03F 7/168* (2013.01); *G03F 7/2004* (2013.01); *G03F 7/322* (2013.01); *G03F 7/38* (2013.01); *C07C 2101/14* (2013.01); *C07C 2103/74* (2013.01); *C08F 2220/283* (2013.01)

(58) Field of Classification Search
CPC .... C08F 220/18; C08F 220/24; C08F 220/30; C07C 381/12
USPC ..... 430/270.1, 322, 325, 331; 526/243, 326, 526/245, 247, 251, 316
See application file for complete search history.

(56) References Cited

U.S. PATENT DOCUMENTS

| | | | |
|---|---|---|---|
| 7,563,558 B2 | 7/2009 | Allen et al. | |
| 8,227,183 B2 | 7/2012 | Tsubaki et al. | |
| 9,040,222 B2 * | 5/2015 | Suka | G03F 7/039 430/270.1 |
| 9,563,125 B2 * | 2/2017 | Masuyama | G03F 7/0045 |
| 9,846,360 B2 * | 12/2017 | Hatakeyama | G03F 7/0046 |
| 2012/0077121 A1 * | 3/2012 | Hasegawa | C07C 69/67 430/270.1 |
| 2012/0214100 A1 * | 8/2012 | Kobayashi | G03F 7/0045 430/285.1 |
| 2013/0034813 A1 * | 2/2013 | Ohsawa | G03F 7/0045 430/281.1 |
| 2013/0084517 A1 * | 4/2013 | Suka | G03F 7/0046 430/5 |

FOREIGN PATENT DOCUMENTS

| | | | |
|---|---|---|---|
| JP | 2005-3862 A | 1/2005 | |
| JP | 2005-3863 A | 1/2005 | |
| JP | 2006-145775 A | 6/2006 | |
| JP | 2006-215067 A | 8/2006 | |
| JP | 2006-317803 A | 11/2006 | |
| JP | 4554665 B2 | 9/2010 | |
| JP | 2014041346 A * | 3/2014 | ............... G03F 7/20 |
| JP | 2016128921 A * | 7/2016 | ........... G03F 7/0046 |
| WO | 2004/074936 A1 | 9/2004 | |

OTHER PUBLICATIONS

Sooriyakumaran et al., "193-nm Negative Resist Based on Acid-Catalyzed Elimination of Polar Molecules", Proceedings of SPIE, 2004, vol. 5376, pp. 71-78. (8 pages).

* cited by examiner

MONOMER, POLYMER, RESIST COMPOSITION, AND PATTERNING PROCESS

CROSS-REFERENCE TO RELATED APPLICATION

This non-provisional application claims priority under 35 U.S.C. § 119(a) on Patent Application No. 2016-023878 filed in Japan on Feb. 10, 2016, the entire contents of which are hereby incorporated by reference.

TECHNICAL FIELD

This invention relates to a monomer useful as a starting reactant for functional, pharmaceutical and agricultural chemicals, a polymer comprising recurring units derived from the monomer, a resist composition comprising the polymer, and a pattern forming process using the composition.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, the self-aligned double patterning (SADP) process of adding film to opposite sidewalls of lines of a resist pattern resulting from ArF lithography for thereby forming two patterns with half line width from one pattern is successful in manufacturing microelectronic devices at the 20-nm node in a mass scale. As the miniaturization technology for microelectronic devices of the next generation 10-nm node, the self-aligned quadruple patterning (SAQP) which is double repetition of SADP is a candidate. It is pointed out that this process is quite expensive because formation of sidewall film by CVD and processing by dry etching are repeated several times. Extreme ultraviolet (EUV) lithography of wavelength 13.5 nm is capable of forming a pattern with a size of the order of 10 nm via single exposure, but suffers from the problems of still low laser power and low productivity. As the miniaturization technology comes to the deadlock, the development of three-dimensional devices such as vertically stacked flash memories typically BiCS is started, but expected to be a high cost process.

Recently, a highlight is put on the organic solvent development again. A positive resist composition featuring a high resolution is subjected to organic solvent development to form a negative pattern. As the ArF resist composition for negative tone development with organic solvent, positive ArF resist compositions of the prior art design may be used. Such a pattern forming process is described in Patent Document 1.

In the process of forming a negative tone pattern via organic solvent development, a film from which a robust protective group such as cyclic structure having dry etch resistance has been eliminated is left as the negative pattern. Thus the film is short of dry etch resistance. This serious problem must be overcome before the negative pattern formation via organic solvent development can be implemented.

On the other hand, studies have also been made on the negative pattern formation via development in alkaline aqueous solution. Known resist compositions used in this process include a negative resist composition of polarity switch type comprising a base resin comprising recurring units having γ-hydroxycarboxylic acid which forms lactone ring by PEB (see Patent Document 2), a negative resist composition comprising a copolymer comprising alcoholic hydroxyl-containing (meth)acrylate units and fluoroalcohol-containing units and a crosslinker (see Patent Document 3), and negative resist compositions of crosslinking type comprising a crosslinker and a combination of α-hydroxyacrylate and lactone units (see Patent Document 4), α-hydroxyacrylate and fluoroalcohol units (see Patent Documents 5 to 7), and mono(meth)acryloyloxypinacol and fluoroalcohol units (see Patent Document 8).

Of these, Patent Document 2 describes a negative resist composition of polarity switch type, not resorting to crosslinking reaction, in which γ-hydroxycarboxylic acid units incur swell of the pattern after development. Patent Documents 3 to 7 relate to negative resist compositions of crosslinking type. Although the negative pattern formation by cooperation of alcoholic hydroxyl group and crosslinker has the problems of bridging between pattern features and pattern collapse due to swell, it is observed that the incorporation of fluoroalcohol units has a swell-reducing effect. Moreover, as recent examples of negative pattern formation by polarity switch, there are proposed base resins having polar units such as tertiary hydroxyl group, tertiary ether bond, tertiary ester bond or acetal bond as the polarity switch group. Of these, a polymer using a polar unit having one tertiary hydroxyl group is unlikely to swell after development. However, the difference of dissolution rate in developer between unexposed and exposed regions is insufficient, which raises the problem that a footing occurs at the bottom of a line-and-space pattern, that is, pattern features take a tapered shape. See Patent Documents 9 and 10 and Non-Patent Document 1.

All the negative pattern forming processes mentioned above are effective to some extent in forming pattern features with a size of the order of 100 nm. However, their performance is insufficient in forming pattern features with a size of finer than 100 nm, because pattern bridging and collapse due to swell, and footing at the pattern bottom inevitably occur. Although active efforts have recently been devoted on the negative pattern forming process via organic solvent development, the organic solvent used as the developer is more expensive than conventional alkaline developers. From the standpoint of etch resistance improvement, it is desired to have a negative resist composition which is amenable to conventional alkaline development at a high resolution and allows a robust backbone structure to be left in the film after development.

CITATION LIST

Patent Document 1: JP 4554665 (U.S. Pat. No. 8,227,183)
Patent Document 2: JP-A 2003-195502
Patent Document 3: WO 2004/074936
Patent Document 4: JP-A 2005-003862
Patent Document 5: JP-A 2005-003863
Patent Document 6: JP-A 2006-145775
Patent Document 7: JP-A 2006-317803
Patent Document 8: JP-A 2006-215067
Patent Document 9: U.S. Pat. No. 7,300,739
Patent Document 10: U.S. Pat. No. 7,563,558
Non-Patent Document 1: Proc. SPIE vol. 5376, p 71 (2004)

DISCLOSURE OF INVENTION

The requirements for further miniaturization continue severer in these years. In the negative pattern forming process via organic solvent development, on which active efforts have been devoted, the negative pattern defined in the resist film has a reduced carbon density as compared with that prior to exposure. It is then desired to improve the resistance to etching of the resist film and the retention of pattern shape after etching.

An object of the invention is to provide a monomer having a substituent group capable of polarity switch under the action of acid, a polymer derived from the monomer, a resist composition comprising the polymer, and a pattern forming process using the composition.

The inventors have found that a resist composition comprising a polymer having a substituent group capable of polarity switch under the action of acid as base resin forms at a high resolution a negative pattern insoluble in alkaline developer and having high etch resistance.

In one aspect, the invention provides a monomer having the formula (1a) or (1b).

carbon atom to which they are attached, $R^a$ is hydrogen, methyl or trifluoromethyl, $X^a$ is a $C_1$-$C_{10}$ alkylene group, $X^b$ is a $C_1$-$C_{10}$ straight, branched or cyclic ($k^1$+1)-valent hydrocarbon group in which any constituent —$CH_2$— moiety may be replaced by —O— or —C(=O)—, with the proviso that $X^b$ is exclusive of a group that forms the O—$X^b$ bond in the formula which is dissociable under the action of acid, $X^c$ is a single bond, methylene or ethylidene, $X^d$ is a single bond, methylene or ethylidene, $Z^a$ is an atomic group necessary to form a $C_3$-$C_{10}$ alicyclic group with the carbon atom to which it is attached, A is a polymerizable functional group, and $k^1$ is 1 or 2. Preferably, A is acryloyl or methacryloyl.

In a second aspect, the invention provides a polymer comprising recurring units containing as pendant a group having the formula (2a) and/or a group having the formula (2b).

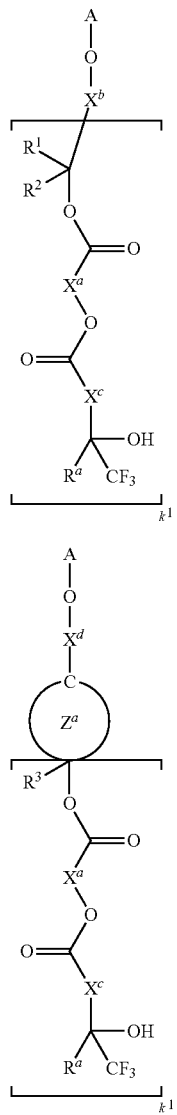

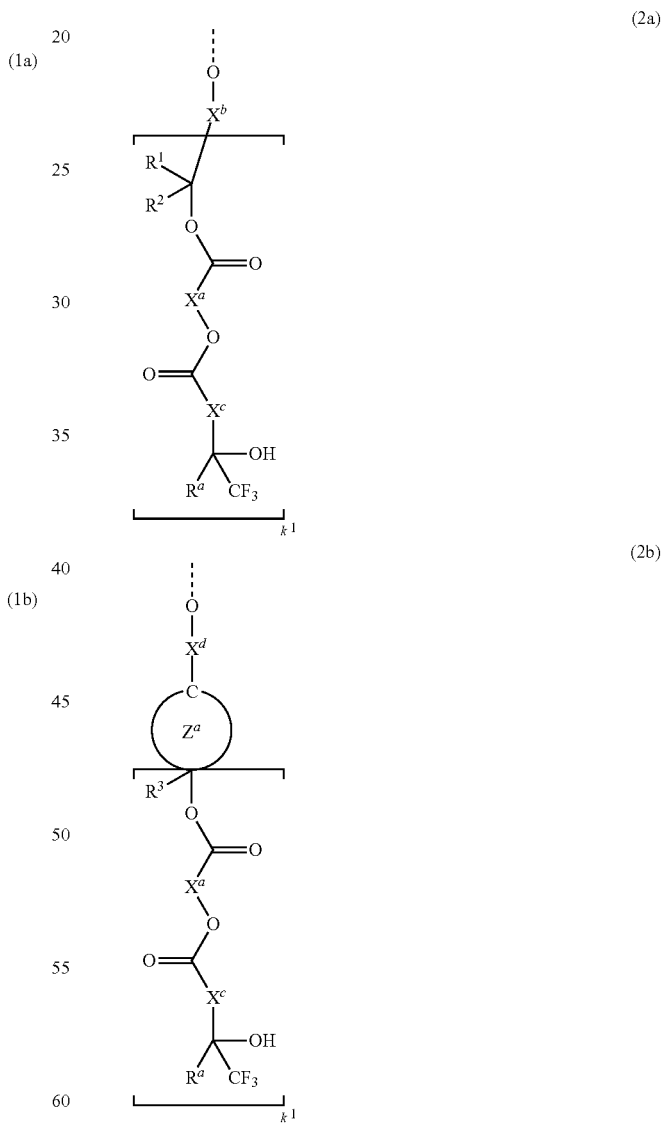

Herein $R^1$ to $R^3$ are each independently a $C_1$-$C_6$ straight, branched or cyclic monovalent hydrocarbon group, $R^1$ and $R^2$ may bond together to form an alicyclic group with the carbon atom to which they are attached, $R^a$ is hydrogen, methyl or trifluoromethyl, $X^a$ is a $C_1$-$C_{10}$ alkylene group, $X^b$ Herein $R^1$ to $R^3$ are each independently a $C_1$-$C_6$ straight, branched or cyclic monovalent hydrocarbon group, $R^1$ and $R^2$ may bond together to form an alicyclic group with the is a $C_1$-$C_{10}$ straight, branched or cyclic ($k^1$+1)-valent hydrocarbon group in which any constituent —$CH_2$— moiety may be replaced by —O— or —C(=O)—, with the proviso that $X^b$ is exclusive of a group that forms the O—$X^b$ bond in the formula which is dissociable under the action of acid, $X^c$ is a single bond, methylene or ethylidene, $X^d$ is a single bond, methylene or ethylidene, $Z^a$ is an atomic group necessary to form a $C_2$-$C_{10}$ alicyclic group with the carbon atom to which it is attached, and $k^1$ is 1 or 2.

Preferably, the recurring units have the formulae (2aa) or (2bb):

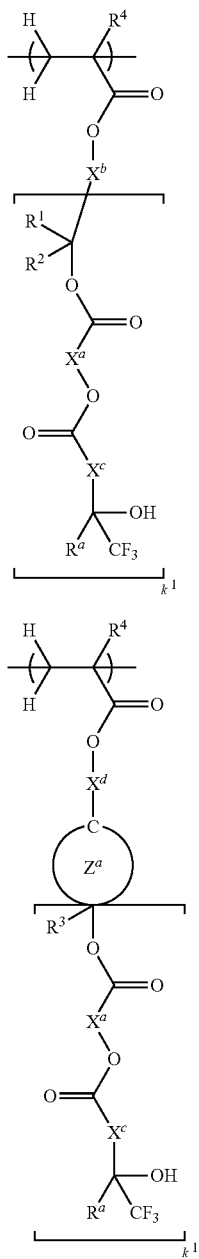

(2aa)

(2bb)

wherein $R^1$ to $R^3$, $R^a$, $X^a$ to $X^d$, $Z^a$ and $k^1$ are as defined above, $R^4$ is hydrogen or methyl.

The polymer may further comprise recurring units of at least one type selected from recurring units having the formulae (3) to (5).

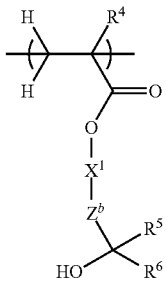

(3)

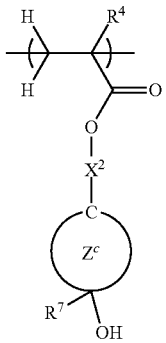

(4)

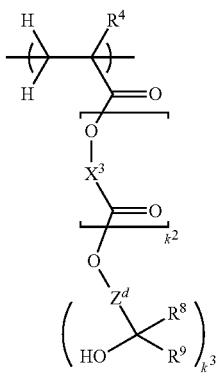

(5)

Herein $R^4$ is hydrogen or methyl; $R^5$ and $R^6$ are each independently a $C_1$-$C_6$ straight, branched or cyclic monovalent hydrocarbon group, $R^5$ and $R^6$ may bond together to form an alicyclic group with the carbon atom to which they are attached; $R^7$ is a $C_1$-$C_6$ straight, branched or cyclic monovalent hydrocarbon group; $R^8$ and $R^9$ are each independently a $C_1$-$C_6$ straight, branched or cyclic monovalent hydrocarbon group, $R^8$ and $R^9$ may bond together to form an alicyclic group with the carbon atom to which they are attached. $X^1$ and $X^2$ are each independently a single bond, methylene or ethylidene; $X^3$ is a $C_1$-$C_{20}$ straight, branched or cyclic divalent hydrocarbon group in which any constituent —$CH_2$— moiety may be replaced by —O— or —C(=O)—. $Z^b$ is a $C_1$-$C_9$ straight, branched or cyclic aliphatic hydrocarbon group; $Z^c$ is an atomic group necessary to form a $C_3$-$C_{10}$ alicyclic group with the carbon atom to which it is attached; $Z^d$ is a $C_1$-$C_{20}$ straight, branched or cyclic aliphatic hydrocarbon group in which any constituent —$CH_2$— moiety may be replaced by —O— or —C(=O)—, with the proviso that $Z^b$ is exclusive of a group that forms the O—$Z^b$ bond in formula (3) which is dissociable under the action of acid, when $X^1$ is a single bond, and $Z^d$ is exclusive of a group that forms the O—$Z^d$ bond in formula (5) which is dissociable under the action of acid.

The total number of carbon atoms in $X^1$, $Z^b$, $R^5$ and $R^6$ is 5 to 12, the total number of carbon atoms in $X^2$, $Z^c$ and $R^7$ is 5 to 12, $k^2$ is 0 or 1, $k^3$ is an integer of 2 to 4.

The polymer may further comprise recurring units of at least one type selected from recurring units having the formulae (A) to (D).

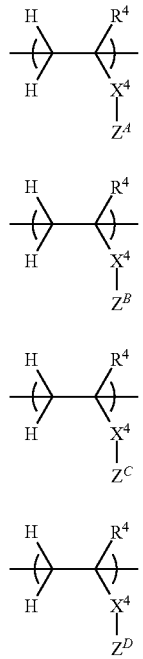

(A)

(B)

(C)

(D)

Herein $R^4$ is hydrogen or methyl, $Z^A$ is a $C_1$-$C_{20}$ fluoroalcohol-containing group, exclusive of a structure undergoing a polarity switch under the action of acid, $Z^B$ is a $C_1$-$C_{20}$ phenolic hydroxyl-containing group, $Z^C$ is a $C_1$-$C_{20}$ carboxyl-containing group, $Z^D$ is a substituent group having a lactone structure, sultone structure, carbonate structure, cyclic ether structure, acid anhydride structure, alcoholic hydroxyl, alkoxycarbonyl, sulfonamide or carbamoyl moiety, $X^4$ is a single bond, methylene, ethylene, phenylene, fluorinated phenylene, naphthylene, —O—$R^{01}$—, or —C(=O)—$Z^X$—$R^{01}$—, $Z^X$ is —O— or —NH—, and $R^{01}$ is a $C_1$-$C_6$ straight, branched or cyclic alkylene, $C_2$-$C_6$ straight, branched or cyclic alkenylene, phenylene or naphthylene group, which may contain a carbonyl, ester, ether or hydroxyl moiety.

The polymer may further comprise recurring units of at least one type selected from recurring units having the formulae (f1) to (f5).

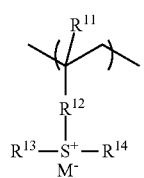

(f1)

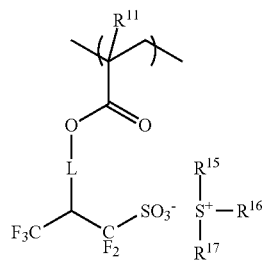

(f2)

(f3)

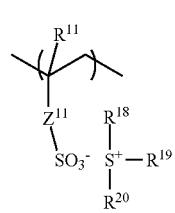

(f4)

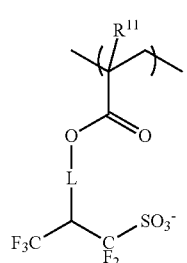

(f5)

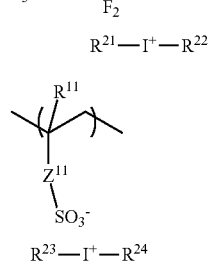

Herein $R^{11}$ is each independently hydrogen or methyl, $R^{12}$ is a single bond, phenylene, —O—$R^{25}$—, or —C(=O)—$Z^{22}$—$R^{25}$—, $Z^{22}$ is —O— or —NH—, $R^{25}$ is a $C_1$-$C_6$ straight, branched or cyclic alkylene group, $C_2$-$C_6$ straight, branched or cyclic alkenylene group or phenylene group, which may contain a carbonyl (—CO—), ester (—COO—), ether (—O—) or hydroxyl moiety, L is a single bond or —$Z^{33}$—C(=O)—O—, $Z^{33}$ is a $C_1$-$C_{20}$ straight, branched or cyclic divalent hydrocarbon group which may contain a heteroatom, $Z^{11}$ is a single bond, methylene, ethylene, phenylene, fluorinated phenylene, —O—$R^{26}$—, or —C(=O)—$Z^{44}$—$R^{26}$—, $Z^{44}$ is oxygen or NH, $R^{26}$ is a $C_1$-$C_6$ straight, branched or cyclic alkylene group, $C_2$-$C_6$ straight, branched or cyclic alkenylene group or phenylene group, which may contain a carbonyl, ester, ether or hydroxyl moiety, $M^-$ is a non-nucleophilic counter ion, $R^{13}$ to $R^{24}$ are each independently a $C_1$-$C_{20}$ straight, branched or cyclic monovalent hydrocarbon group which may contain a heteroatom, $R^{13}$ and $R^{14}$ may bond together to form a ring with the sulfur atom to which they are attached, any two or more of $R^{15}$, $R^{16}$ and $R^{17}$ or any two or more of $R^{18}$, $R^{19}$ and $R^{20}$ may bond together to form a ring with the sulfur atom to which they are attached.

The polymer may further comprise recurring units of at least one type selected from recurring units having the formulae (X-1) to (X-4).

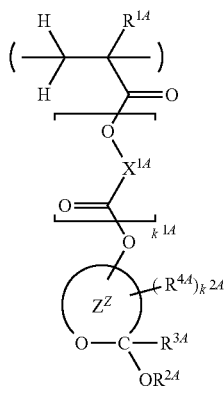

(X-1)

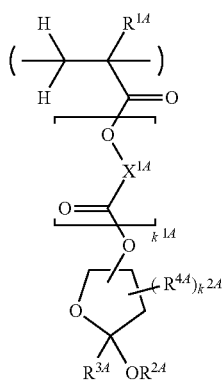

(X-2)

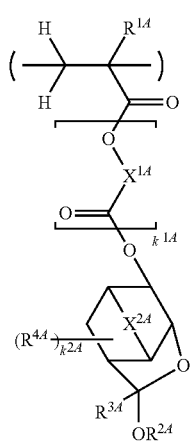

(X-3)

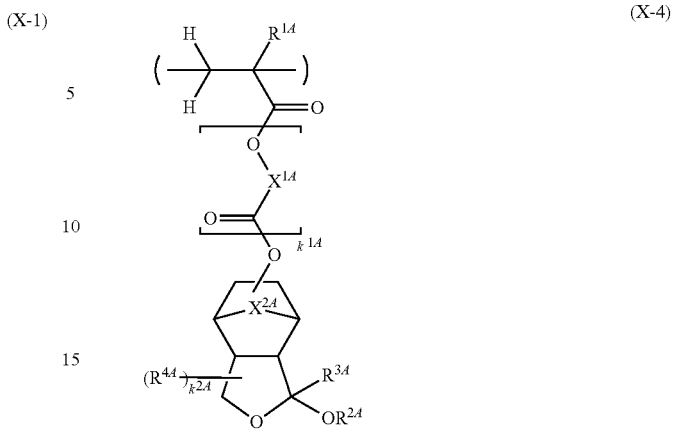

Herein $R^{1A}$ is hydrogen, methyl or trifluoromethyl, $R^{2A}$ to $R^{4A}$ are each independently hydrogen or a $C_1$-$C_{15}$ straight, branched or cyclic monovalent hydrocarbon group in which any constituent —$CH_2$— moiety may be replaced by —O— or —C(=O)—, $X^{1A}$ is a $C_1$-$C_{15}$ straight, branched or cyclic divalent hydrocarbon group in which any constituent —$CH_2$— moiety may be replaced by —O— or —C(=O)—, $X^{2A}$ is —$CH_2$— or —O—, $Z^Z$ represents a $C_4$-$C_{20}$ non-aromatic mono- or polycyclic ring having a hemiacetal structure, $k^{1A}$ is 0 or 1, and $k^{2A}$ is an integer of 0 to 3.

In a third aspect, the invention provides a resist composition comprising a base resin, an acid generator, and an organic solvent, the base resin comprising the polymer defined above.

In a fourth aspect, the invention provides a pattern forming process comprising the steps of applying the resist composition onto a substrate, baking to form a resist film, exposing the resist film to high-energy radiation to define exposed and unexposed regions, baking, and developing the exposed resist film in a developer to form a pattern.

In a preferred embodiment, the developing step uses an alkaline developer in which the unexposed region of resist film is dissolved and the exposed region of resist film is not dissolved, for forming a negative tone pattern.

ADVANTAGEOUS EFFECTS OF INVENTION

Using a polymer comprising recurring units derived from the inventive monomer as base resin, a resist composition having high transparency to radiation of wavelength 500 nm or less, especially 300 nm or less, e.g., KrF, ArF or $F_2$ laser radiation is formulated. From the resist composition having improved development properties, a negative pattern insoluble in alkaline developer and having a high resolution and etch resistance can be formed.

DESCRIPTION OF EMBODIMENTS

Figure 1:
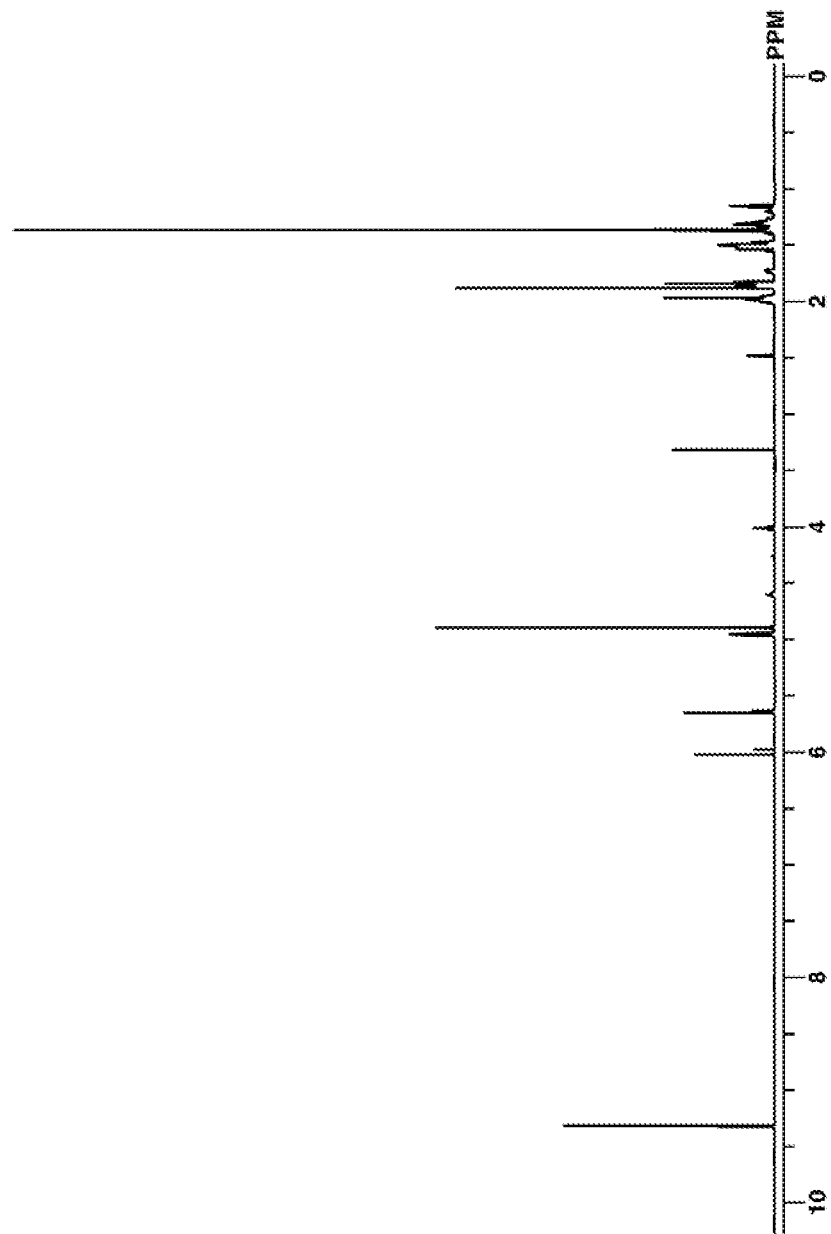
FIG. 1 is a diagram showing $^1$H-NMR spectrum of Monomer 1 in Example 1.

In the disclosure, the singular forms "a," "an" and "the" include plural referents unless the context clearly dictates otherwise. The notation (Cn-Cm) means a group containing from n to m carbon atoms per group. In the chemical formulae, the broken line denotes a valence bond. Me stands for methyl, Ph for phenyl, and Ac for acetyl.

The abbreviations and acronyms have the following meaning.

EUV: extreme ultraviolet
PAG: photoacid generator
Mw: weight average molecular weight
Mn: number average molecular weight
Mw/Mn: molecular weight distribution or dispersity
GPC: gel permeation chromatography
PEB: post-exposure bake
LWR: line width roughness It is understood that for some structures represented by chemical formulae, there can exist enantiomers and diastereomers because of the presence of asymmetric carbon atoms. In such a case, a single formula collectively represents all such isomers. The isomers may be used alone or in admixture.

Monomer

The invention provides a monomer having the formula (1a) or (1b).

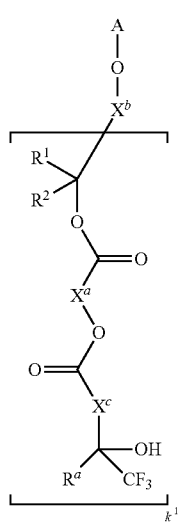

(1a)

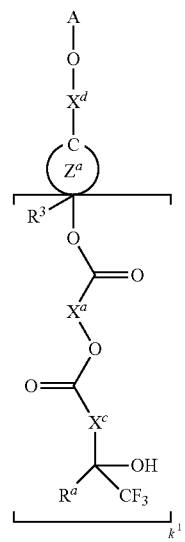

(1b)

Herein $R^1$ to $R^3$ are each independently a $C_1$-$C_6$ straight, branched or cyclic monovalent hydrocarbon group, $R^1$ and $R^2$ may bond together to form an alicyclic group with the carbon atom to which they are attached. $R^a$ is hydrogen, methyl or trifluoromethyl. $X^a$ is a $C_1$-$C_{10}$ alkylene group. $X^b$ is a $C_1$-$C_{10}$ straight, branched or cyclic ($k^1$+1)-valent hydrocarbon group in which any constituent —$CH_2$— moiety may be replaced by —O— or —C(=O)—, with the proviso that $X^b$ is exclusive of a group that forms the O—$X^b$ bond in the formula which is dissociable under the action of acid. $X^c$ is a single bond, methylene or ethylidene. $X^d$ is a single bond, methylene or ethylidene. $Z^a$ is an atomic group necessary to form a $C_3$-$C_{10}$ alicyclic group with the carbon atom to which it is attached. A is a polymerizable functional group, and $k^1$ is 1 or 2.

Suitable $C_1$-$C_6$ straight, branched or cyclic monovalent hydrocarbon groups include alkyl groups such as methyl, ethyl, propyl, isopropyl, n-butyl, s-butyl, t-butyl, cyclopentyl, and cyclohexyl.

Typical of the alicyclic group are cyclopropane, cyclobutane, cyclopentane and cyclohexane.

Examples of the $C_1$-$C_{10}$ alkylene group are given below, but not limited thereto.

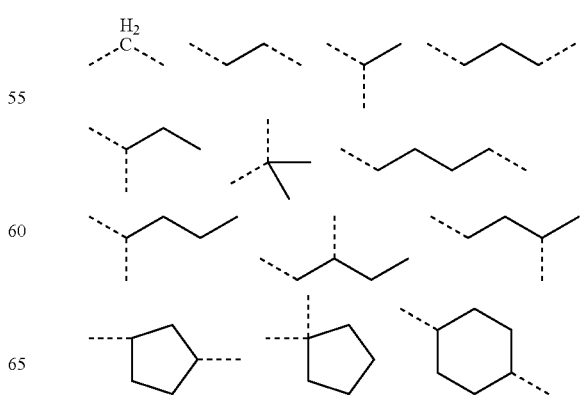

-continued
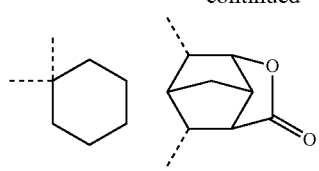
Examples of the $C_3$-$C_{10}$ alicyclic group that $Z^a$ forms with the carbon atom to which it is attached are given below, but not limited thereto.
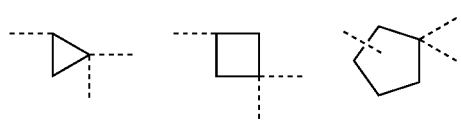
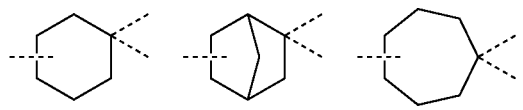
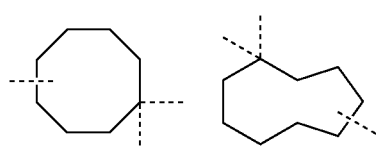
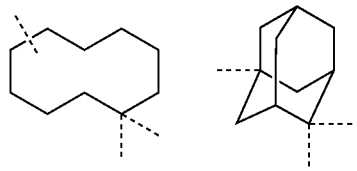
Examples of the monomers having formulae (1a) and (1b) are shown below, but not limited thereto. In the formulae, A is as defined above.
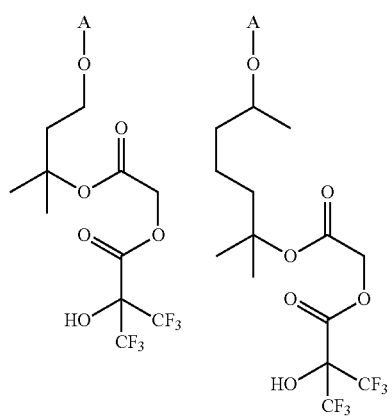
-continued
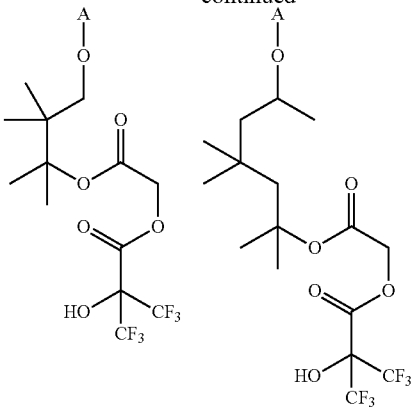
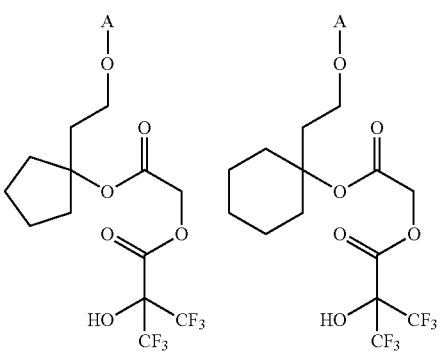
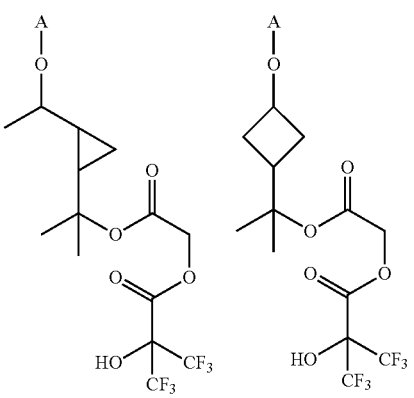
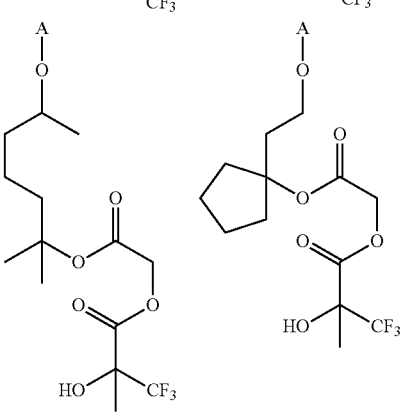

-continued
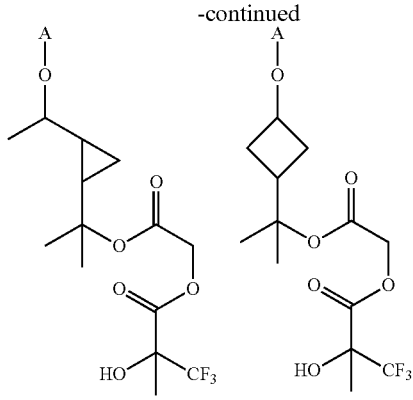
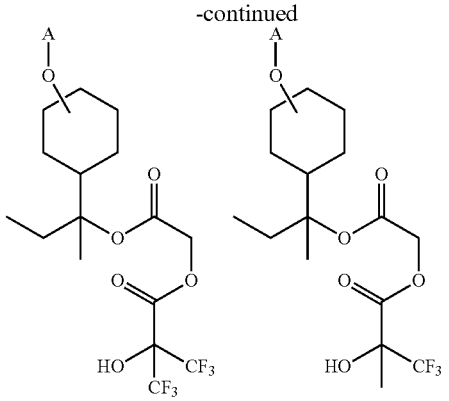
-continued
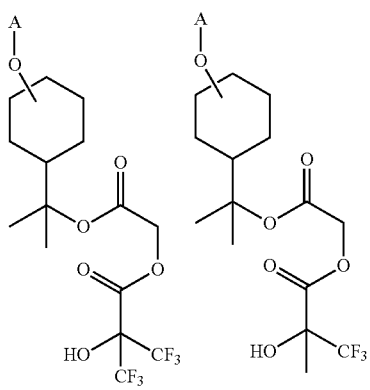
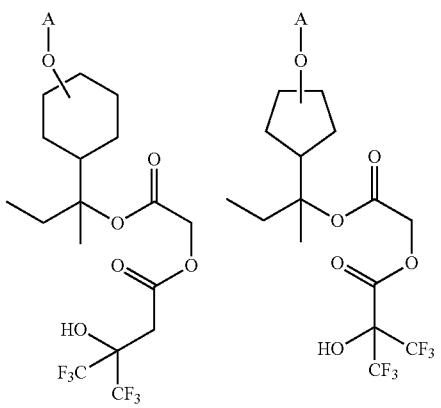
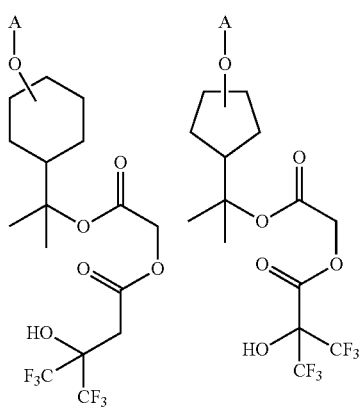
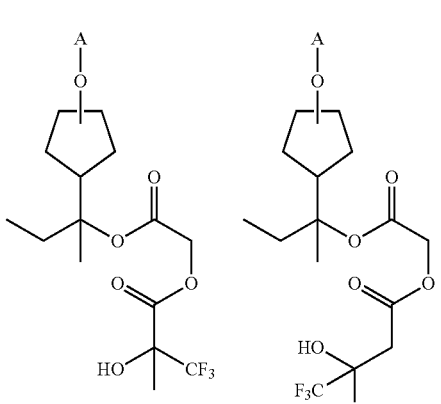
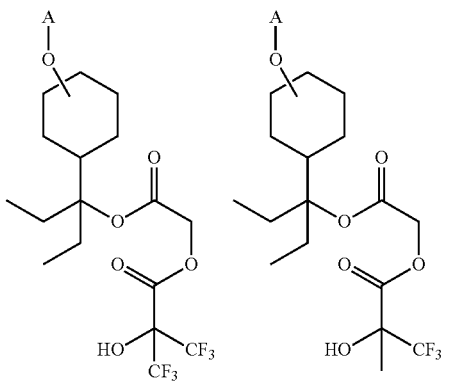

-continued
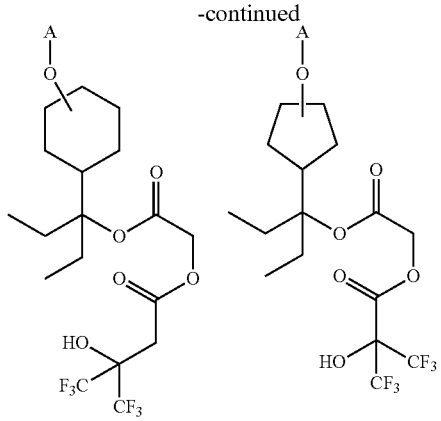 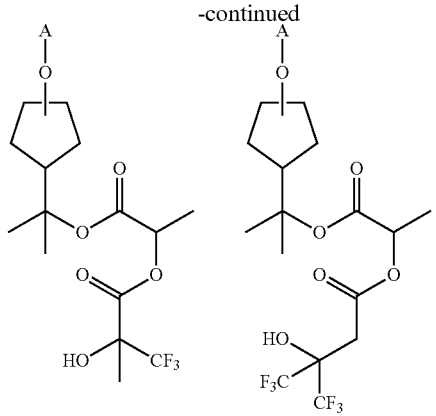
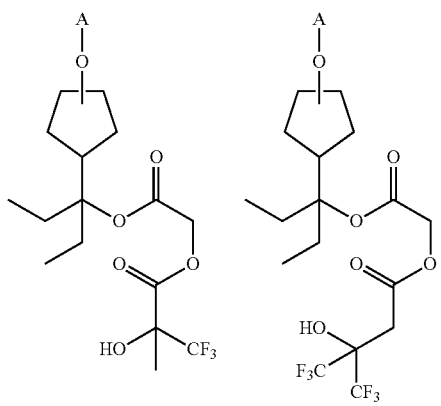 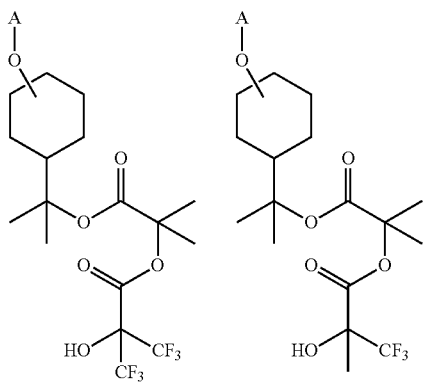
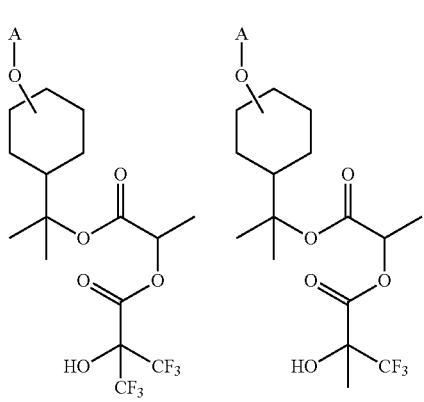 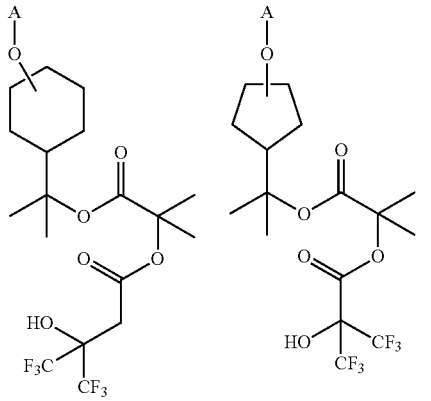
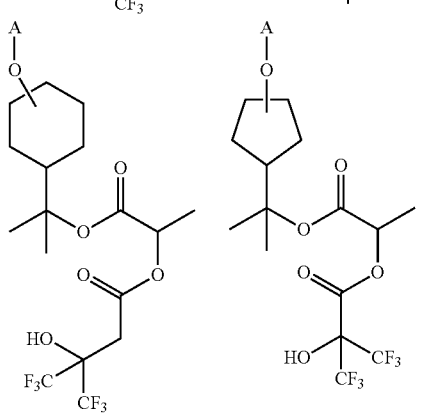 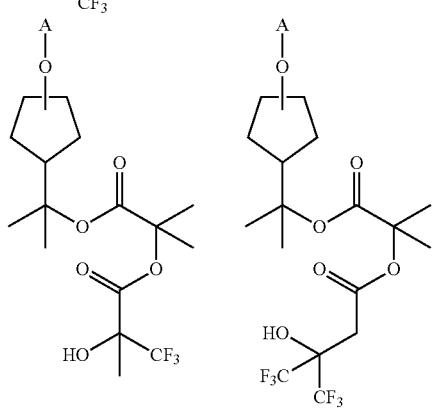

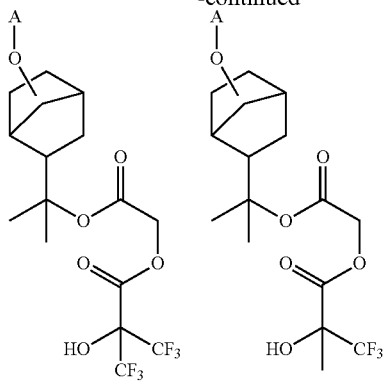
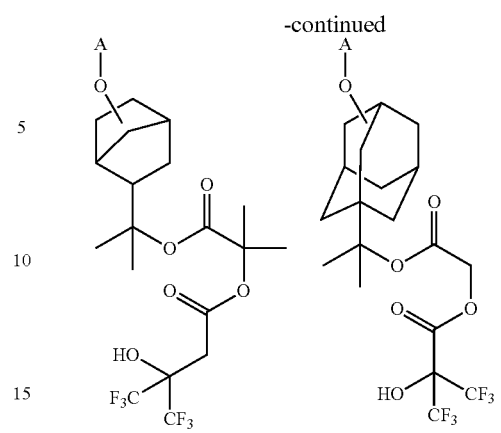
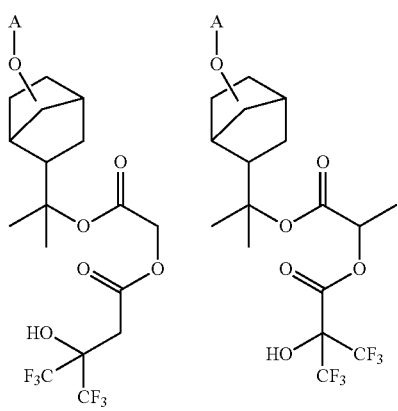
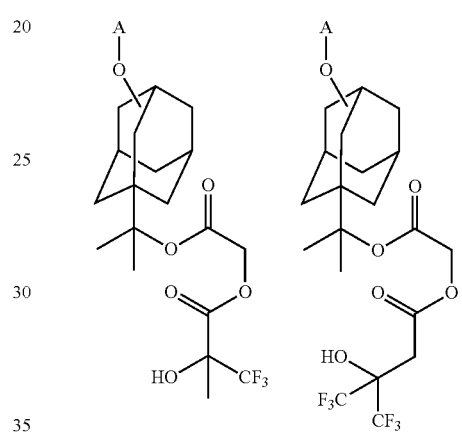
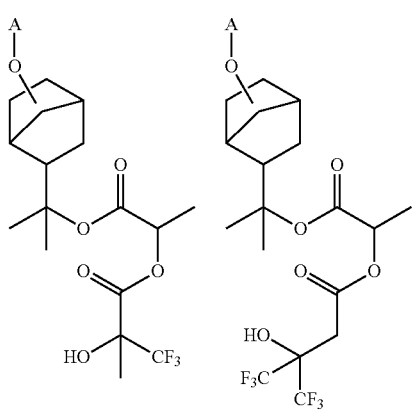
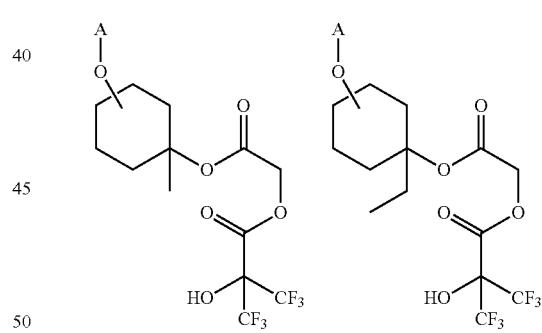
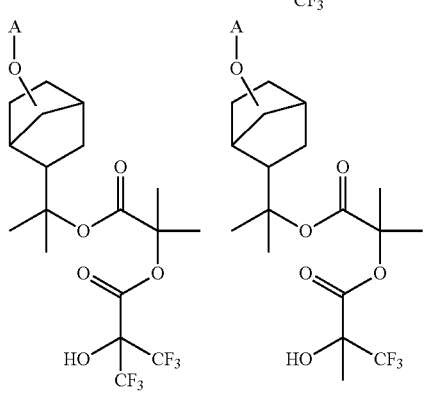
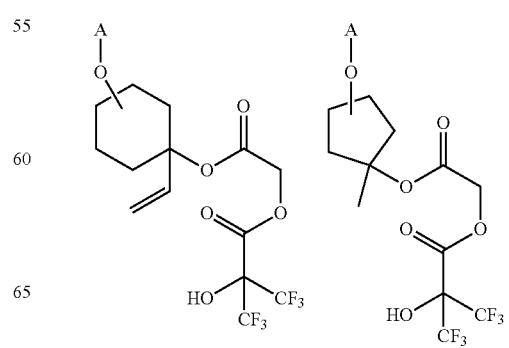

-continued
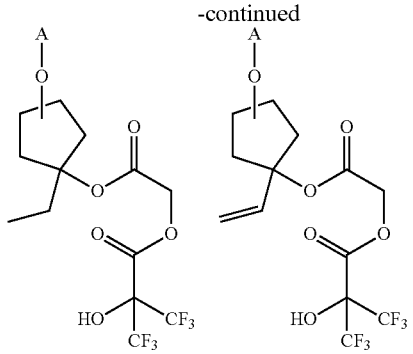
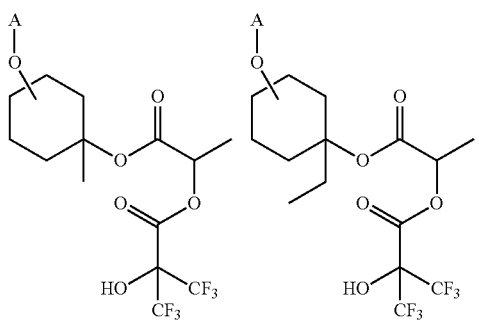
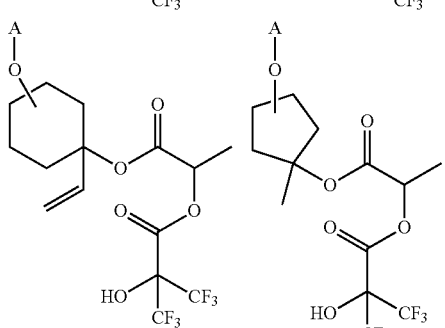
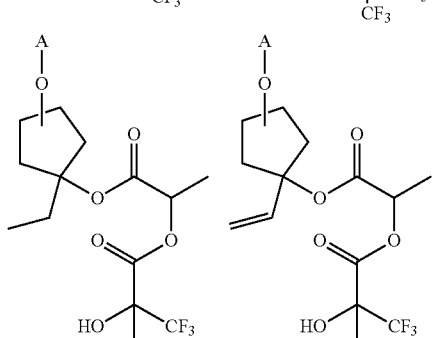
-continued
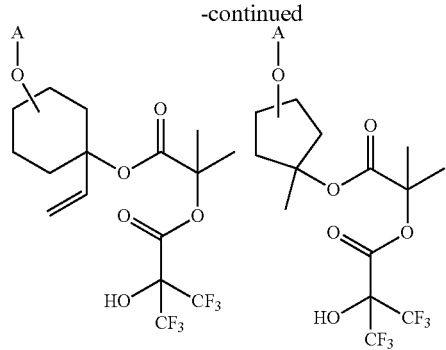
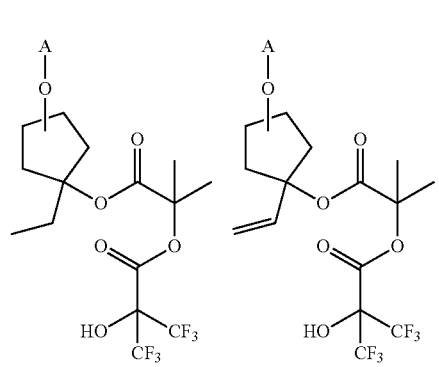
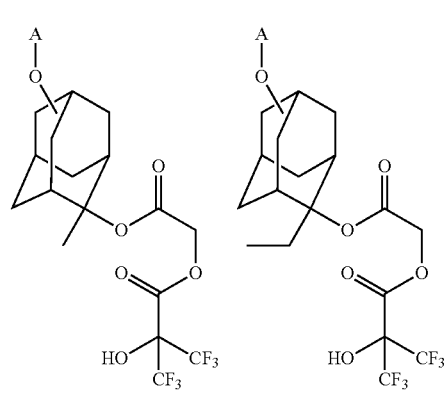
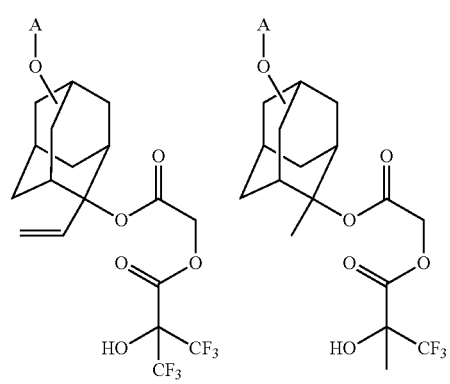

-continued
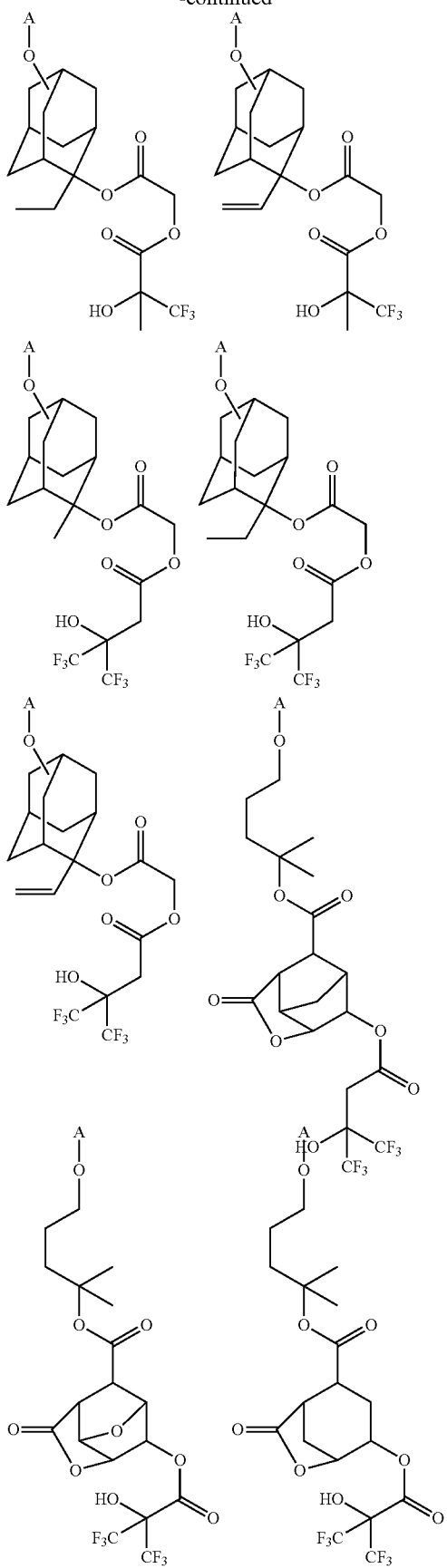
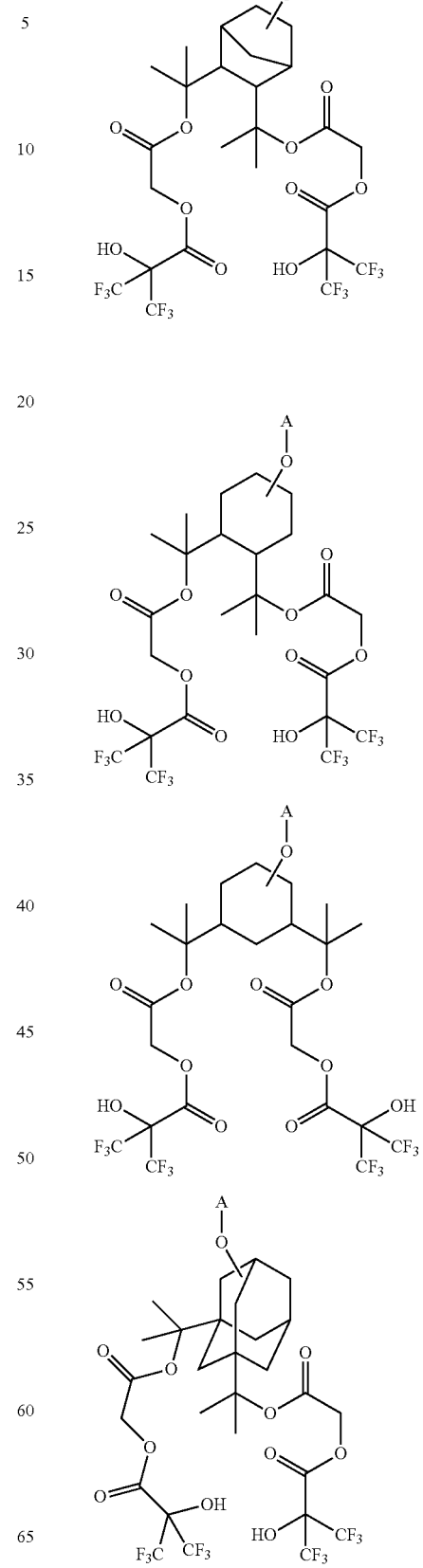

25
-continued
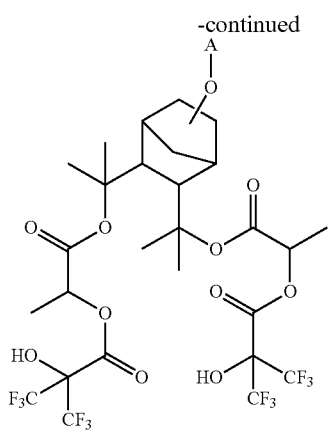
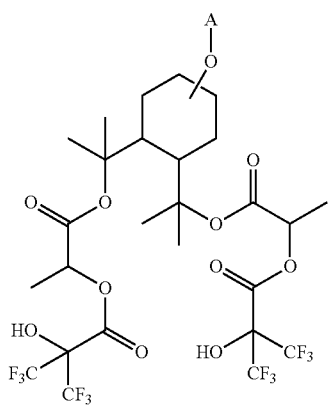
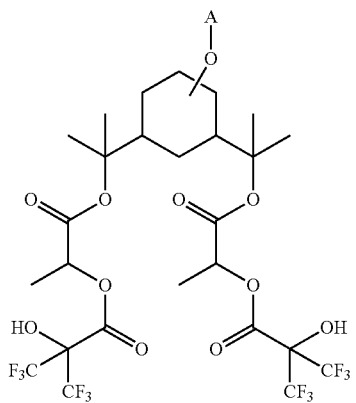
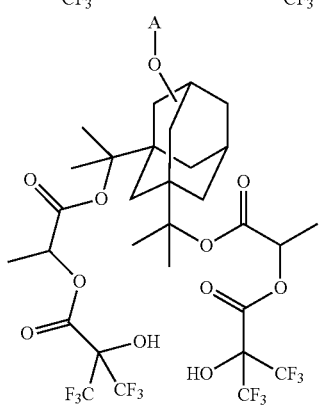
26
-continued
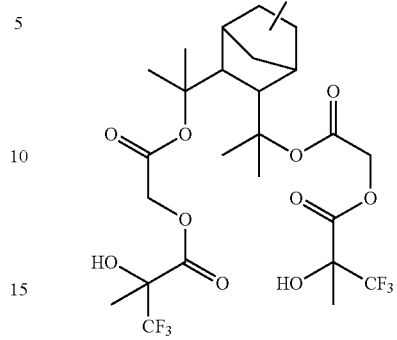
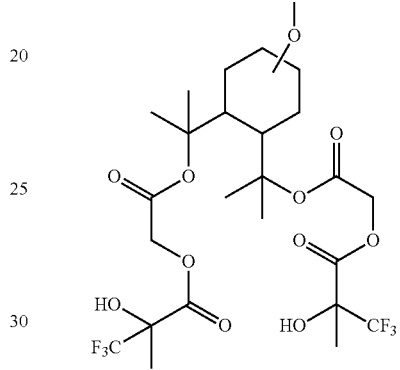
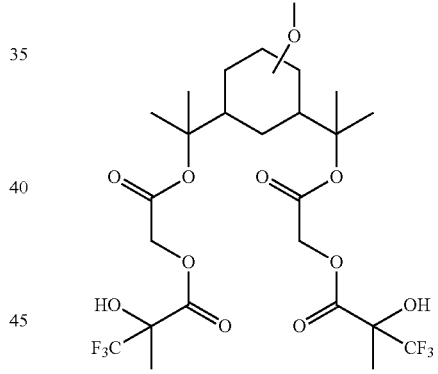
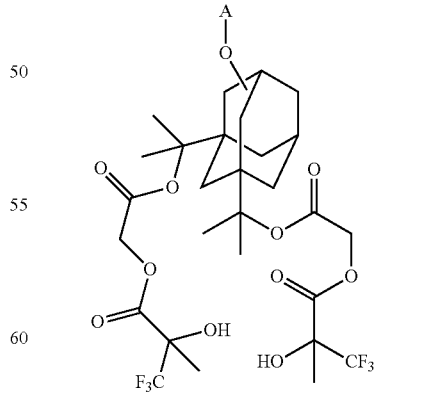
In formulae (1a) and (1b), A is a polymerizable functional group, examples of which are shown below, but not limited thereto.

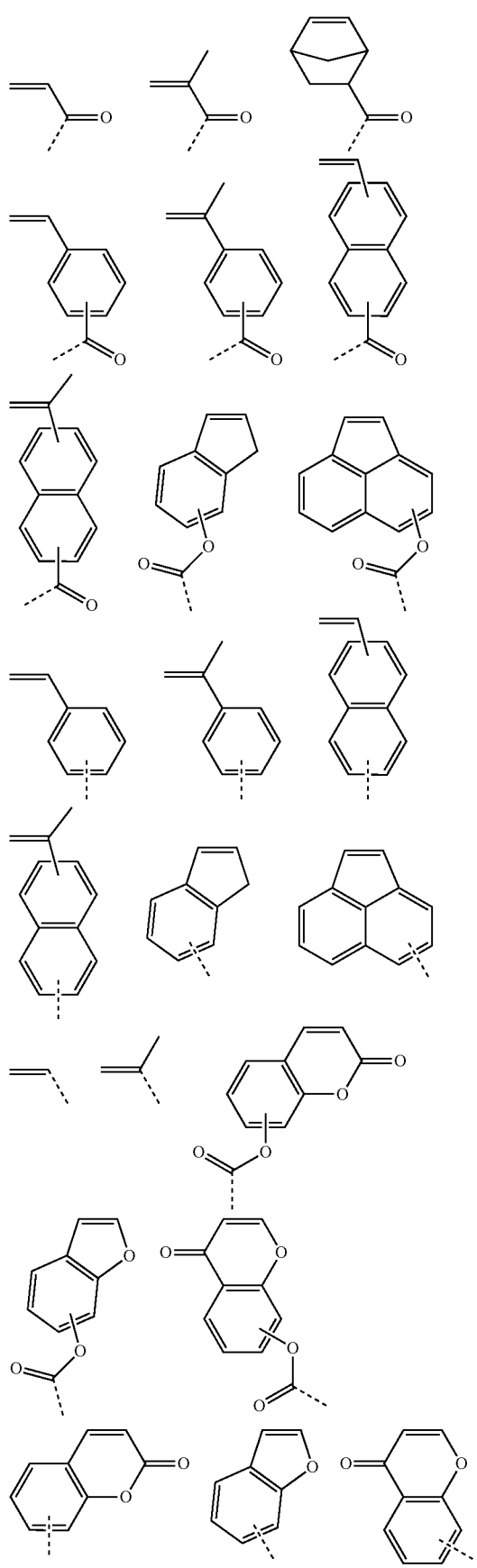

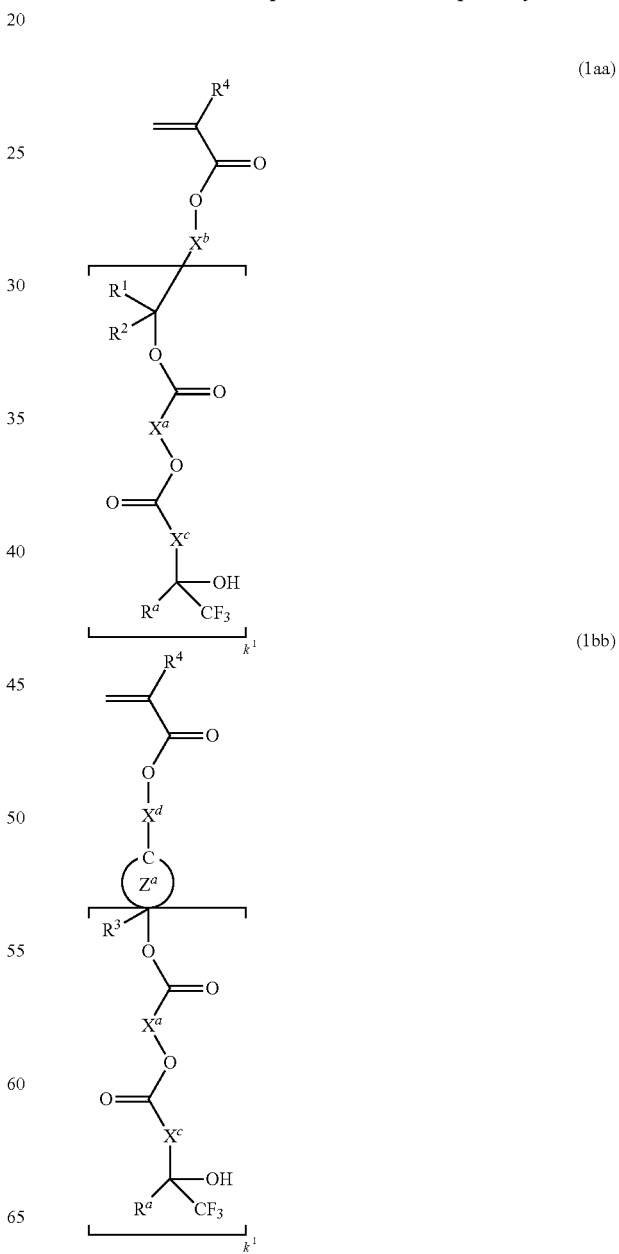

Of the foregoing, A is preferably selected from acryloyl, methacryloyl, cycloalkenyl-containing groups, and vinyl. Most preferably A is acryloyl or methacryloyl. Those monomers wherein A is acryloyl or methacryloyl, as represented by the formula (1aa) or (1bb), are preferable in that monomers of widely varying structures can be prepared owing to ease of introduction of (meth)acryloyl group, and polymerization reaction can be performed in a simple way.

Herein $R^1$ to $R^3$, $R^a$, $X^a$ to $X^d$, $Z^a$ and $k^1$ are as defined above, $R^4$ is hydrogen or methyl.

Among others, those (meth)acrylate monomers having the formulae (1aa-1), (1bb-1) and (1bb-2) are most preferred for the reasons that since they have an alicyclic structure and a high carbon density, polymers obtained therefrom are expectable to be rigid, and that the monomers themselves may be prepared from reactants which are readily available.

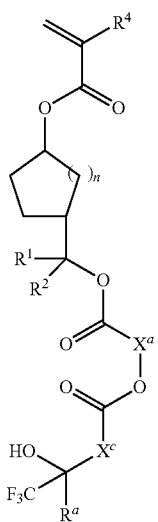

(1aa-1)

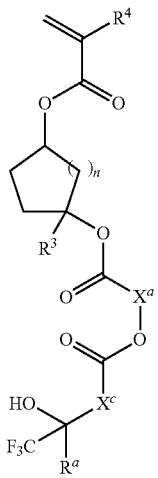

(1bb-1)

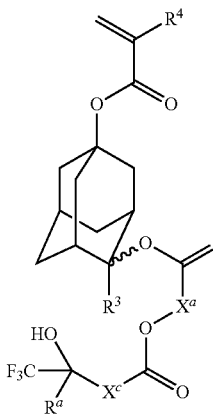

(1bb-2)

Herein $R^1$ to $R^4$, $R^a$, $X^a$ and $X^c$ are as defined above, n is 1 or 2.

The method for preparing the polymerizable monomer of the invention is described by referring to a (meth)acrylate monomer having formula (1aa) or (1bb), but the method is not limited thereto. The method is illustrated by the reaction scheme below.

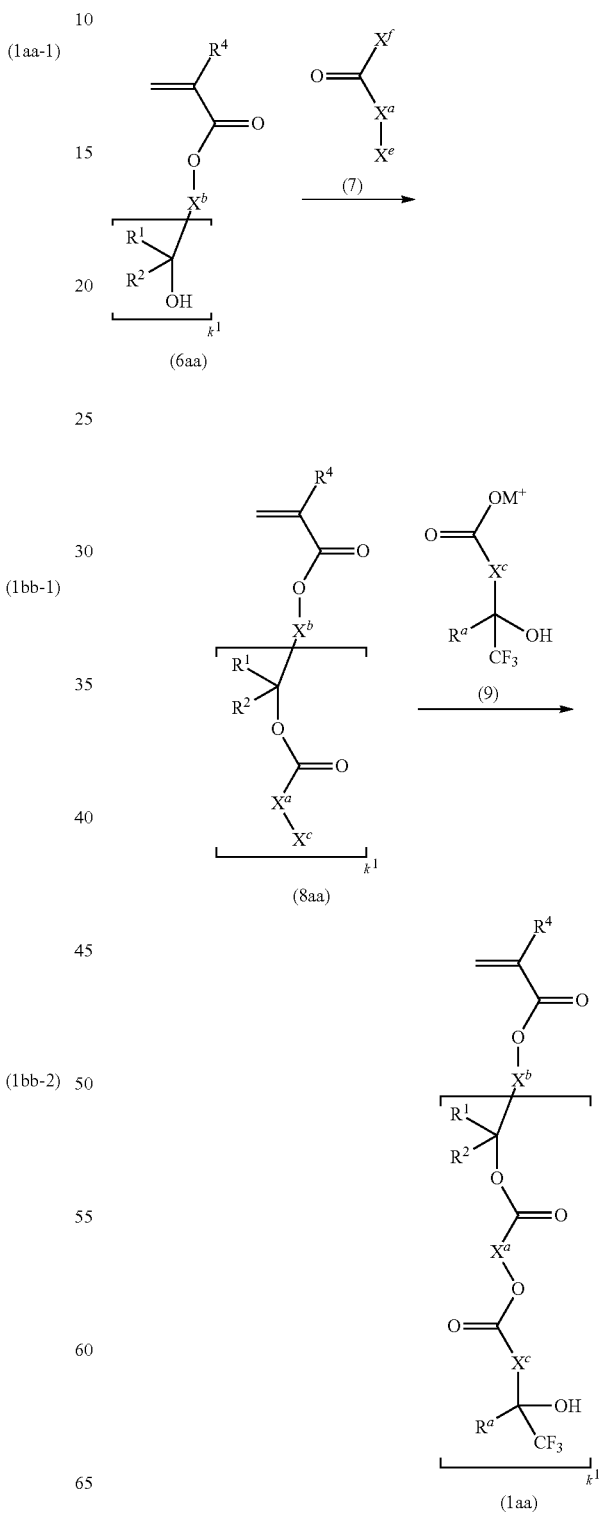

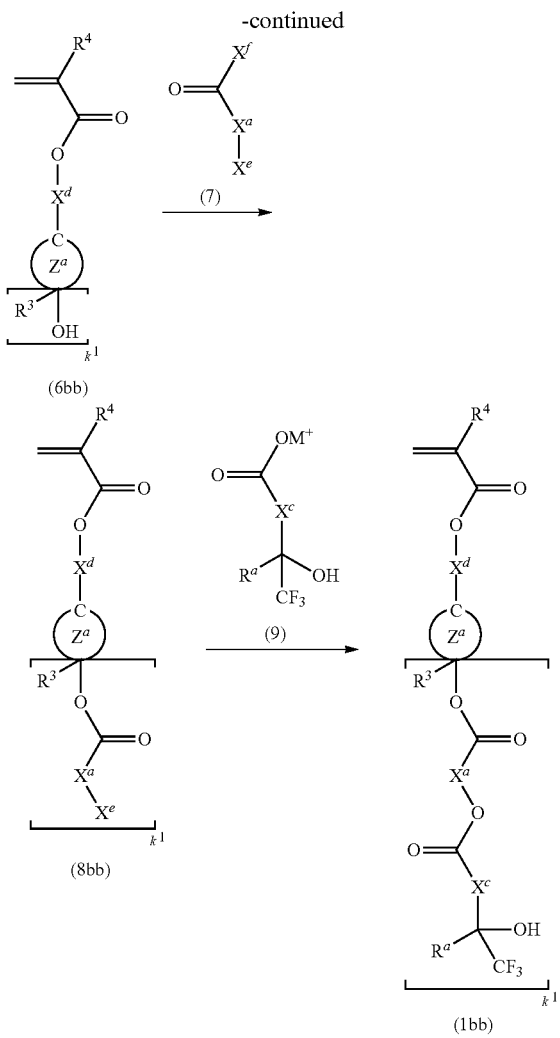

Herein $R^1$ to $R^4$, $R^a$, $X^a$ to $X^d$, $Z^a$ and $k^1$ are as defined above, $X^e$ and $X^f$ are each independently chlorine, bromine or iodine, and $M^+$ is a monovalent metal ion or optionally substituted ammonium ion.

A first step starting with (meth)acrylate (6aa) or (6bb) is an esterification reaction with a halocarboxylic acid chloride to form a halo-ester (8aa) or (8bb).

The reactant, (meth)acrylate (6aa) or (6bb) may be synthesized by a well-known method or purchased from a commercial supplier. The reaction may be performed in a solventless system or in a solvent (e.g., methylene chloride, acetonitrile, tetrahydrofuran, diisopropyl ether, toluene or hexane) by sequentially or simultaneously adding (meth)acrylate (6aa) or (6bb), a corresponding halocarboxylic acid chloride (7) such as chloroacetyl chloride (of formula (7) wherein $X^a$ is —$CH_2$—, both $X^e$ and $X^f$ are chlorine) or 4-chlorobutyric acid chloride (of formula (7) wherein $X^a$ is —$CH_2CH_2CH_2$—, both $X^e$ and $X^f$ are chlorine), and a base (e.g., triethylamine, pyridine or 4-dimethylaminopyridine), and optionally cooling or heating the reaction system. It is desirable from the standpoint of yield that the reaction time is determined so as to drive the reaction to completion by monitoring the reaction process by gas chromatography (GC) or silica gel thin layer chromatography (TLC). Usually, the reaction time is about 0.5 to 48 hours. From the reaction mixture, the halo-ester (8aa) or (8bb) is recovered through an ordinary aqueous workup. If necessary, it may be purified by a standard technique such as distillation, chromatography or recrystallization.

A second step is a reaction of halo-ester (8aa) or (8bb) with a fluoroalcohol structure-containing carboxylic acid salt compound (9) to form a (meth)acrylate monomer (1aa) or (1bb).

The fluoroalcohol structure-containing carboxylic acid salt compound (9) may be previously prepared by mixing a fluoroalcohol structure-containing carboxylic acid with a corresponding alkali compound (e.g., sodium hydroxide, triethylamine or tetrabutylammonium hydroxide) in a molar ratio of 1:1. Alternatively, the fluoroalcohol structure-containing carboxylic acid salt compound (9) may be formed in situ by mixing halo-ester (8aa) or (8bb) with a fluoroalcohol structure-containing carboxylic acid, and adding a corresponding alkali compound (e.g., sodium hydroxide, triethylamine or tetrabutylammonium hydroxide) to the mixture. The reaction may be performed in a solventless system or in a solvent (e.g., acetonitrile, N,N-dimethylformamide (DMF), N,N-dimethylacetamide (DMAc) or —N-methylpyrrolidone (NMP)) by combining halo-ester (8aa) or (8bb) with the fluoroalcohol structure-containing carboxylic acid salt compound (9) at room temperature or elevated temperature. When the reaction system is heated, a temperature of about 40 to 80° C. is preferred. It is desirable from the standpoint of yield that the reaction time is determined so as to drive the reaction to completion by monitoring the reaction process by GC or silica gel TLC. Usually, the reaction time is about 1 to 48 hours. From the reaction mixture, the (meth)acrylate monomer (1aa) or (1bb) is recovered through an ordinary aqueous workup. If necessary, the monomer may be purified by a standard technique such as distillation, chromatography or recrystallization.

Polymer

The invention also provides a polymer comprising recurring units containing as pendant a group having the formula (2a) and/or a group having the formula (2b).

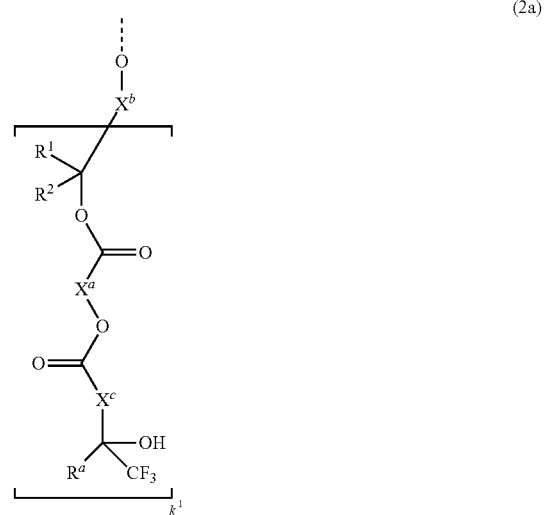

(2a)

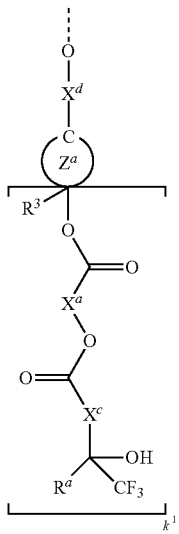

(2b)

Herein $R^1$ to $R^3$, $R^a$, $X^a$ to $X^d$, $Z^a$ and $k^1$ are as defined above, and the broken line designates a valence bond to the polymer backbone.

The recurring unit of formula (2a) or (2b) has a tertiary alkyl ester structure which is an acid labile group and a fluoroalcohol-containing ester structure having at least one trifluoromethyl group substituted at α-position relative to the alcoholic hydroxyl group, at the end of a corresponding carboxylic acid moiety. This terminal structure containing a tertiary ester of carboxylic acid functions as an eliminatable group having high acid reactivity. Then the polymer reacts with acid at a high efficiency, whereupon the fluoroalcohol structure having high acidity is lost and an olefin forms. An exemplary reaction is shown below.

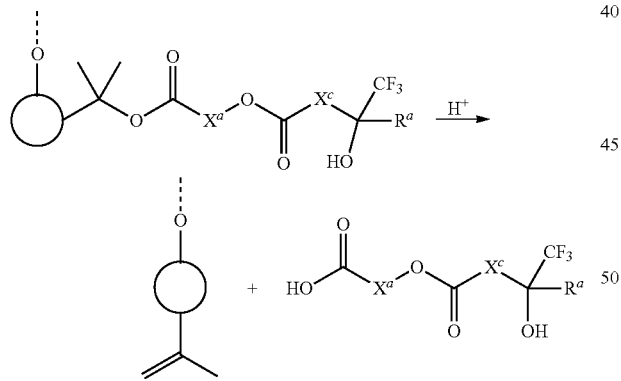

Herein $R^a$, $X^a$ and $X^c$ are as defined above.

As mentioned above, a resist composition comprising the inventive polymer as a base resin has a very high affinity to and high solubility in alkaline developer prior to exposure, due to the presence of a fluoroalcohol structure exhibiting a high acidity. After exposure, in the exposed region, the terminal fluoroalcohol-containing carboxylic acid structure is eliminated and lost via reaction with the acid generated in the exposed region, and as a result, the resist in the exposed region undergoes a substantial drop of solubility in alkaline developer and becomes insoluble in the developer. In the unexposed region where the fluoroalcohol structure having alkaline affinity is retained intact in the resin, the resist is rapidly dissolved in the developer without being swollen. In this sense, the inventive polymer is a base resin having a very high dissolution contrast or a very large difference of dissolution rate in alkaline developer between the exposed region and the unexposed region. In addition, since the resist maintains a high carbon density and resin film thickness even after the switch of developer solubility after exposure, it is quite effective for restraining bridging between pattern features and pattern collapse due to swell, which are regarded problematic with prior art negative tone resist materials of polarity switch type and negative tone resist materials utilizing crosslinking reaction. Also the polymer has excellent etch resistance, enabling resolution of finer size patterns.

The recurring unit containing a group of formula (2a) or the recurring unit containing a group of formula (2b) is preferably derived from a monomer having formula (1a) or a monomer having formula (1b). Of these recurring units, those units derived from monomers of the corresponding formula wherein A is acryloyl or methacryloyl, that is, units having formula (2aa) or (2bb) are especially preferred.

(2aa)

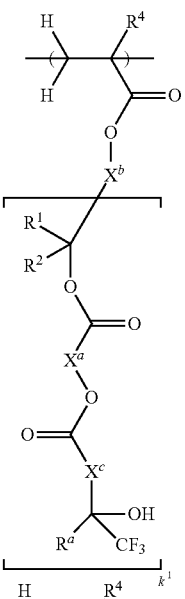

(2bb)

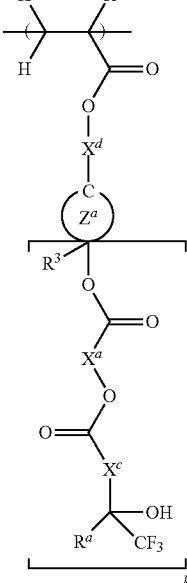

Herein $R^1$ to $R^3$, $R^a$, $X^a$ to $X^d$, $Z^a$ and $k^1$ are as defined above, $R^4$ is hydrogen or methyl.

The inventive polymer may further comprise recurring units of at least one type selected from recurring units having the formulae (3) to (5).

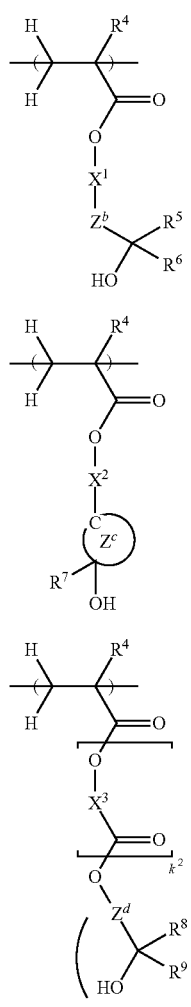

Herein $R^4$ is hydrogen or methyl. $R^5$ and $R^6$ are each independently a $C_1$-$C_6$ straight, branched or cyclic monovalent hydrocarbon group, $R^5$ and $R^6$ may bond together to form an alicyclic group with the carbon atom to which they are attached. $R^7$ is a $C_1$-$C_6$ straight, branched or cyclic monovalent hydrocarbon group. $R^8$ and $R^9$ are each independently a $C_1$-$C_6$ straight, branched or cyclic monovalent hydrocarbon group, $R^8$ and $R^9$ may bond together to form an alicyclic group with the carbon atom to which they are attached. $X^1$ and $X^2$ are each independently a single bond, methylene or ethylidene. $X^3$ is a $C_1$-$C_{20}$ straight, branched or cyclic divalent hydrocarbon group in which any constituent —$CH_2$— moiety may be replaced by —O— or —C(=O)—. $Z^b$ is a $C_1$-$C_9$ straight, branched or cyclic aliphatic hydrocarbon group, $Z^c$ is an atomic group necessary to form a $C_3$-$C_{10}$ alicyclic group with the carbon atom to which it is attached, $Z^d$ is a $C_1$-$C_{20}$ straight, branched or cyclic aliphatic hydrocarbon group in which any constituent —$CH_2$— moiety may be replaced by —O— or —C(=O)—, with the proviso that $Z^b$ is exclusive of a group that forms the O—$Z^b$ bond in formula (3) which is dissociable under the action of acid, when $X^1$ is a single bond, and $Z^d$ is exclusive of a group that forms the O—$Z^d$ bond in formula (5) which is dissociable under the action of acid. The total number of carbon atoms in $X^1$, $Z^b$, $R^5$ and $R^6$ is 5 to 12, the total number of carbon atoms in $X^2$, $Z^c$ and $R^7$ is 5 to 12, $k^2$ is 0 or 1, $k^3$ is an integer of 2 to 4.

Now that recurring units having the formulae (3) to (5) are incorporated in addition to the recurring units having the formula (2a) and/or recurring units having the formula (2b), the dissolution rate in alkaline developer of the polymer or base resin in the unexposed region is further improved. The recurring unit having the formula (3), (4) or (5) is a unit having 1 to 4 tertiary alcoholic hydroxyl groups which are acid labile groups. Prior to exposure, the polymer has a high affinity to and solubility in alkaline developer due to the presence of hydrophilic hydroxyl groups. After exposure, hydroxyl groups are lost in the exposed region, and the polymer in the exposed region experiences a substantial drop of solubility in alkaline developer and becomes insoluble in the developer.

Examples of the recurring units having the formulae (3) to (5) are given below, but not limited thereto. $R^4$ is as defined above.

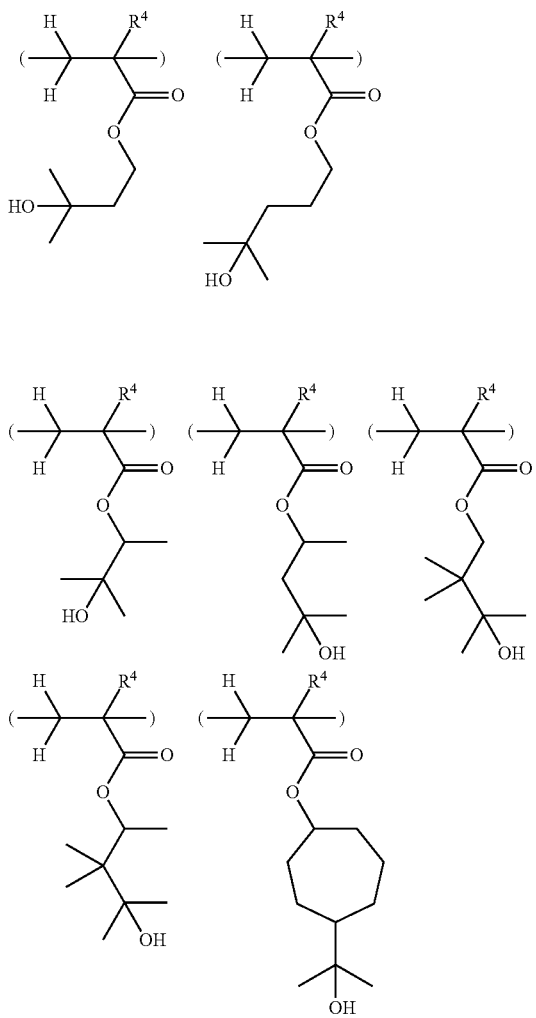

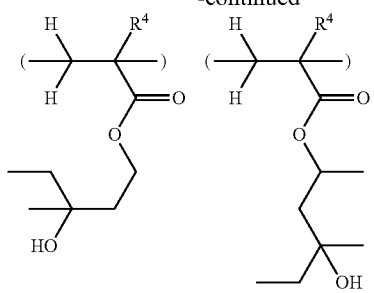
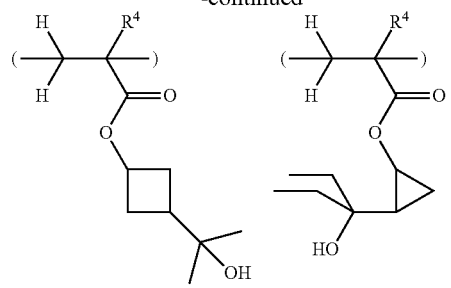
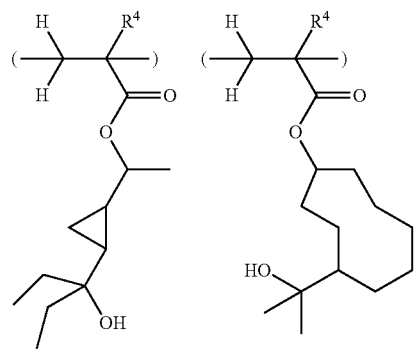
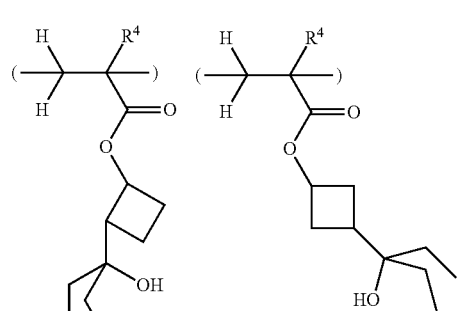
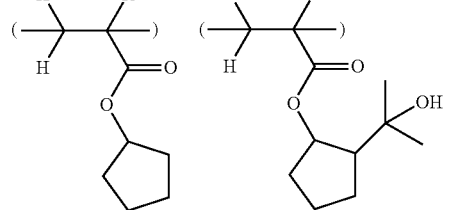
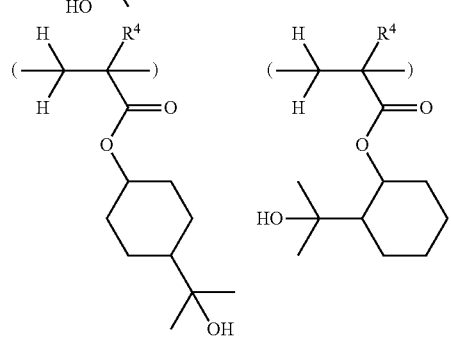

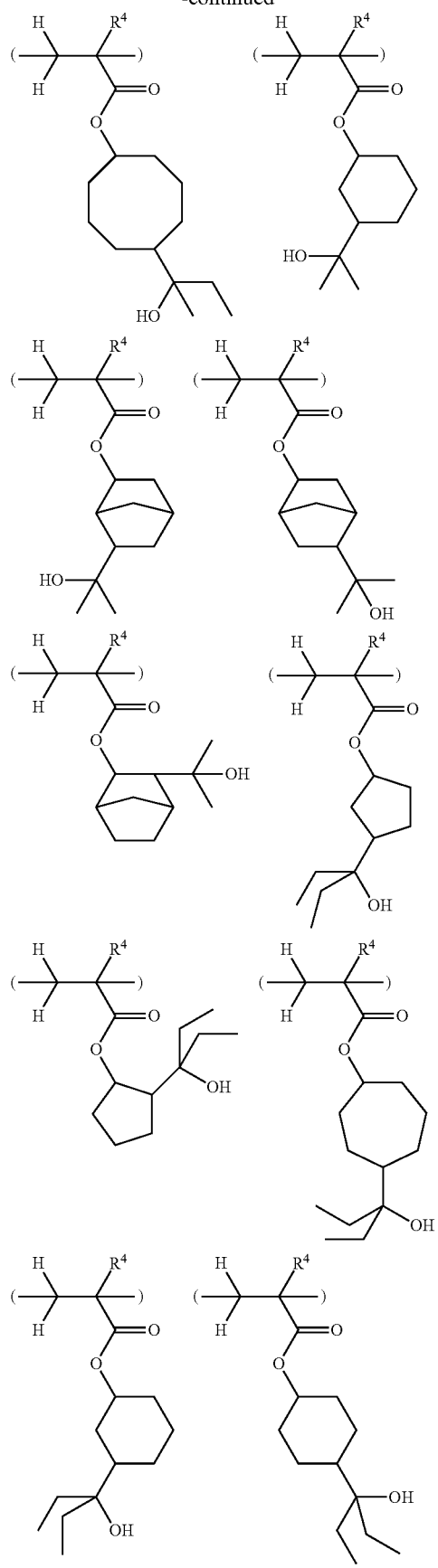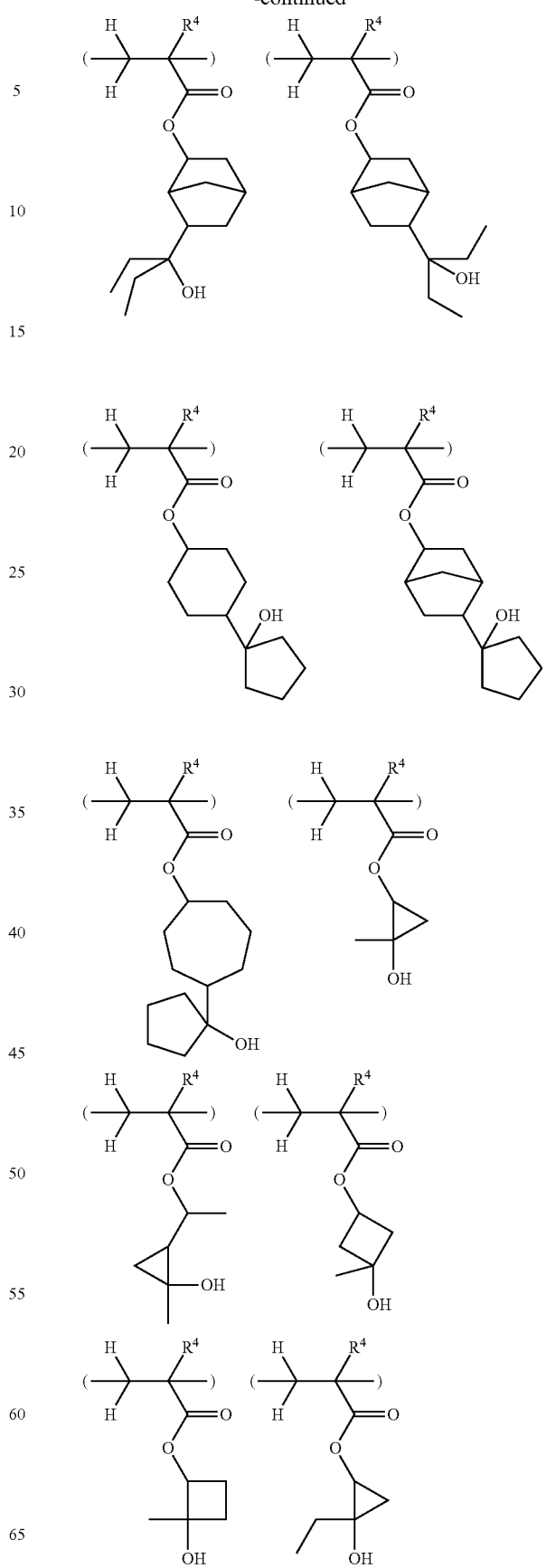

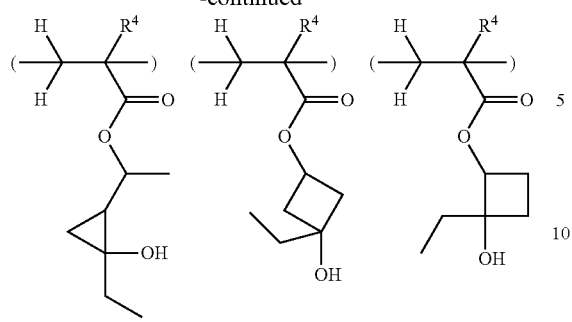
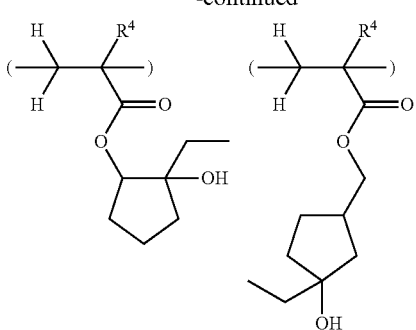
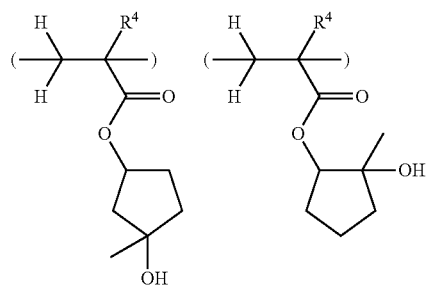
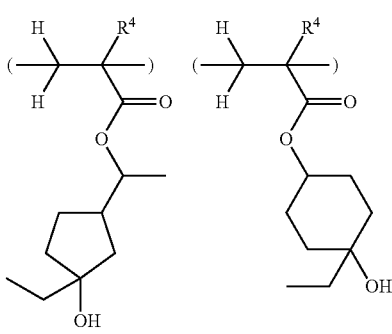
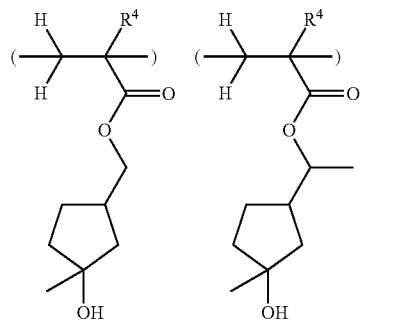
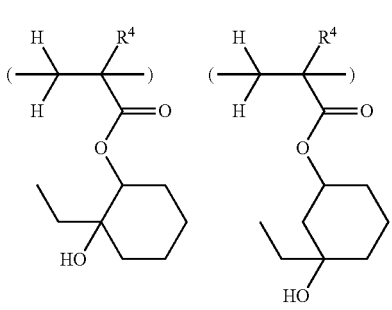
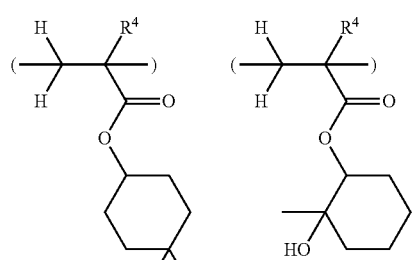
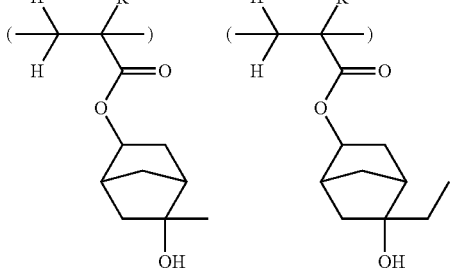
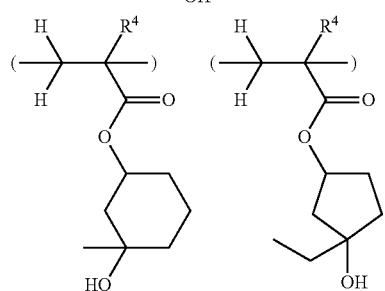
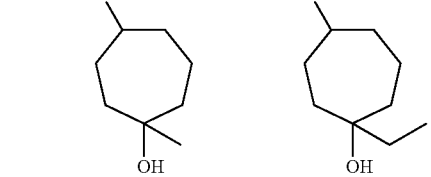

-continued
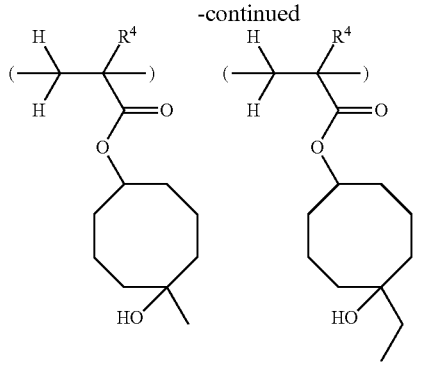
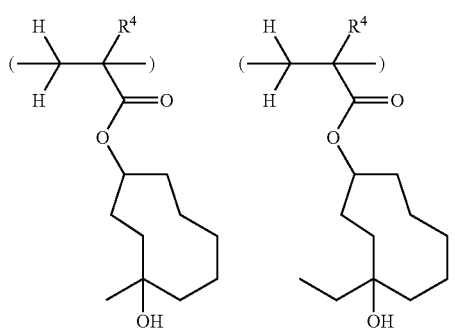
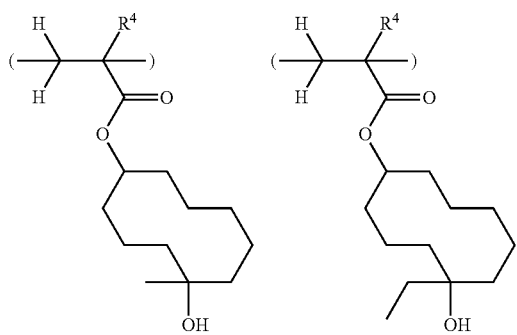
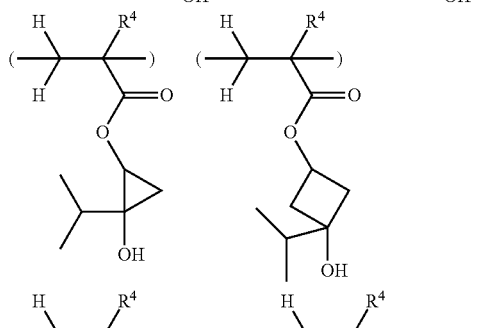
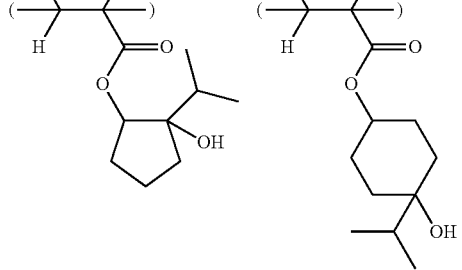
-continued
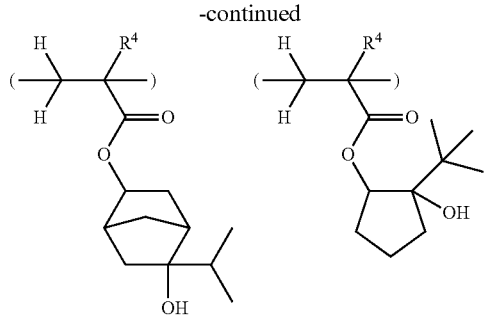
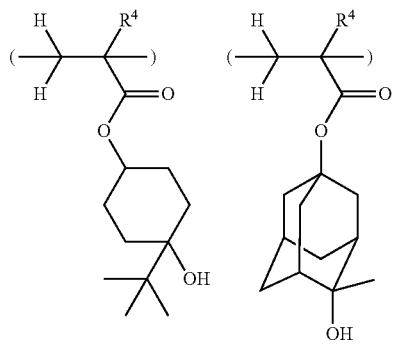
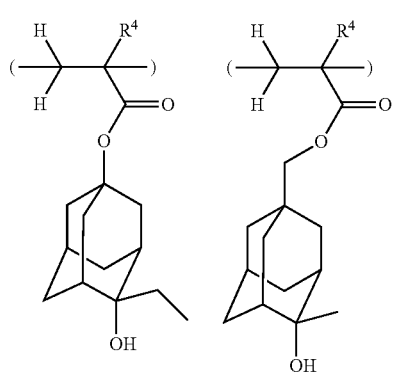
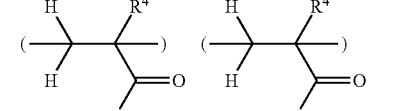
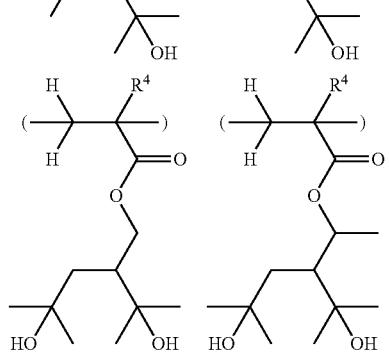

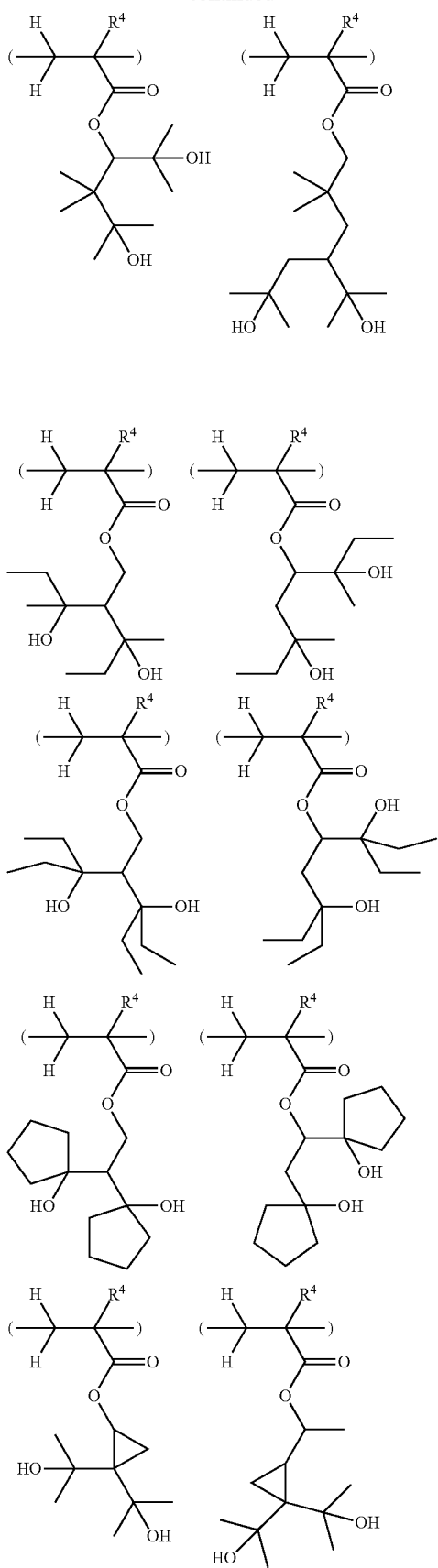
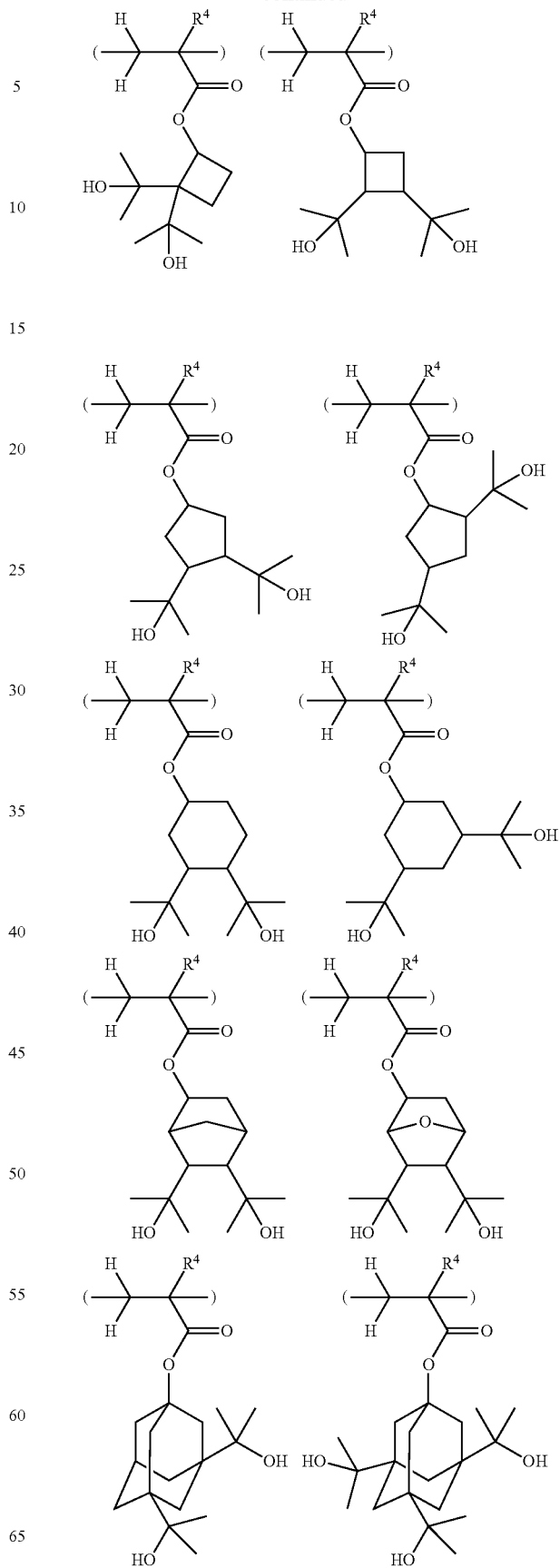

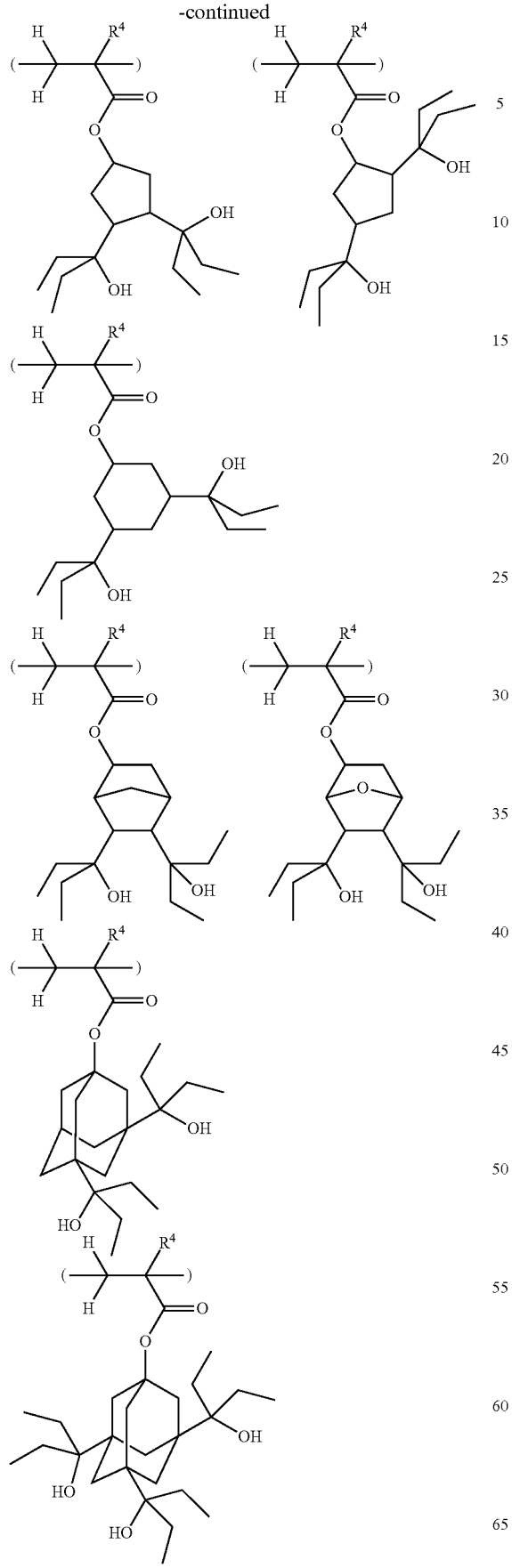
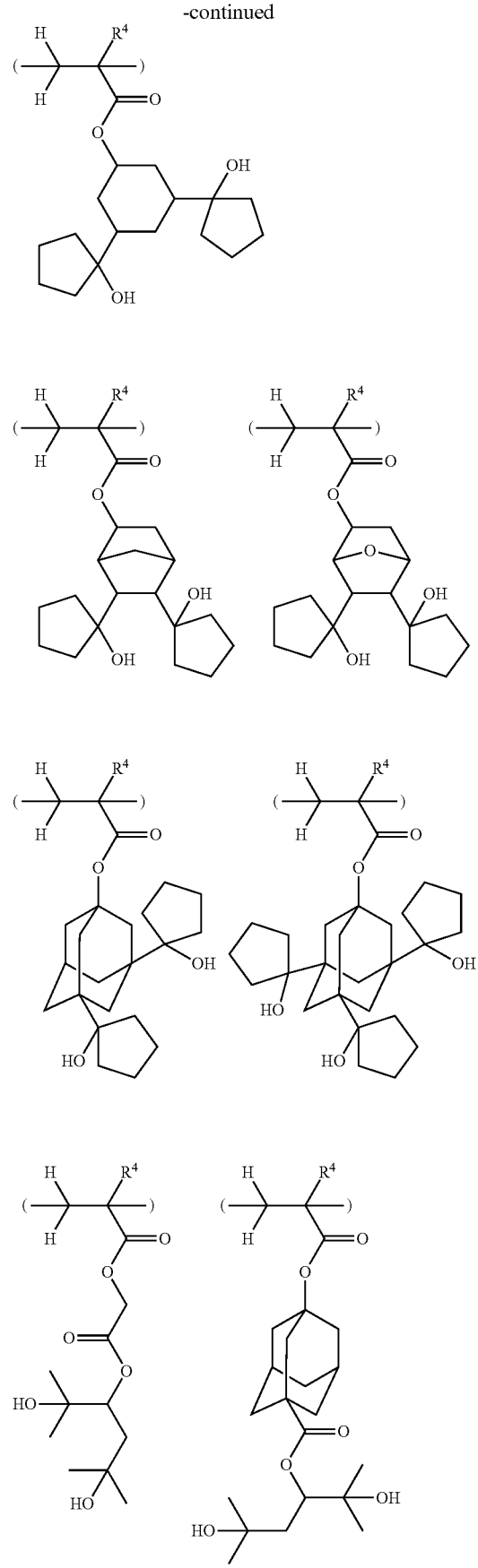

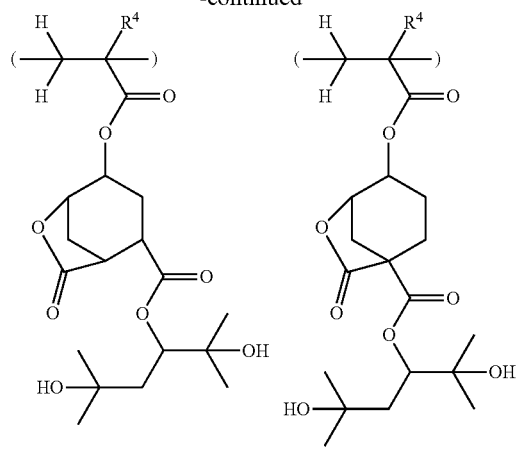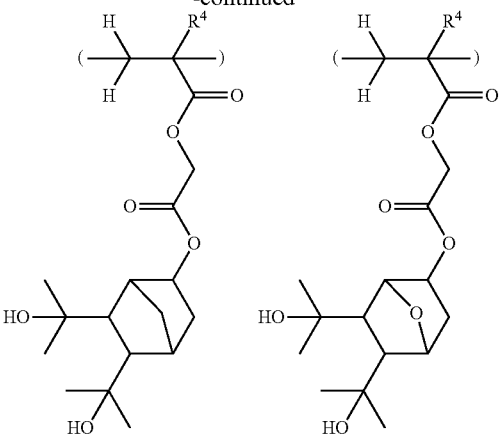
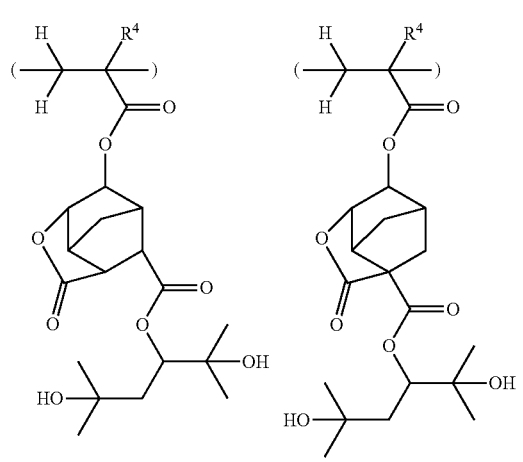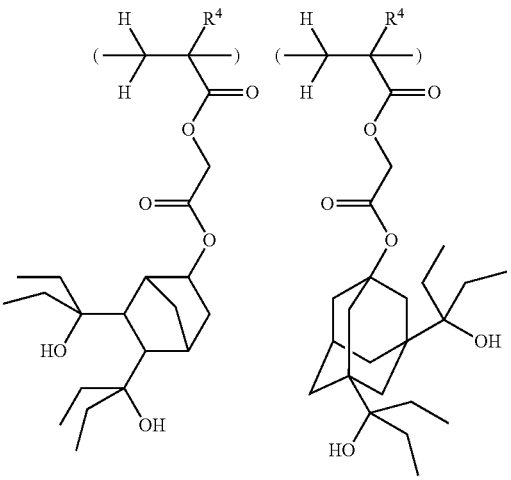
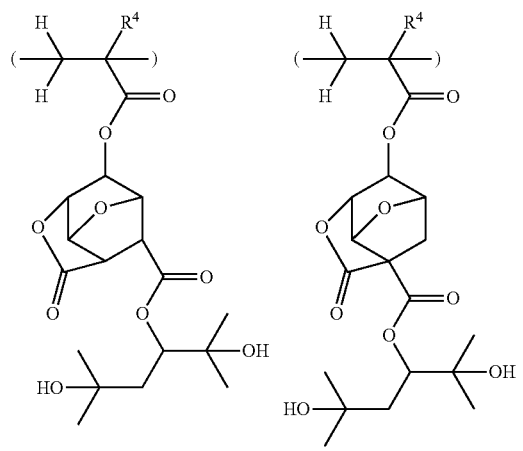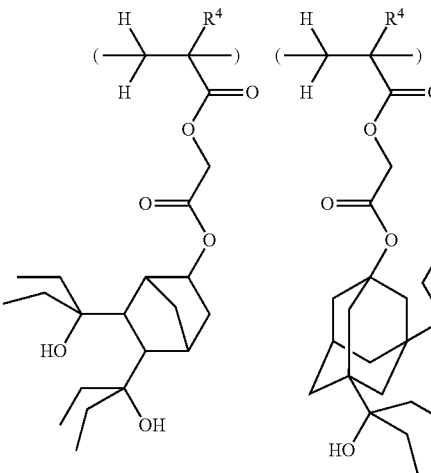

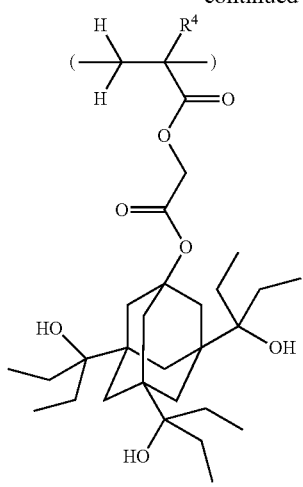

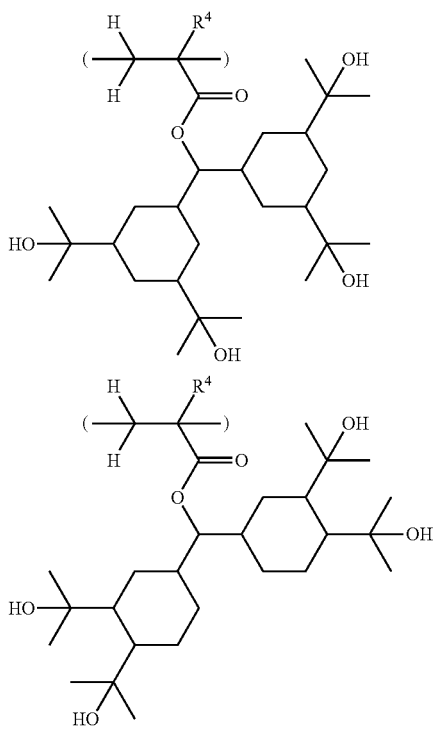

In the inventive polymer, recurring units of at least one type selected from recurring units having the formulae (A) to (D) may further be incorporated for the purposes of controlling solubility and improving adhesion to the substrate.

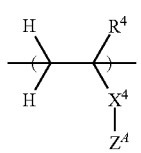
(A)

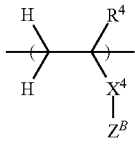
(B)

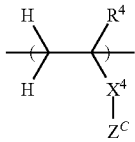
(C)

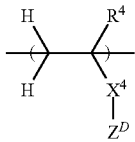
(D)

Herein $R^4$ is hydrogen or methyl. $Z^A$ is a $C_1$-$C_{20}$ fluoroalcohol-containing group, exclusive of a structure undergoing a polarity switch under the action of acid. $Z^B$ is a $C_1$-$C_{20}$ phenolic hydroxyl-containing group. $Z^C$ is a $C_1$-$C_{20}$ carboxyl-containing group. $Z^D$ is a substituent group having a lactone structure, sultone structure, carbonate structure, cyclic ether structure, acid anhydride structure, alcoholic hydroxyl, alkoxycarbonyl, sulfonamide or carbamoyl moiety. $X^4$ is a single bond, methylene, ethylene, phenylene, fluorinated phenylene, naphthylene, —O—$R^{01}$—, or —C(=O)—$Z^X$—$R^{01}$—, wherein $Z^X$ is —O— or —NH—, and $R^{01}$ is a $C_1$-$C_6$ straight, branched or cyclic alkylene, $C_2$-$C_6$ straight, branched or cyclic alkenylene, phenylene or naphthylene group, which may contain a carbonyl, ester, ether or hydroxyl moiety.

The recurring unit of formula (A) has a fluoroalcohol-containing group having high affinity to alkaline aqueous solution. Preferred examples of the fluoroalcohol-containing unit include recurring units having a 1,1,1,3,3,3-hexafluoro-2-propanol residue and 2-hydroxy-2-trifluoromethyloxolane structure, as described in JP-A 2007-297590, JP-A 2008-111103, JP-A 2008-122932, and JP-A 2012-128067. Although these units have a tertiary alcoholic hydroxyl group or hemiacetal structure, they are not reactive with acid because of fluorine substitution.

Since the recurring units of formulae (A) to (D) are structural units having hydroxyl group's proton, the polymer becomes higher in alkaline solubility as the proportion of these units incorporated is increased. On the other hand, excessive incorporation of these units can adversely affect a polarity switch (or alkali insolubilizing effect) that is brought about by elimination reaction taking place in recurring unit of formula (2a) and/or (2b) by acid. Accordingly, the recurring units of formulae (A) to (D) are preferably incorporated in such proportions that the alkali solubility of the unexposed region may be supplemented and the alkali insolubilizing effect of the exposed region not be impaired.

Illustrative, non-limiting examples of the recurring unit having formula (A) are shown below. Notably $R^4$ is as defined above.

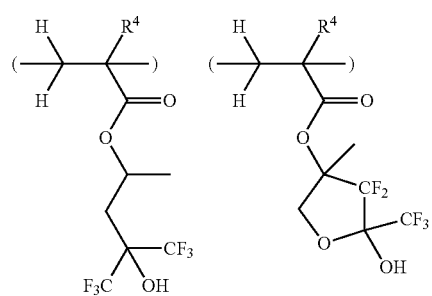
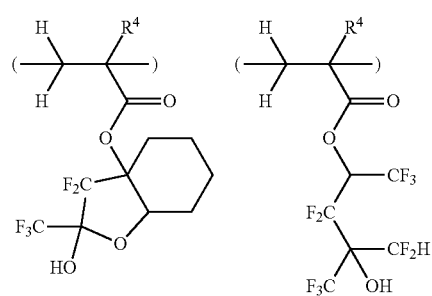
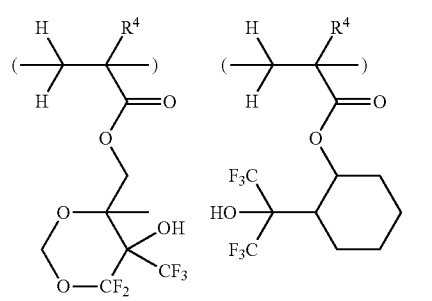
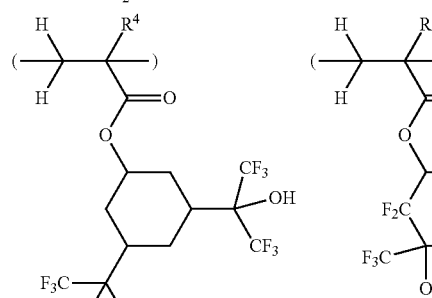
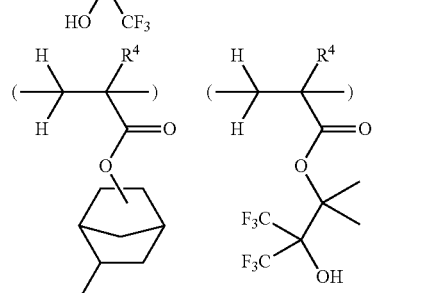
-continued
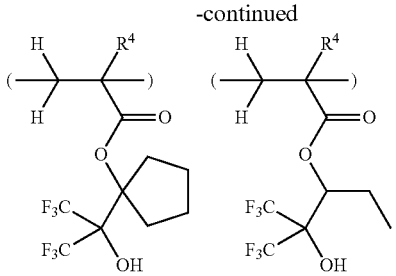
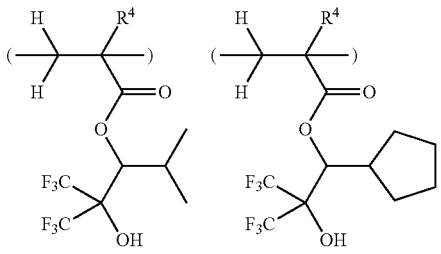
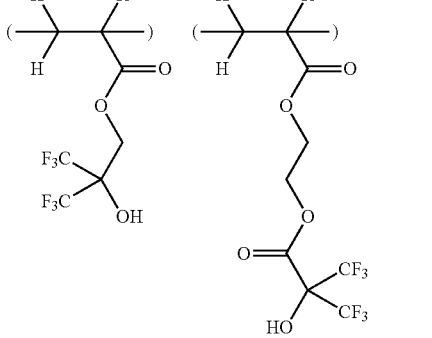
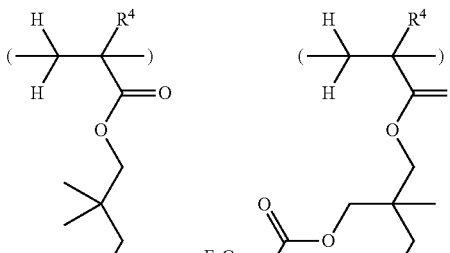
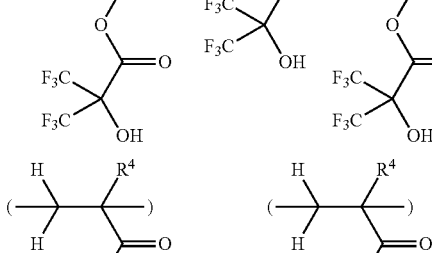
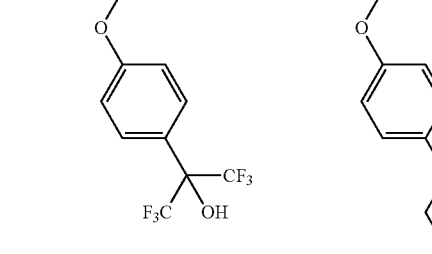

-continued
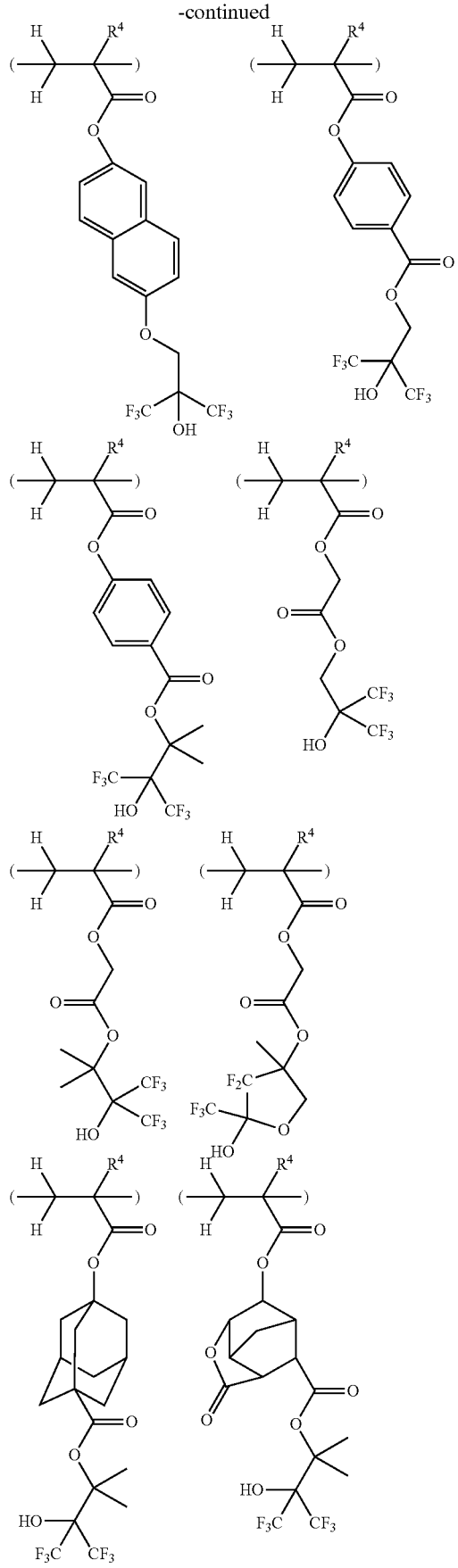
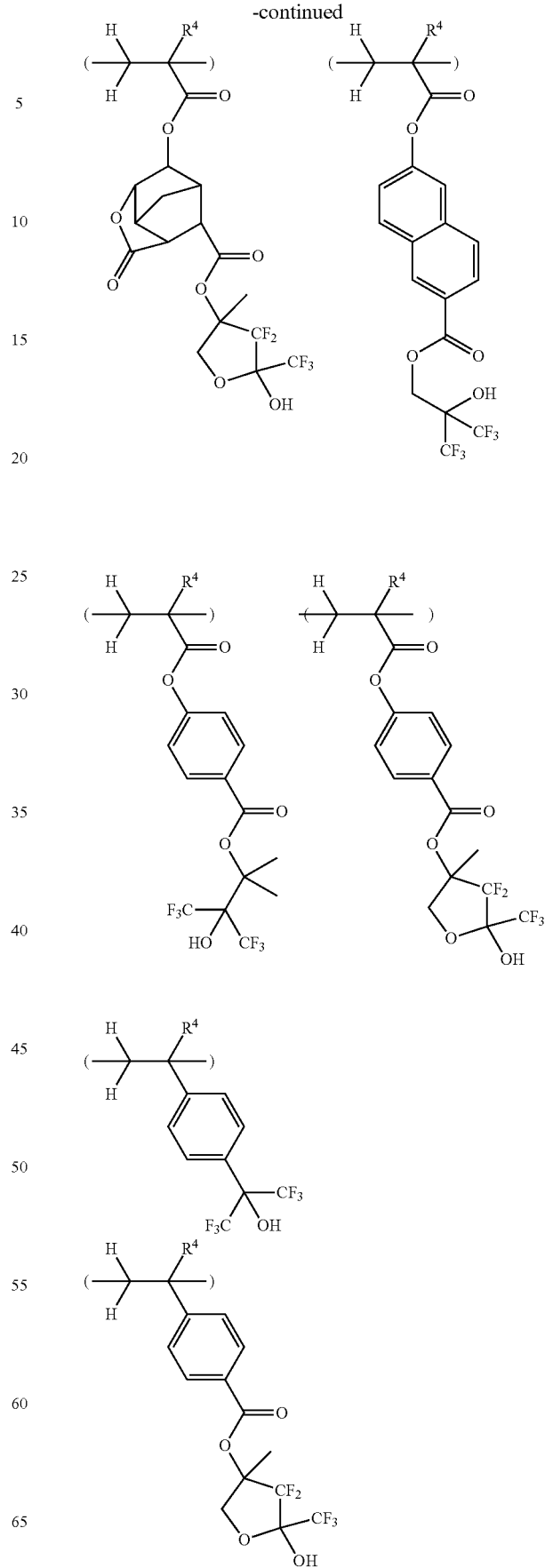

-continued
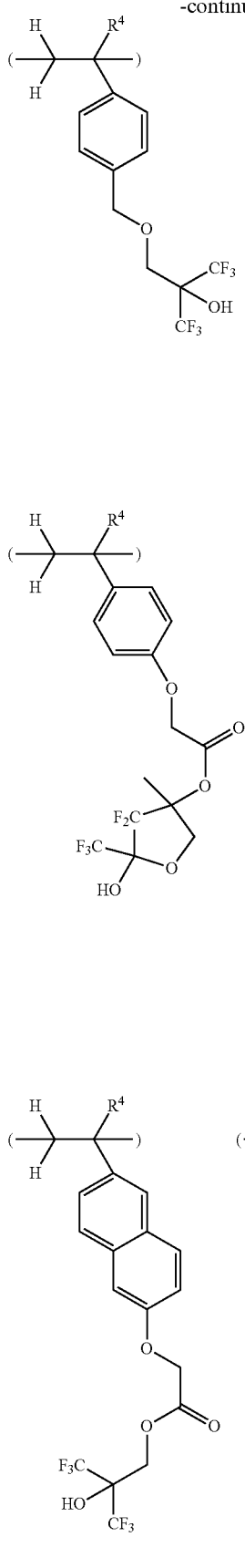
Illustrative, non-limiting examples of the recurring unit having formula (B) are shown below. Notably $R^4$ is as defined above.
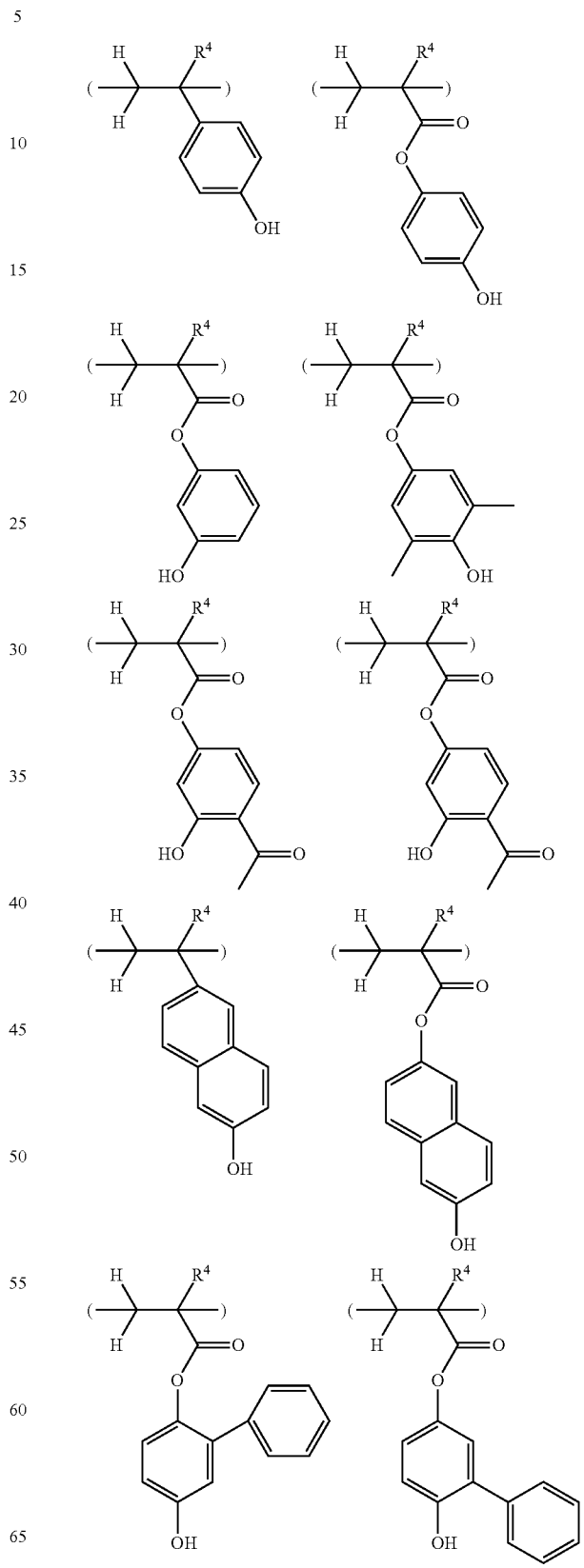

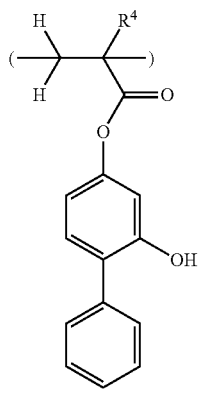

Illustrative, non-limiting examples of the recurring unit having formula (C) are shown below. Notably R⁴ is as defined above.

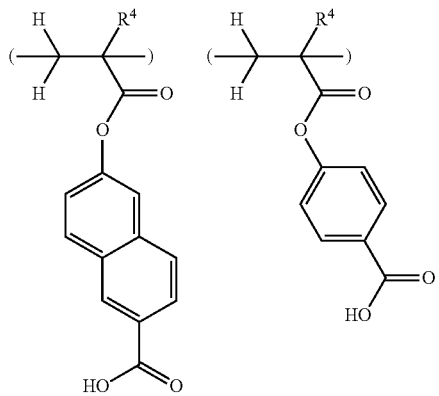

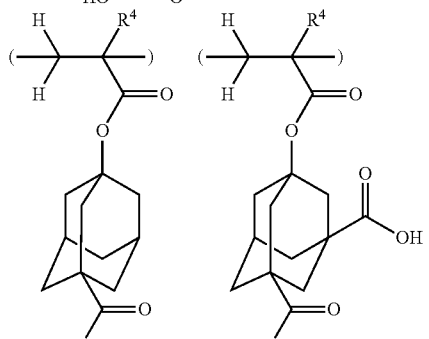

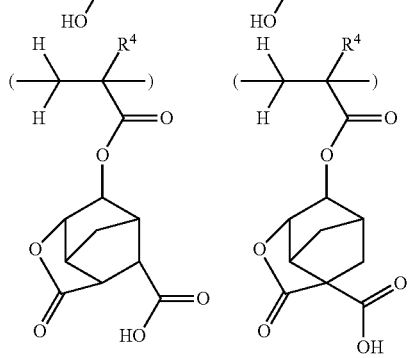

It is possible that the fluoroalcohol is protected with an acyl group or acid labile group in the polymer, so that the fluoroalcohol-containing unit corresponding to formula (A) may be generated by hydrolysis in alkaline developer or deprotection with the acid generated after exposure. Suitable such recurring units include the units described in JP-A 2012-128067 (U.S. Pat. No. 8,916,331), specifically units in paragraphs [0036]-[0040] and units (2a), (2b) and (2f) in paragraph [0041].

Illustrative, non-limiting examples of the recurring unit having formula (D) are shown below. Notably R⁴ is as defined above.

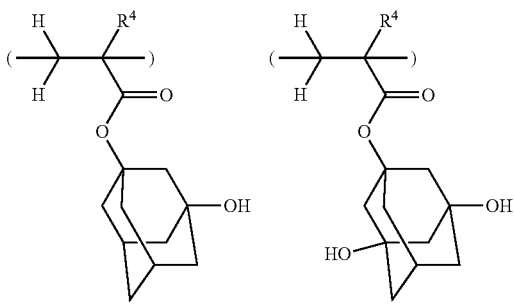

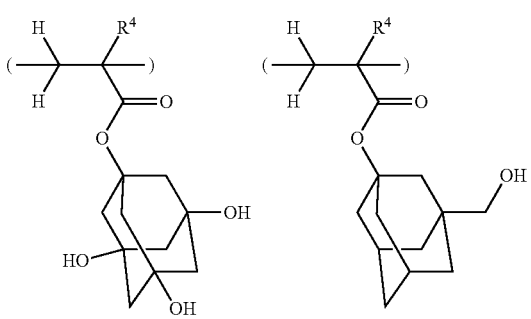

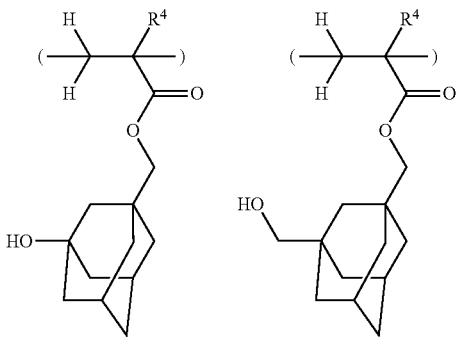

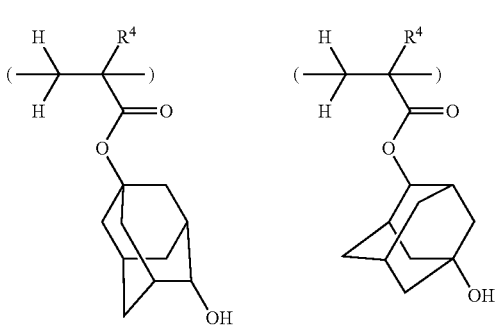

-continued
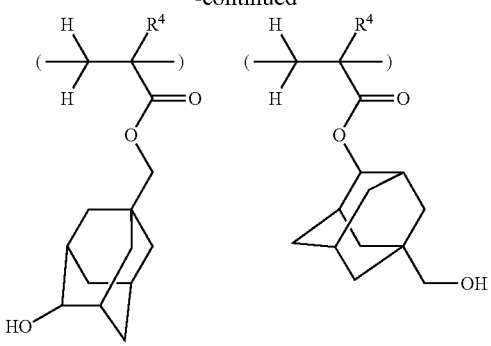
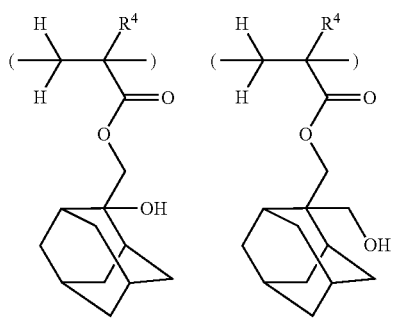
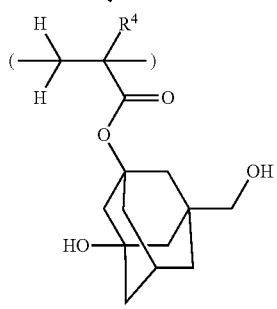
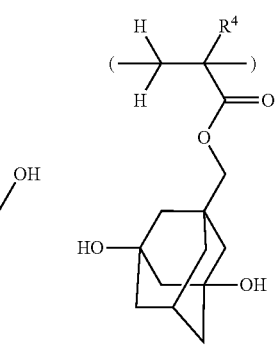
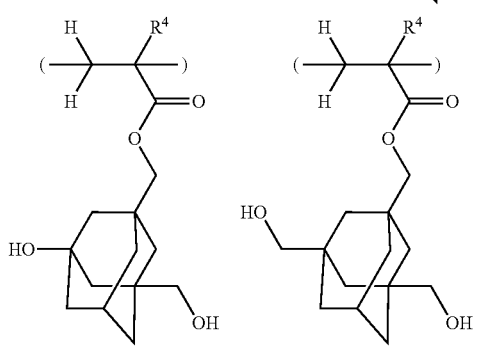
-continued
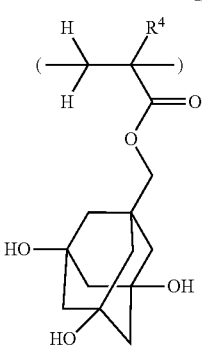
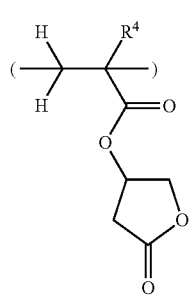
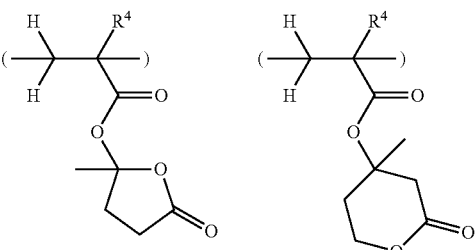
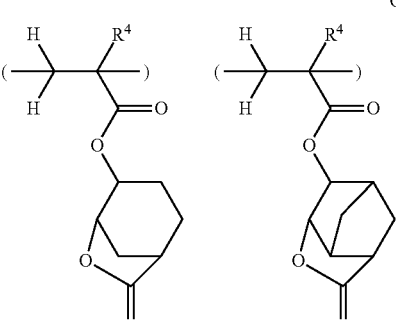
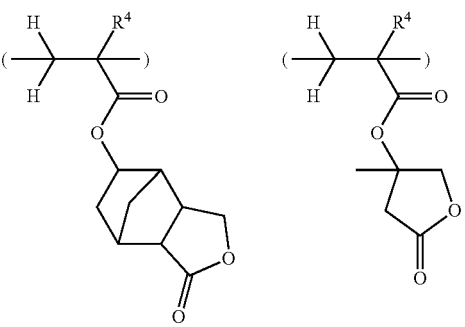

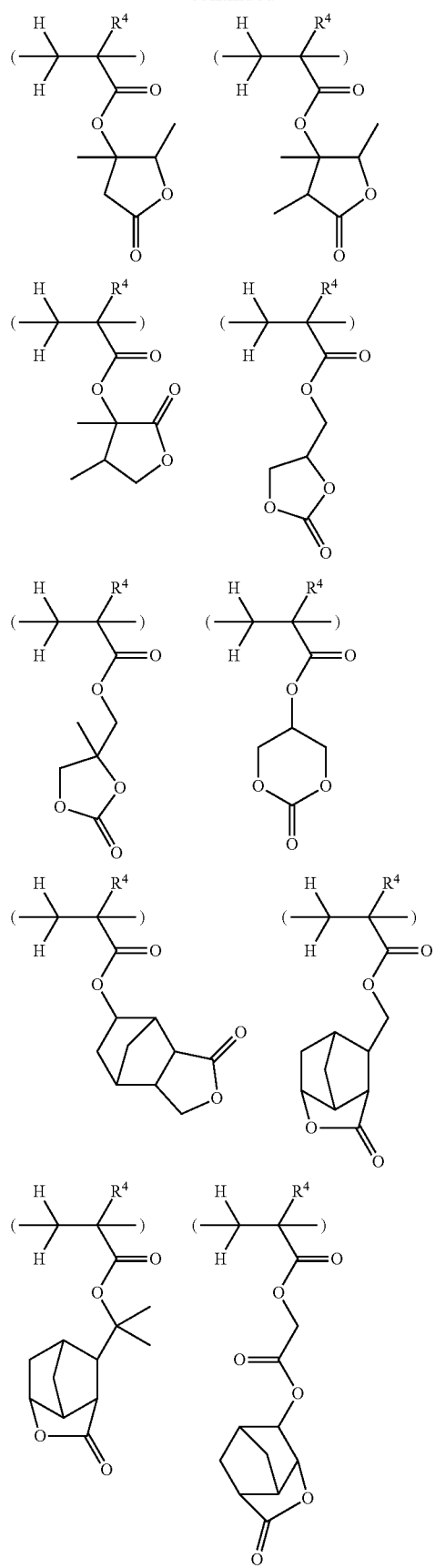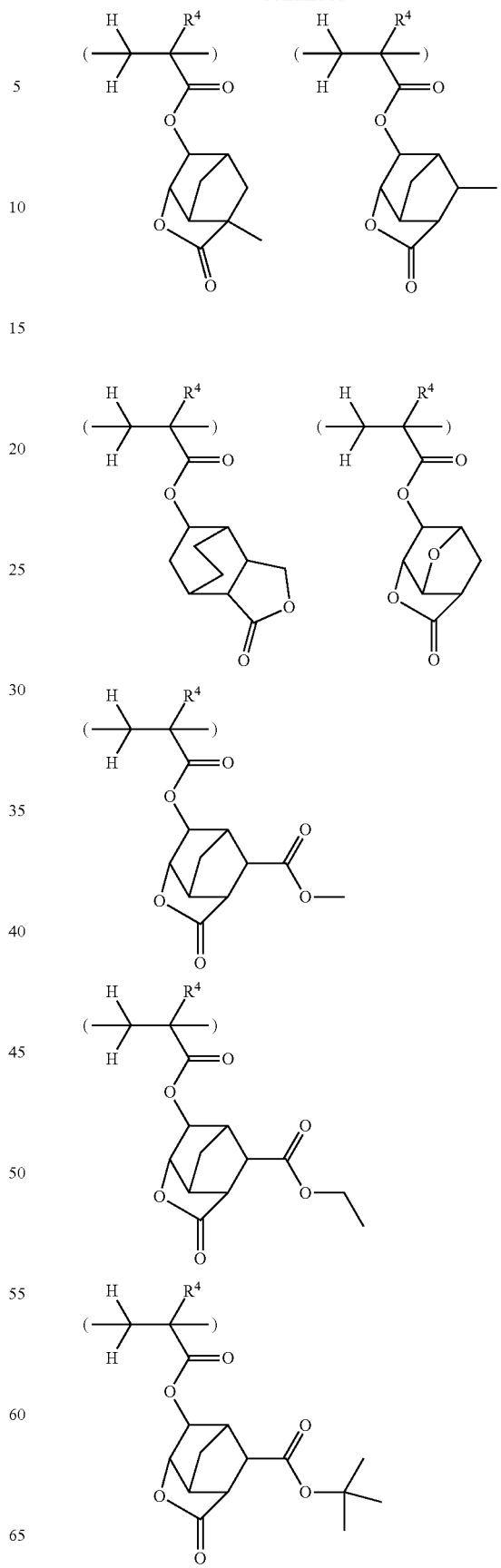

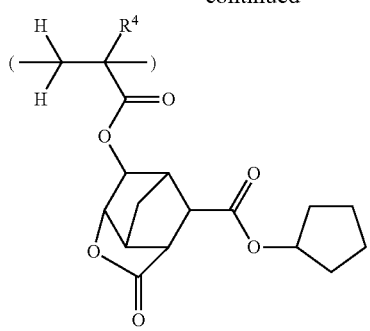
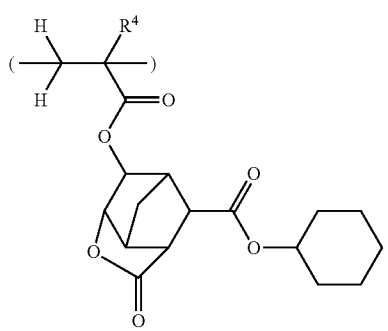
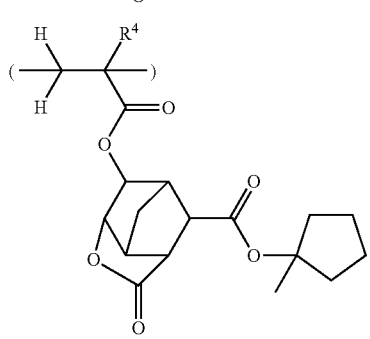
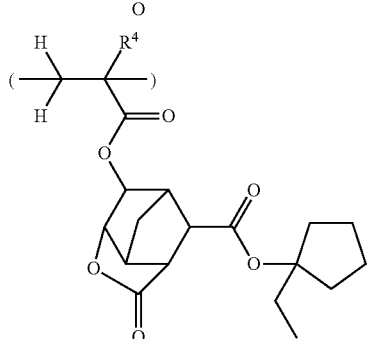
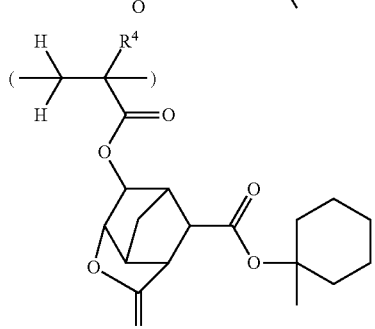
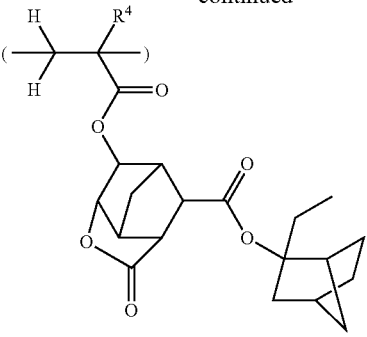
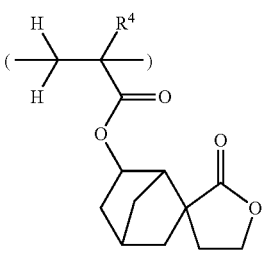
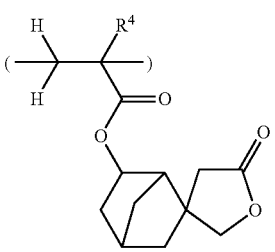
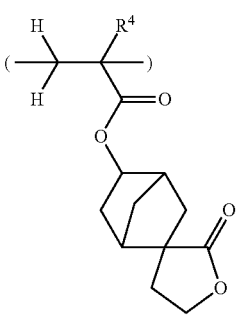
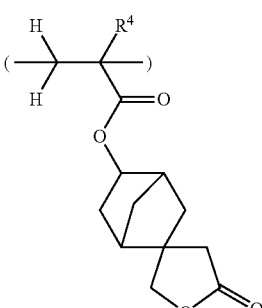
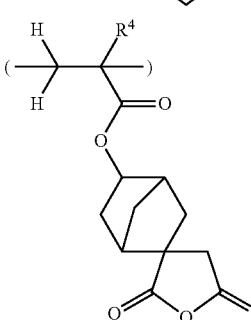

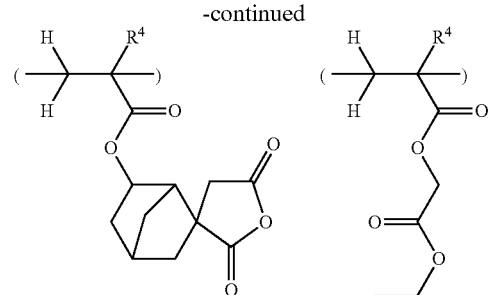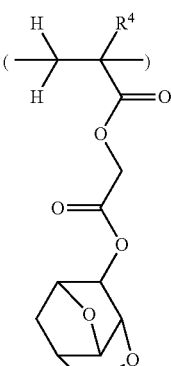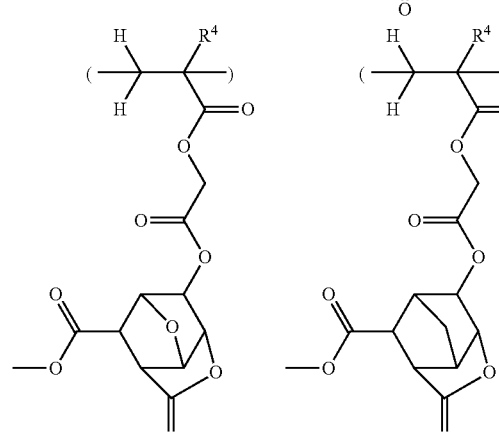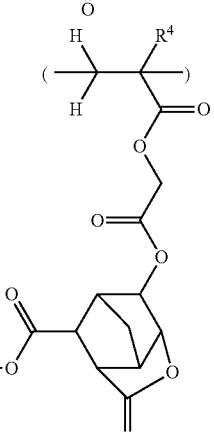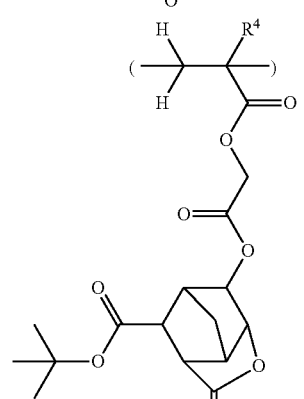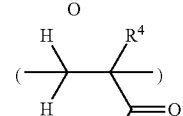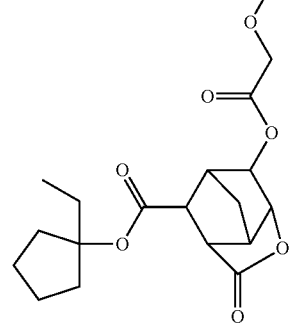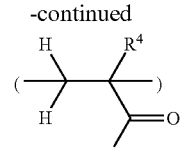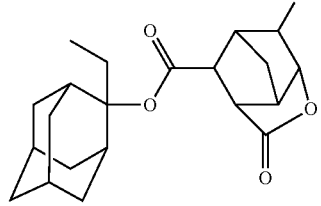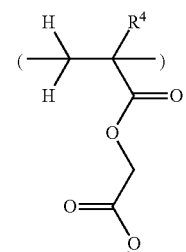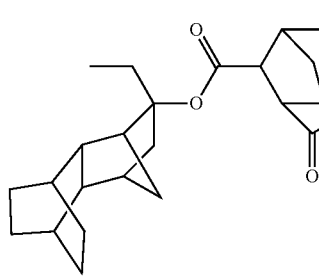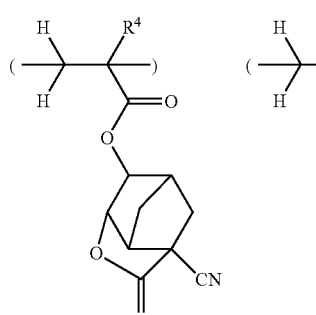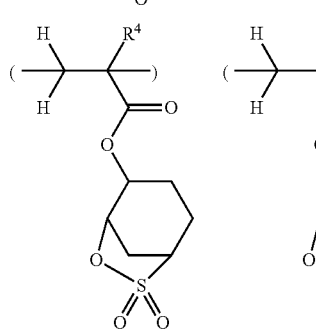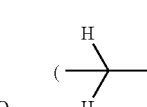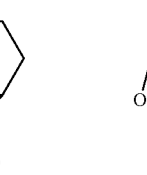

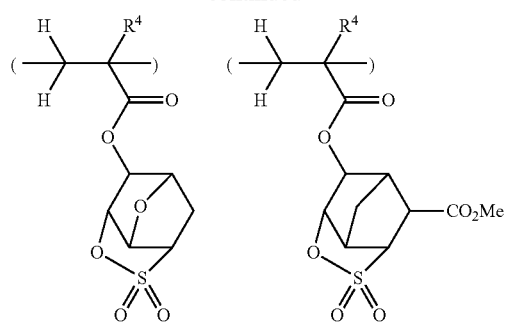
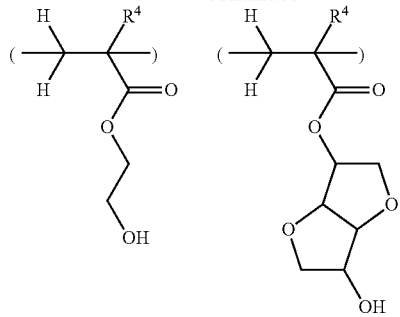
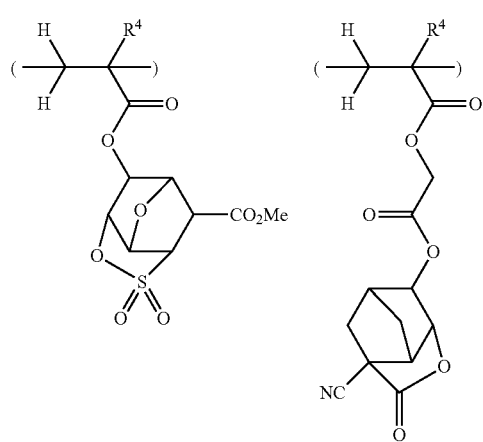
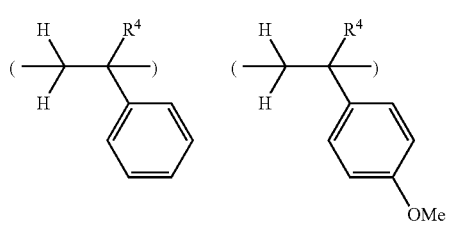
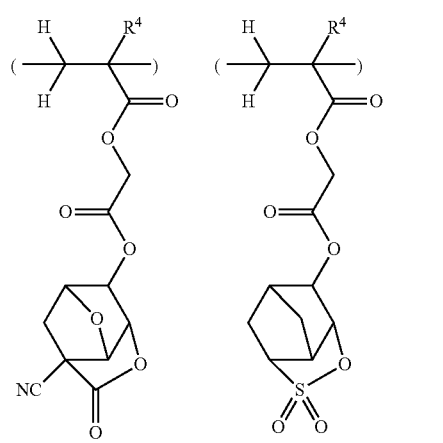
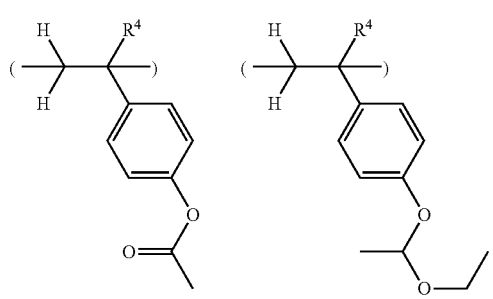
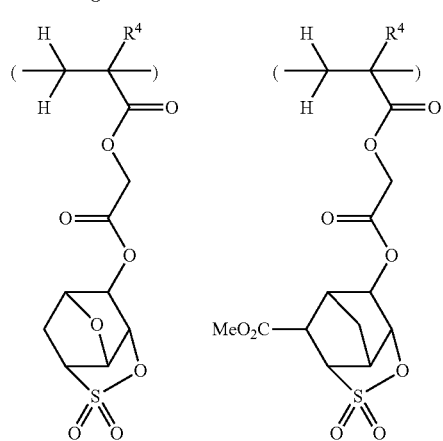
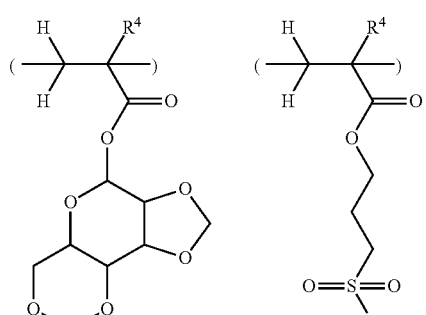
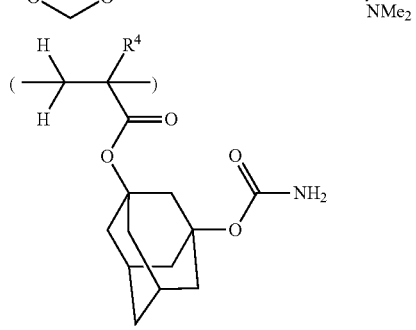

-continued

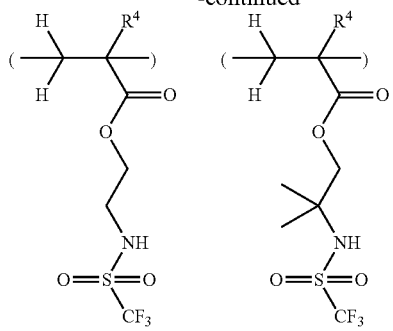

In addition to the foregoing units, the inventive polymer may further comprise recurring units of at least one type selected from recurring units having formulae (f1) to (f5).

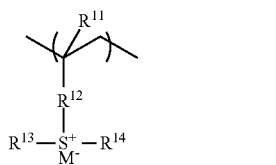 (f1)

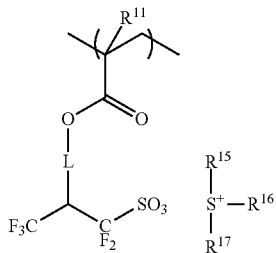 (f2)

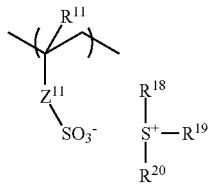 (f3)

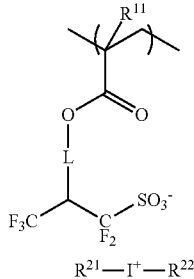 (f4)

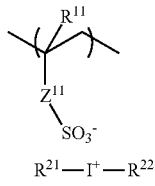 (f5)

Herein $R^{11}$ is each independently hydrogen or methyl. $R^{12}$ is a single bond, phenylene, —O—$R^{25}$—, or —C(=O)—$Z^{22}$—$R^{25}$— wherein $Z^{22}$ is —O— or —NH— and $R^{25}$ is a $C_1$-$C_6$ straight, branched or cyclic alkylene group, $C_2$-$C_6$ straight, branched or cyclic alkenylene group or phenylene group, which may contain a carbonyl (—CO—), ester (—COO—), ether (—O—) or hydroxyl moiety. L is a single bond or —$Z^{33}$—C(=O)—O— wherein $Z^{33}$ is a $C_1$-$C_{20}$ straight, branched or cyclic divalent hydrocarbon group which may contain a heteroatom. $Z^{11}$ is a single bond, methylene, ethylene, phenylene, fluorinated phenylene, —O—$R^{26}$—, or —C(=O)—$Z^{44}$—$R^{26}$— wherein $Z^{44}$ is oxygen or NH and $R^{26}$ is a $C_1$-$C_6$ straight, branched or cyclic alkylene group, $C_2$-$C_6$ straight, branched or cyclic alkenylene group or phenylene group, which may contain a carbonyl, ester, ether or hydroxyl moiety. $R^{13}$ to $R^{24}$ are each independently a $C_1$-$C_{20}$ straight, branched or cyclic monovalent hydrocarbon group which may contain a heteroatom. $M^-$ is a non-nucleophilic counter ion.

$R^{13}$ to $R^{24}$ are each independently a $C_1$-$C_{20}$ straight, branched or cyclic monovalent hydrocarbon group which may contain a heteroatom. Suitable monovalent hydrocarbon groups include alkyl groups such as methyl, ethyl, n-propyl, isopropyl, n-butyl, t-butyl, cyclopropyl, cyclopentyl, cyclohexyl, cyclopropylmethyl, 4-methylcyclohexyl, cyclohexylmethyl, norbornyl, and adamantyl; alkenyl groups such as vinyl, allyl, propenyl, butenyl, hexenyl, and cyclohexenyl; aryl groups such as phenyl, naphthyl, and thienyl; and aralkyl groups such as benzyl, 1-phenylethyl, and 2-phenylethyl, with the aryl groups being preferred. Also included are modified forms of the foregoing groups in which at least one hydrogen atom (one or more hydrogen atoms) is replaced by a moiety containing a heteroatom such as oxygen, sulfur, nitrogen or halogen, or in which a heteroatom such as oxygen, sulfur or nitrogen intervenes between carbon atoms, so that the group may contain a hydroxyl, cyano, carbonyl, sulfonyl moiety, ether bond, ester bond, sulfonic acid ester bond, carbonate bond, lactone ring, sultone ring, carboxylic acid anhydride, or haloalkyl moiety. Also, a pair of $R^{13}$ and $R^{14}$ may bond together to form a ring with the sulfur atom to which they are attached, and any two or more of $R^{15}$, $R^{16}$ and $R^{17}$, or any two or more of $R^{18}$, $R^{19}$ and $R^{20}$ may bond together to form a ring with the sulfur atom to which they are attached.

When L is —$Z^{33}$—C(=O)—O—, examples of the optionally heteroatom-containing, $C_1$-$C_{20}$ straight, branched or cyclic divalent hydrocarbon group represented by $Z^{33}$ are shown below, but not limited thereto.

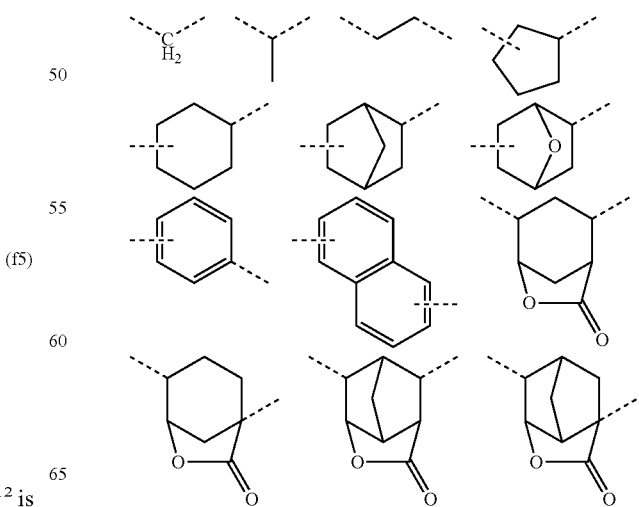

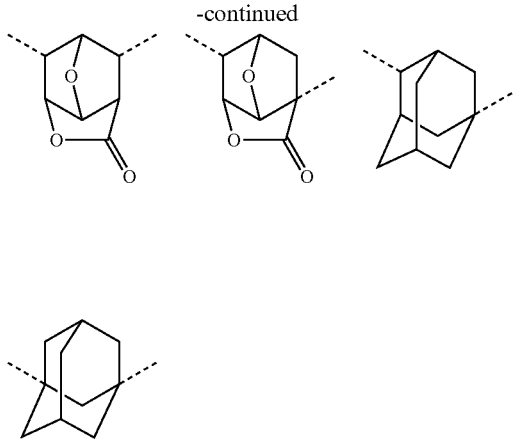

When a pair of $R^{13}$ and $R^{14}$ bond together to form a ring with the sulfur atom to which they are attached, and any two or more of $R^{15}$, $R^{16}$ and $R^{17}$, or any two or more of $R^{18}$, $R^{19}$ and $R^{20}$ bond together to form a ring with the sulfur atom to which they are attached, examples of the ring are shown below, but not limited thereto.

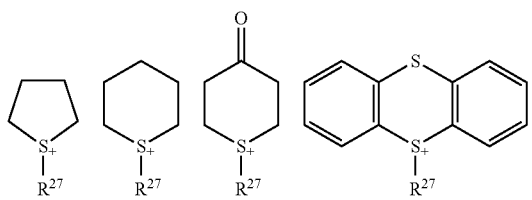

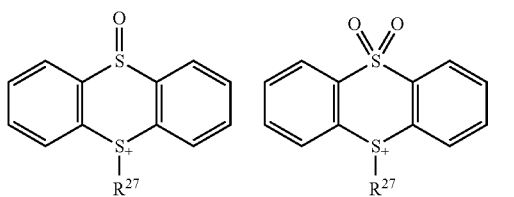

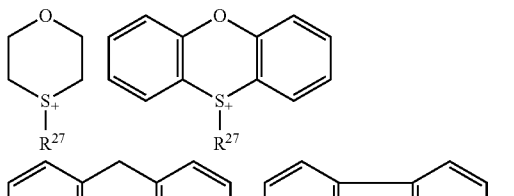

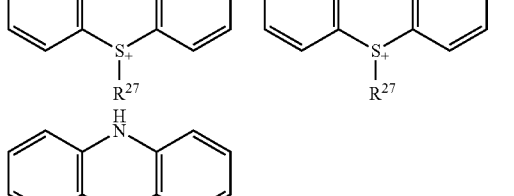

In the formulae, $R^{27}$ is a $C_1$-$C_{20}$ straight, branched or cyclic monovalent hydrocarbon group which may contain a heteroatom. Suitable monovalent hydrocarbon groups are as exemplified above for $R^{13}$ to $R^{20}$.

Illustrative, non-limiting examples of the sulfonium cation in formulae (f2) and (f3) are given below.

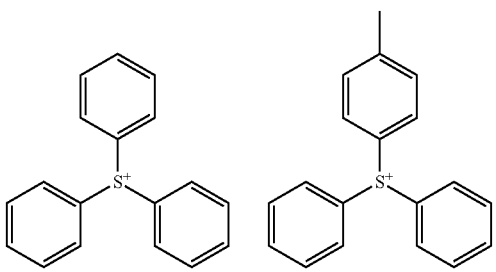

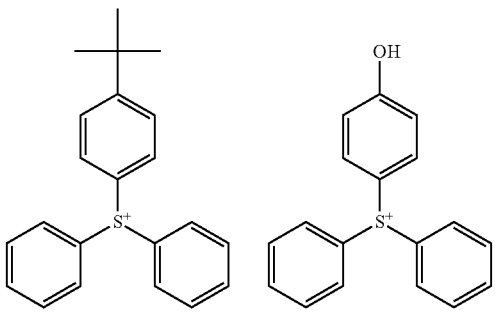

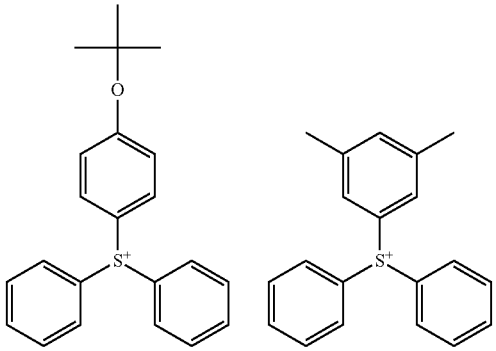

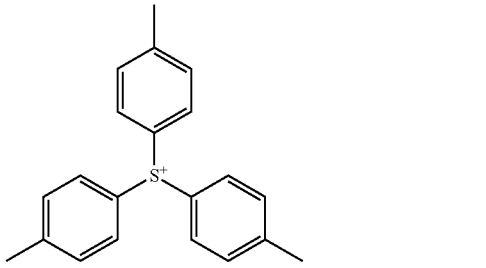

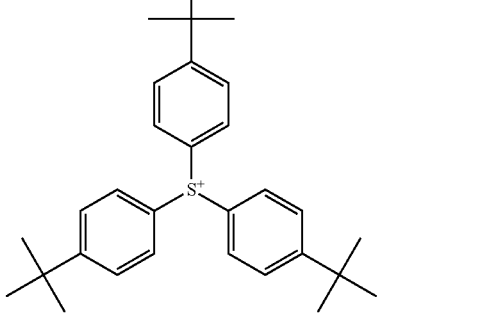

75
-continued
76
-continued
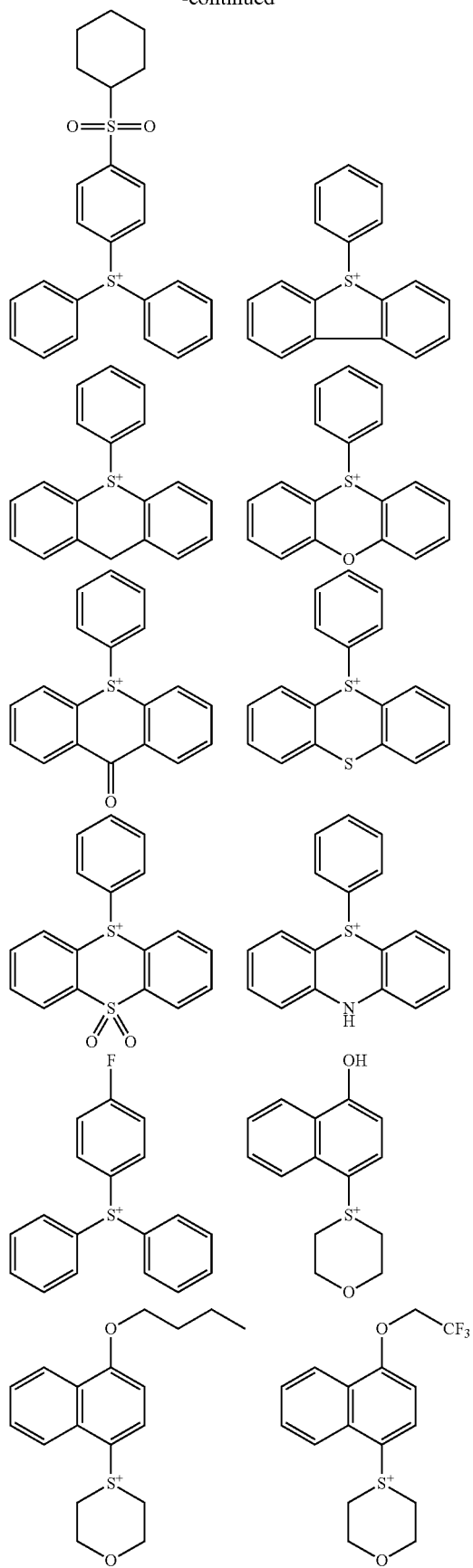
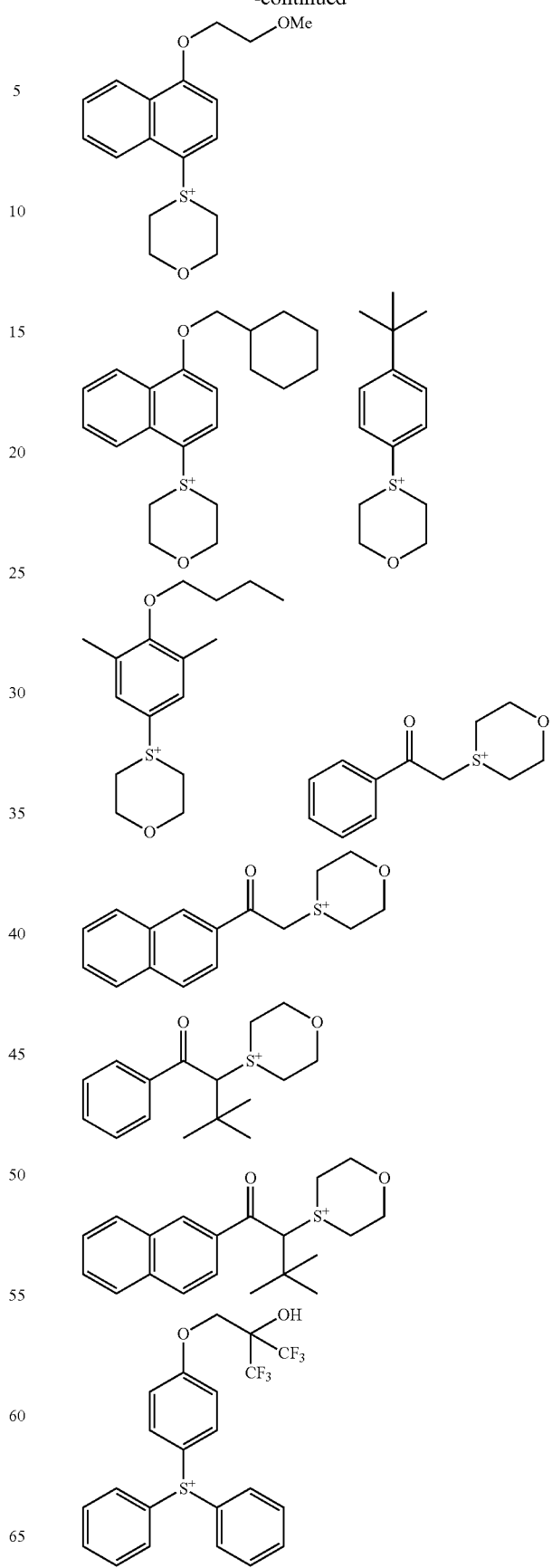

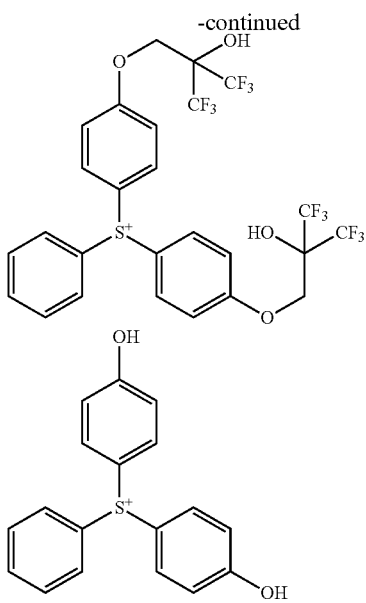

Illustrative, non-limiting examples of the iodonium cation in formulae (f4) and (f5) are given below.

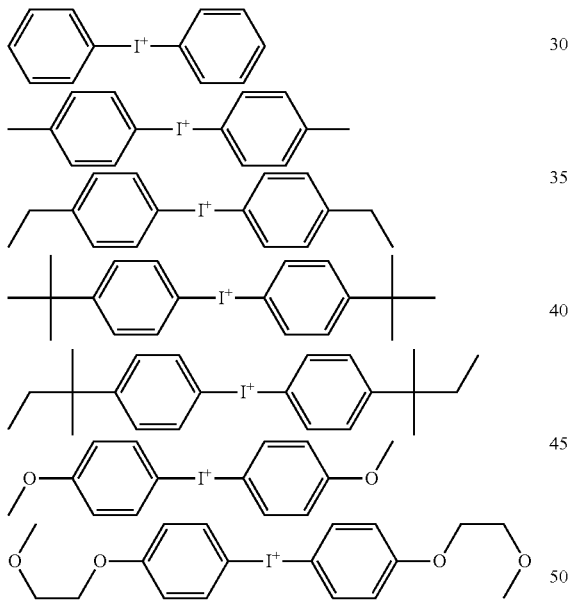

Examples of the non-nucleophilic counter ion represented by M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; and methidates such as tris(trifluoromethylsulfonyl)methide and tris(perfluoroethylsulfonyl)methide.

Also included are a sulfonate which is fluorinated at α-position as represented by the formula (F-1) and a sulfonate which is fluorinated at α- and β-positions as represented by the formula (F-2).

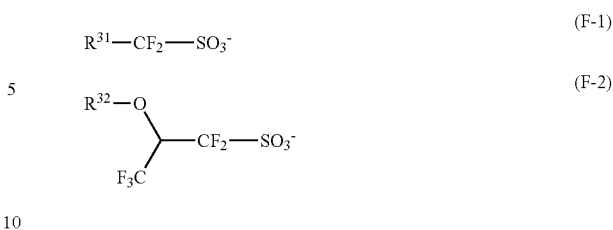

In formula (F-1), $R^{31}$ is hydrogen, or a $C_1$-$C_{20}$ straight, branched or cyclic alkyl group, $C_2$-$C_{20}$ straight, branched or cyclic alkenyl group or $C_6$-$C_{20}$ aryl group, which may have an ether, ester, carbonyl moiety, lactone ring or fluorine atom. In formula (F-2), $R^{32}$ is hydrogen, or a $C_1$-$C_{30}$ straight, branched or cyclic alkyl group, $C_2$-$C_{20}$ straight, branched or cyclic acyl group, $C_2$-$C_{20}$ straight, branched or cyclic alkenyl group, $C_6$-$C_{20}$ aryl group or $C_6$-$C_{20}$ aryloxy group, which may have an ether, ester, carbonyl moiety or lactone ring.

Examples of the recurring units having formulae (f1) to (f5) are given below, but not limited thereto. Notably $R^{11}$ is as defined above.

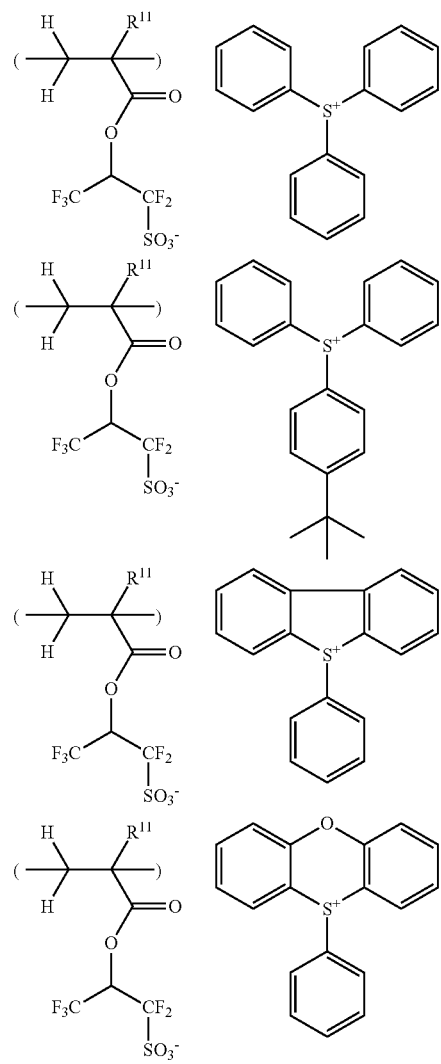

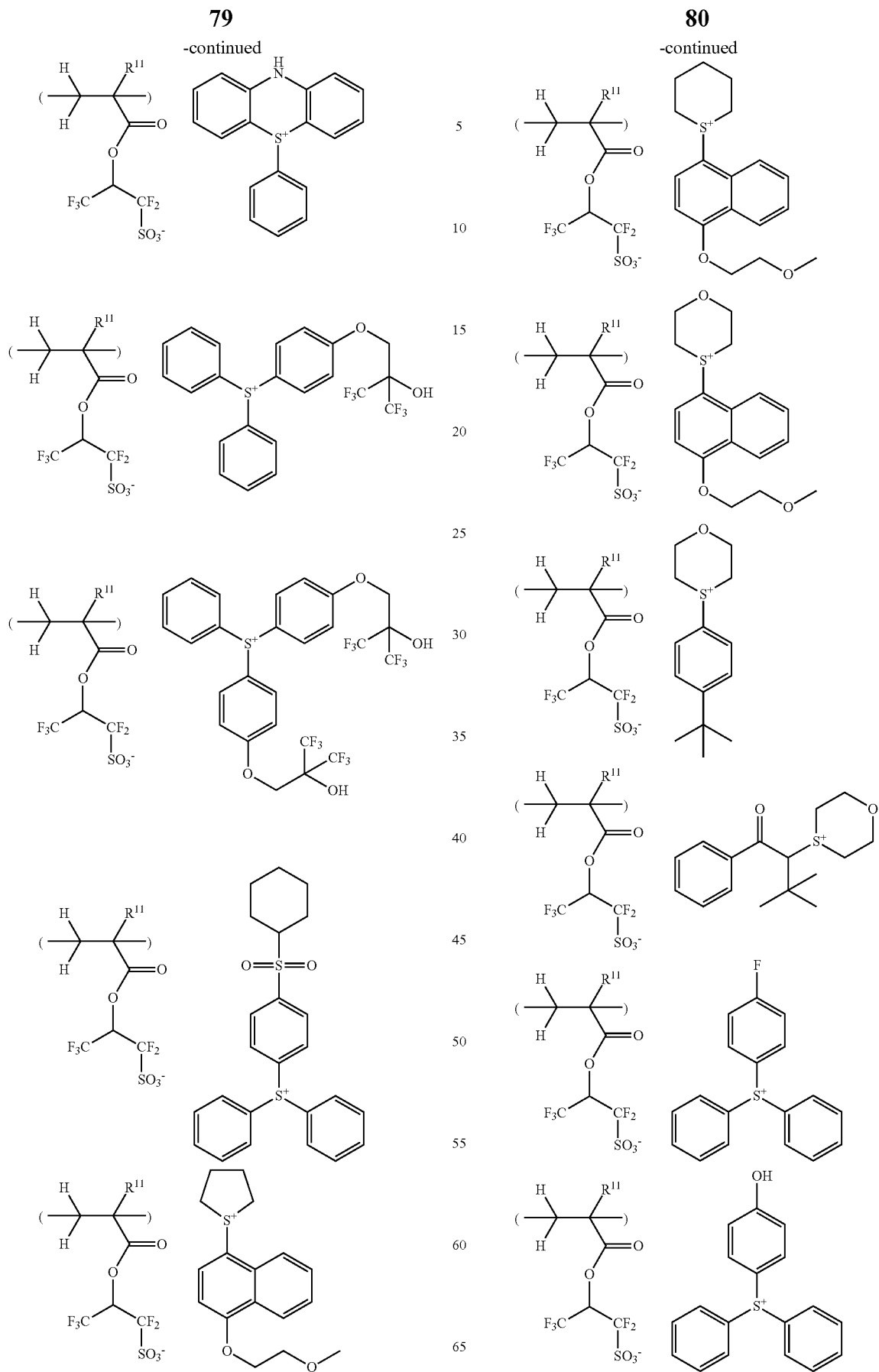

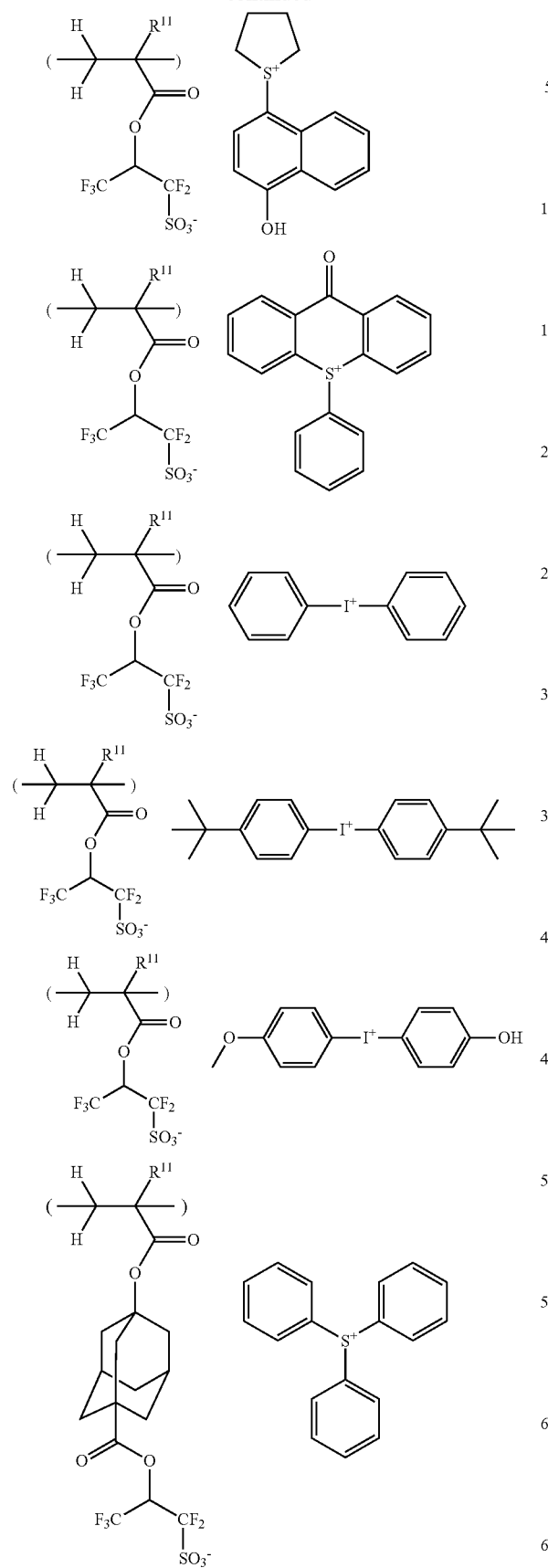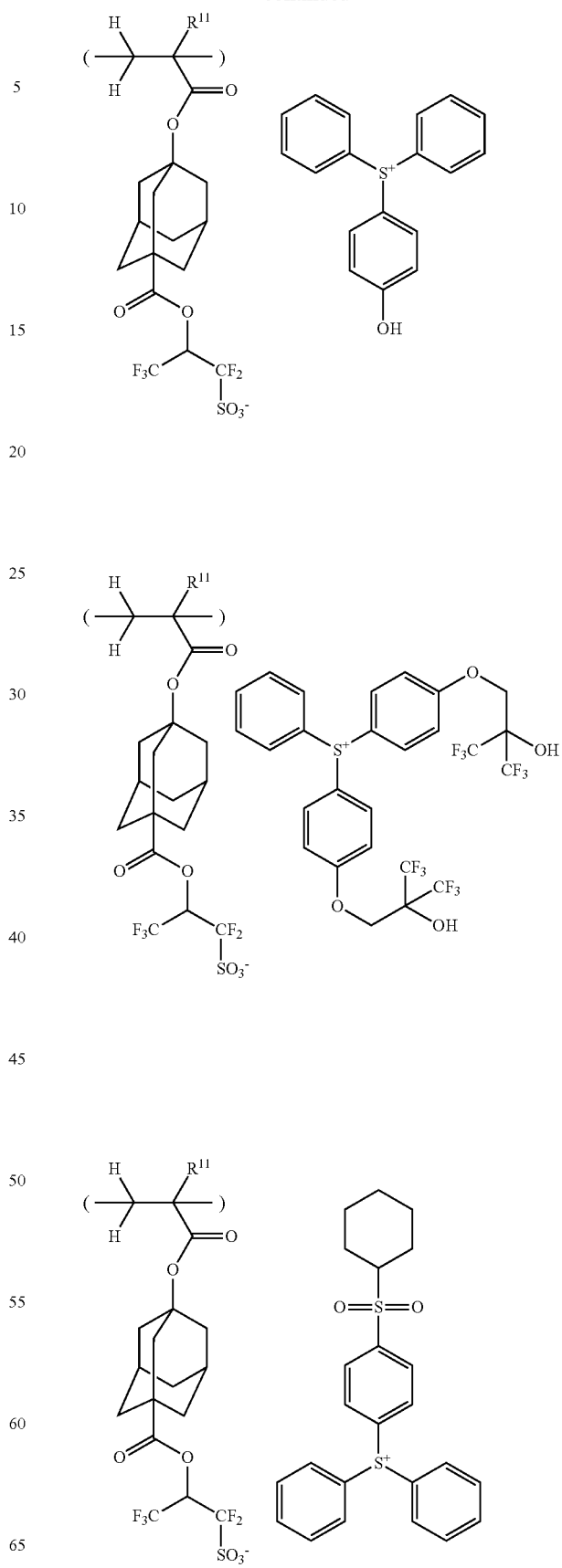

83
-continued
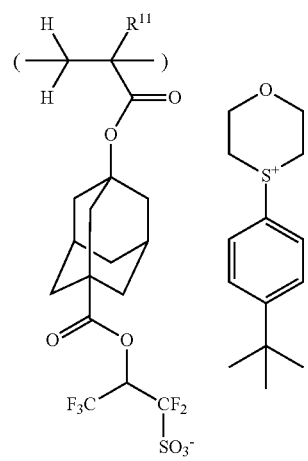
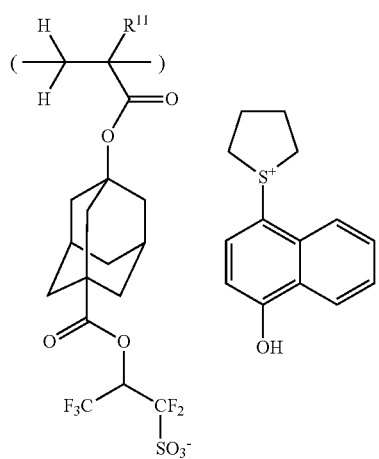
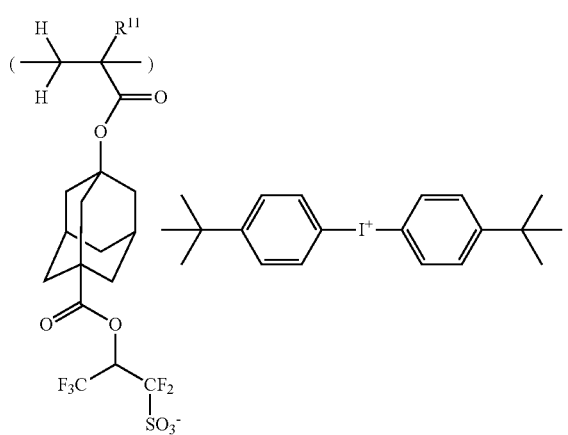
84
-continued
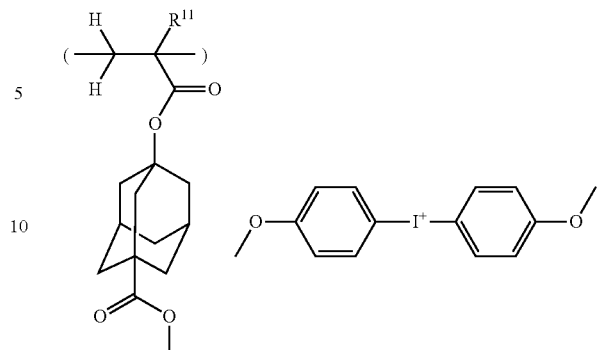
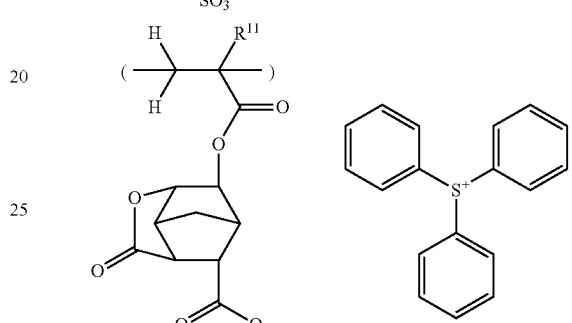
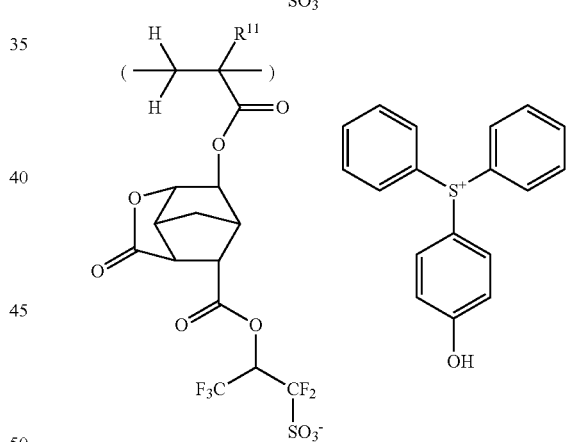
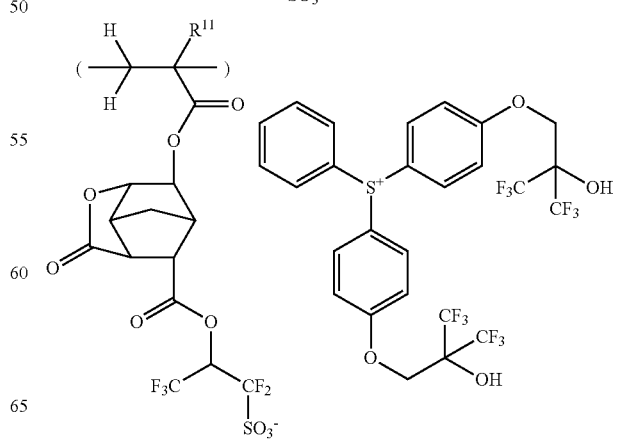

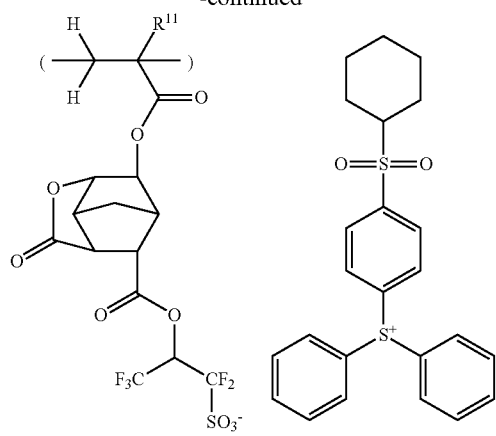
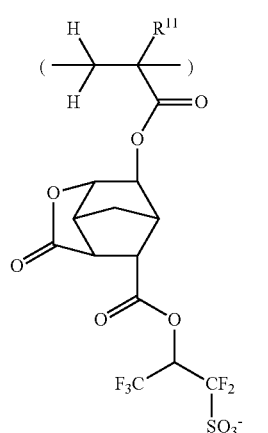
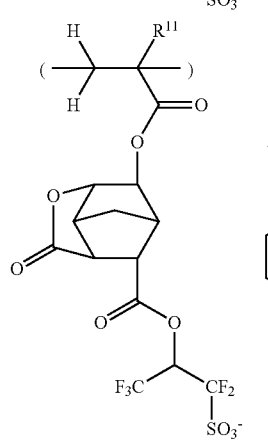
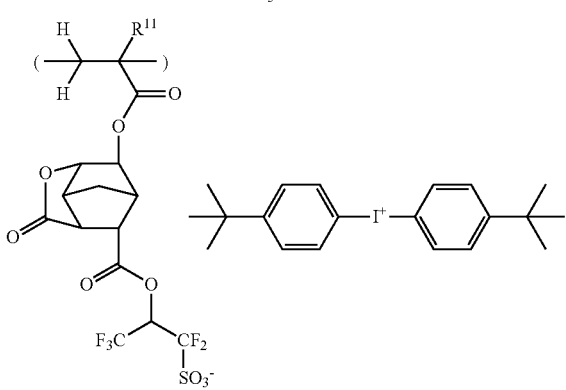
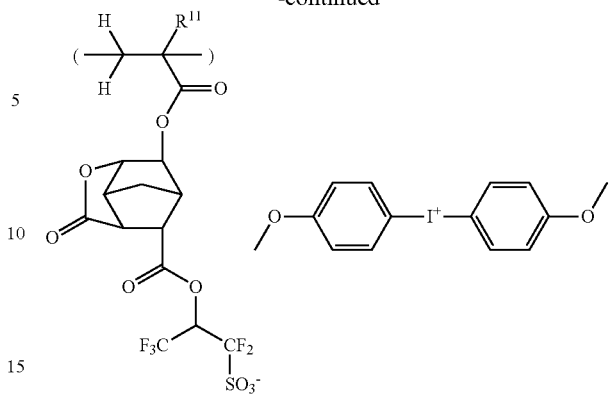
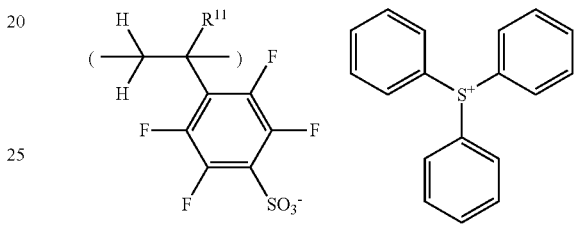
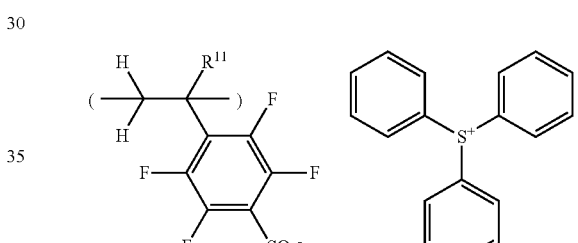
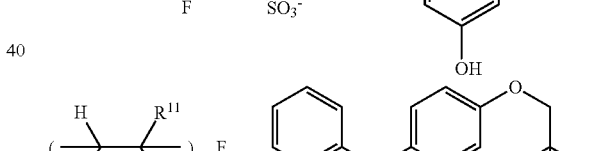
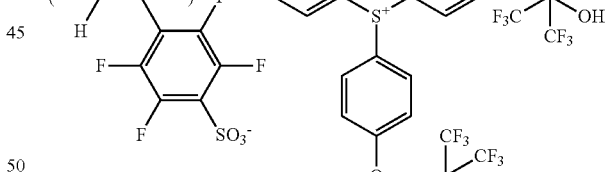
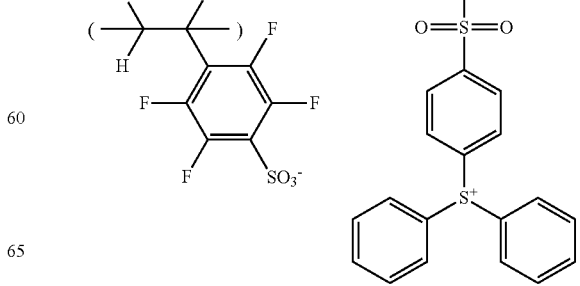

-continued

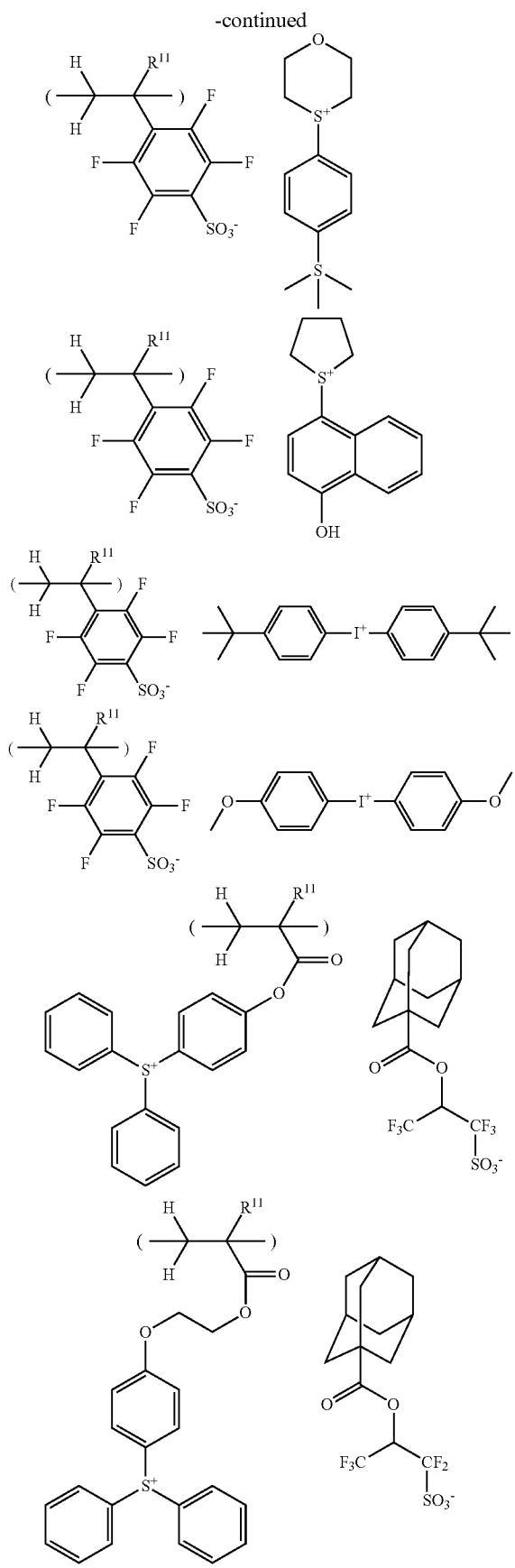

Besides the recurring units having a sulfonium cation or sulfonic acid anion bonded to the backbone as represented by formulae (f1) to (f5), the inventive polymer may comprise recurring units having a sulfonic acid, imidic acid or methide acid anion bonded to the backbone or recurring units having a sulfonium cation bonded to the backbone as described in JP 5548473, paragraphs [0129]-[0151], or recurring units derived from a monomer containing a sulfonic acid anion as described in WO 2011/070947, paragraphs [0034]-[0038].

The inventive polymer may further comprise recurring units of at least one type selected from recurring units having the formulae (X-1) to (X-4).

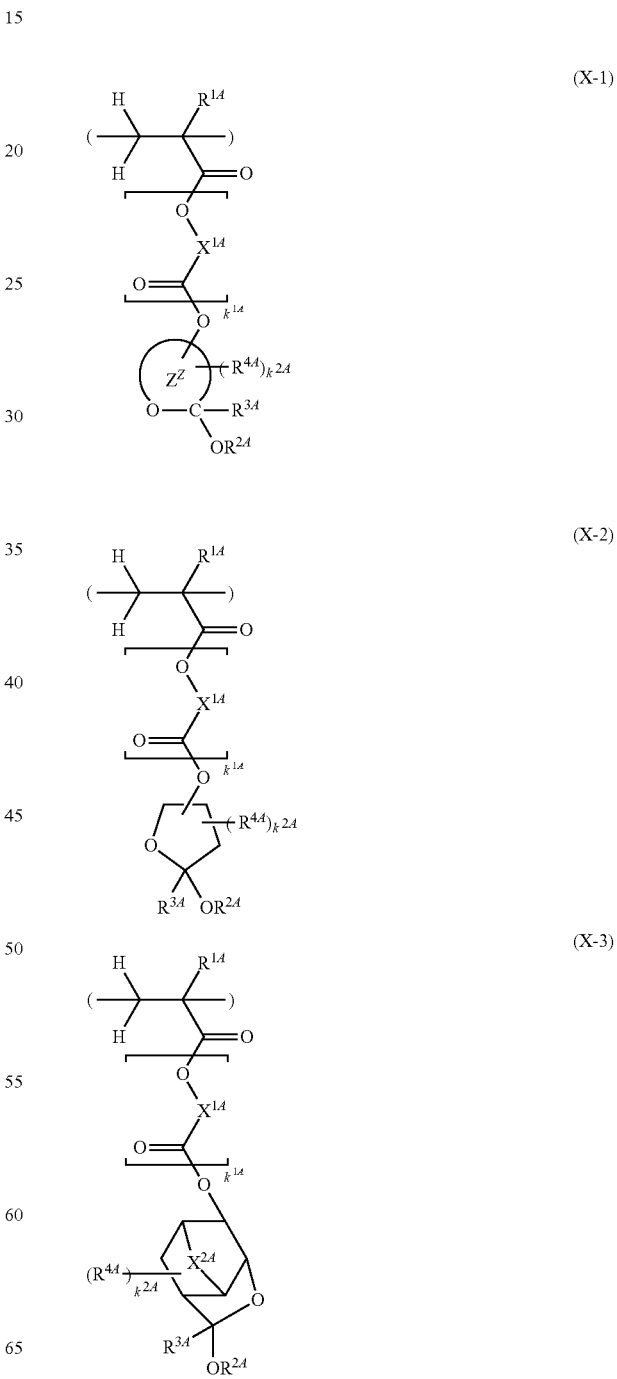

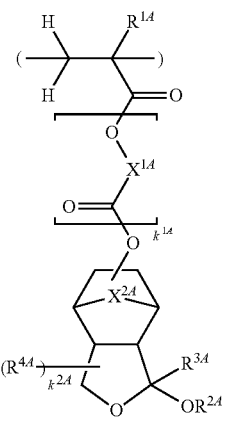

(X-4)

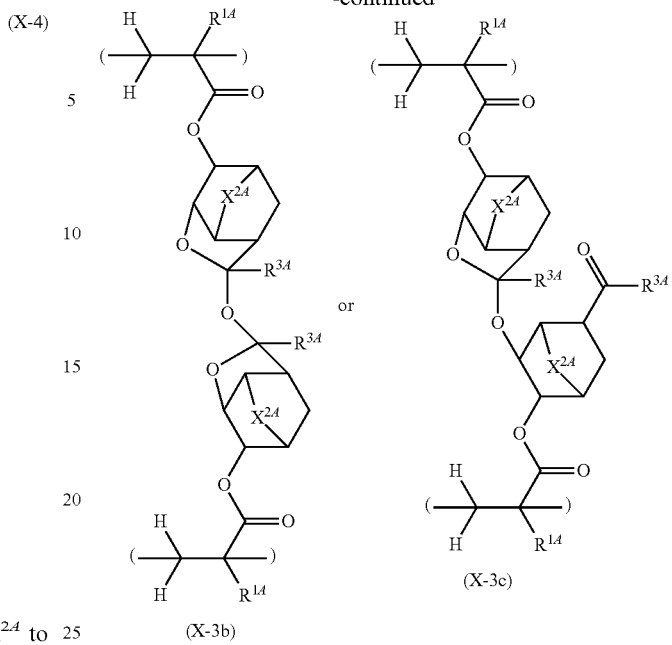

(X-3b)

(X-3c)

Herein $R^{1A}$ is hydrogen, methyl or trifluoromethyl. $R^{2A}$ to $R^{4A}$ are each independently hydrogen or a $C_1$-$C_{15}$ straight, branched or cyclic monovalent hydrocarbon group in which any constituent —$CH_2$— moiety may be replaced by —O— or —C(=O)—. $X^{1A}$ is a $C_1$-$C_{15}$ straight, branched or cyclic divalent hydrocarbon group in which any constituent —$CH_2$— moiety may be replaced by —O— or —C(=O)—. $X^{2A}$ is —$CH_2$— or —O—. $Z^Z$ represents a $C_4$-$C_{20}$ non-aromatic mono- or polycyclic ring having a hemiacetal structure, $k^{1A}$ is 0 or 1, and $k^{2A}$ is an integer of 0 to 3.

The recurring unit having formulae (X-1) to (X-4) has a chemically active hemiacetal or acetal structure. As a typical example, reference is made to a polymer (X-3a) having formula (X-3) wherein $k^{1A}=k^{2A}=0$. When a polymer comprising recurring units of formulae (X-3) as well as recurring units of formula (2a) and/or (2b) is used as a base resin, it is expected that in the exposed region, acetal exchange readily occurs under the action of acid generated therein, to force conversion to a higher molecular weight compound as shown by the formula (X-3b) or (X-3c), eventually contributing to a substantial drop of solubility of the resin in alkaline developer after exposure.

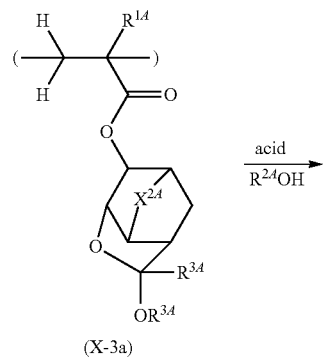

(X-3a)

Herein $R^{1A}$ to $R^{3A}$ and $X^{2A}$ are as defined above.

Examples of the monomers from which the recurring units having formulae (X-1) to (X-4) are derived are given below, but not limited thereto. Notably $R^{1A}$ is as defined above.

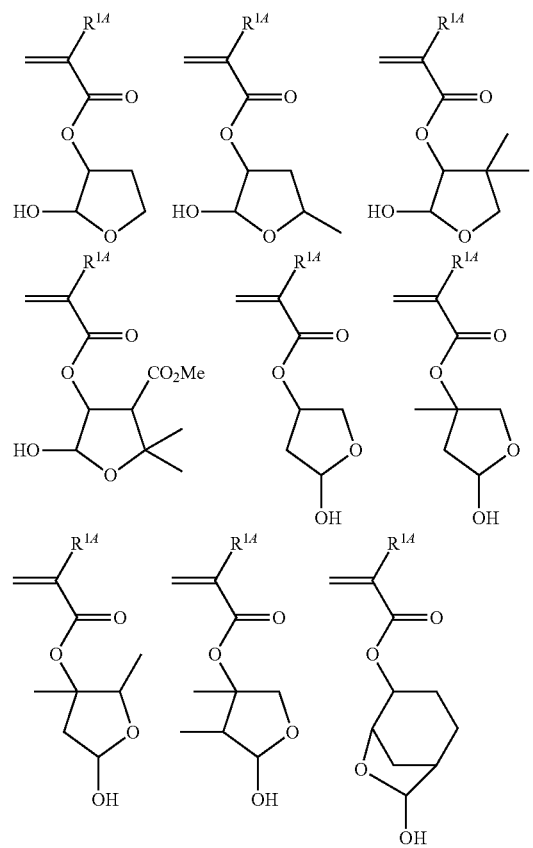

-continued
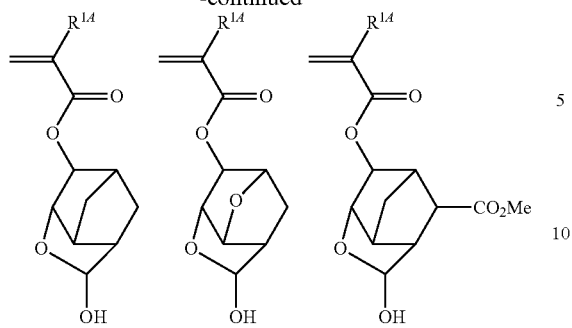
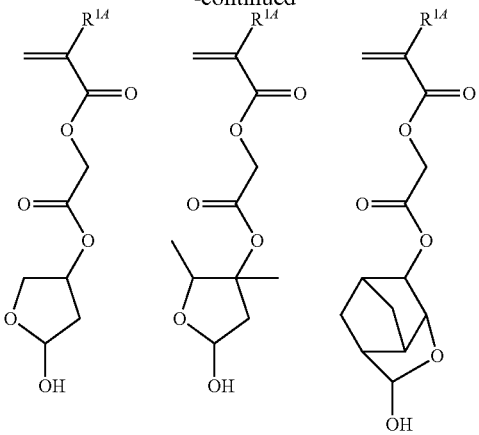
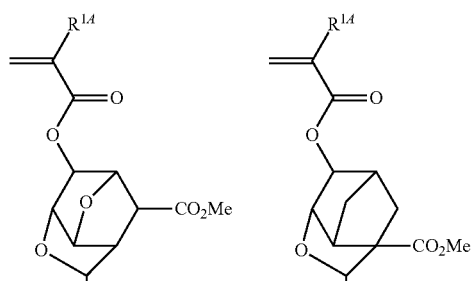
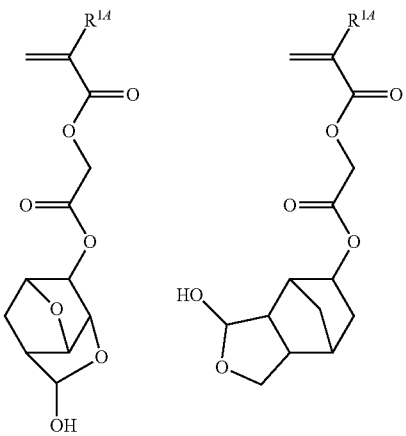
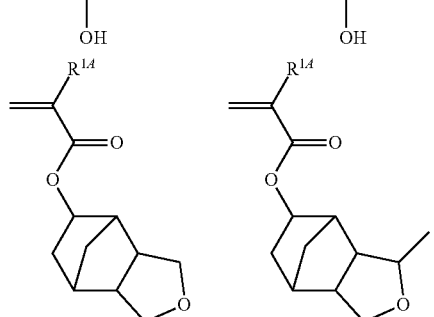
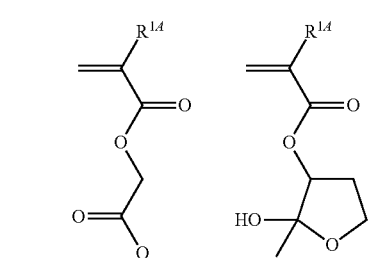
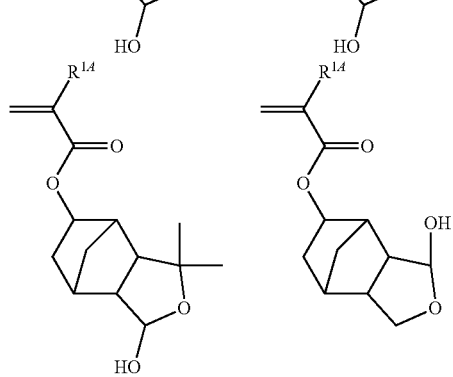
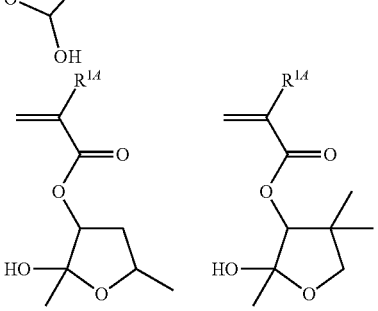
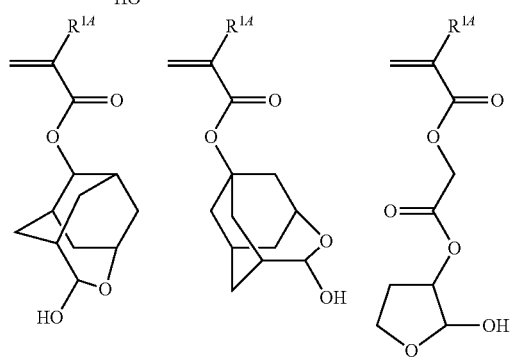

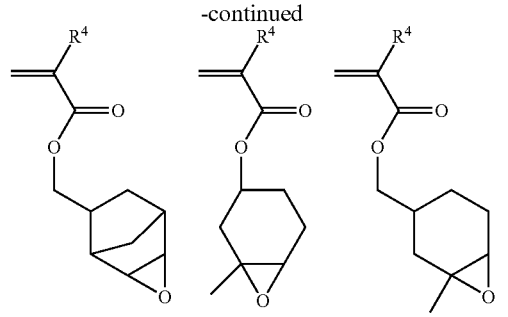

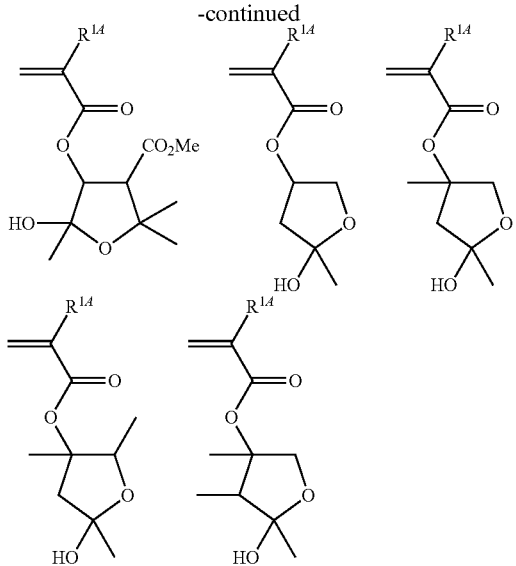

Furthermore, recurring units (g) having an oxirane or oxetane ring may be copolymerized. When recurring units (g) are copolymerized, it is expected that when the polymer is used in a resist composition, the exposed region of a resist film is crosslinked, leading to improvements in insolubilization in alkaline developer and etch resistance of negative pattern. Examples of the monomers from which the recurring units (g) having an oxirane or oxetane ring are derived are shown below, but not limited thereto. Notably $R^4$ is as defined above.

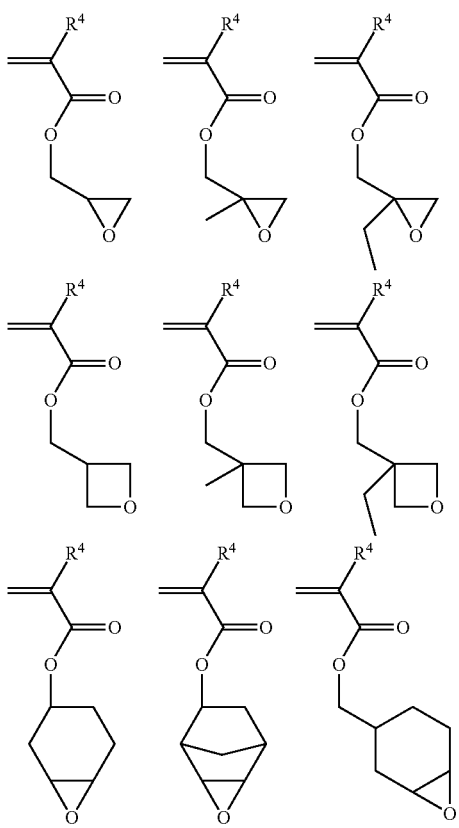

95
-continued
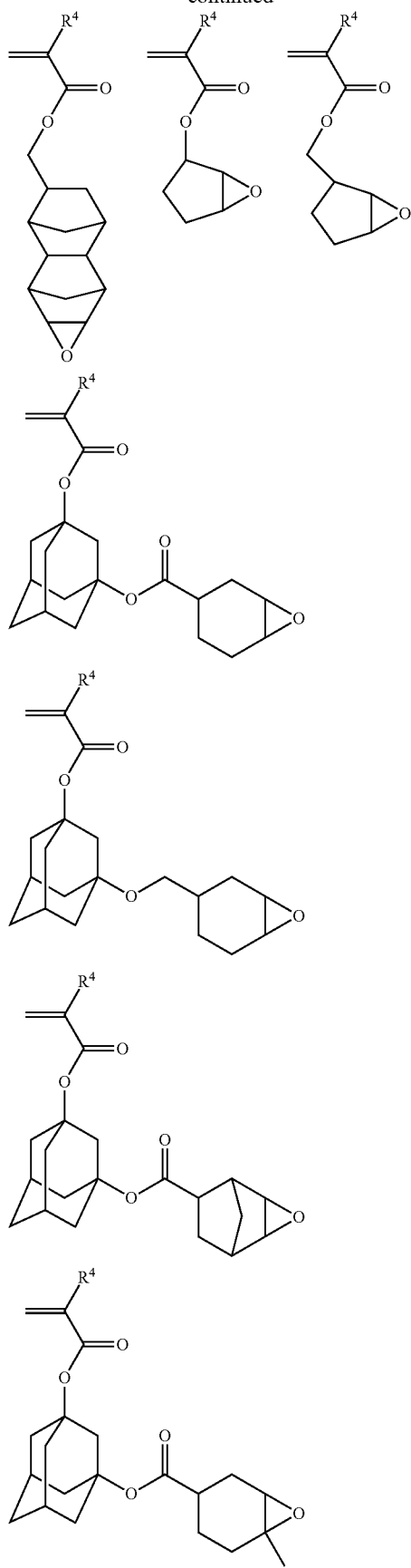
96
-continued
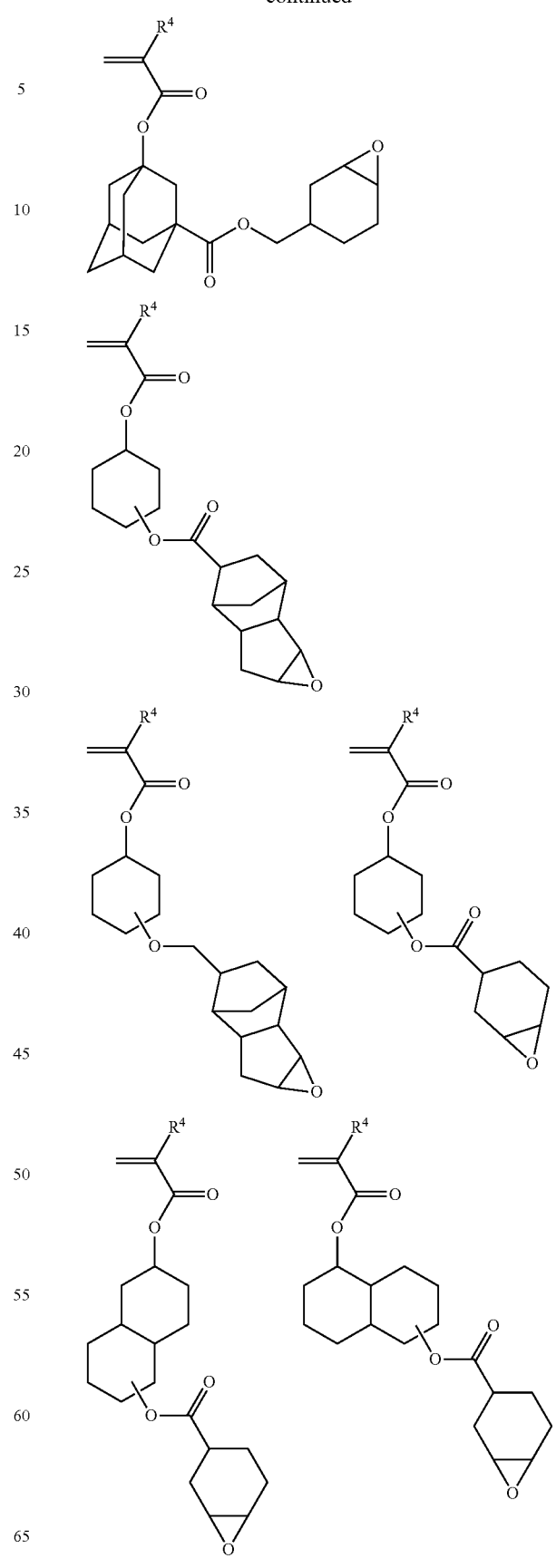

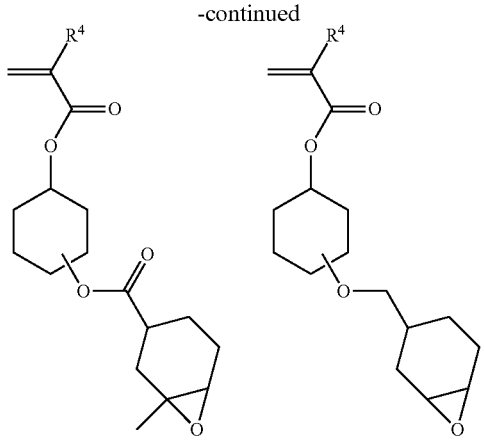
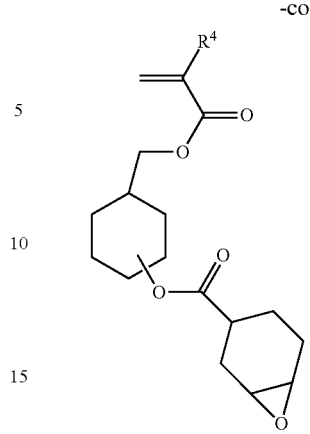
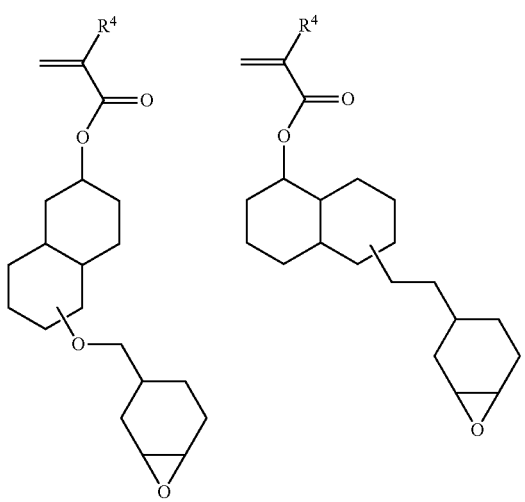
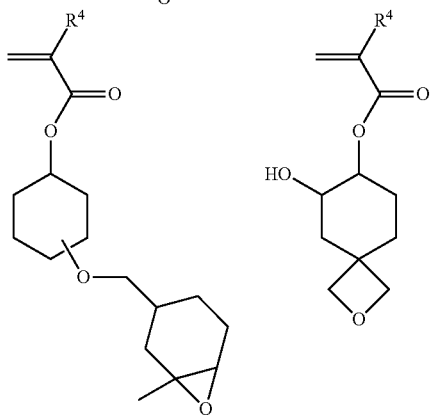
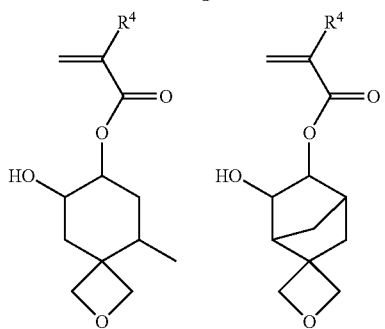

In addition to the foregoing units, the polymer may further comprise recurring units (h) derived from carbon-to-carbon double bond-bearing monomers. Examples include recurring units derived from substituted acrylic acid esters such as methyl methacrylate, methyl crotonate, dimethyl maleate and dimethyl itaconate, unsaturated carboxylic acids such as maleic acid, fumaric acid, and itaconic acid, cyclic olefins such as norbornene, norbornene derivatives, and tetracyclo[$4.4.0.1^{2,5}.1^{7,10}$]dodecene derivatives, unsaturated acid anhydrides such as itaconic anhydride, and other monomers shown below. Notably $R^4$ is as defined above.

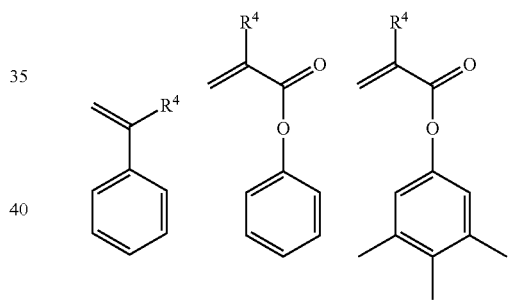
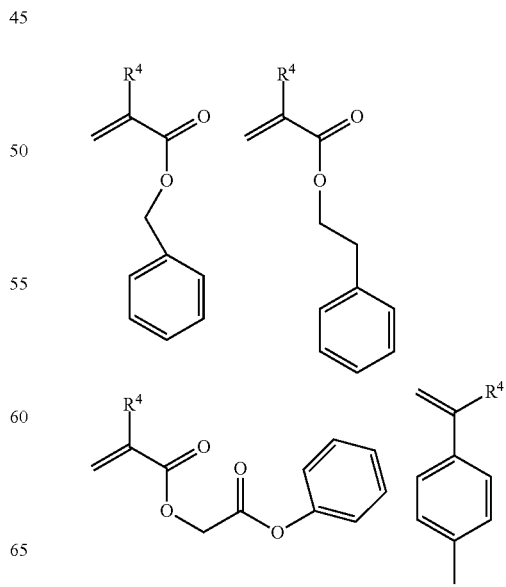

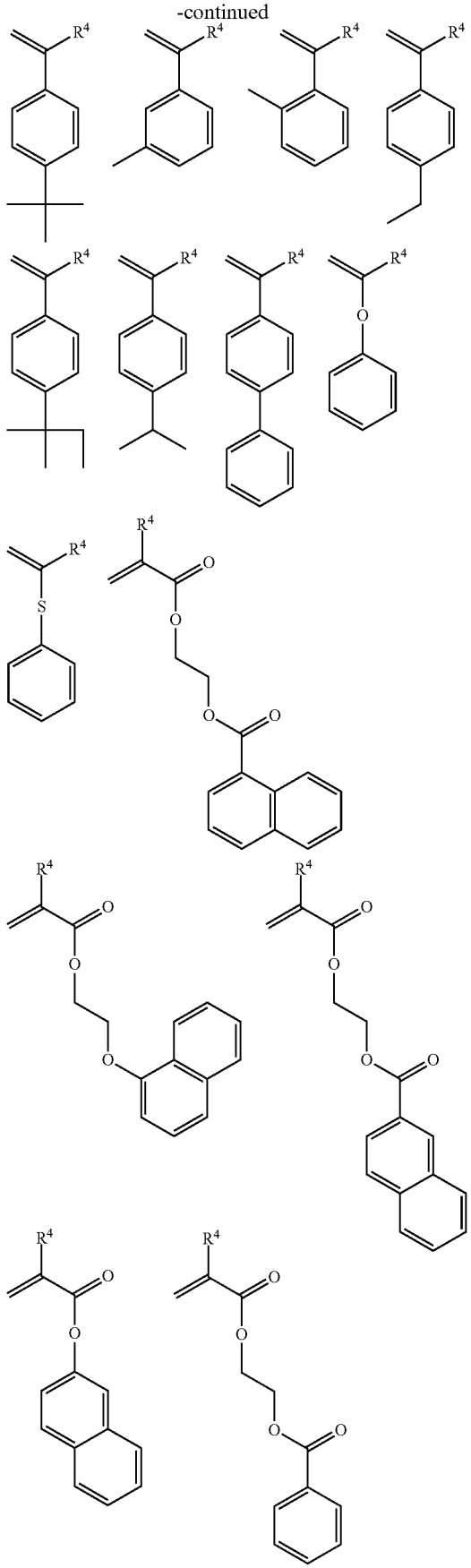
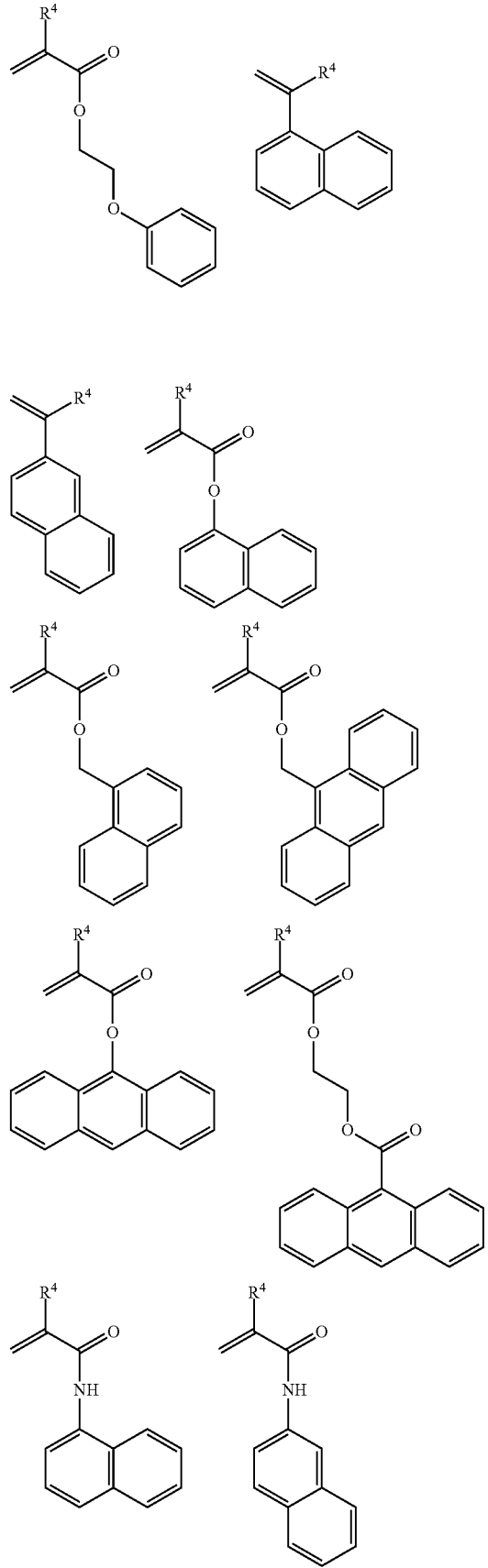

-continued
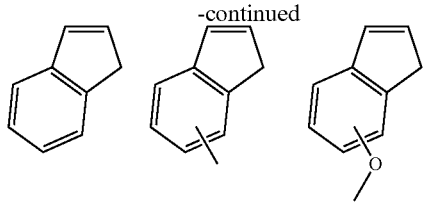
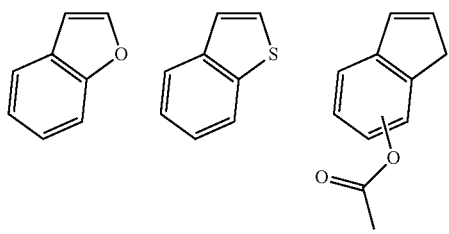
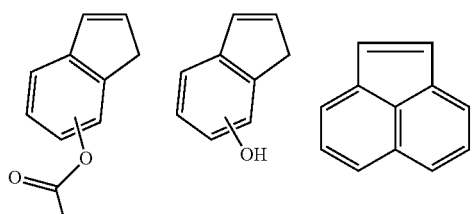
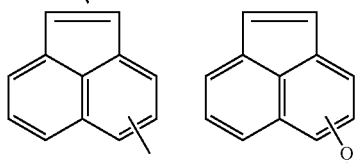
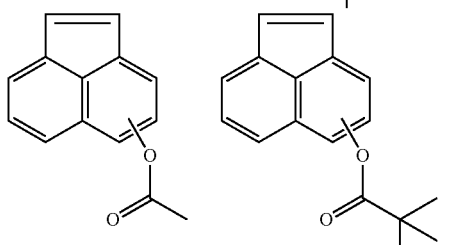
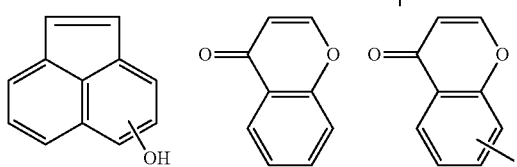
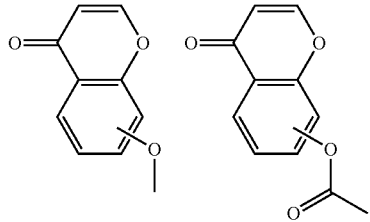
-continued
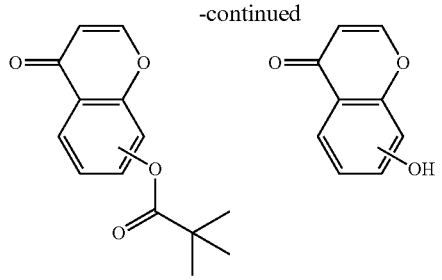
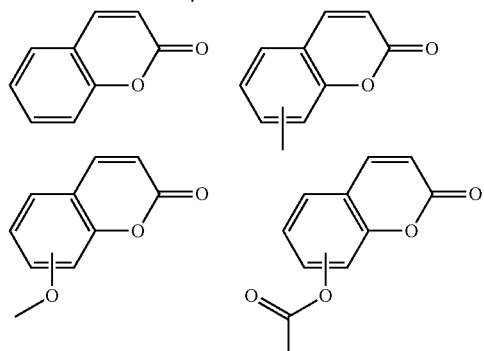
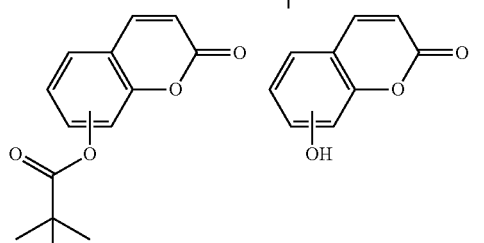
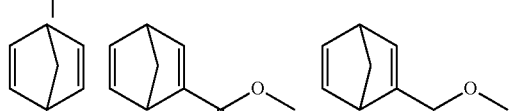
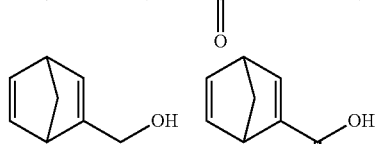
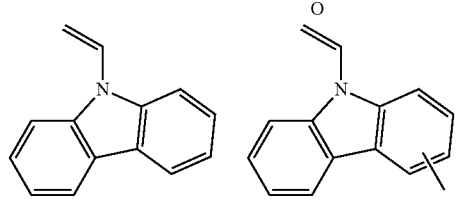
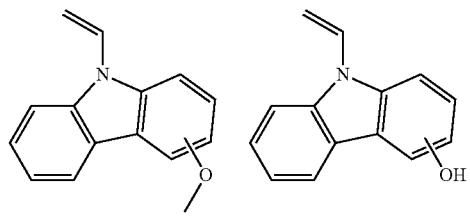
In the polymer, the recurring units derived from the inventive monomer and other monomers are preferably incorporated in the following molar fractions (mol %):
(I) more than 0 mol % to 100 mol %, preferably 5 to 80 mol %, and more preferably 10 to 60 mol % of recurring units of at least one type selected from formulae (2a) and (2b);

(II) 0 mol % to less than 100 mol %, preferably 0 to 90 mol %, and more preferably 0 to 80 mol % of recurring units of at least one type selected from formulae (3) to (5);

(III) 0 mol % to less than 100 mol %, preferably 20 to 95 mol %, and more preferably 40 to 90 mol % of recurring units of at least one type selected from formulae (A) to (D);

(IV) 0 to 30 mol %, preferably 0 to 20 mol %, and more preferably 0 to 10 mol % of recurring units of at least one type selected from formulae (f1) to (f5);

(V) 0 to 30 mol %, preferably 0 to 20 mol %, and more preferably 0 to 10 mol % of recurring units of at least one type selected from formulae (X-1) to (X-4); and (VI) 0 to 80 mol %, preferably 0 to 70 mol %, and more preferably 0 to 50 mol % of recurring units of at least one type selected from units (g) and (h).

The polymer may be synthesized by any desired methods, for example, by dissolving one or more monomers corresponding to the selected recurring units in an organic solvent, adding a radical polymerization initiator thereto, and effecting heat polymerization. Examples of the organic solvent which can be used for polymerization include toluene, benzene, tetrahydrofuran, diethyl ether, dioxane, cyclohexane, cyclopentane, methyl ethyl ketone (MEK), propylene glycol monomethyl ether acetate (PGMEA), and γ-butyrolactone (GBL). Examples of the polymerization initiator used herein include 2,2'-azobisisobutyronitrile (AIBN), 2,2'-azobis(2,4-dimethyl-valeronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, a copolymer may be obtained by dissolving hydroxystyrene or hydroxyvinylnaphthalene and another monomer(s) in an organic solvent, adding a radical polymerization initiator, and heat polymerization. Alternatively, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to polyhydroxystyrene or hydroxypolyvinylnaphthalene. For alkaline hydrolysis, a base such as aqueous ammonia or triethylamine may be used. The reaction temperature is −20° C. to 100° C., preferably 0° C. to 60° C., and the reaction time is 0.2 to 100 hours, preferably 0.5 to 20 hours.

The polymer should preferably have a weight average molecular weight (Mw) in the range of 1,000 to 500,000, and more preferably 3,000 to 50,000, as measured versus polystyrene standards by GPC using tetrahydrofuran solvent. Outside the range, there may result an extreme decline of etch resistance, a failure to provide a differential dissolution rate before and after exposure, and a lowering of resolution. Also preferably, the polymer has a molecular weight distribution or dispersity (Mw/Mn) of 1.20 to 2.20, more preferably 1.30 to 1.80.

Resist Composition

The inventive polymer is advantageously used as a base resin in a resist composition. Specifically, the polymer is used as a base resin and combined with any desired components including an organic solvent, acid generator, dissolution regulator, basic compound, surfactant, and acetylene alcohol to formulate a resist composition.

The resist composition comprising the inventive polymer has a very high sensitivity in that the dissolution rate in alkaline developer of the polymer in the exposed region is reduced by catalytic reaction. In addition, the resist film has a high dissolution contrast, resolution, exposure latitude, and process adaptability, and provides a good pattern profile after exposure, yet better etch resistance, and minimal proximity bias because of restrained acid diffusion. By virtue of these advantages, the composition is fully useful in commercial application and suited as a pattern-forming material for the fabrication of VLSIs. Particularly when an acid generator is included to formulate a chemically amplified resist composition capable of utilizing acid catalyzed reaction, the composition has a higher sensitivity and is further improved in the properties described above.

Inclusion of a dissolution regulator may lead to an increased difference in dissolution rate between exposed and unexposed regions and a further improvement in resolution. Addition of a basic compound may be effective in suppressing the diffusion rate of acid in the resist film, achieving a further improvement in resolution. Addition of a surfactant may improve or control the coating characteristics of the resist composition.

The resist composition may include an acid generator in order for the composition to function as a chemically amplified negative resist composition. Typical of the acid generator used herein is a photoacid generator (PAG) capable of generating an acid in response to actinic light or radiation. Preferably the PAG is used in an amount of 0.5 to 30 parts, more preferably 1 to 20 parts by weight per 100 parts by weight of the base resin.

Examples of the PAG include those described in JP-A 2008-111103, paragraphs [0122]-[0142] (U.S. Pat. No. 7,537,880). Preferred structures are also described in JP-A 2014-001259, paragraphs [0088]-[0092], JP-A 2012-041320, paragraphs [0015]-[0017], and JP-A 2012-106986, paragraphs [0015]-[0029]. These PAGs capable of generating partially fluorinated sulfonic acid are advantageously used in the ArF lithography because the generated acid has an appropriate strength and diffusion length.

Examples of the acid generated by the acid generator include sulfonic acids, imidic acids and methide acids. Of these, sulfonic acids which are fluorinated at α-position are most commonly used. Fluorination at α-position is not essential when the acid labile group used is an acetal group susceptible to deprotection.

Where the base resin contains recurring units of at least one type selected from formulae (f1) to (f5), the acid generator of addition type is not essential.

The preferred acid generators are those having the formulae (Z1) and (Z2).

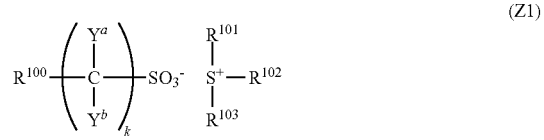
(Z1)

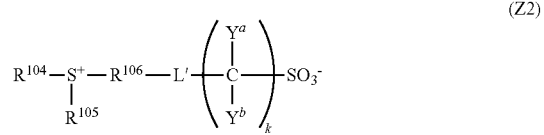
(Z2)

Herein $R^{100}$ is hydrogen, fluorine, or a $C_1$-$C_{35}$ straight, branched or cyclic monovalent hydrocarbon group which may contain a heteroatom. $Y^a$ and $Y^b$ are each independently hydrogen, fluorine, or trifluoromethyl, k is an integer of 1 to 4. $R^{101}$, $R^{102}$, and $R^{103}$ are each independently an optionally substituted, $C_1$-$C_{10}$ straight or branched alkyl or oxoalkyl, $C_2$-$C_{10}$ straight or branched alkenyl group, or an optionally substituted $C_6$-$C_{18}$, aryl, $C_7$-$C_{19}$ aralkyl or aryloxoalkyl group, or any two or more of $R^{101}$, $R^{102}$, and $R^{103}$ may bond together to form a ring with the sulfur atom to which they are attached. $R^{104}$ and $R^{105}$ are each independently a $C_1$-$C_{20}$ straight, branched or cyclic monovalent hydrocarbon group which may contain a heteroatom, or $R^{104}$ and $R^{105}$ may bond together to form a ring with the sulfur atom to which they are attached. $R^{106}$ is a $C_1$-$C_{20}$ straight, branched or cyclic divalent hydrocarbon group which may contain a heteroatom. L' is a single bond, ether bond or a $C_1$-$C_{20}$ straight, branched or cyclic divalent hydrocarbon group which may contain a heteroatom.

Also preferred are acid generators having the formulae (Z3) and (Z4).

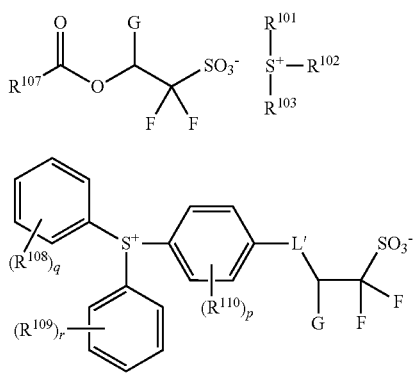

Herein $R^{101}$, $R^{102}$, and $R^{103}$ are as defined above. G is hydrogen or trifluoromethyl. $R^{107}$ is a $C_1$-$C_{35}$ straight, branched or cyclic monovalent hydrocarbon group which may contain a heteroatom. $R^{108}$, $R^{109}$, and $R^{110}$ are each independently hydrogen or a $C_1$-$C_{20}$ straight, branched or cyclic monovalent hydrocarbon group which may contain a heteroatom. Each of q and r is an integer of 0 to 5, p is an integer of 0 to 4. L' is a single bond, ether bond, or a $C_1$-$C_{20}$ straight, branched or cyclic divalent hydrocarbon group which may contain a heteroatom.

When the acid generator is one having formula (Z3) or (Z4), preferably formula (Z3) or (Z4) wherein G is trifluoromethyl, a pattern with improved properties, for example, a line-and-space pattern having low roughness (LWR) and improved control of acid diffusion length or a hole pattern having improved roundness and dimensional control can be formed.

Illustrative, non-limiting examples of the acid generators having formulae (Z1) to (Z4) are shown below. Notably G is as defined above.

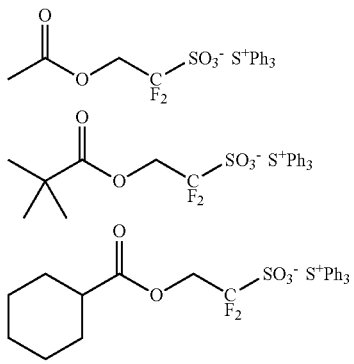

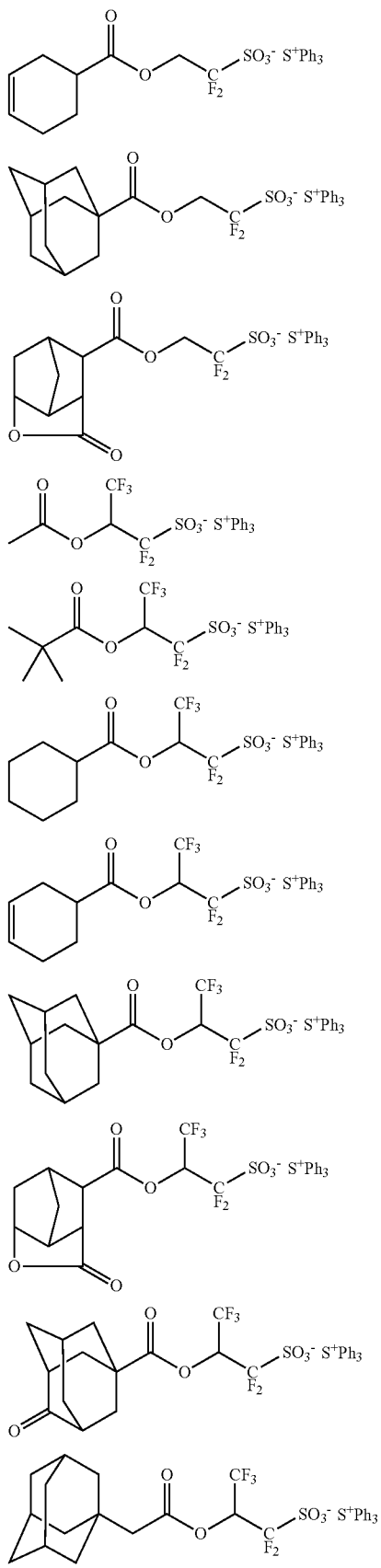

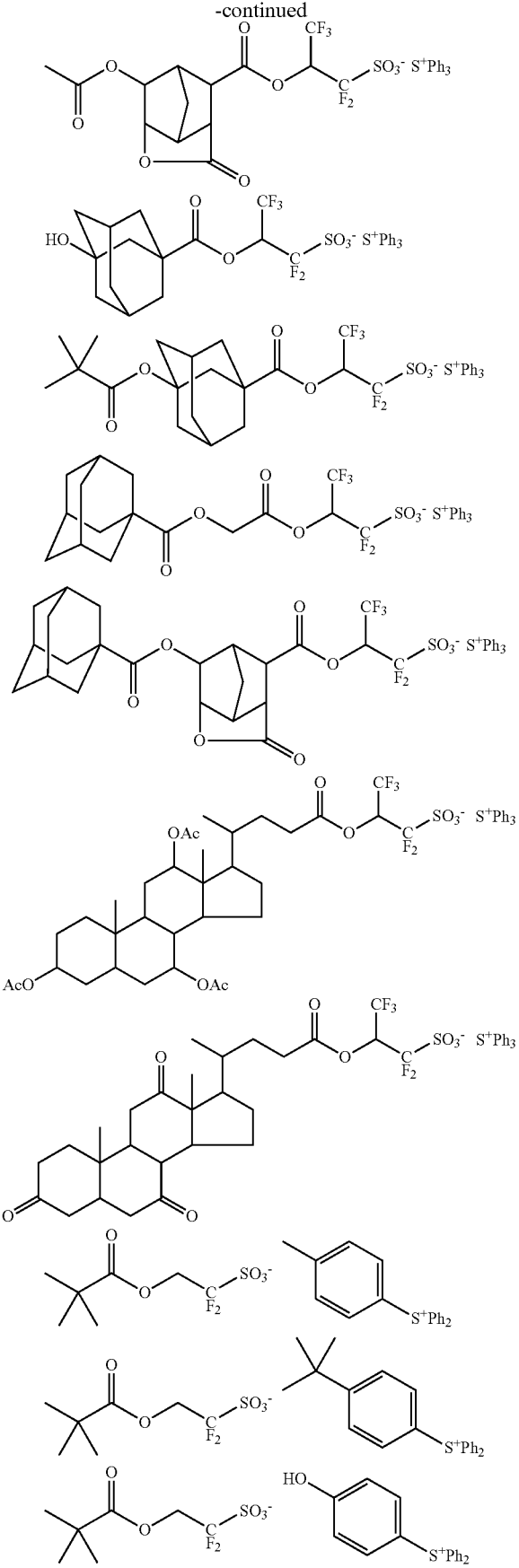
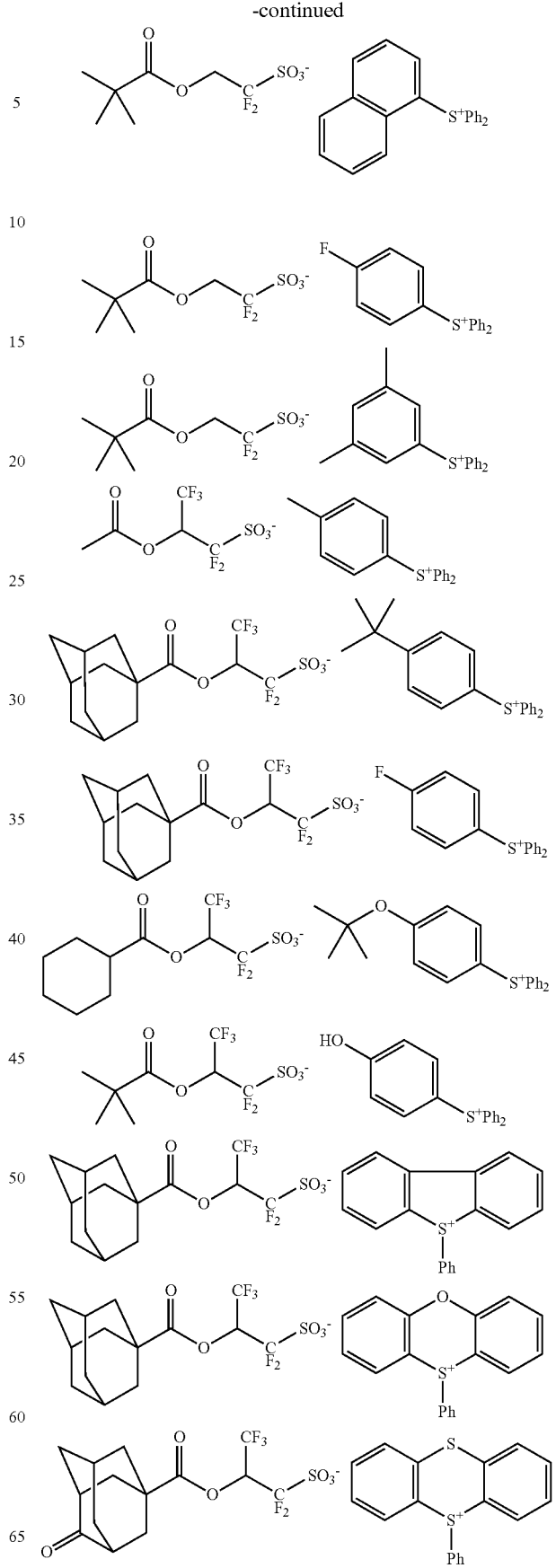

109
-continued
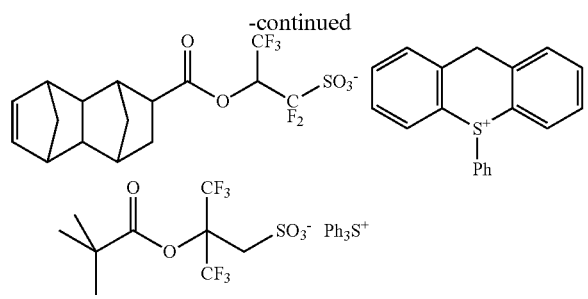
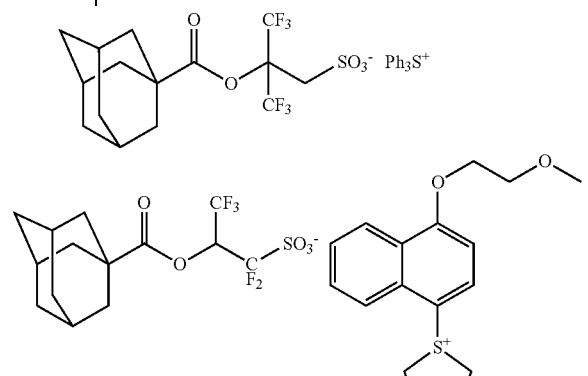
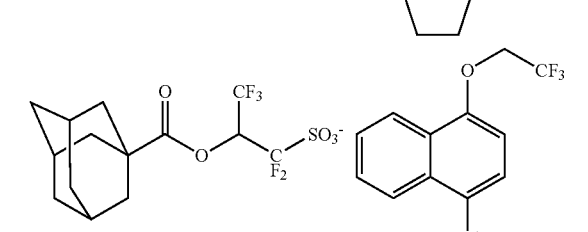
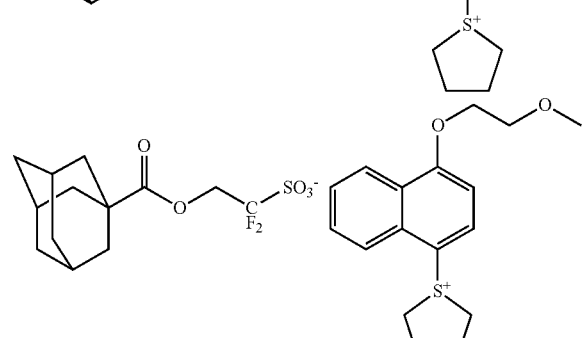
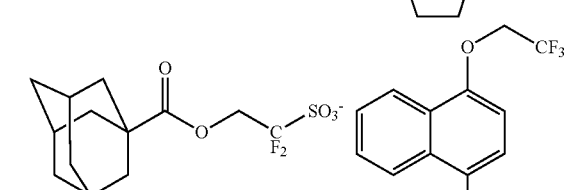
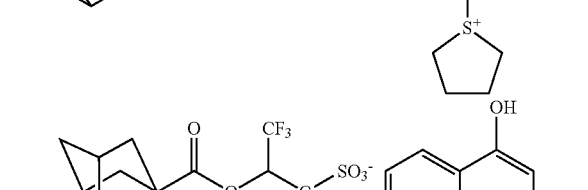
110
-continued
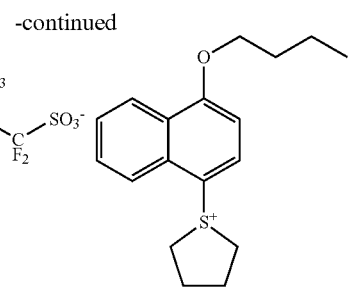
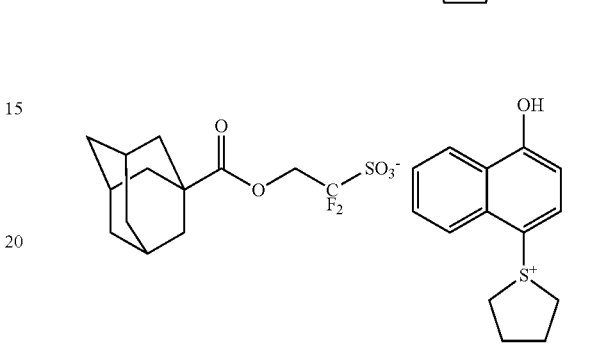
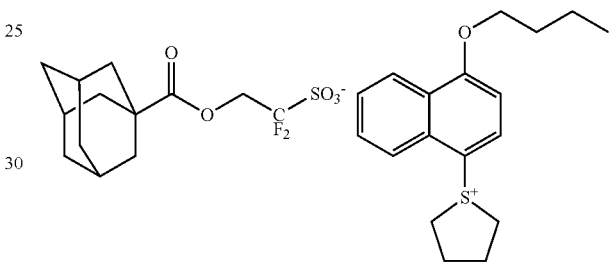
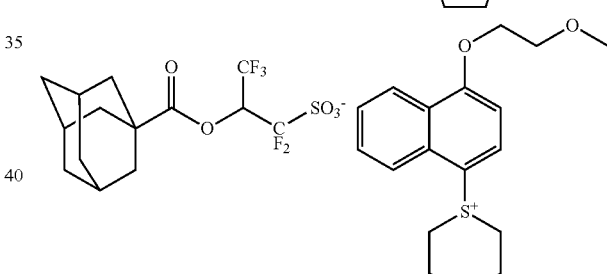
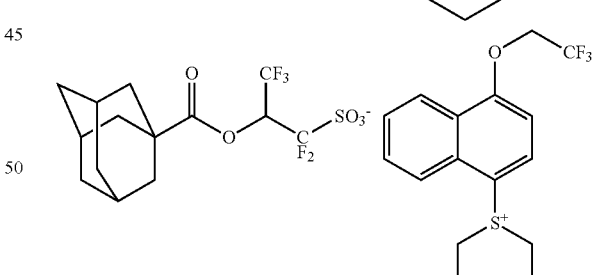
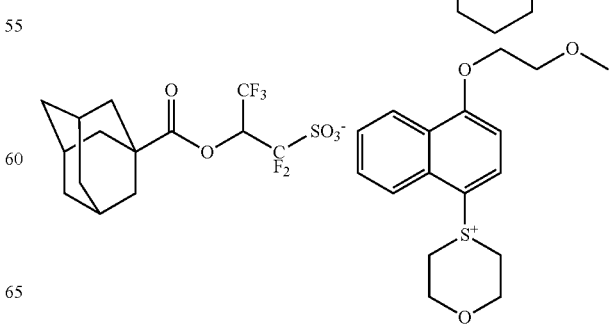

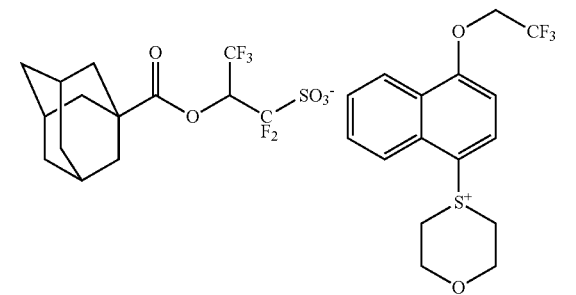
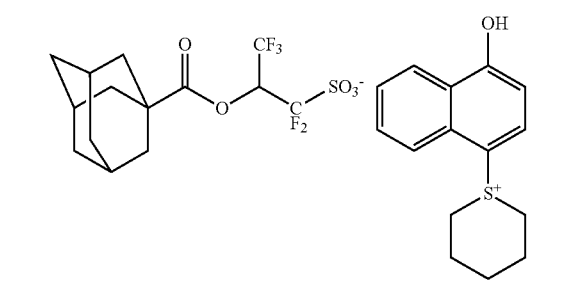
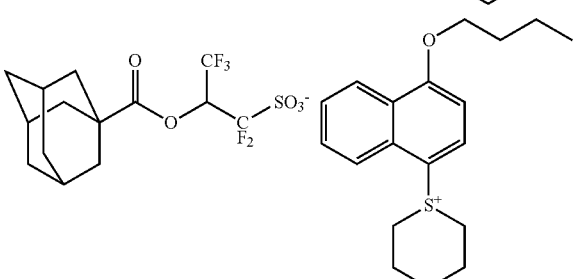
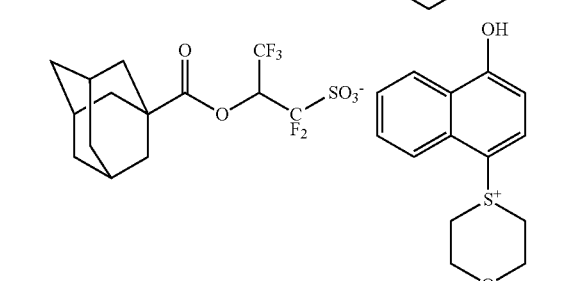
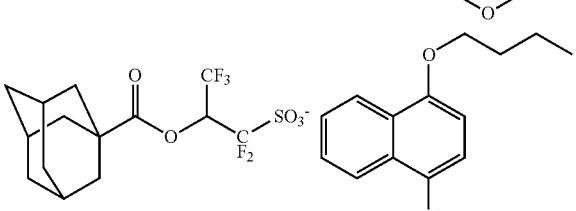
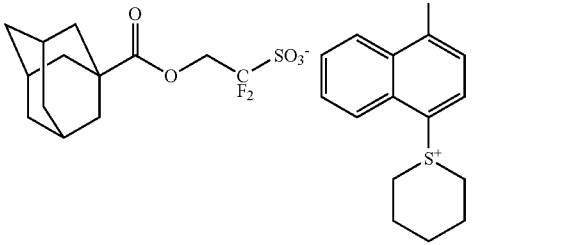
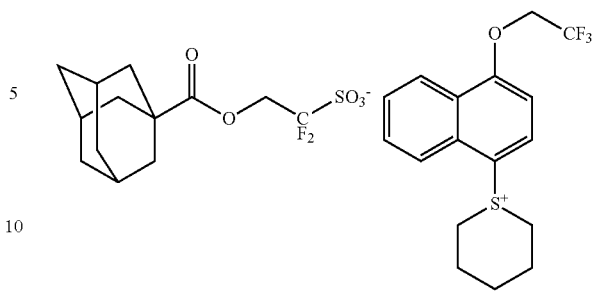
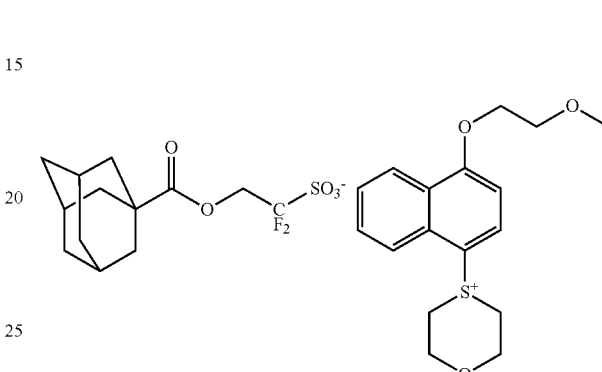
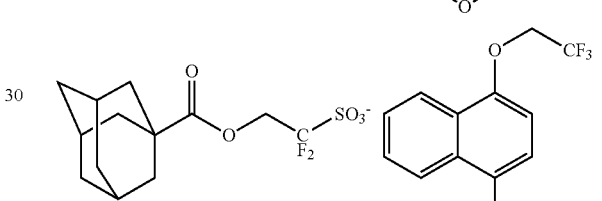
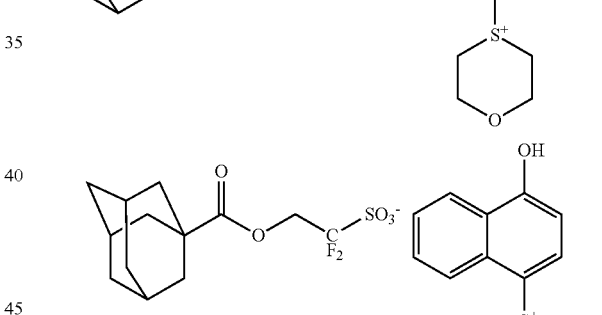
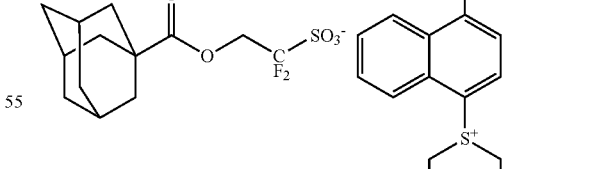
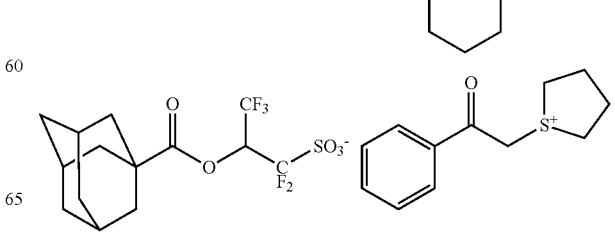

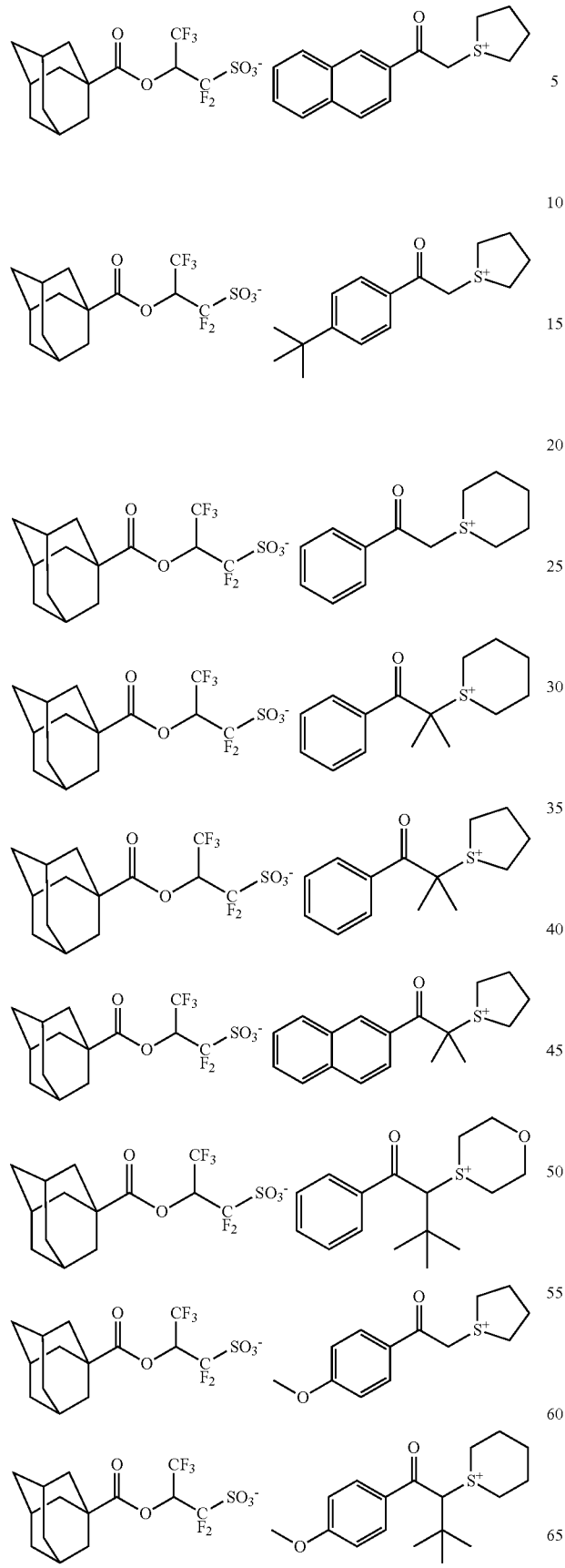

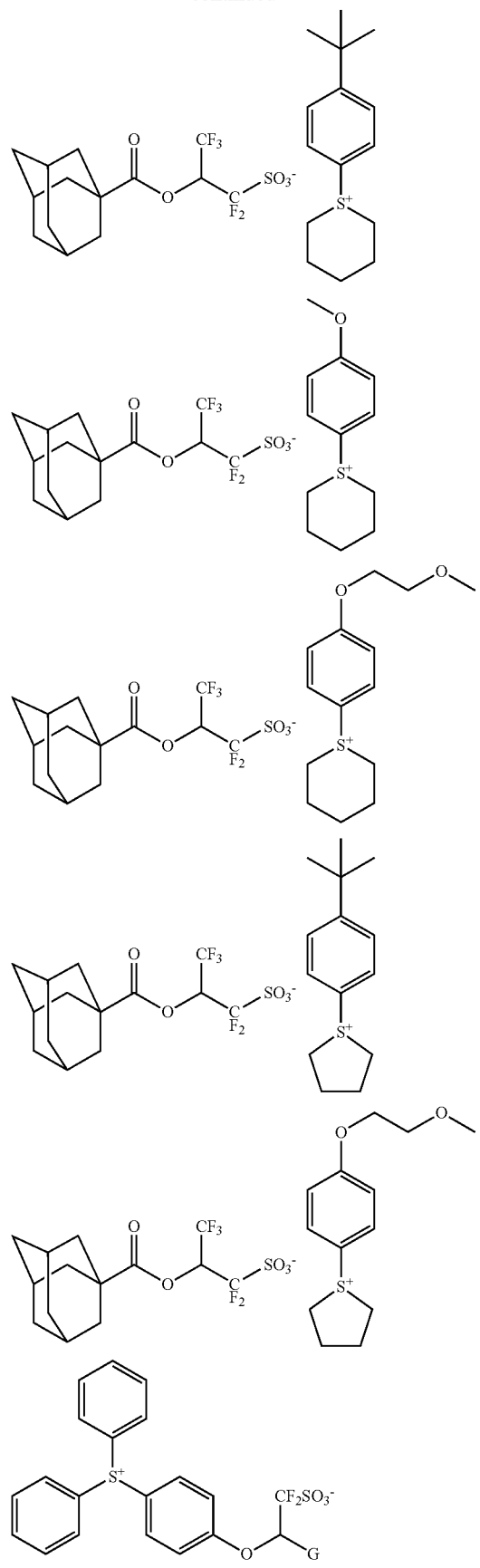
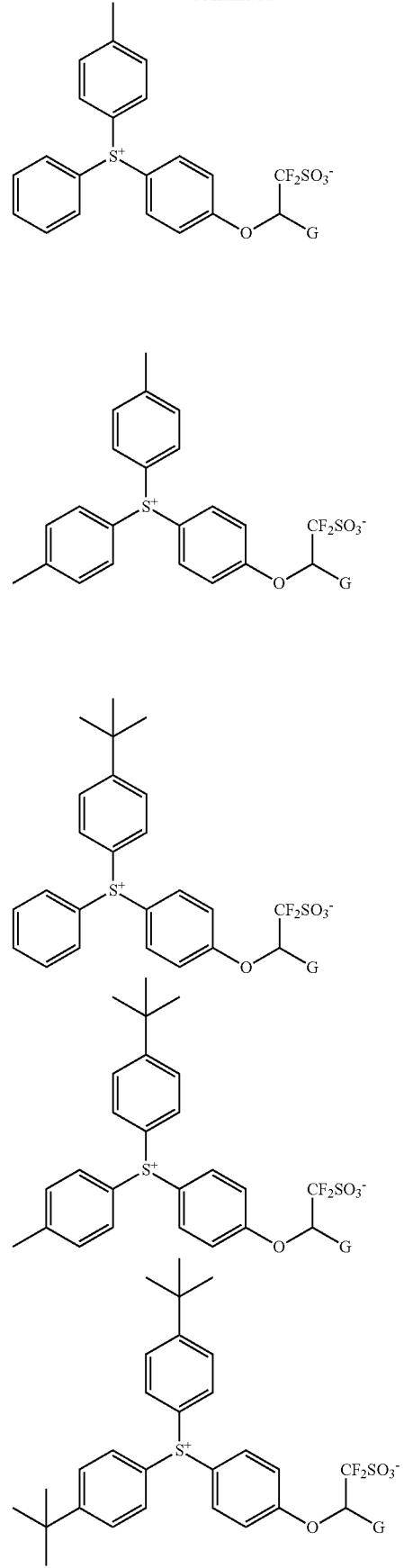

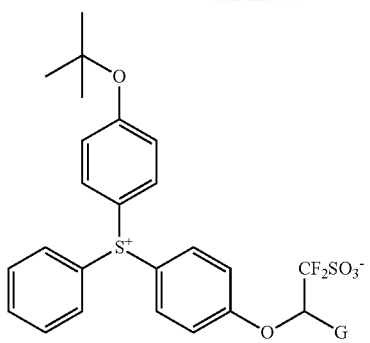
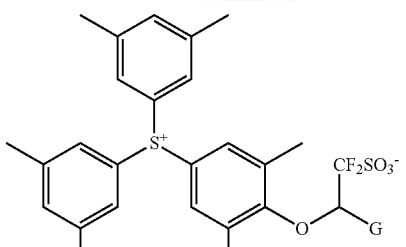
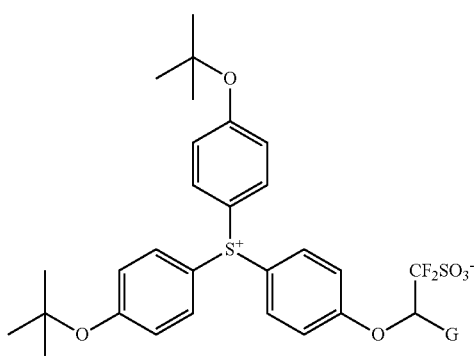
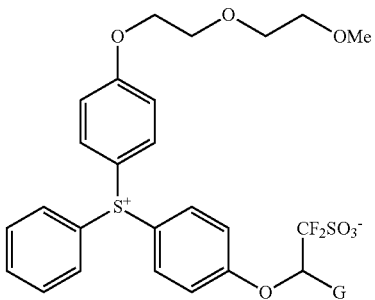
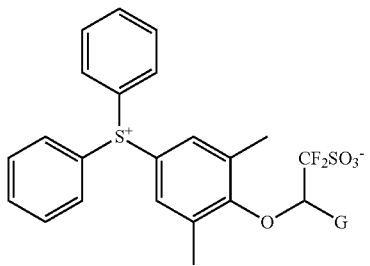
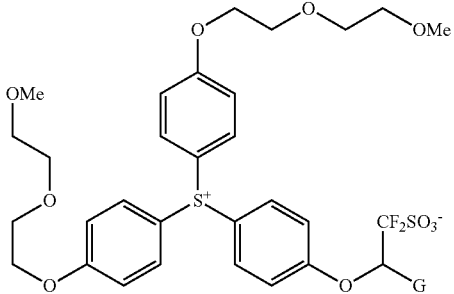
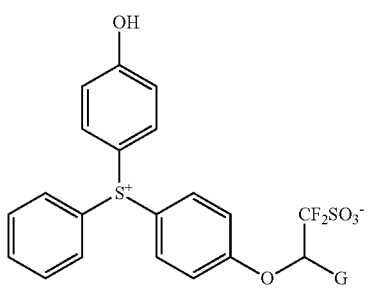
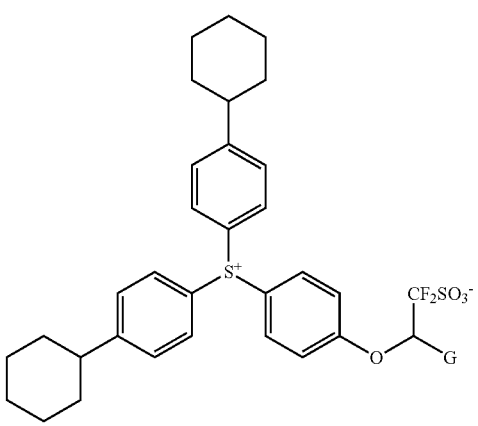
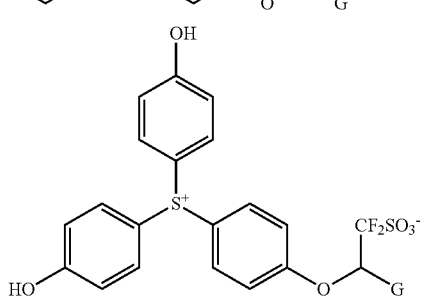
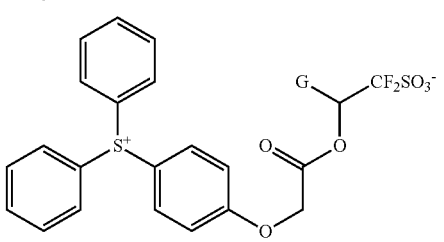

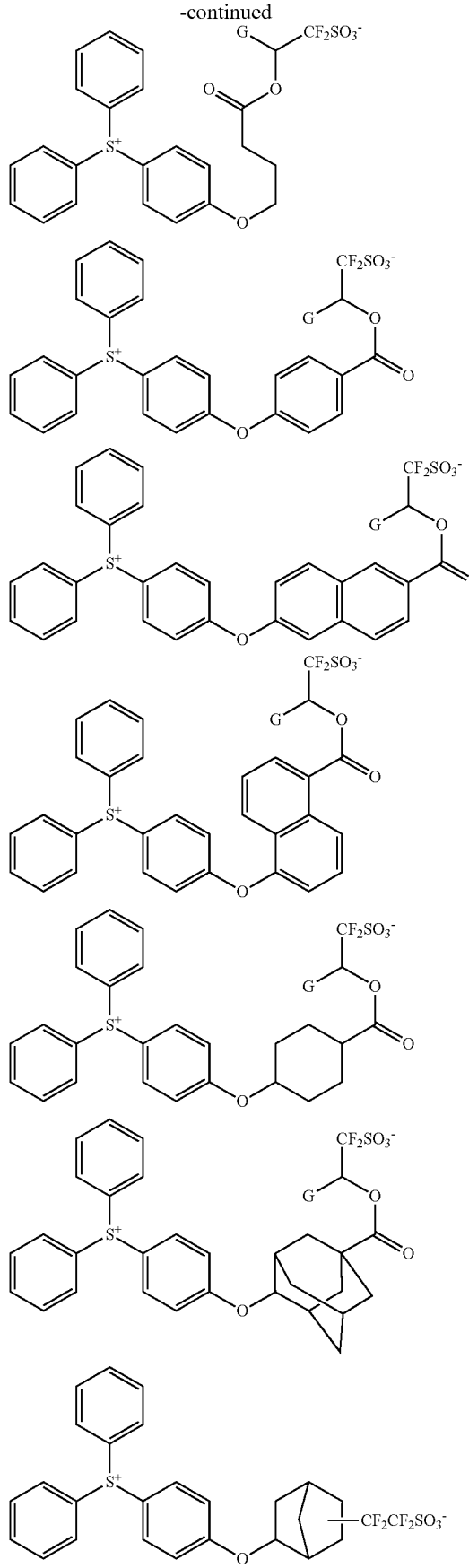
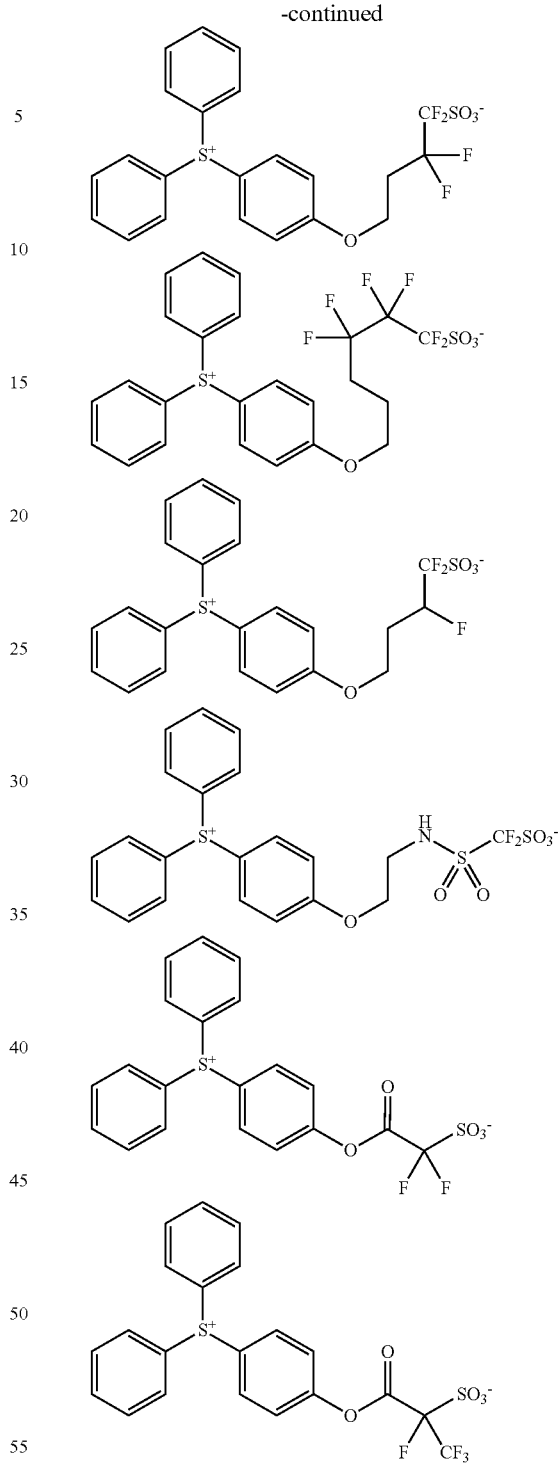

Suitable organic solvents include ketones such as cyclohexanone, cyclopentanone, methyl-2-n-pentyl ketone, and diacetone alcohol; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, methyl lactate, ethyl lactate, n-butyl lactate, ethyl pyruvate, butyl acetate, methyl 3-methoxypropionate, ethyl 3-ethoxypropionate, t-butyl acetate, t-butyl propionate, propylene glycol mono-t-butyl ether acetate, methyl 2-hydroxyisobutyrate, isopropyl 2-hydroxyisobutyrate, isobutyl 2-hydroxyisobutyrate, and n-butyl 2-hydroxyisobutyrate; and lactones such as γ-butyrolactone, which may be used alone or in admixture.

Examples of the basic compound used herein include primary, secondary, and tertiary amine compounds as described in JP-A 2008-111103 (U.S. Pat. No. 7,537,880), paragraphs [0146]-[0164], specifically amine compounds having a hydroxyl, ether, ester, lactone, cyano or sulfonic ester group, and compounds having a carbamate group as described in JP 3790649.

In the resist composition, an onium salt having the formula (xa) or (xb) may also be included.

$$R^{q1}-SO_3^-Mq^+ \quad (xa)$$

$$R^{q2}-CO_2^-Mq^+ \quad (xb)$$

Herein $R^{q1}$ is hydrogen or a $C_1$-$C_{40}$ straight, branched or cyclic monovalent hydrocarbon group which may contain a heteroatom. Notably, those groups wherein the hydrogen atom bonded to the carbon atom at α- and/or β-position relative to the sulfo group is replaced by fluorine or fluoroalkyl are excluded. $R^{q2}$ is hydrogen or a $C_1$-$C_{40}$ straight, branched or cyclic monovalent hydrocarbon group which may contain a heteroatom. $Mq^+$ is an onium cation having the formula (c1), (c2) or (c3).

(c1)

(c2)

(c3)

Herein $R^{201}$, $R^{202}$, $R^{203}$, $R^{204}$, $R^{205}$, $R^{206}$, $R^{207}$, $R^{208}$, and $R^{209}$ are each independently a $C_1$-$C_{40}$ straight, branched or cyclic monovalent hydrocarbon group which may contain a heteroatom, or a pair of $R^{201}$ and $R^{202}$, or $R^{206}$ and $R^{207}$ may bond together to form a ring with the atom to which they are attached.

$R^{q1}$ is hydrogen or a monovalent hydrocarbon group, examples of which include methyl, ethyl, propyl, isopropyl, n-butyl, s-butyl, t-butyl, t-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl and anthracenyl. In these hydrocarbon groups, one or more hydrogen atoms may be substituted by a heteroatom such as oxygen, sulfur, nitrogen or halogen, or a moiety containing a heteroatom such as oxygen, sulfur or nitrogen may intervene between carbon atoms, so that the group may contain a hydroxyl, cyano, carbonyl, ether bond, ester bond, sulfonic acid ester bond, carbonate bond, lactone ring, sultone ring, carboxylic anhydride or haloalkyl moiety.

Examples of group $R^{q2}$ include the substituent groups exemplified above for $R^{q1}$ as well as fluorinated alkyl groups such as trifluoromethyl and trifluoroethyl, and fluorinated aryl groups such as pentafluorophenyl and 4-trifluoromethylphenyl.

Examples of the anion moiety in formula (xa) include the following structures, but are not limited thereto.

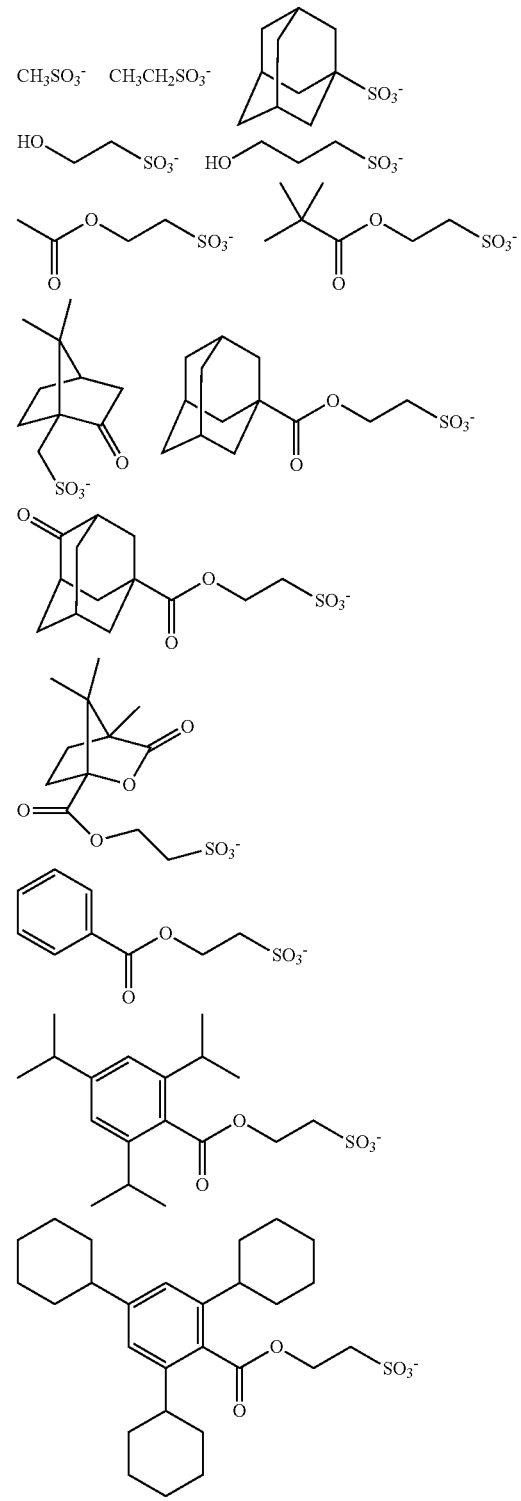

123
-continued
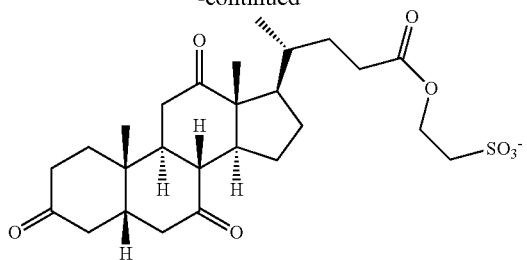
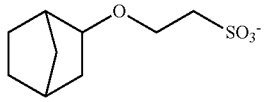
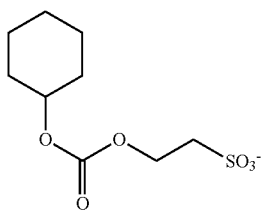
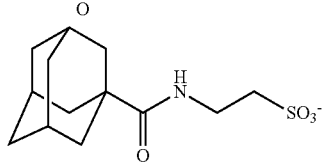
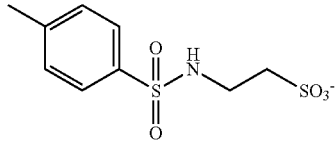
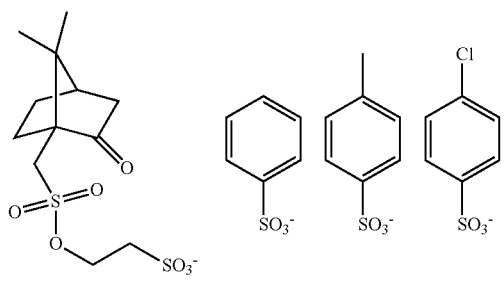
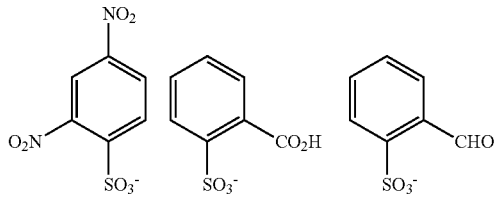
124
-continued
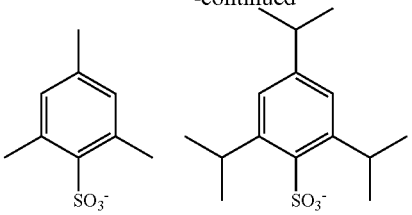
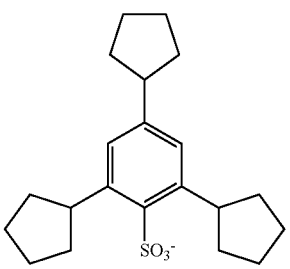
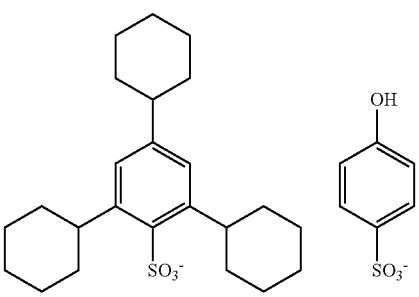
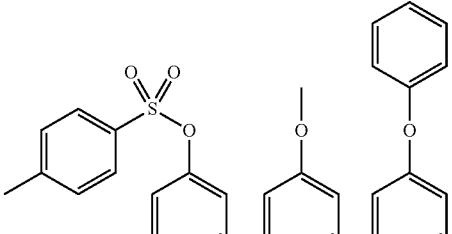
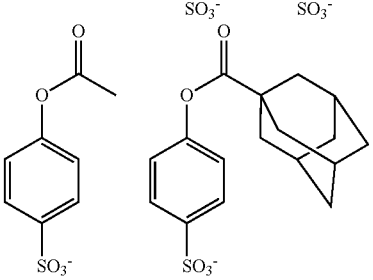
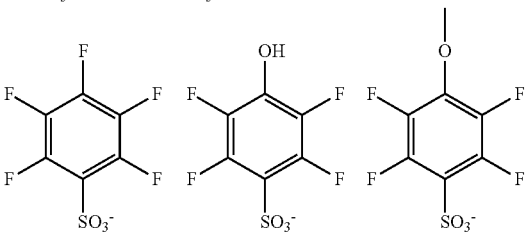

125
-continued
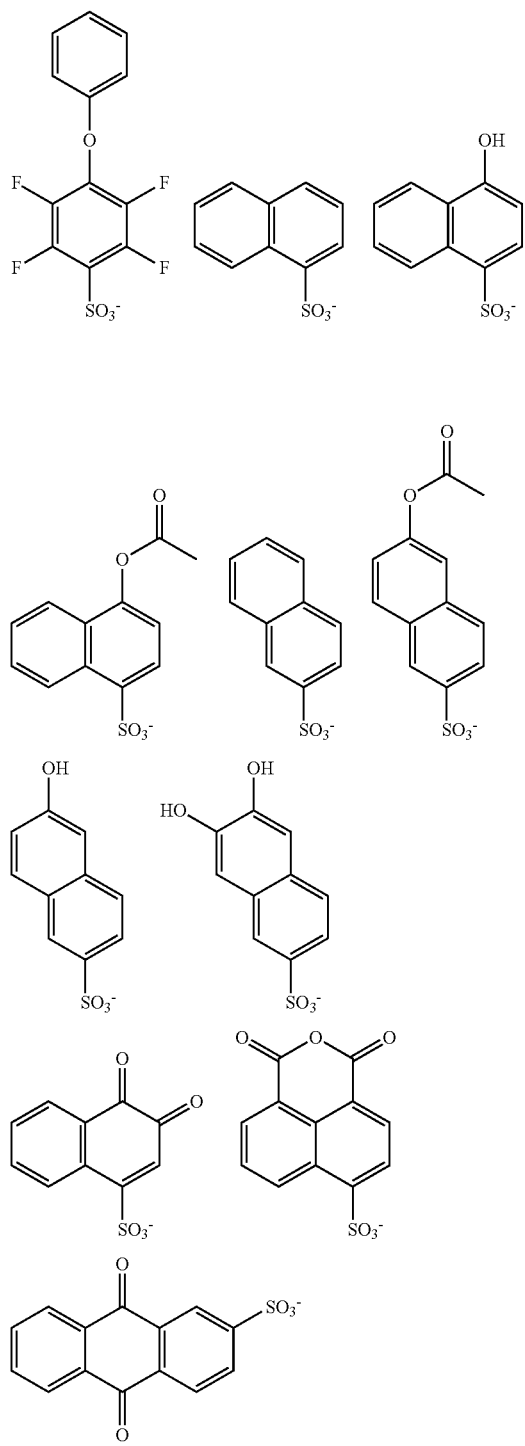
Examples of the anion moiety in formula (xb) include the following structures, but are not limited thereto.
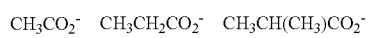 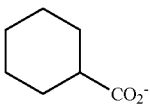
126
-continued
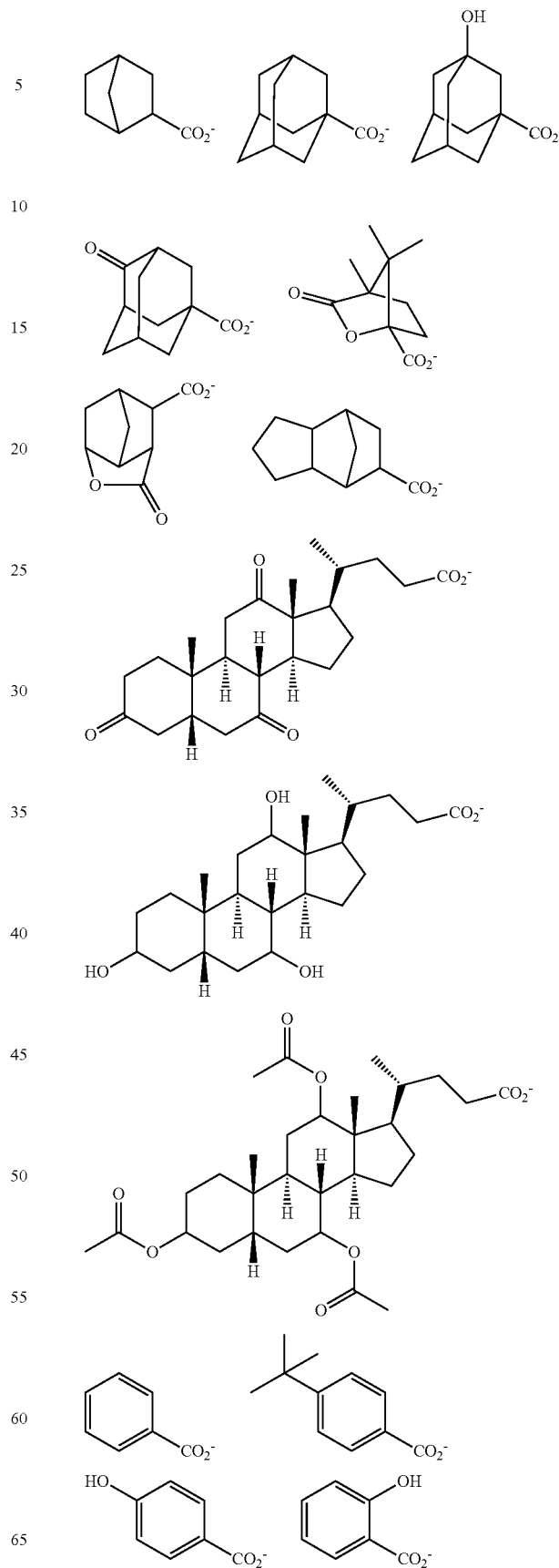

-continued
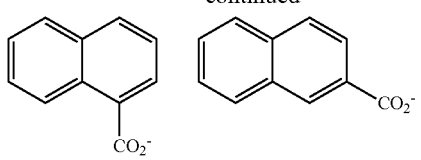
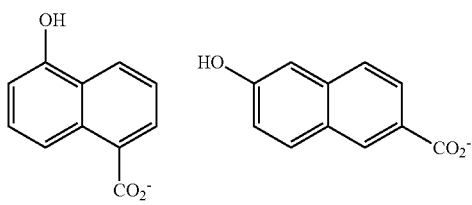
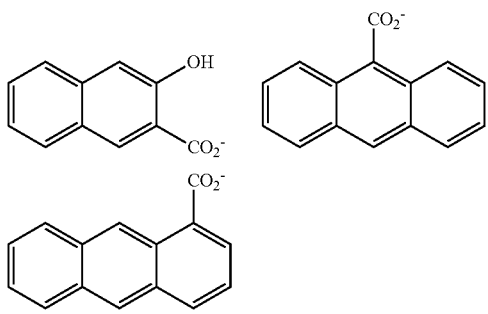
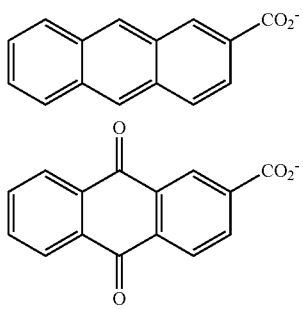
CF₃CF₂CO₂⁻   CF₃C(CF₃)(OH)CO₂⁻   CF₃CO₂⁻   CF₃CH₂CO₂⁻
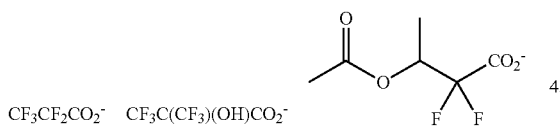
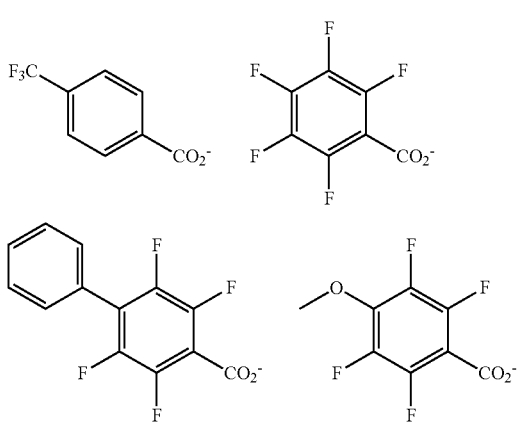
In formulae (c1), (c2) and (c3), examples of monovalent hydrocarbon groups $R^{201}$ to $R^{209}$ include the same groups as exemplified for $R^{q1}$ in formula (xa).
Examples of the cation moiety ($Mq^+$) in formulae (xa) and (xb) include the following structures, but are not limited thereto.
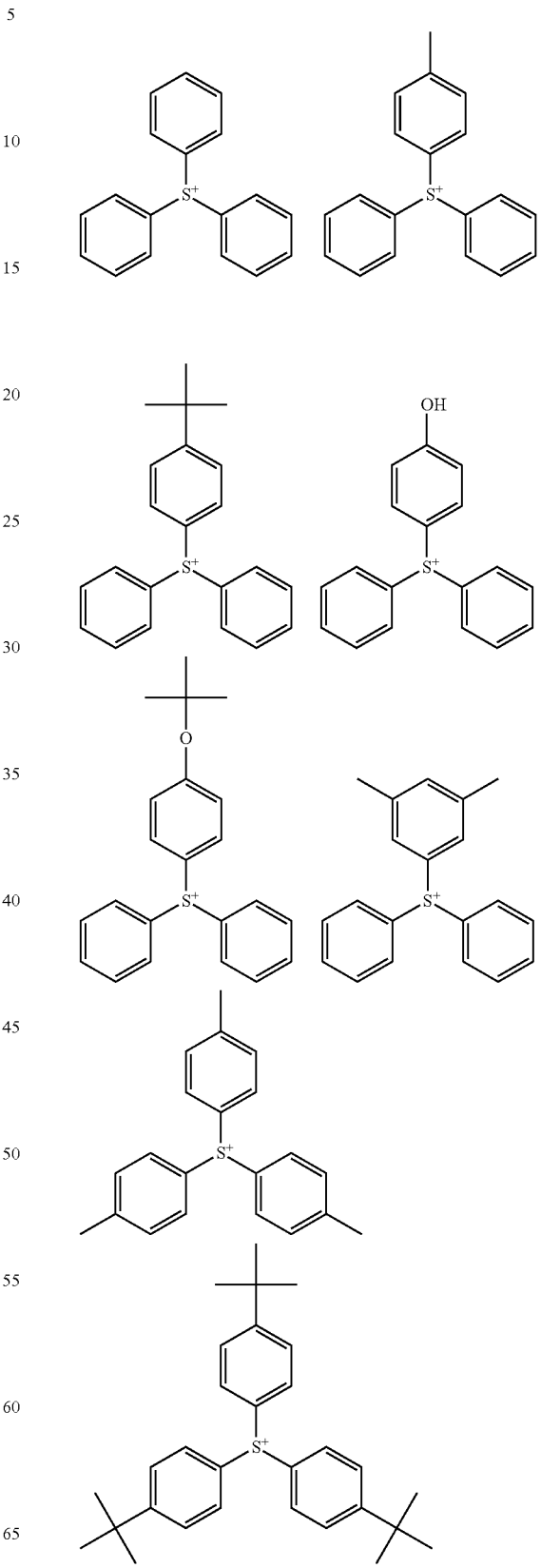

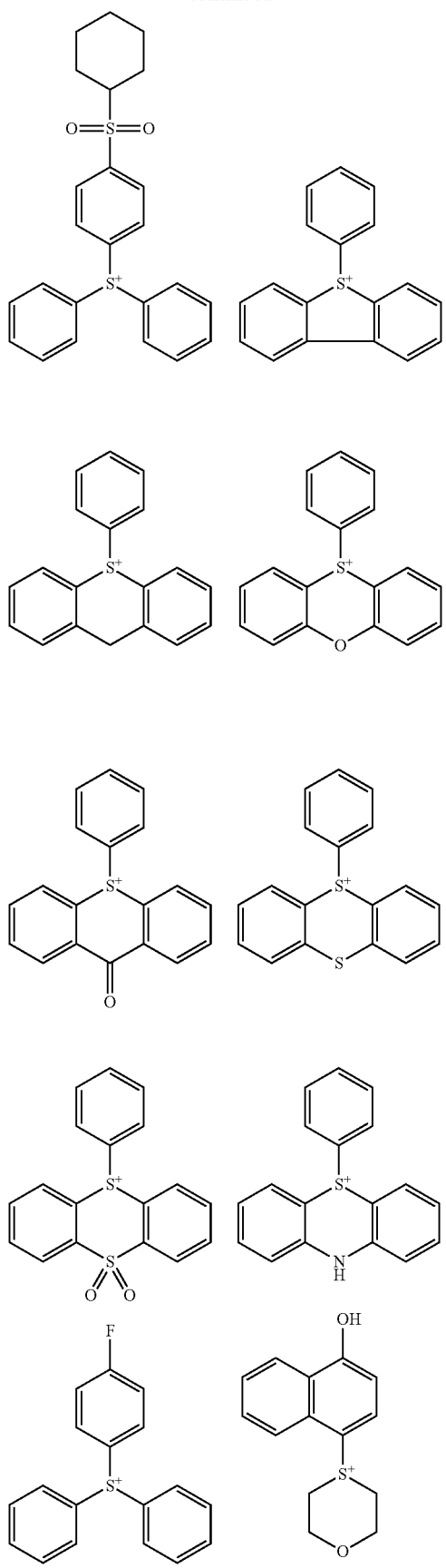
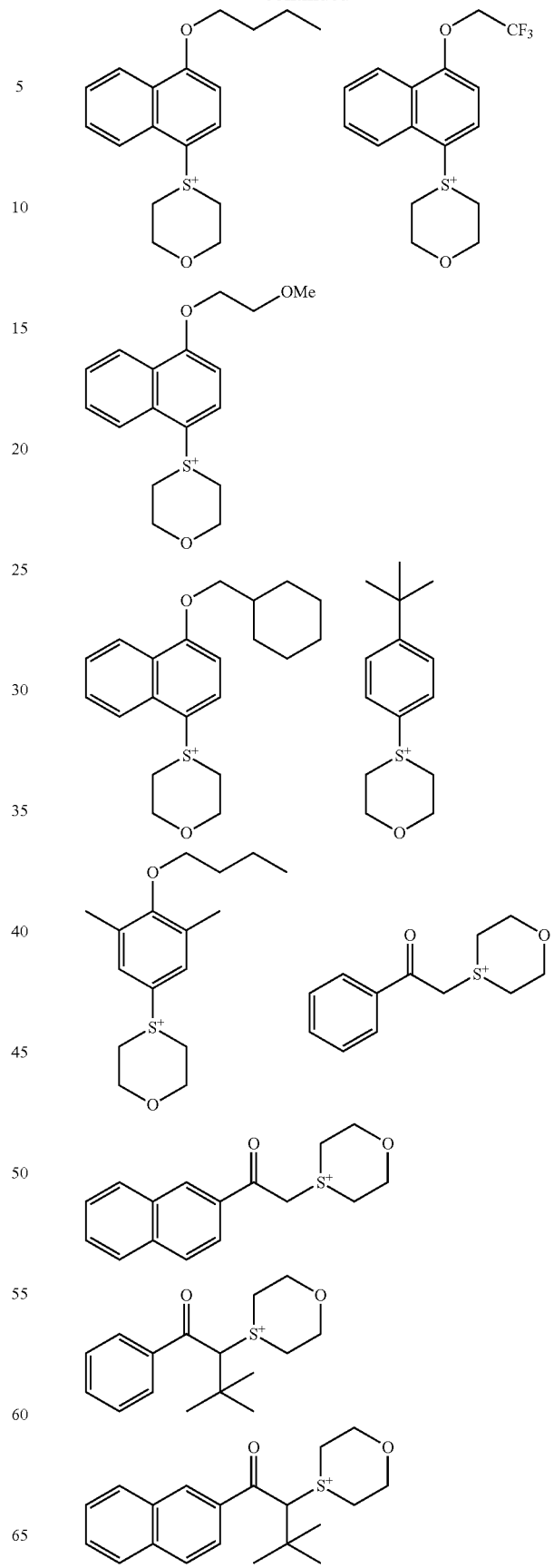

131
-continued

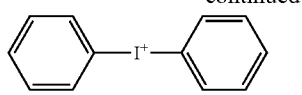

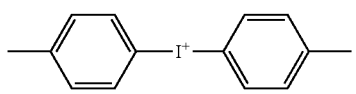

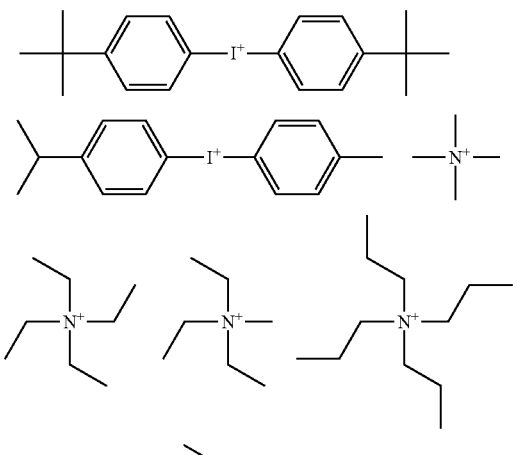

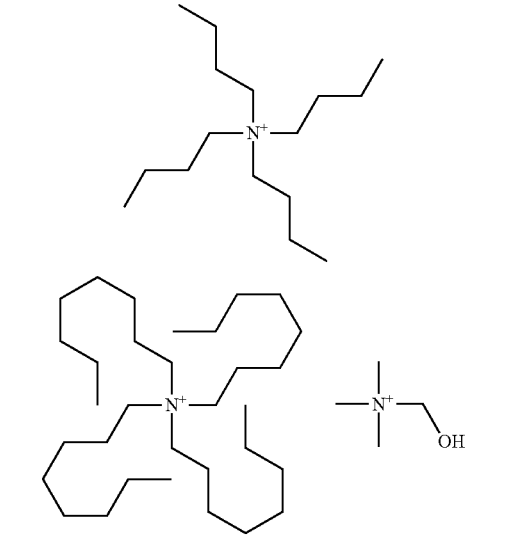

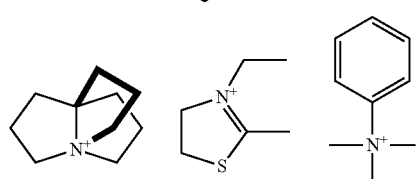

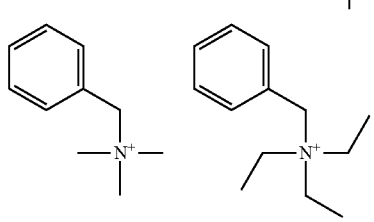

132
-continued

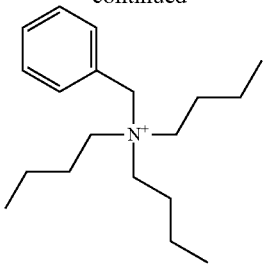

Examples of the onium salt having formula (xa) or (xb) include any combinations of the anion structure with the cation structure, both exemplified above. These onium salts may be readily prepared via ion exchange reaction by any well-known organic chemistry techniques. With respect to the ion exchange reaction, reference may be made to JP-A 2007-145797.

The onium salt having formula (xa) or (xb) functions as the acid diffusion regulator or quencher because the counter anion of the onium salt is a conjugated base of weak acid. As used herein, the weak acid indicates an acidity insufficient to deprotect an acid labile group from an acid labile group-containing unit in the base resin. The onium salt having formula (xa) or (xb) functions as a quencher when used in combination with an onium salt type PAG having a conjugated base of a strong acid, typically a sulfonic acid which is fluorinated at α-position as the counter anion. In a system using a mixture of an onium salt capable of generating a strong acid (e.g., α-position fluorinated sulfonic acid) and an onium salt capable of generating a weak acid (e.g., α-position non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If a PAG capable of generating a strong acid is an onium salt, an exchange from the strong acid generated upon exposure to high-energy radiation to a weak acid as above can take place, but it scarcely happens that the weak acid generated upon exposure to high-energy radiation collides with the unreacted onium salt capable of generating a strong acid to induce a salt exchange. This is because of a likelihood of an onium cation forming an ion pair with a stronger acid anion.

A compound having the formula (YB) may be used as an onium salt of weak acid.

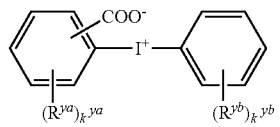

(YB)

Herein $R^{ya}$ and $R^{yb}$ are each independently a $C_1$-$C_{12}$ monovalent hydrocarbon group, nitro, acyl, alkoxy or acyloxy group, $k^{ya}$ and $k^{yb}$ each are an integer of 0 to 4.

Examples of the onium salt of weak acid having formula (YB) are given below, but not limited thereto.

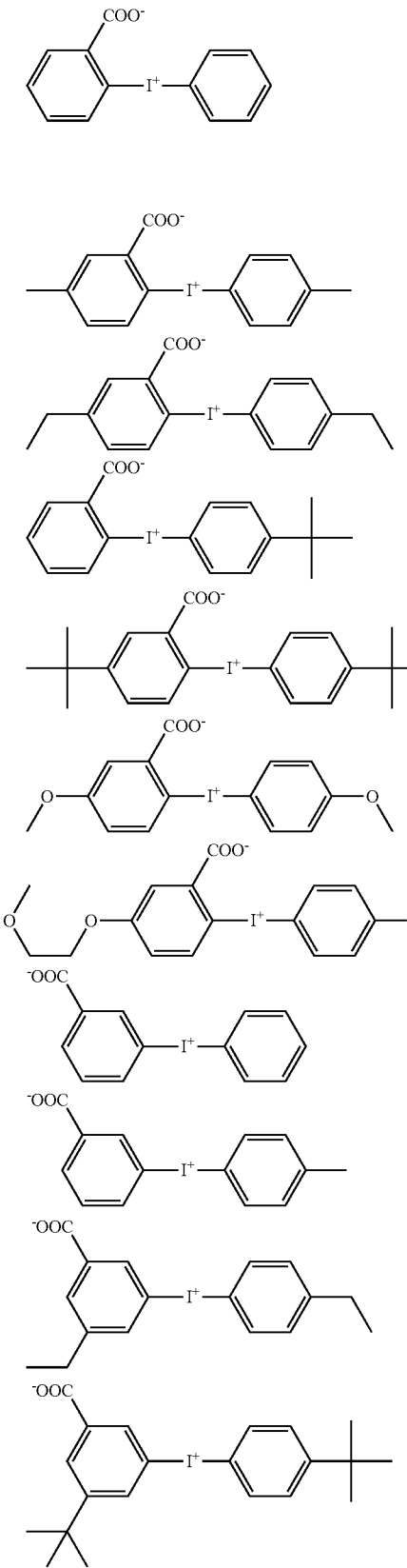

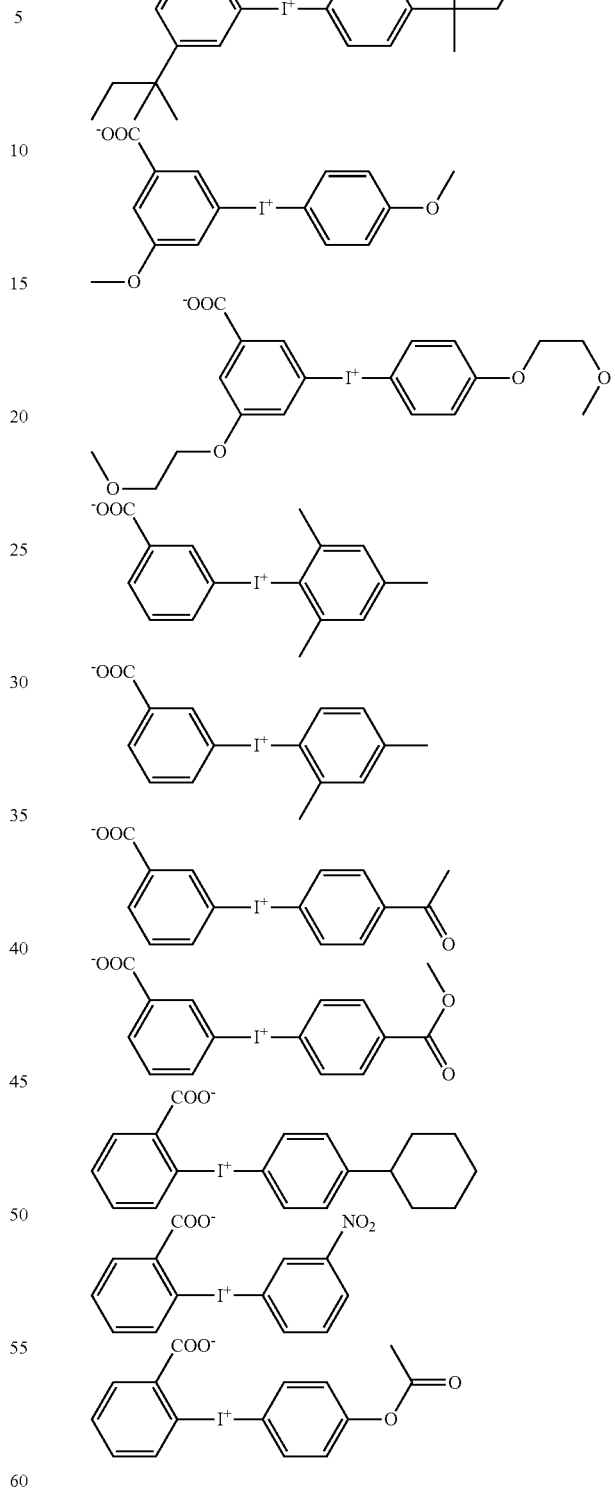

Useful surfactants are described in JP-A 2008-111103, paragraphs [0165]-[0166]. Useful dissolution regulators are described in JP-A 2008-122932, paragraphs [0155]-[0178]. Useful acetylene alcohols are described in JP-A 2008-122932, paragraphs [0179]-[0182].

Notably an appropriate amount of the organic solvent is 50 to 10,000 parts, more preferably 100 to 5,000 parts by weight, an appropriate amount of the dissolution regulator is 0 to 50 parts, more preferably 0 to 40 parts by weight, and an appropriate amount of the basic compound or acid diffusion regulator having formula (xa) or (xb) as the quencher is 0 to 100 parts, more preferably 0.001 to 50 parts by weight, per 100 parts by weight of the base resin. Amounts of the surfactant and acetylene alcohol may be determined as appropriate for a particular purpose.

Also a polymeric additive may be added for improving the water repellency on surface of a resist film as spin coated. This water repellency improver may be used in the topcoatless immersion lithography. These water repellency improvers have a specific structure with a 1,1,1,3,3,3-hexafluoro-2-propanol residue and are described in JP-A 2007-297590, JP-A 2008-111103, JP-A 2008-122932, JP-A 2012-128067, and JP-A 2013-057836.

The water repellency improver is described in more detail. Preferred are a homopolymer consisting of fluorine-containing units of one type, a copolymer consisting of fluorine-containing units of more than one type, and a copolymer consisting of fluorine-containing units and other units. Suitable fluorine-containing units and other units are shown below, but not limited thereto. Notably $R^{55}$ is hydrogen or methyl.

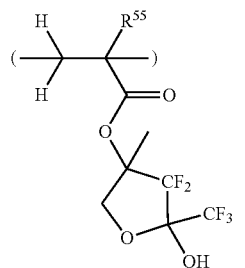
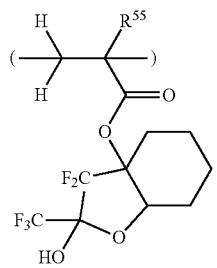

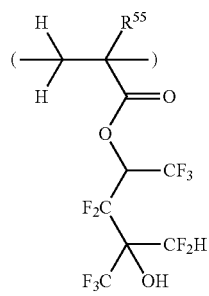
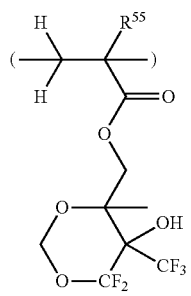

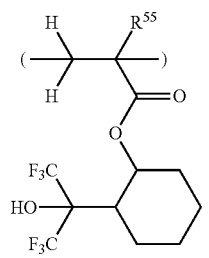
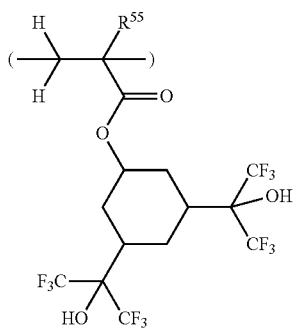

-continued

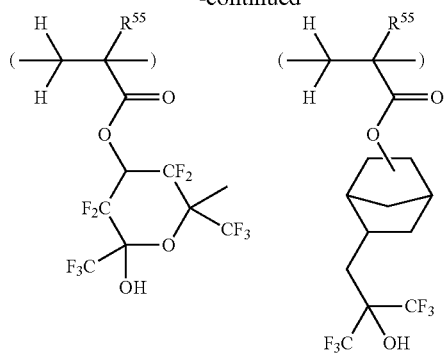

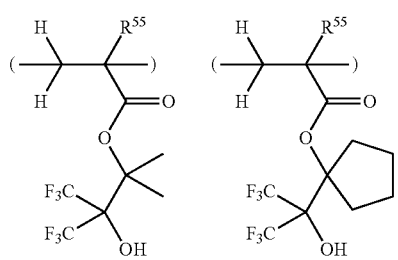

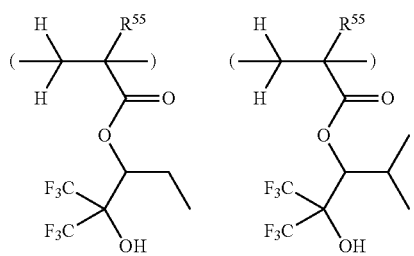

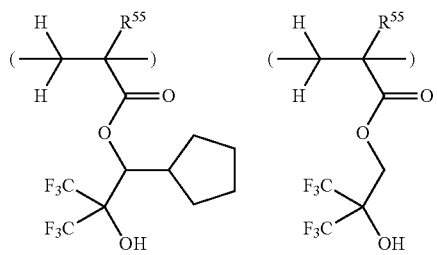

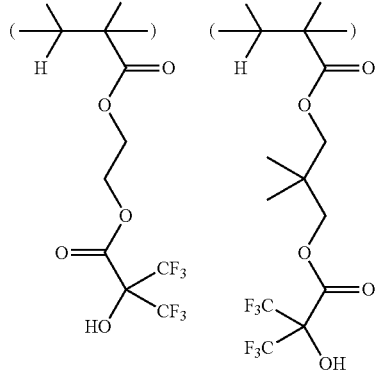

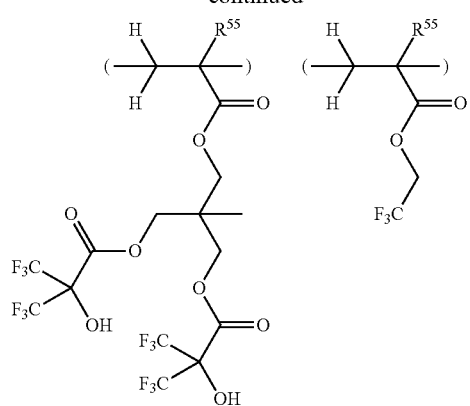
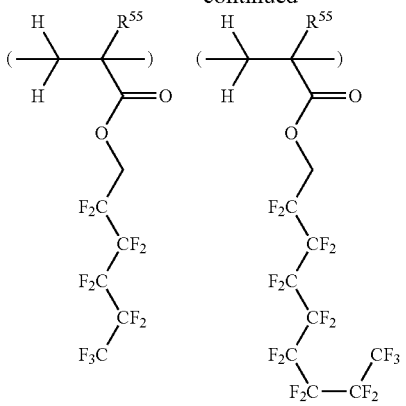
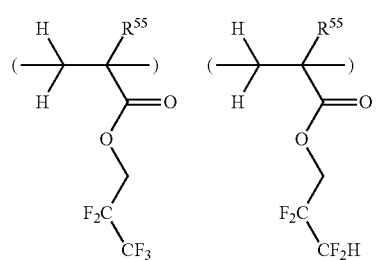
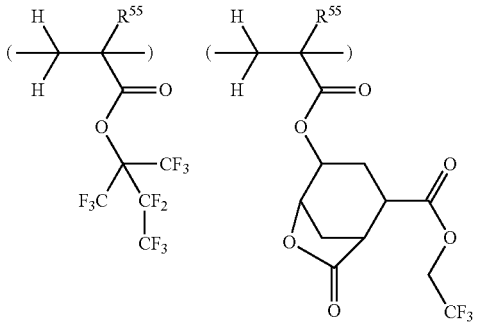
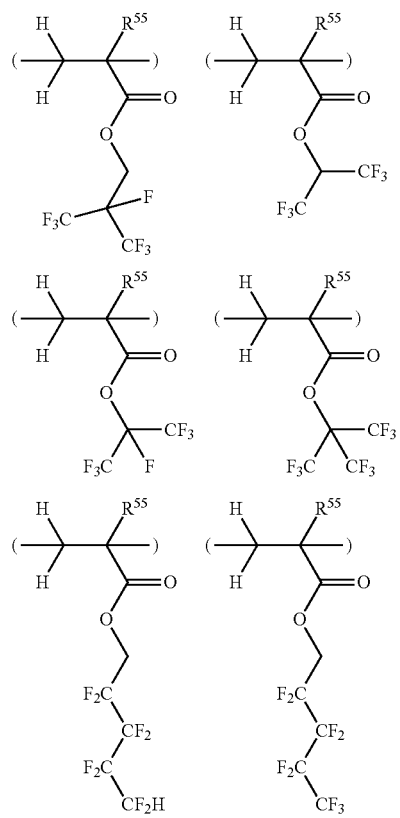
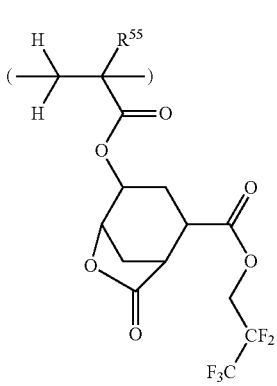
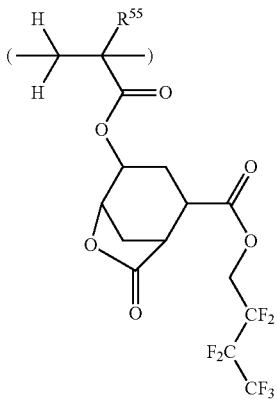

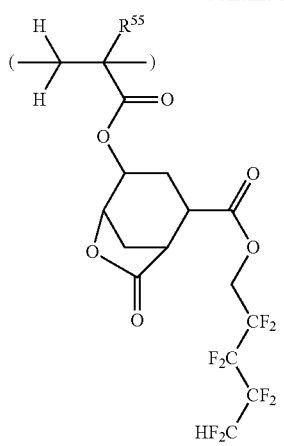
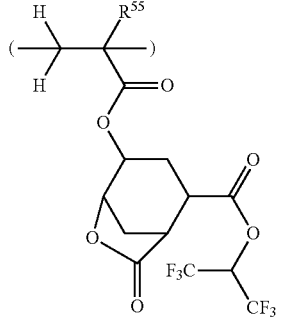
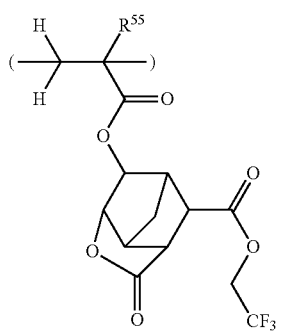
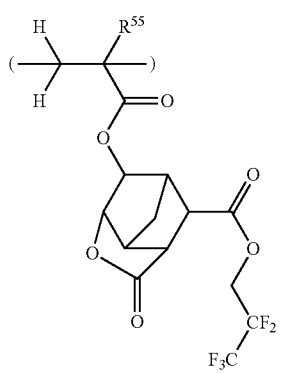
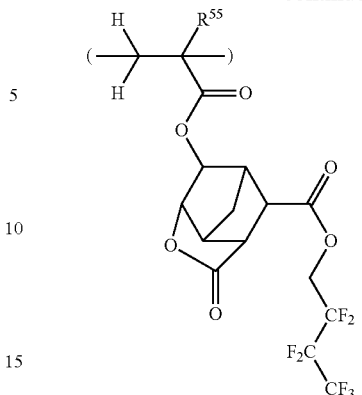
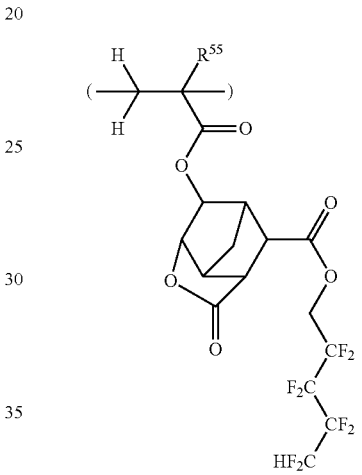
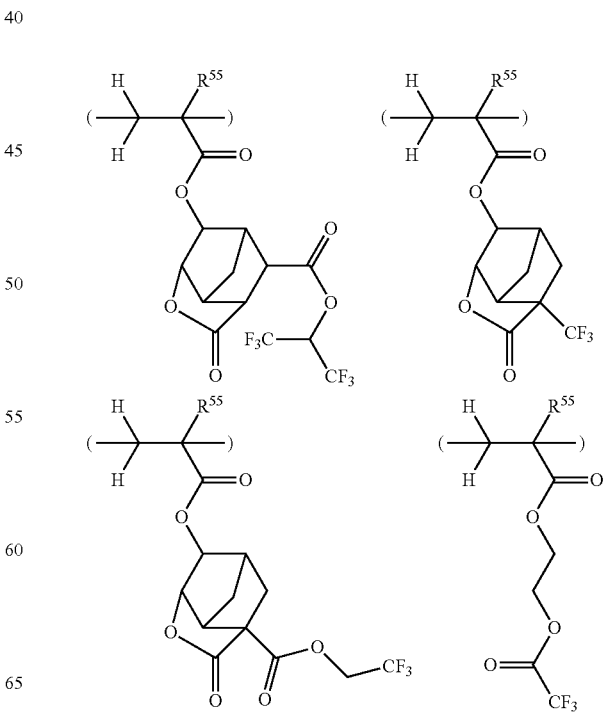

141
-continued
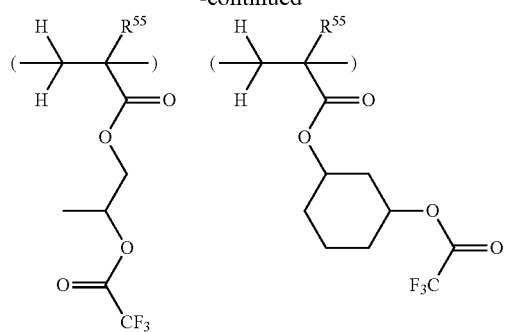
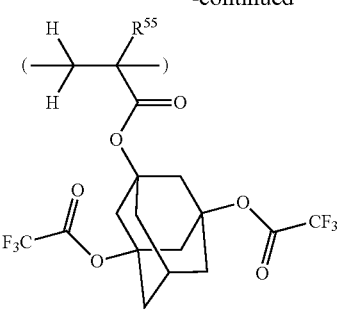
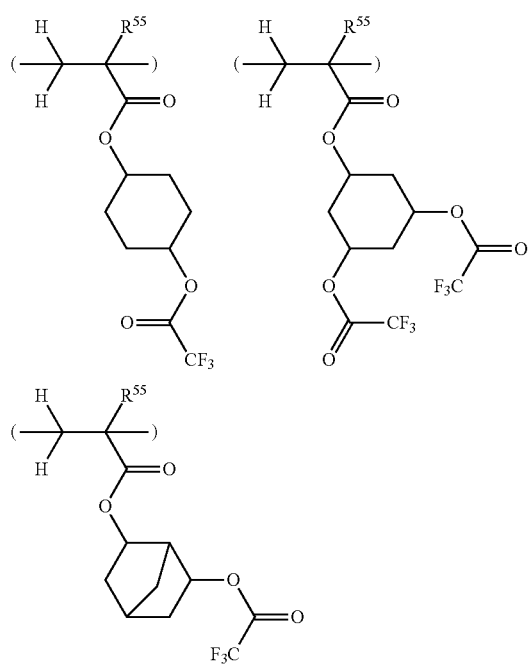
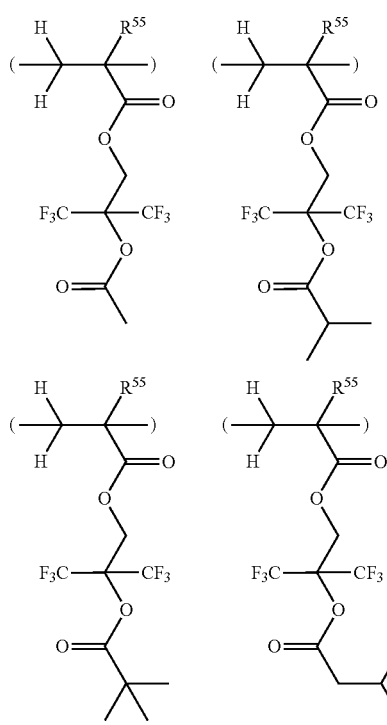
142
-continued
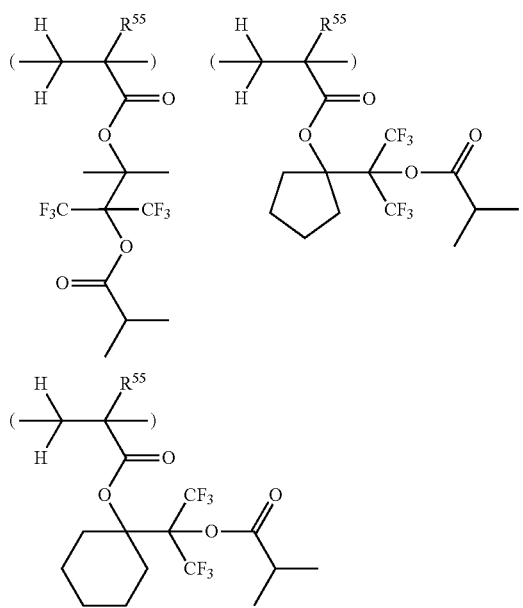

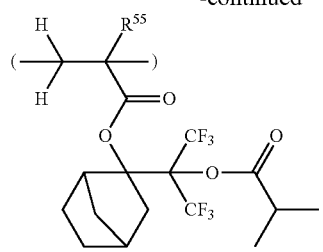
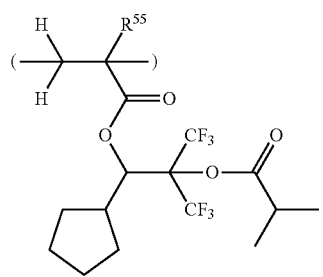
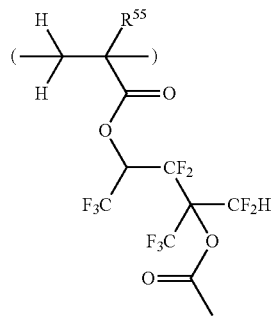
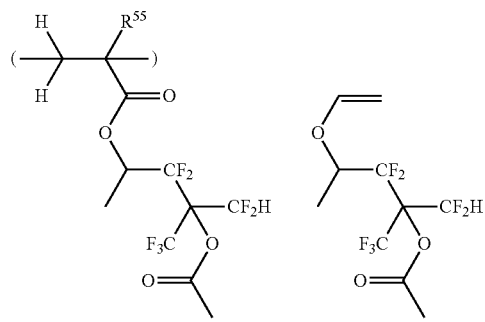
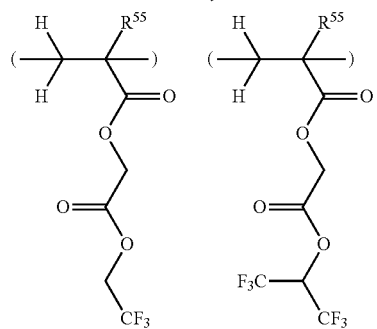
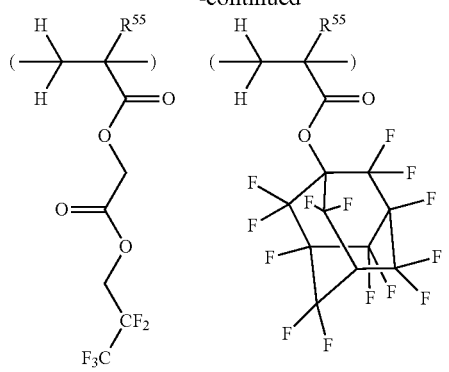
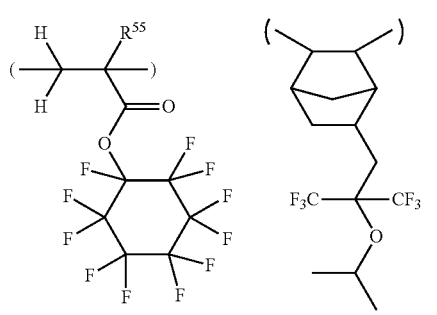
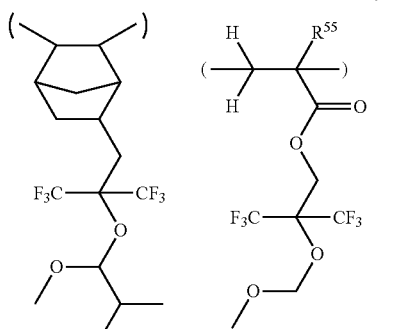
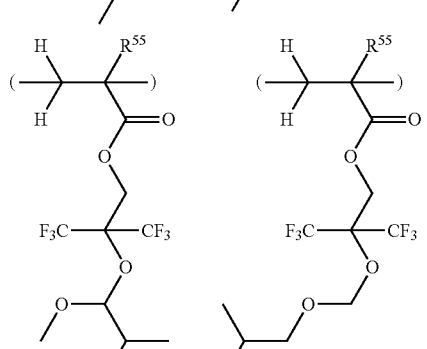
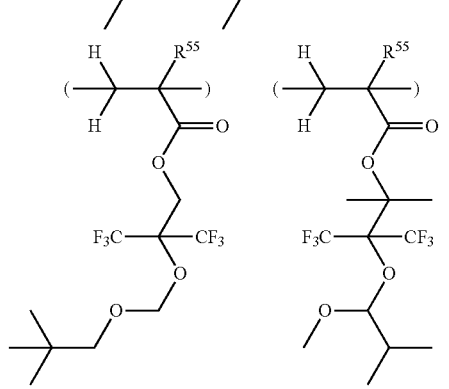

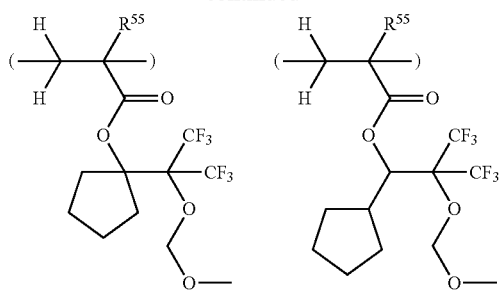
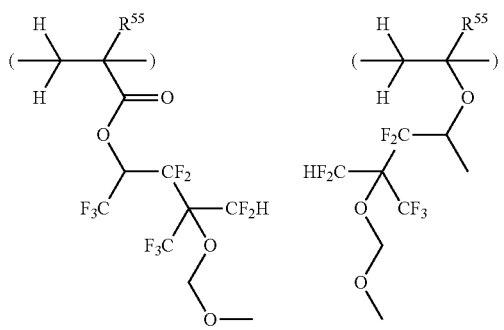
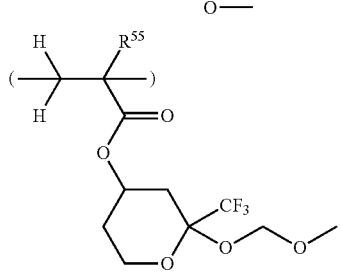
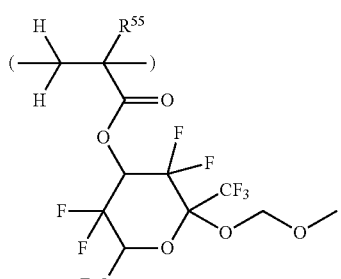
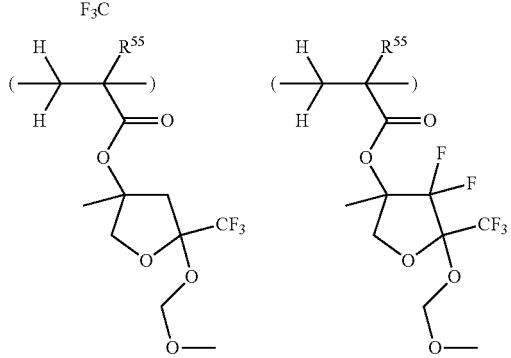
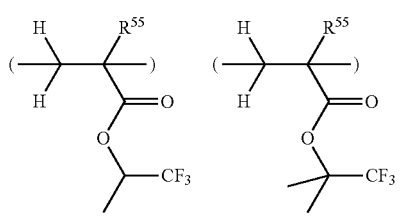
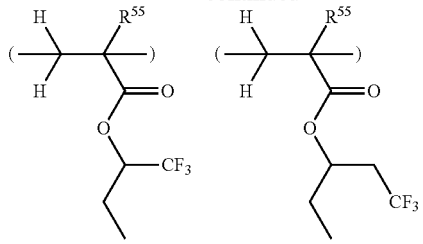
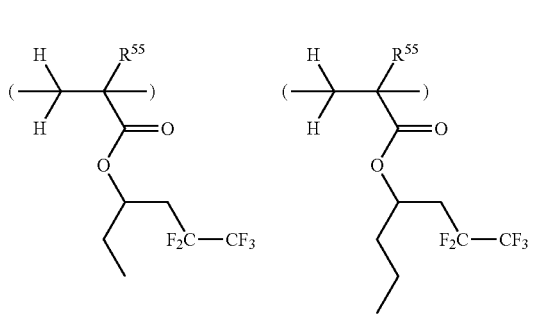
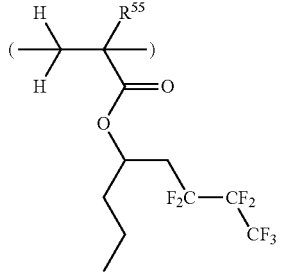
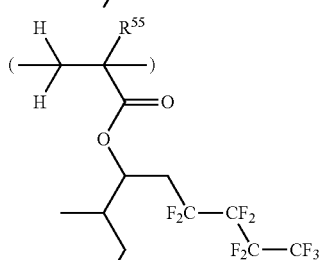
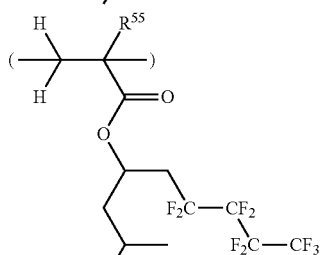
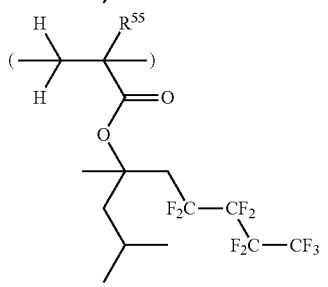

147
-continued
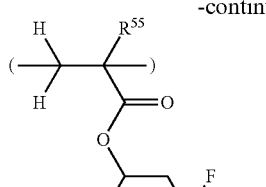
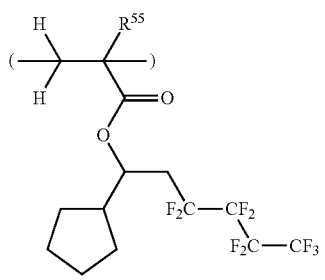
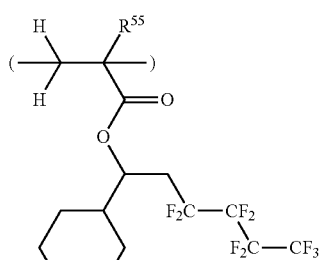
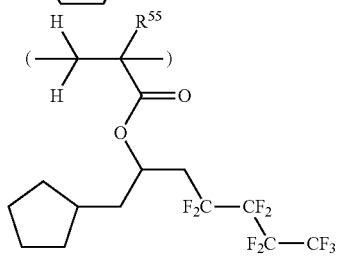
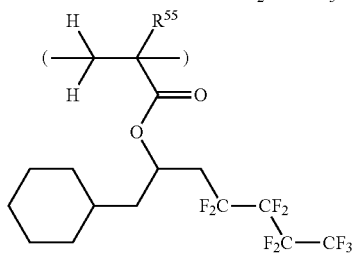
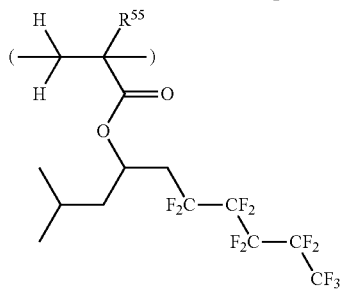
148
-continued
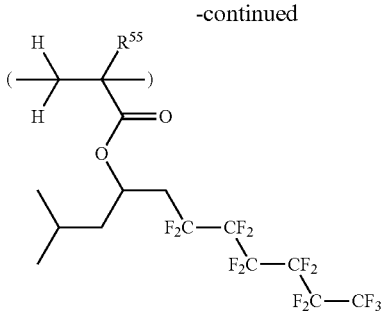
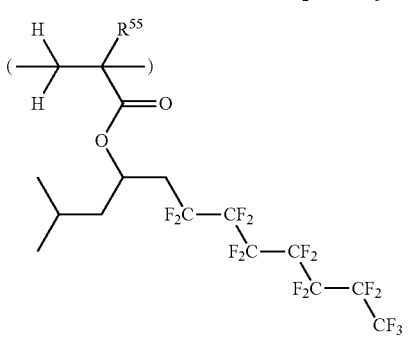
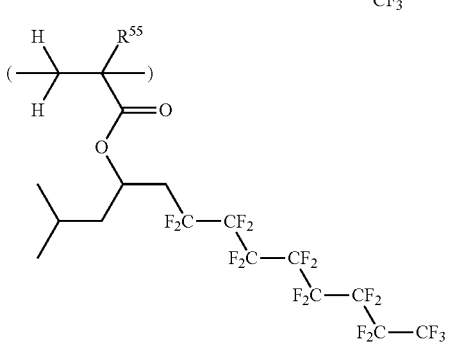
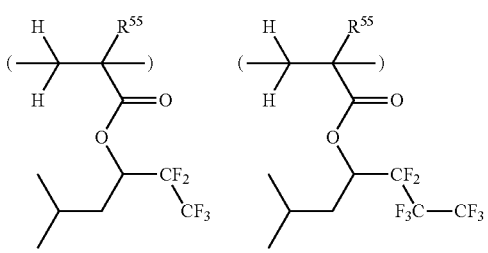
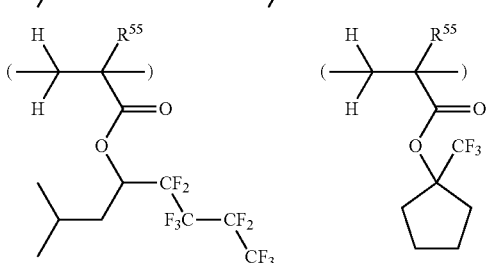
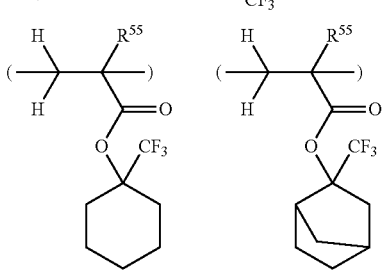

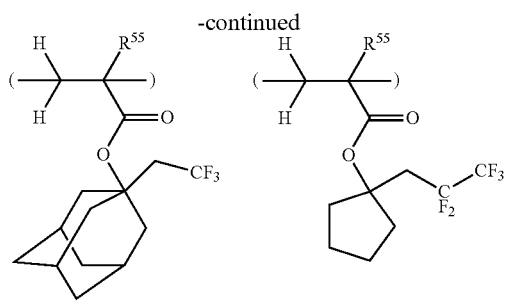
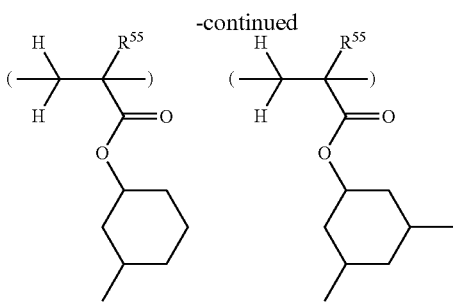
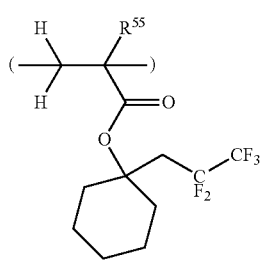
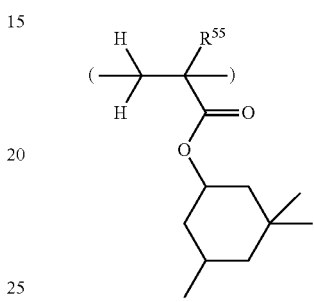
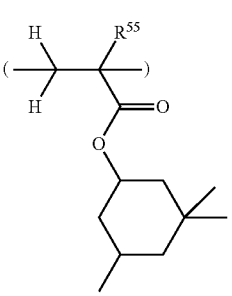
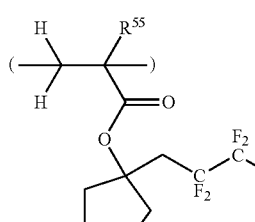
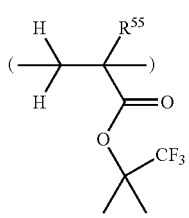
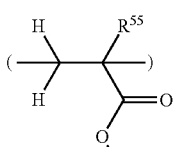
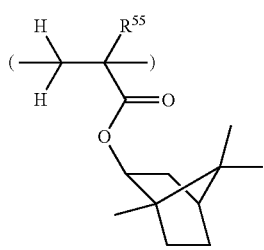
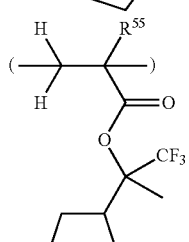
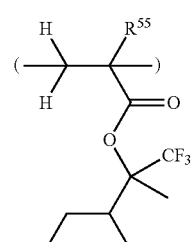
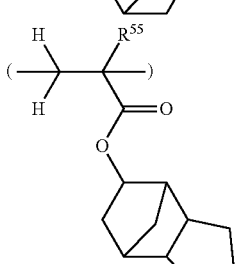
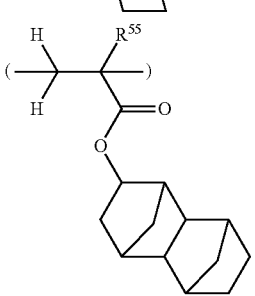
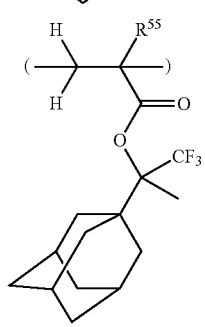
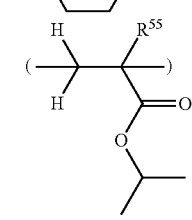
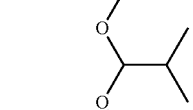
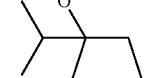
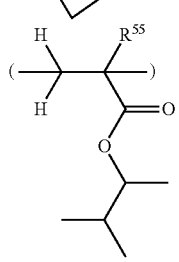
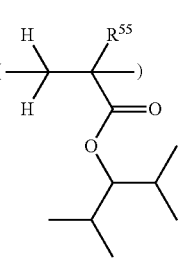
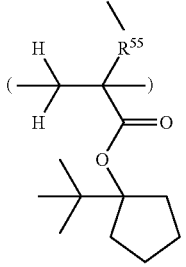
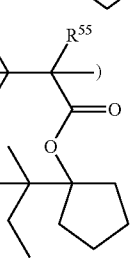

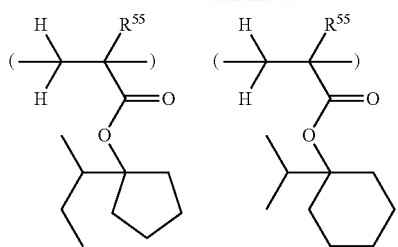

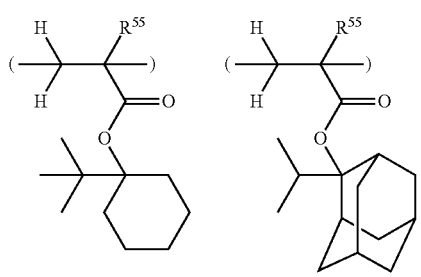

The water repellency improver to be added to the resist composition should be soluble in alkaline aqueous solution as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, any hole pattern opening failure after development, and bridging of a line-and-space pattern. An amount of the water repellency improver is 0 to 20 parts, preferably 0.1 to 20 parts, more preferably 0.5 to 10 parts by weight per 100 parts by weight of the base resin.

Though optional, a crosslinker may be added to the resist composition to facilitate formation of a negative pattern via a polarity switch of the inventive polymer. Suitable crosslinkers are described in JP-A 2006-145755. The crosslinker is preferably used in such an amount as not to interfere with high resolution performance due to a polarity switch and solubility change induced by dehydration reaction of the recurring unit derived from the inventive monomer. An amount of the crosslinker is 0 to 30 parts, preferably 1 to 30 parts, more preferably 3 to 20 parts by weight per 100 parts by weight of the base resin.

Process

The resist composition comprising the inventive polymer, typically chemically amplified resist composition comprising the inventive polymer, a basic compound and an acid generator in an organic solvent is used in the fabrication of various integrated circuits. Pattern formation using the resist composition may be performed by well-known lithography processes. The process generally involves coating, prebaking, exposure, PEB, and development. If necessary, any additional steps may be added.

The negative resist composition is first applied onto a substrate on which an integrated circuit is to be formed (e.g., Si, $SiO_2$, SiN, SiON, TiN, WSi, BPSG, SOG, or a multilayer film including silicon-containing antireflective coating or organic hydrocarbon film) or a substrate on which a mask circuit is to be formed (e.g., Cr, CrO, CrON, MoSi, or $SiO_2$) by a suitable coating technique such as spin coating, roll coating, flow coating, dipping, spraying or doctor coating. The coating is prebaked on a hot plate preferably at a temperature of 60 to 150° C. for 10 seconds to 30 minutes, more preferably at 80 to 120° C. for 30 seconds to 20 minutes. The resulting resist film is generally 0.01 to 2 μm thick.

The resist film is then exposed to a desired pattern of high-energy radiation such as UV, deep-UV, EB, x-ray, excimer laser light, γ-ray, synchrotron radiation, EUV or soft x-ray, directly or through a mask. The exposure dose is preferably about 1 to 200 $mJ/cm^2$, more preferably about 10 to 100 $mJ/cm^2$, or about 0.1 to 100 $μC/cm^2$, more preferably about 0.5 to 50 $μC/cm^2$. The resist film is further baked (PEB) on a hot plate preferably at 60 to 150° C. for 10 seconds to 30 minutes, more preferably at 80 to 120° C. for 30 seconds to 20 minutes.

Thereafter the resist film is developed in an alkaline developer for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed region is not dissolved in the developer whereas the resist film in the unexposed region is dissolved. In this way, the desired negative pattern is formed on the substrate. After the development step, the patterned resist film is rinsed with water, preferably for 3 seconds to 3 minutes, more preferably 5 seconds to 2 minutes, by conventional techniques such as dip, puddle and spray techniques. It is appreciated that the resist composition of the invention is best suited for micro-patterning using such high-energy radiation as KrF and ArF excimer laser, EB, EUV, soft x-ray, x-ray, γ-ray and synchrotron radiation.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLE

Examples of the invention are given below by way of illustration and not by way of limitation. The abbreviation "pbw" is parts by weight, THF stands for tetrahydrofuran, PGME for propylene glycol monomethyl ether, and NMP for N-methyl-2-pyrrolidone. For all polymers, Mw and Mn are determined versus polystyrene standards by GPC using THF solvent, and dispersity Mw/Mn is computed therefrom.

[1] Synthesis of Monomers

Example 1

Synthesis of Monomer 1

Monomer 1 was synthesized according to the following scheme.

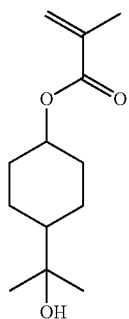

Methacrylate 1

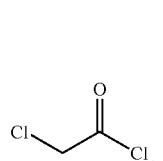

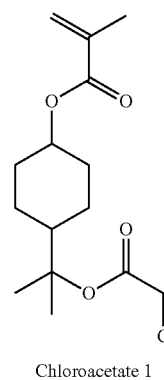

Chloroacetate 1

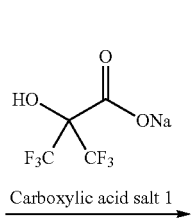

Monomer 1

Example 1-1

Synthesis of Chloroacetate 1

In nitrogen atmosphere, 113 g of Methacrylate 1 (cis:trans molar ratio=80:20), 107 g of chloroacetyl chloride and 500 g of diisopropyl ether were mixed and ice cooled at 5° C. To the solution, 71 g of pyridine was added dropwise below 15° C. At the end of dropwise addition, the solution was stirred at room temperature for 24 hours. The reaction solution was ice cooled again, to which 600 g of water was added dropwise below 15° C. to quench the reaction. This was followed by ordinary aqueous workup and solvent distillation, obtaining 153 g of Chloroacetate 1 as oily matter. The product was used in the subsequent reaction without further purification.

Example 1-2

Synthesis of Monomer 1

In nitrogen atmosphere, 153 g of Chloroacetate 1, 233 g of Carboxylic acid salt 1, 7.5 g of sodium iodide, and 600 g of NMP were mixed and stirred at 60° C. for 24 hours. The reaction solution was cooled to room temperature, to which 1,000 g of water was added to quench the reaction. This was followed by ordinary aqueous workup, solvent distillation, and purification by silica gel column chromatography, obtaining 190 g of Monomer 1 (cis:trans molar ratio=80:20) as oily matter (two-step yield 80%). The product was analyzed by $^1$H-NMR and IR spectroscopy. FIG. 1 shows the $^1$H-NMR spectrum of Monomer 1 and the IR spectrum is shown below.

IR (D-ATR): ν=3355, 2950, 2873, 1774, 1755, 1715, 1637, 1450, 1430, 1376, 1321, 1297, 1227, 1194, 1163, 1125, 1043, 976, 944, 869, 815, 748, 730, 671, 588, 569 cm$^{-1}$

Example 2

Synthesis of Monomer 2

Monomer 2 was synthesized according to the following scheme.

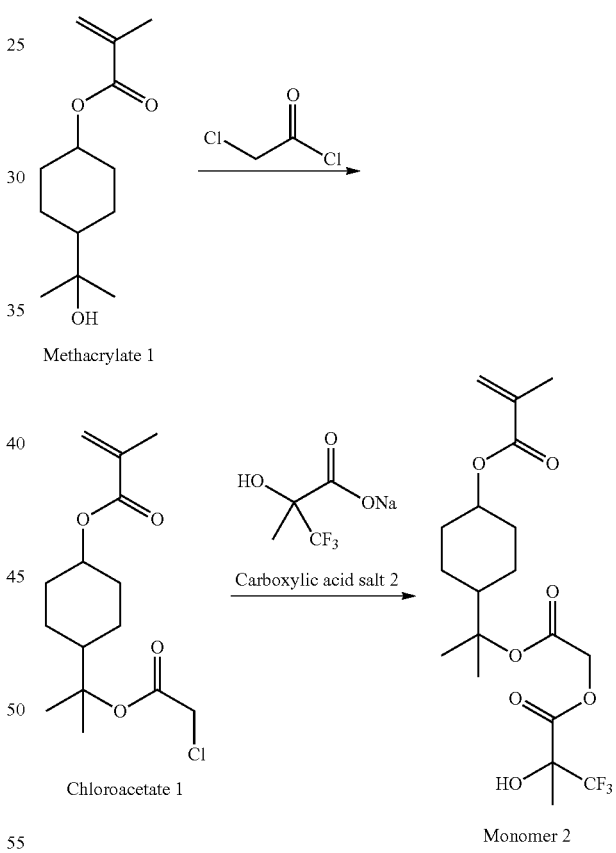

Figure 2:
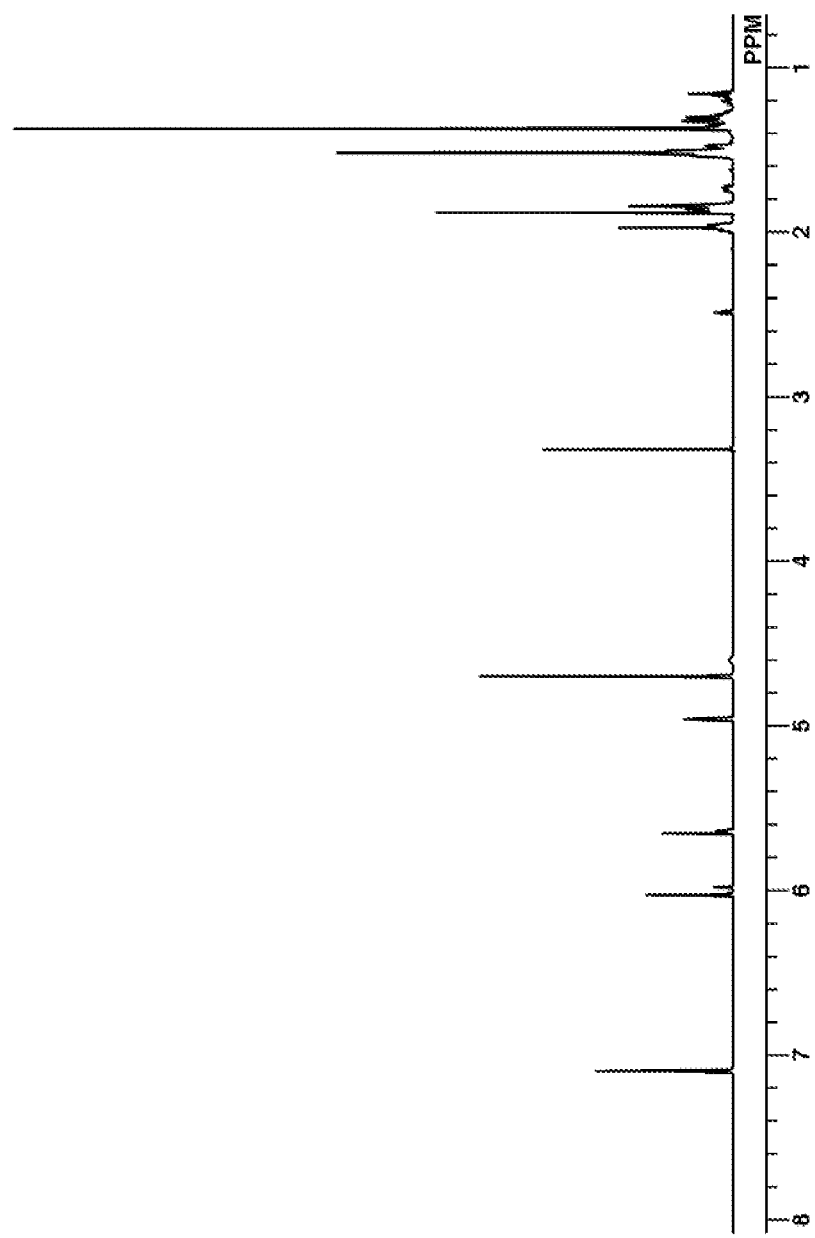
FIG. 2 is a diagram showing $^1$H-NMR spectrum of Monomer 2 in Example 2.

By following the same procedure as in Example 1 aside from using Carboxylic acid salt 2 instead of Carboxylic acid salt 1, 83 g of Monomer 2 (cis:trans molar ratio=78:22) was obtained as oily matter (two-step yield 73%). FIG. 2 shows the $^1$H-NMR spectrum of Monomer 2 and the IR spectrum is shown below.

IR (D-ATR): ν=3438, 2950, 2870, 1749, 1716, 1637, 1451, 1387, 1296, 1228, 1170, 1127, 1100, 1030, 942, 869, 815, 760, 733, 708, 646, 602, 586, 567 cm$^{-1}$

Example 3

Synthesis of Monomer 3

Monomer 3 was synthesized according to the following scheme.

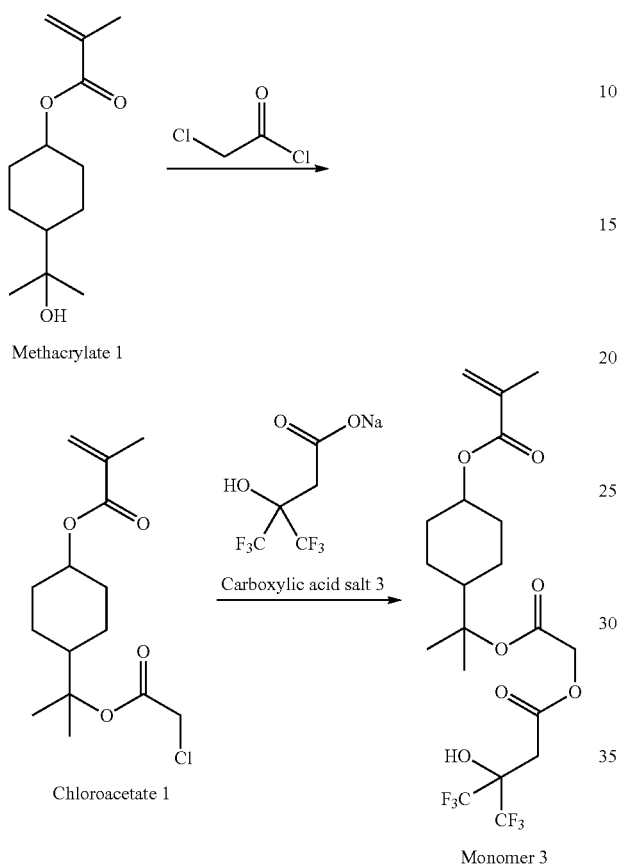

Figure 3:
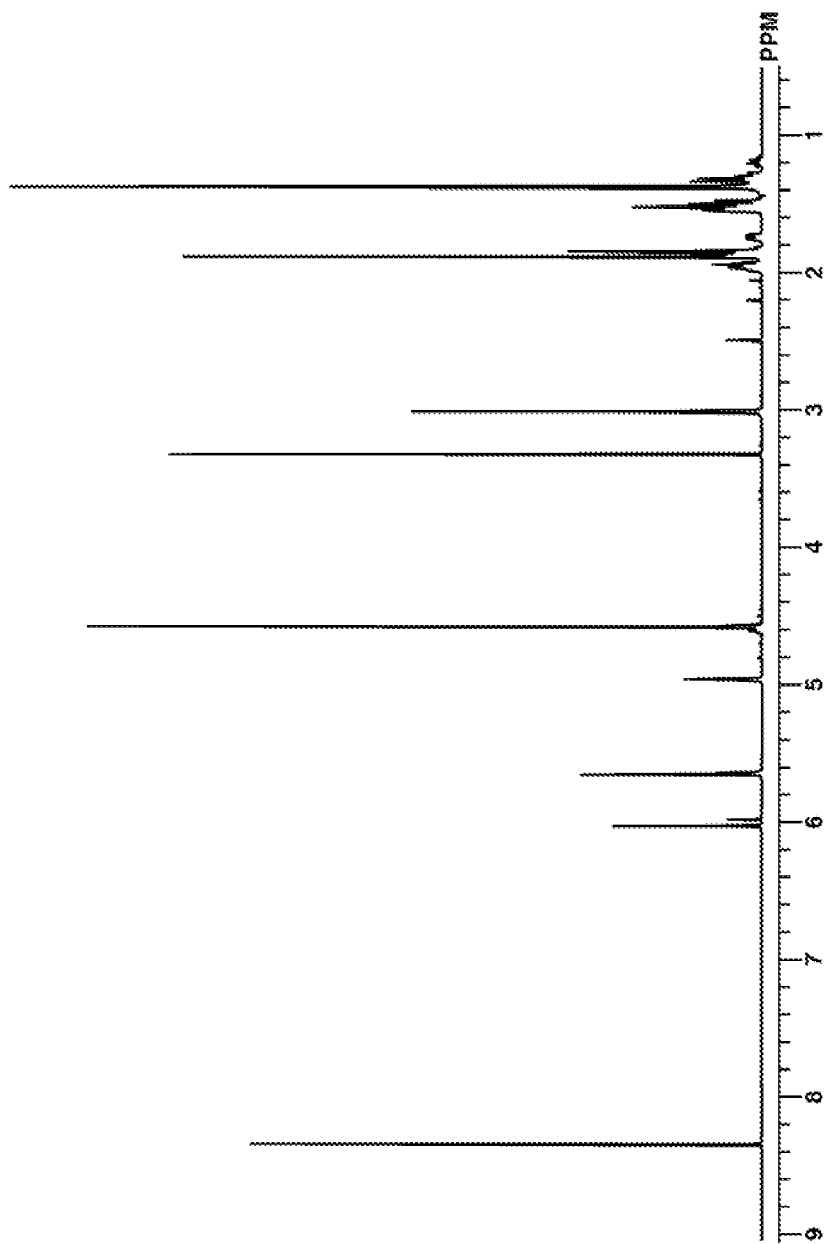
FIG. 3 is a diagram showing $^1$H-NMR spectrum of Monomer 3 in Example 3.

By following the same procedure as in Example 1 aside from using Carboxylic acid salt 3 instead of Carboxylic acid salt 1, 70 g of Monomer 3 (cis:trans molar ratio=79:21) was obtained as oily matter (two-step yield 75%). FIG. 3 shows the $^1$H-NMR spectrum of Monomer 3 and the IR spectrum is shown below.

IR (D-ATR): ν=3361, 2950, 1755, 1716, 1638, 1430, 1387, 1321, 1295, 1274, 1216, 1188, 1125, 1040, 986, 942, 868, 815, 737, 701, 688, 599, 576, 559 cm$^{-1}$

Example 4

Synthesis of Monomer 4

Monomer 4 was synthesized according to the following scheme.

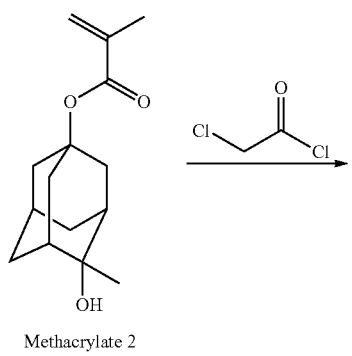

Methacrylate 2

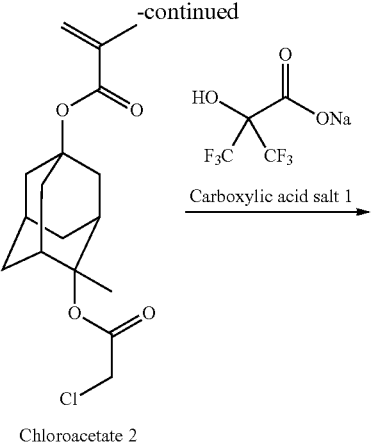

Chloroacetate 2

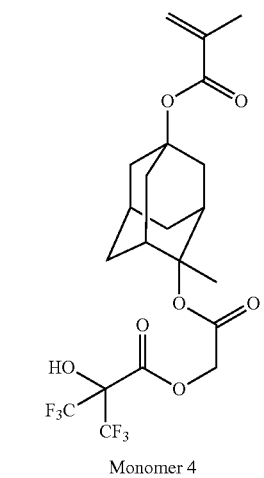

Monomer 4

Example 4-1

Synthesis of Chloroacetate 2

In nitrogen atmosphere, 97 g of Methacrylate 2 (main: minor isomer molar ratio=70:30), 83 g of chloroacetyl chloride and 500 g of diisopropyl ether were mixed and ice cooled at 5° C. To the solution, 55 g of pyridine was added dropwise below 15° C. At the end of dropwise addition, the solution was stirred at room temperature for 24 hours. The reaction solution was ice cooled again, to which 600 g of water was added dropwise below 15° C. to quench the reaction. This was followed by ordinary aqueous workup and solvent distillation, obtaining 126 g of Chloroacetate 2 as oily matter. The product was used in the subsequent reaction without further purification.

Example 4-2

Synthesis of Monomer 4

Figure 4:
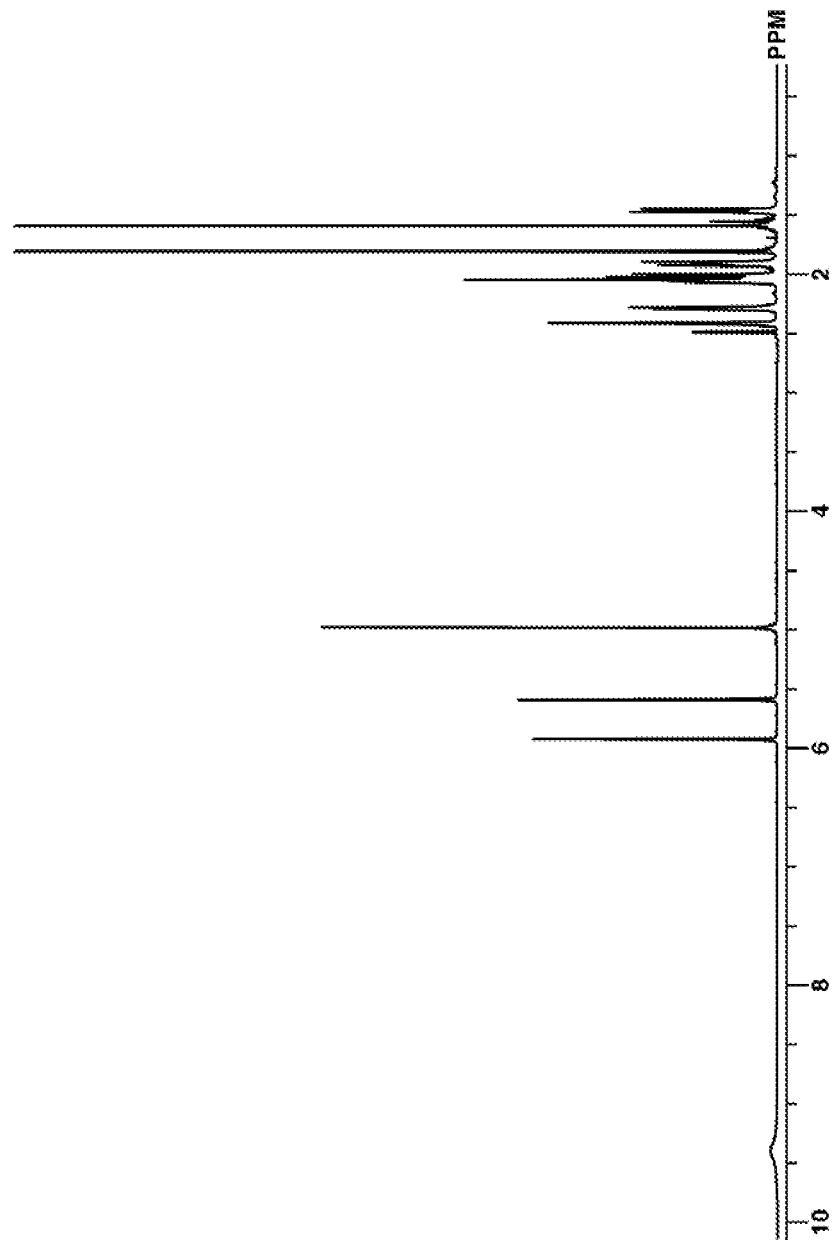
FIG. 4 is a diagram showing $^1$H-NMR spectrum of Monomer 4 in Example 4.

In nitrogen atmosphere, 126 g of Chloroacetate 2, 180 g of Carboxylic acid salt 1, 5.8 g of sodium iodide, and 500 g of NMP were mixed and stirred at 60° C. for 24 hours. The reaction solution was cooled to room temperature, to which 1,000 g of water was added to quench the reaction. This was followed by ordinary aqueous workup, solvent distillation, and recrystallization from ethyl acetate/hexane, obtaining 96 g of Monomer 4 (main:minor isomer molar ratio=96:4) as white crystal (two-step yield 50%). The product was analyzed by $^1$H-NMR and IR spectroscopy. FIG. 4 shows the $^1$H-NMR spectrum of Monomer 4 and the IR spectrum is shown below.

IR (D-ATR): ν=3310, 2958, 2928, 2906, 2871, 1778, 1753, 1699, 1633, 1452, 1427, 1381, 1344, 1330, 1314, 1298, 1257, 1221, 1188, 1162, 1101, 1063, 1043, 1029, 975, 957, 939, 915, 898, 885, 853, 816, 807, 748, 727, 705, 662, 639, 573 cm$^{-1}$

Example 5

Synthesis of Monomer 5

Monomer 5 was synthesized according to the following scheme.

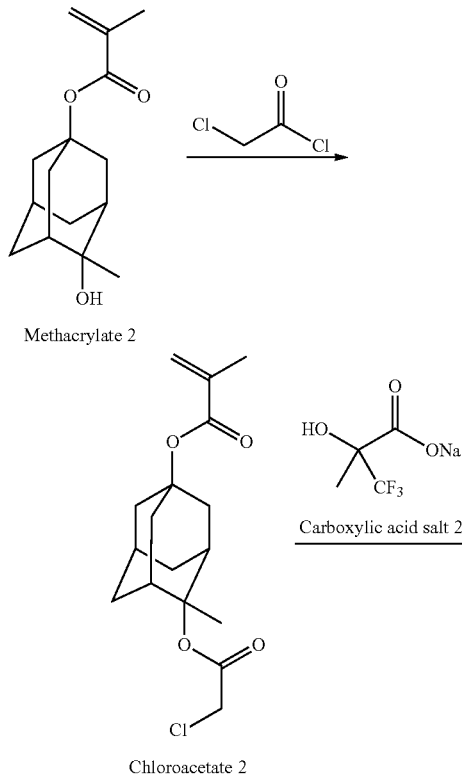

IR (D-ATR): ν=3437, 2921, 2874, 1761, 1745, 1705, 1694, 1631, 1453, 1427, 1383, 1340, 1314, 1295, 1280, 1225, 1183, 1163, 1117, 1098, 1030, 949, 916, 899, 850, 817, 801, 760, 730, 696, 652, 616, 598, 589, 580, 558 cm$^{-1}$

Example 6

Synthesis of Monomer 6

Monomer 6 was synthesized according to the following scheme.

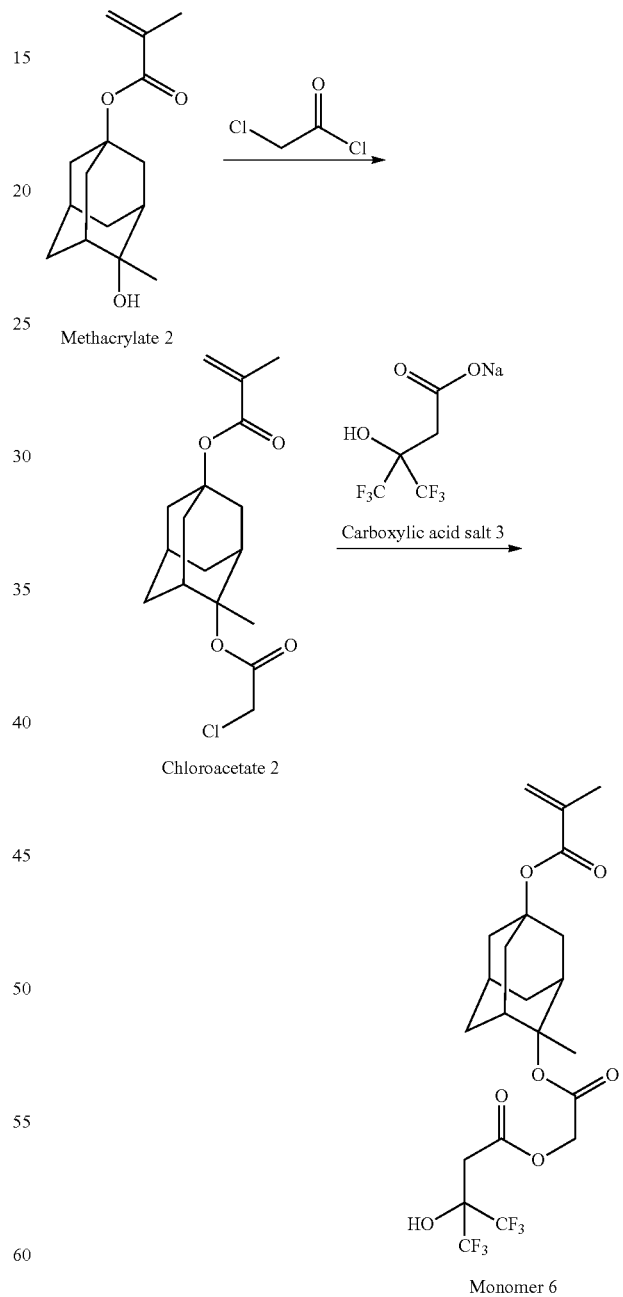

Figure 5:
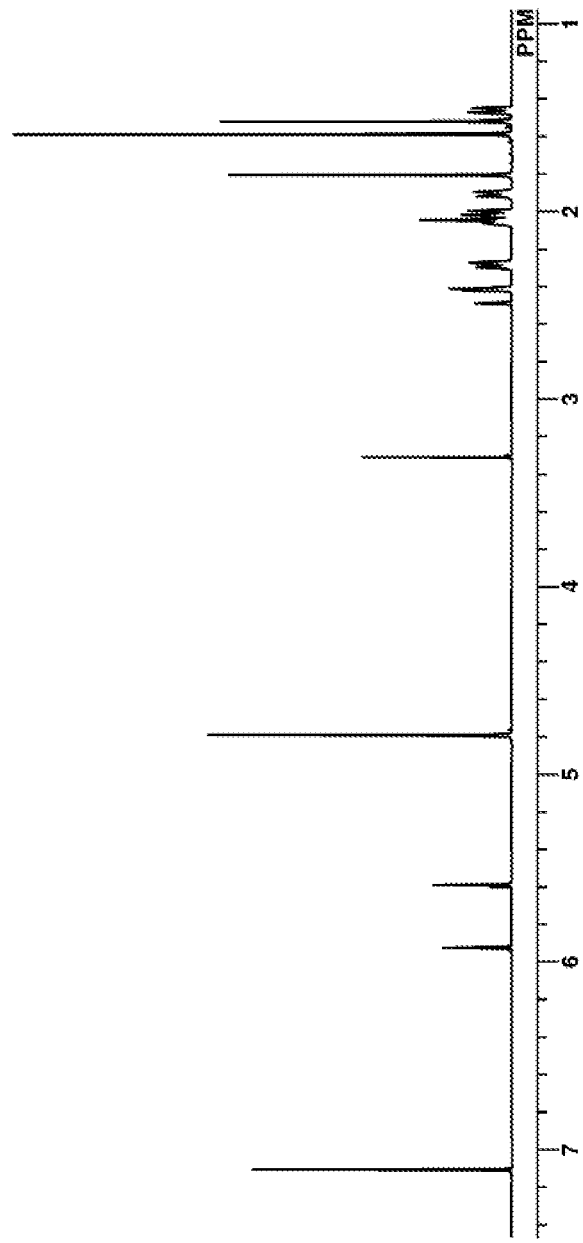
FIG. 5 is a diagram showing ¹H-NMR spectrum of Monomer 5 in Example 5.

By following the same procedure as in Example 4 aside from using Carboxylic acid salt 2 instead of Carboxylic acid salt 1, 53 g of Monomer 5 (main:minor isomer molar ratio=98:2) was obtained as white crystal (two-step yield 47%). FIG. 5 shows the $^1$H-NMR spectrum of Monomer 5 and the IR spectrum is shown below.

Figure 6:
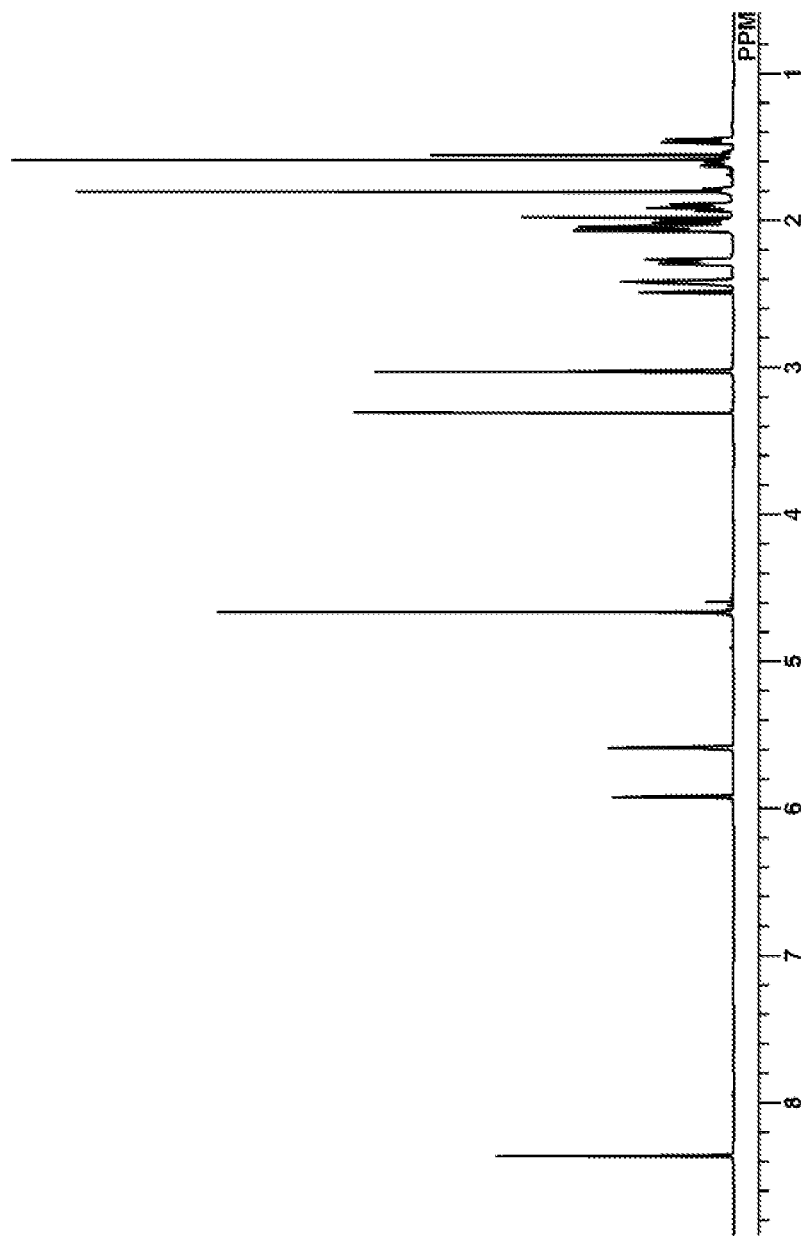
FIG. 6 is a diagram showing ¹H-NMR spectrum of Monomer 6 in Example 6.

By following the same procedure as in Example 4 aside from using Carboxylic acid salt 3 instead of Carboxylic acid salt 1, 46 g of Monomer 6 (main:minor isomer molar ratio=68:32) was obtained as oily matter (two-step yield 74%). FIG. 6 shows the $^1$H-NMR spectrum of Monomer 6 and the IR spectrum is shown below.

IR (D-ATR): ν=3375, 2929, 2871, 1713, 1637, 1451, 1429, 1384, 1332, 1295, 1274, 1238, 1217, 1183, 1101, 1045, 986, 941, 916, 900, 848, 815, 733, 701, 684, 663, 619, 609, 583, 568 cm$^{-1}$

Example 7

Synthesis of Monomer 7
Monomer 7 was synthesized according to the following scheme.

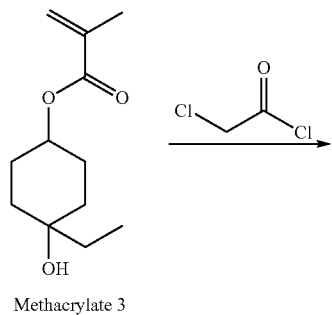

Methacrylate 3

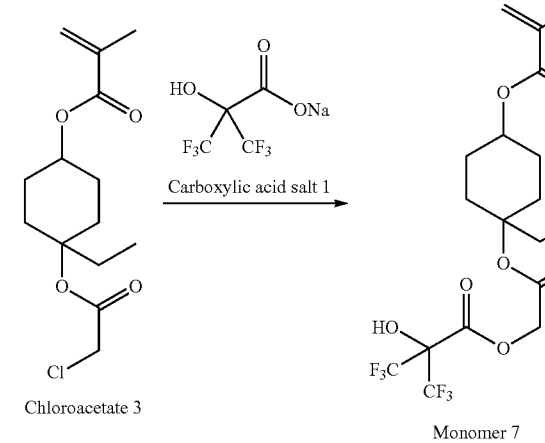

Example 7-1

Synthesis of Chloroacetate 3
In nitrogen atmosphere, 32 g of Methacrylate 3 (main:minor isomer molar ratio=94:6), 32 g of chloroacetyl chloride and 200 g of diisopropyl ether were mixed and ice cooled at 5° C. To the solution, 22 g of pyridine was added dropwise below 15° C. At the end of dropwise addition, the solution was stirred at room temperature for 24 hours. The reaction solution was ice cooled again, to which 200 g of water was added dropwise below 15° C. to quench the reaction. This was followed by ordinary aqueous workup and solvent distillation, obtaining 46 g of Chloroacetate 3 as oily matter. The product was used in the subsequent reaction without further purification.

Example 7-2

Figure 7:
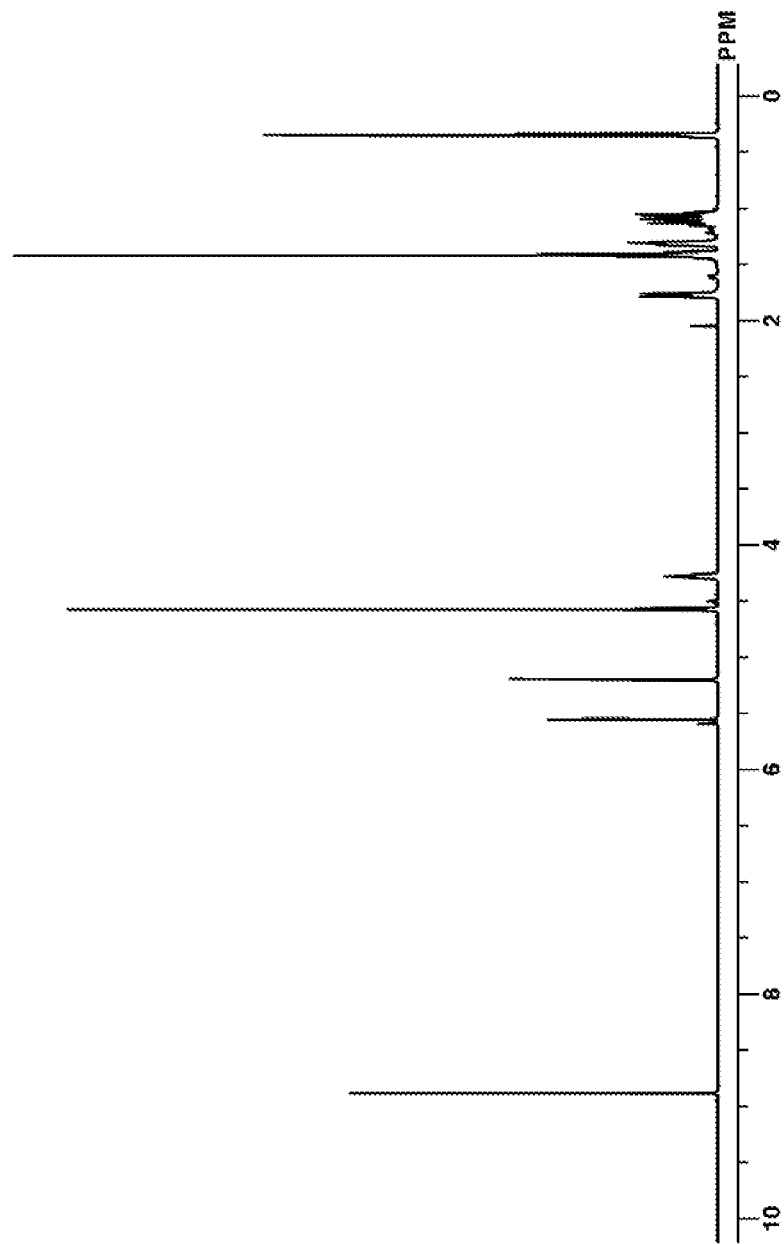
FIG. 7 is a diagram showing ¹H-NMR spectrum of Monomer 7 in Example 7.

Synthesis of Monomer 7
In nitrogen atmosphere, 46 g of Chloroacetate 3, 70 g of Carboxylic acid salt 1, 2.3 g of sodium iodide, and 200 g of NMP were mixed and stirred at 60° C. for 24 hours. The reaction solution was cooled to room temperature, to which 300 g of water was added to quench the reaction. This was followed by ordinary aqueous workup, solvent distillation, and purification by silica gel column chromatography, obtaining 58 g of Monomer 7 (main:minor isomer molar ratio=92:8) as oily matter (two-step yield 83%). The product was analyzed by $^1$H-NMR and IR spectroscopy. FIG. 7 shows the $^1$H-NMR spectrum of Monomer 7 and the IR spectrum is shown below.

IR (D-ATR): ν=3344, 2959, 2887, 1773, 1756, 1714, 1637, 1453, 1430, 1381, 1321, 1295, 1222, 1164, 1125, 1044, 1021, 976, 953, 927, 897, 814, 748, 730, 667, 604, 585, 555 cm$^{-1}$

Example 8

Synthesis of Monomer 8
Monomer 8 was synthesized according to the following scheme.

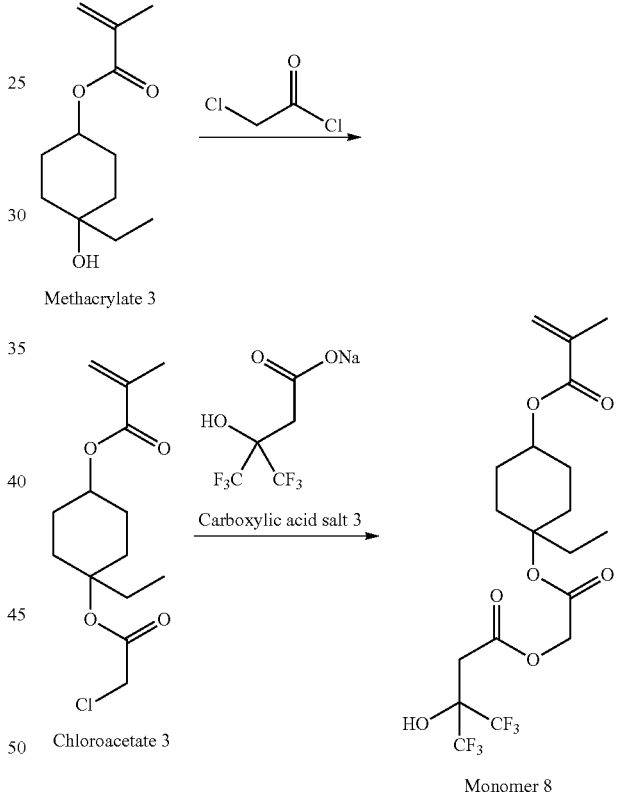

Figure 8:
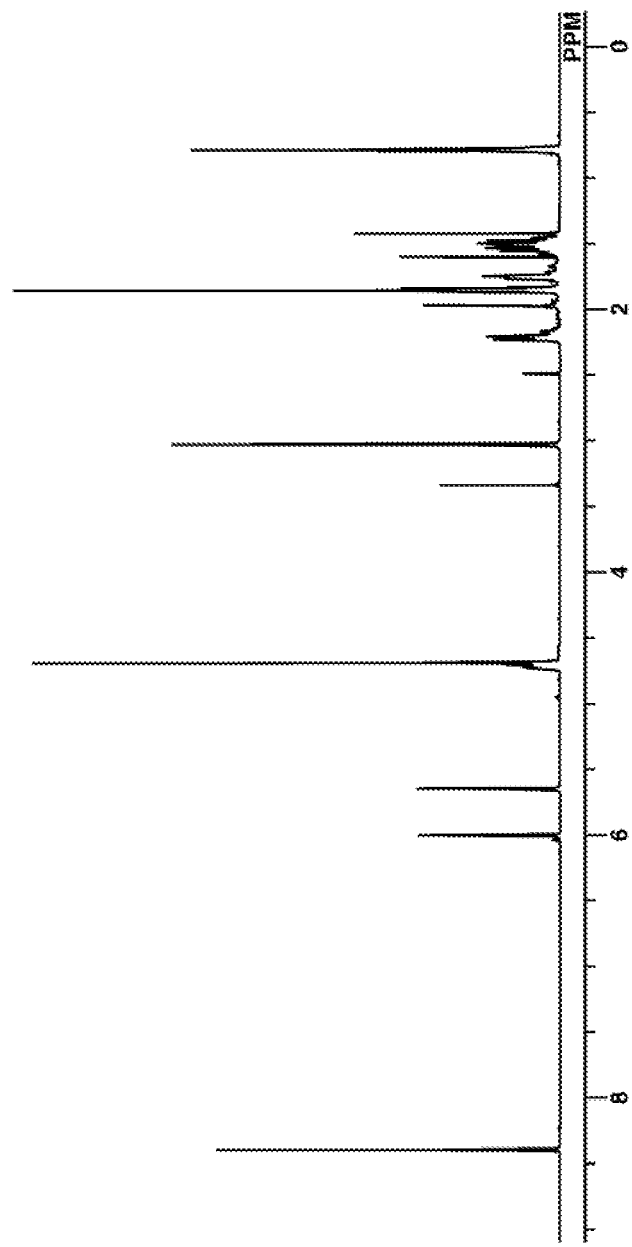
FIG. 8 is a diagram showing ¹H-NMR spectrum of Monomer 8 in Example 8.

By following the same procedure as in Example 7 aside from using Carboxylic acid salt 3 instead of Carboxylic acid salt 1, 47 g of Monomer 8 (main:minor isomer molar ratio=92:8) was obtained as oily matter (two-step yield 76%). FIG. 8 shows the $^1$H-NMR spectrum of Monomer 8.

[2] Synthesis of Polymers

Examples 9 to 31 & Comparative Examples 1 to 10

Each of polymers (Polymers 1 to 23 and Comparative Polymers 1 to 10) for use in resist compositions was prepared by combining monomers in PGME solvent, effecting copolymerization reaction, crystallizing from a water-methanol mixture, washing with water-methanol several times, isolation and drying. The polymer was analyzed for composition by ¹H-NMR and ¹³C-NMR spectroscopy.
Example 9: Polymer 1
Mw=8,800
Mw/Mn=1.67
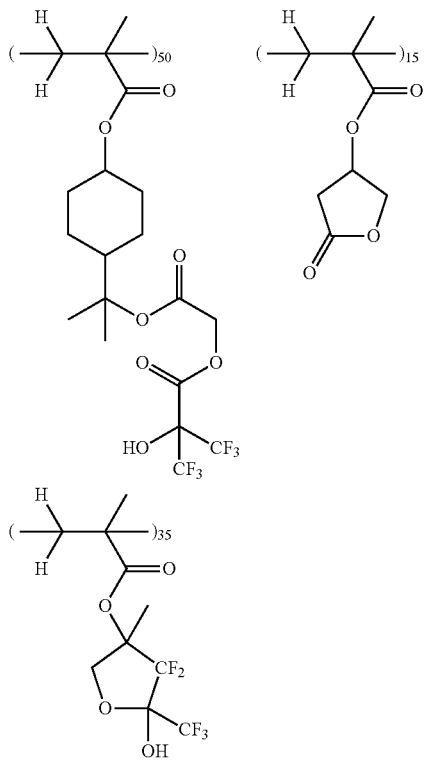
Example 10: Polymer 2
Mw=8,600
Mw/Mn=1.64
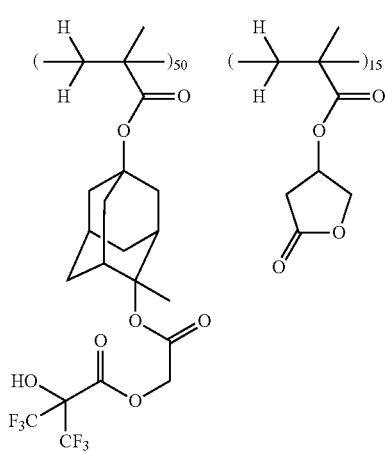
-continued
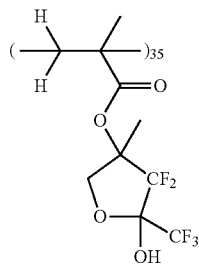
Example 11: Polymer 3
Mw=8,700
Mw/Mn=1.62
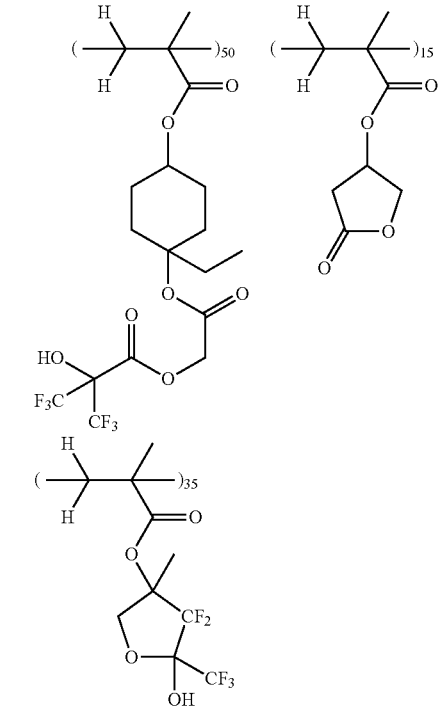
Example 12: Polymer 4
Mw=8,900
Mw/Mn=1.66
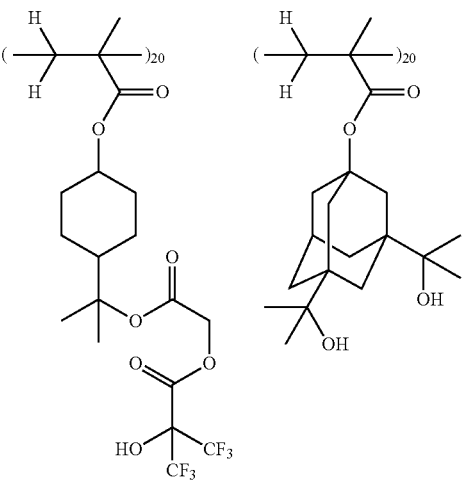

-continued
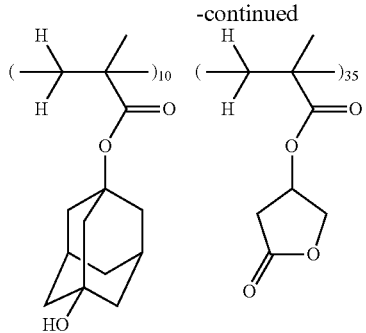
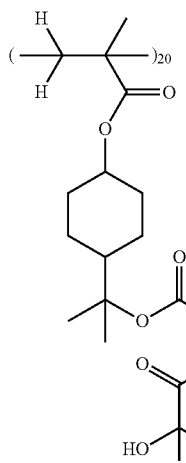
Example 13: Polymer 5
Mw=9,000
Mw/Mn=1.65
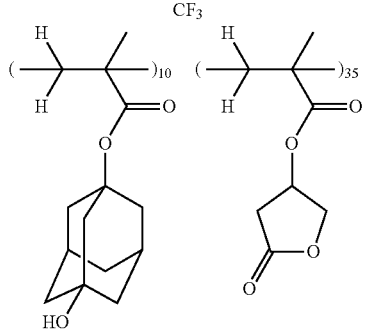
-continued
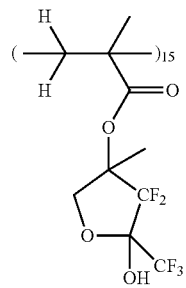
Example 14: Polymer 6
Mw=9,100
Mw/Mn=1.70
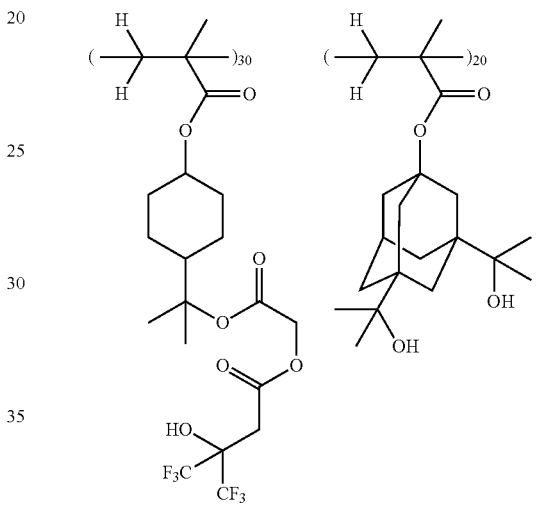
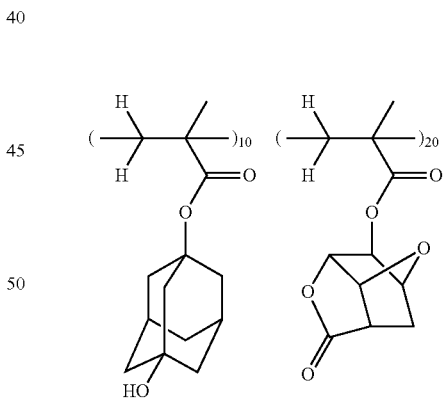
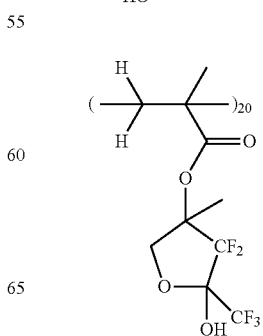

Example 15: Polymer 7
Mw=8,800
Mw/Mn=1.66
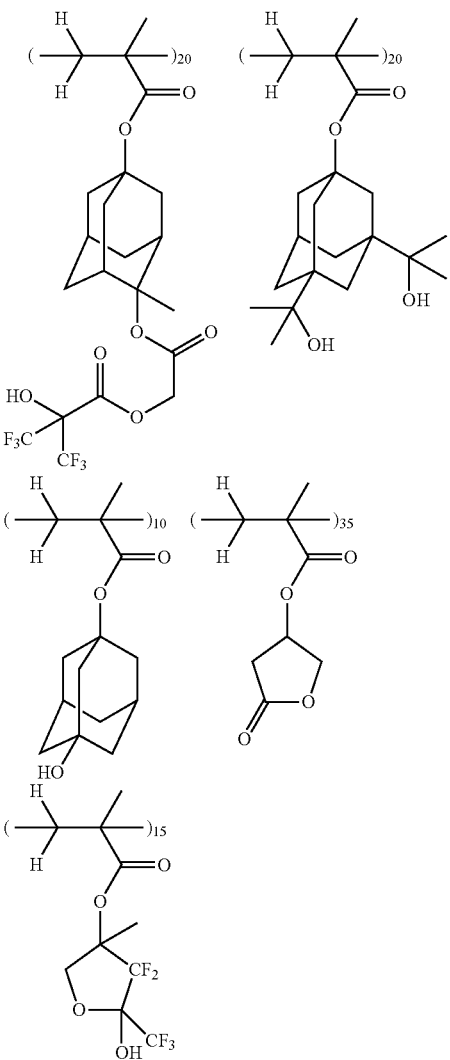
Example 16: Polymer 8
Mw=8,900
Mw/Mn=1.65
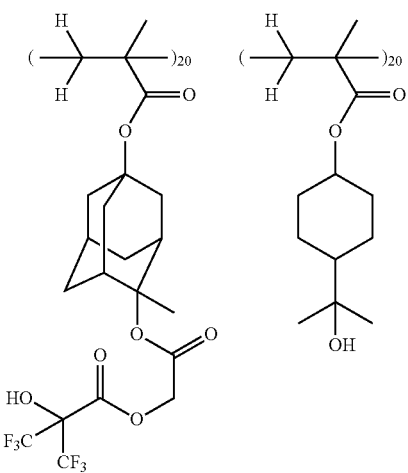
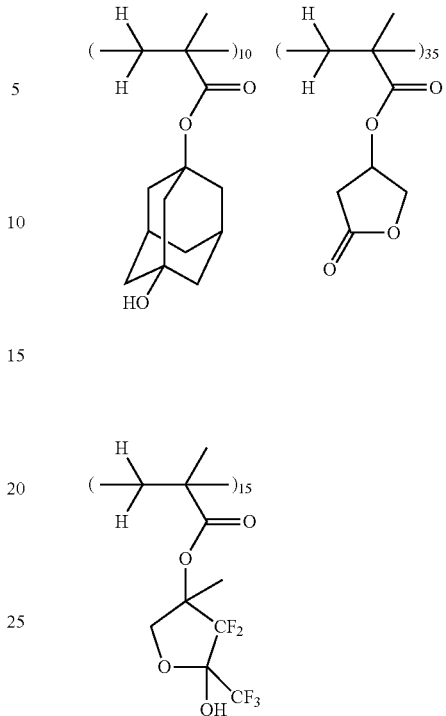
Example 17: Polymer 9
Mw=8,700
Mw/Mn=1.63
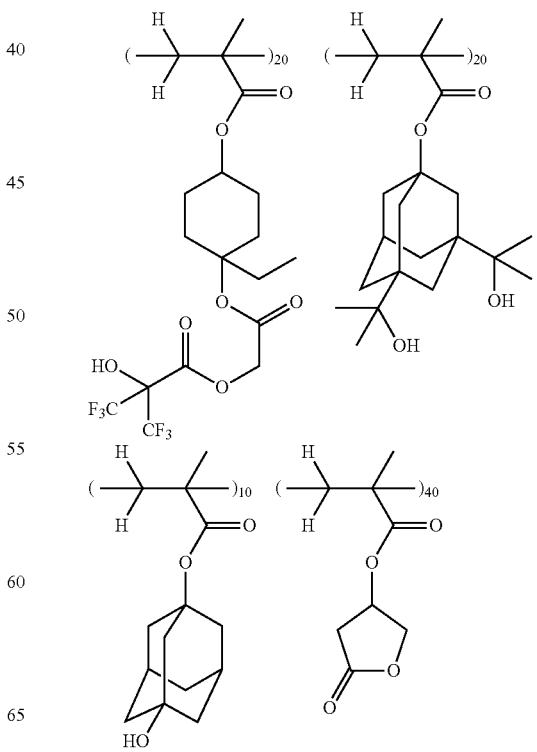

-continued
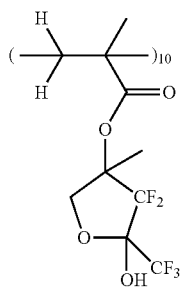
Example 18: Polymer 10
Mw=8,700
Mw/Mn=1.67
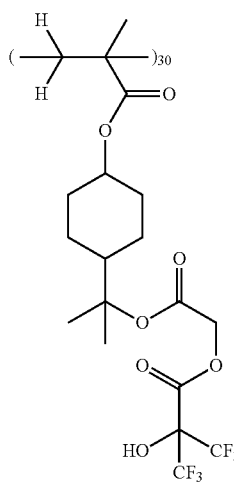
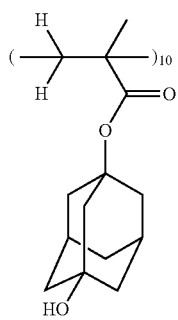
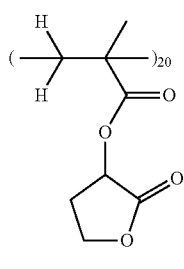
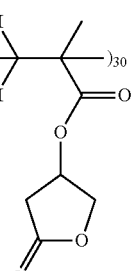
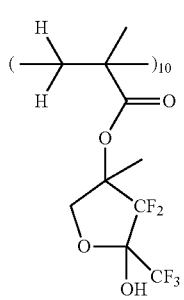
Example 19: Polymer 11
Mw=9,200
Mw/Mn=1.65
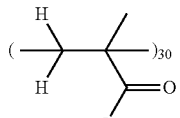
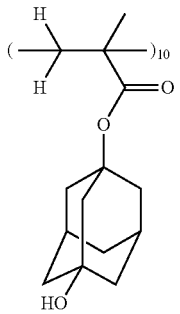
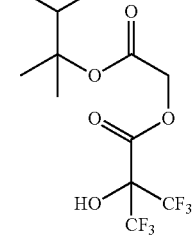
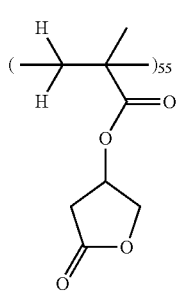
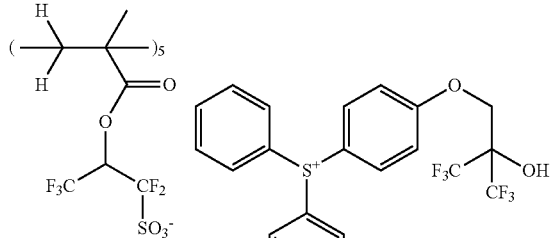
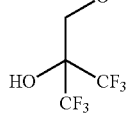

Example 20: Polymer 12
Mw=8,800
Mw/Mn=1.68
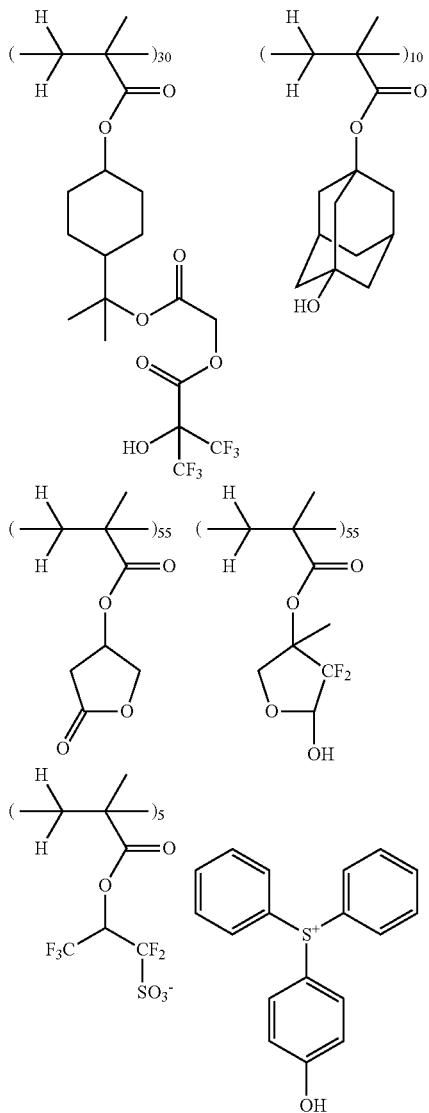
Example 21: Polymer 13
Mw=9,000
Mw/Mn=1.70
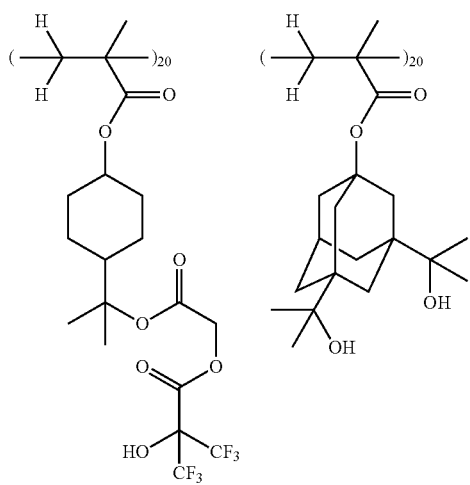
-continued
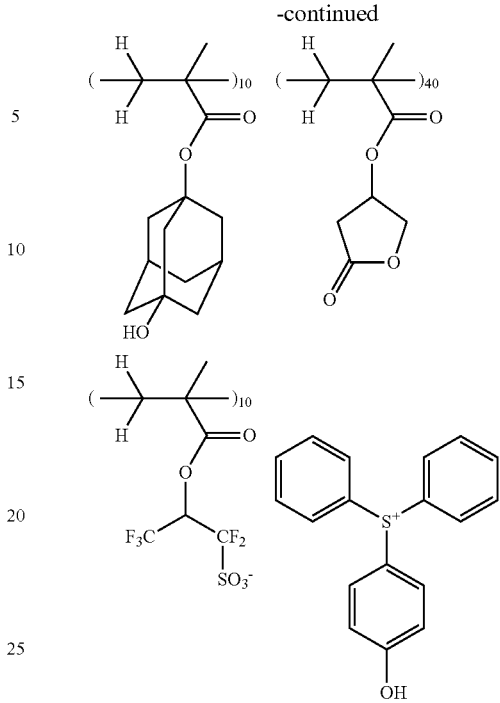
Example 22: Polymer 14
Mw=9,300
Mw/Mn=1.68
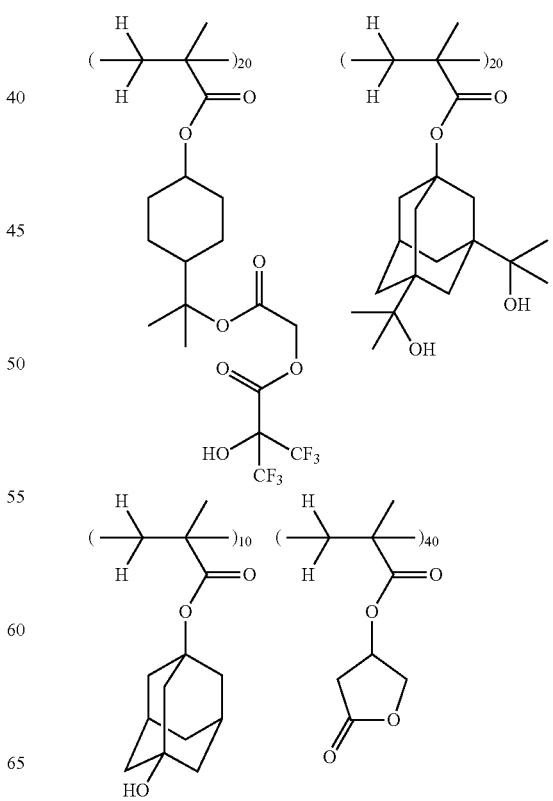

-continued
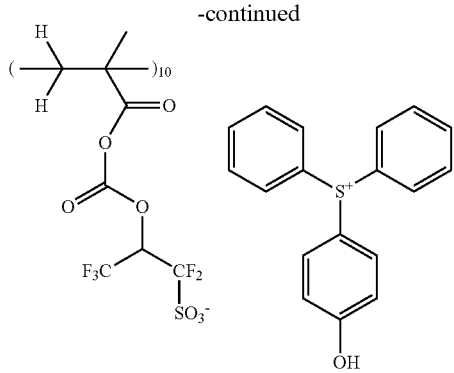
Example 23: Polymer 15
Mw=9,300
Mw/Mn=1.68
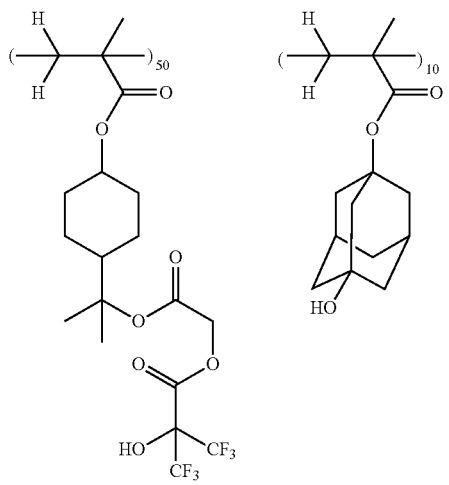
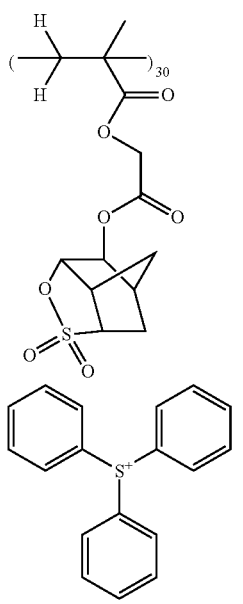
Example 24: Polymer 16
Mw=9,300
Mw/Mn=1.68
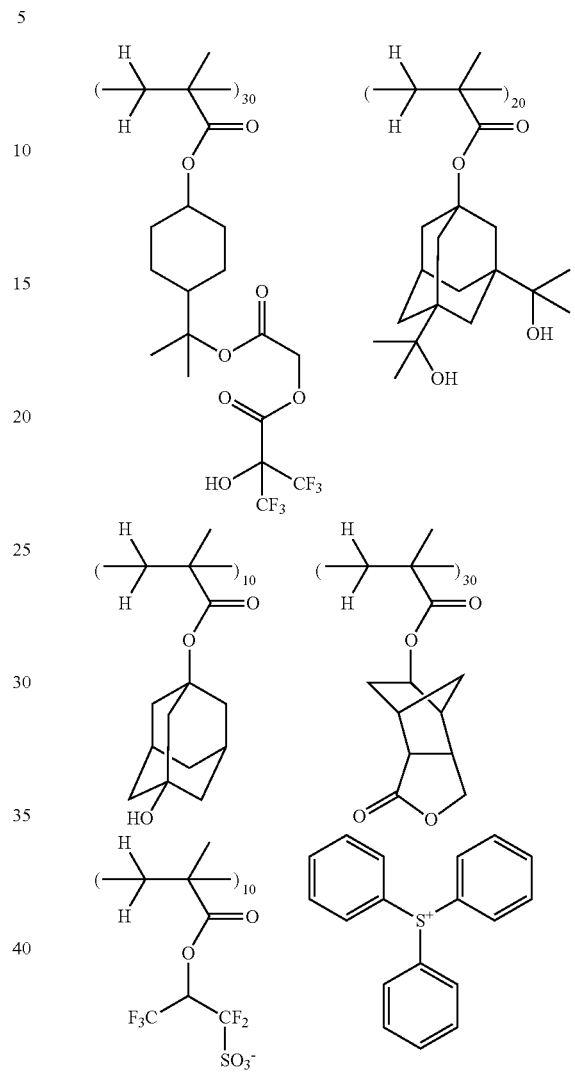
Example 25: Polymer 17
Mw=9,100
Mw/Mn=1.68
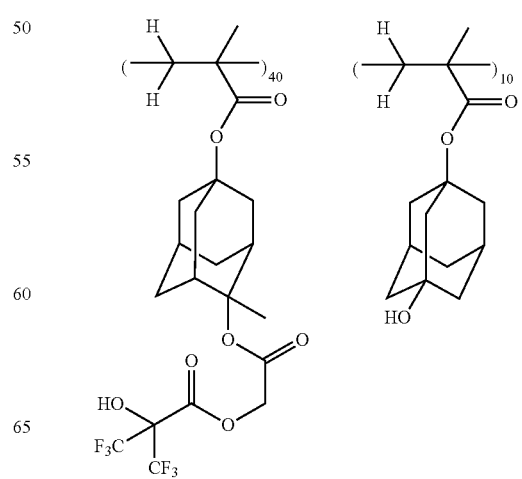

-continued
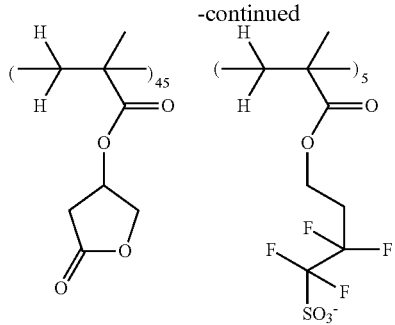
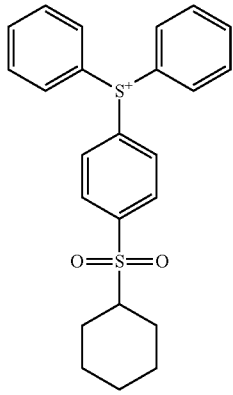
Example 26: Polymer 18
Mw=9,000
Mw/Mn=1.64
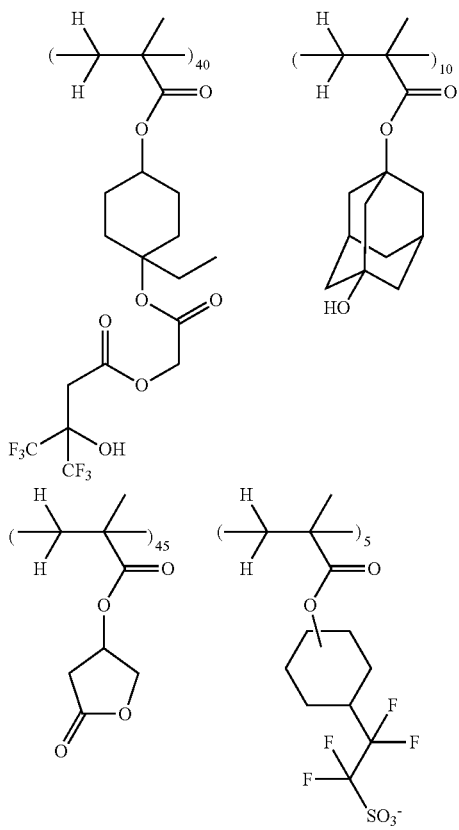
-continued
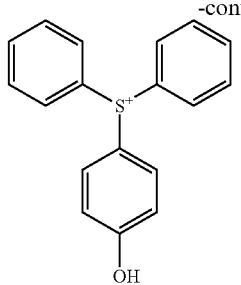
Example 27: Polymer 19
Mw=9,000
Mw/Mn=1.64
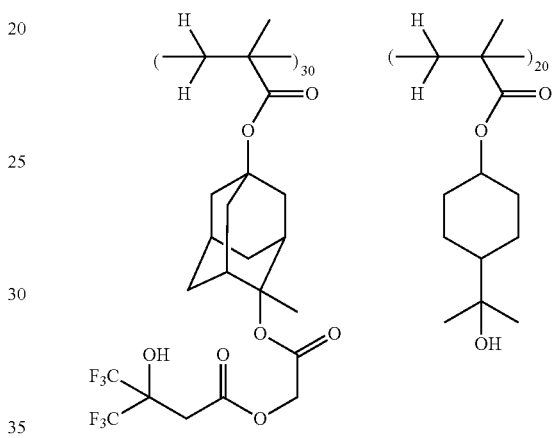
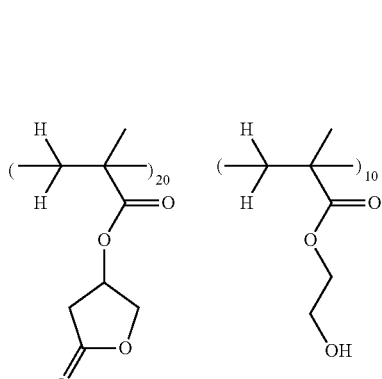
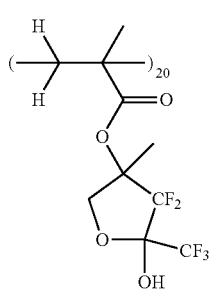

Example 28: Polymer 20
Mw=8,700
Mw/Mn=1.63
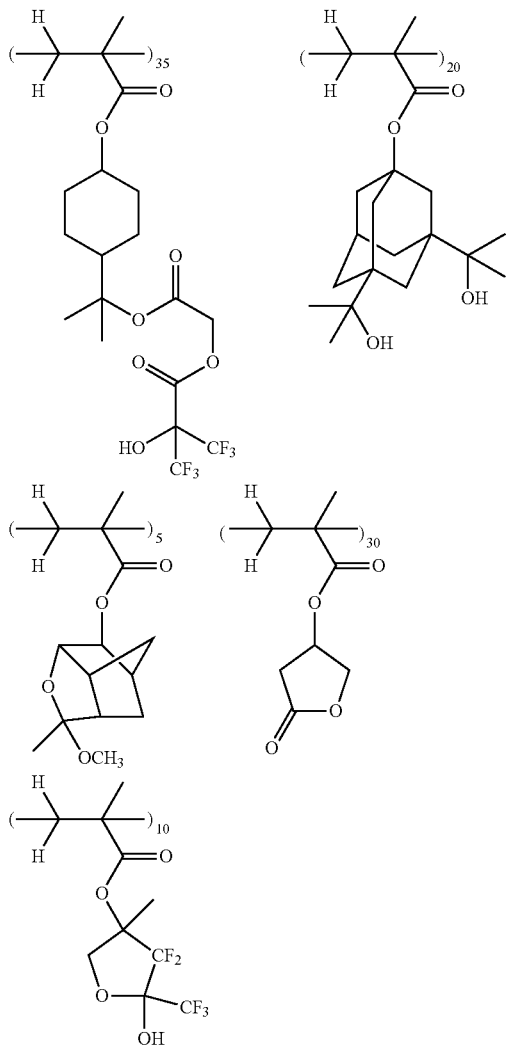
Example 29: Polymer 21
Mw=8,700
Mw/Mn=1.63
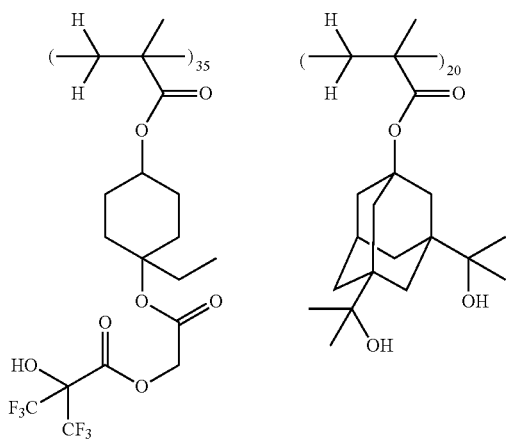
-continued
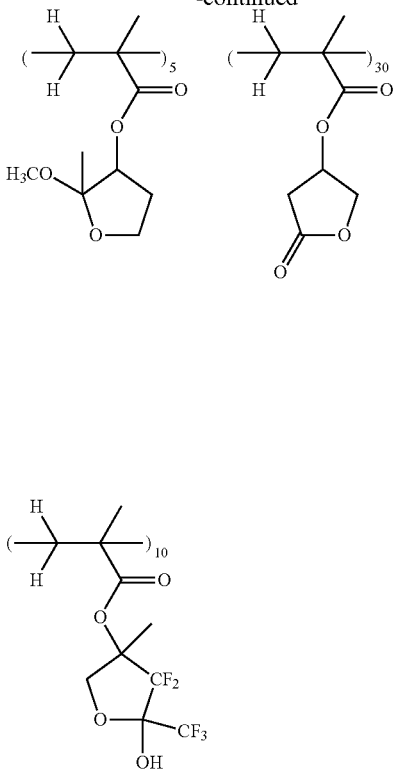
Example 30: Polymer 22
Mw=9,000
Mw/Mn=1.69
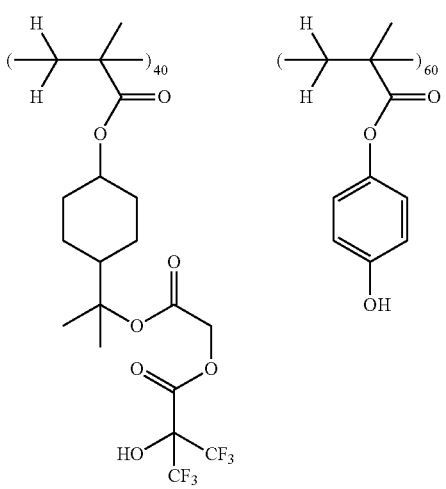 [SMILES: CCC(C)(C)C(=O)OC1CCC(C(C)(C)OC(=O)COC(=O)C(O)(C(F)(F)F)C(F)(F)F)CC1 ; CCC(C)(C)C(=O)Oc1ccc(O)cc1]

Example 31: Polymer 23
Mw=9,000
Mw/Mn=1.68
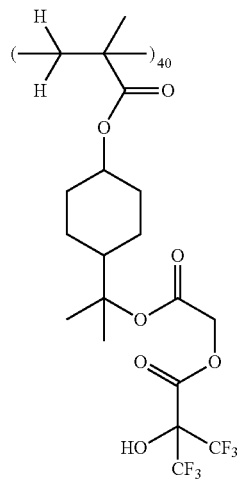
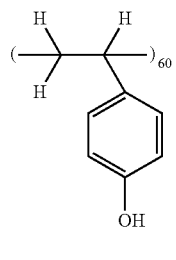
Comparative Example 2: Comparative Polymer 2
Mw=8,500
Mw/Mn=1.63
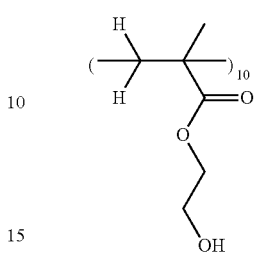
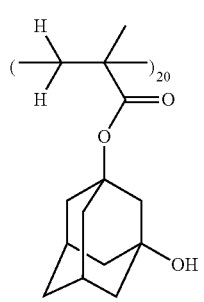
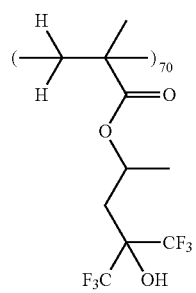
Comparative Example 1: Comparative Polymer 1
Mw=8,400
Mw/Mn=1.65
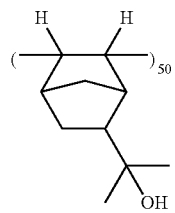
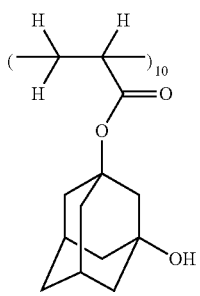
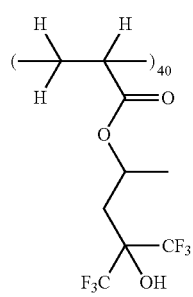
Comparative Example 3: Comparative Polymer 3
Mw=8,700
Mw/Mn=1.65
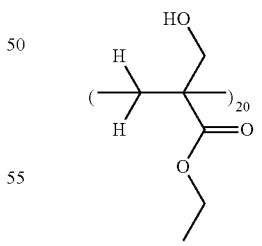
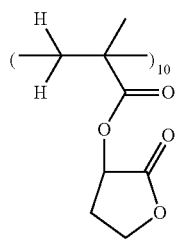
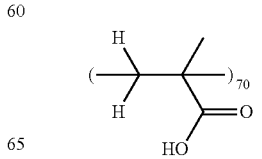

Comparative Example 4: Comparative Polymer 4
Mw=8,600
Mw/Mn=1.62
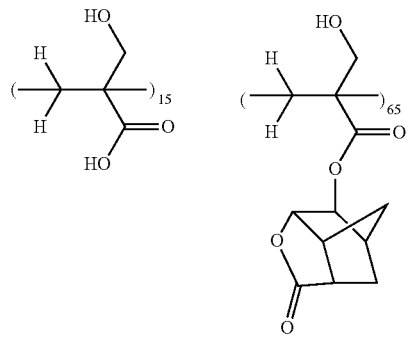
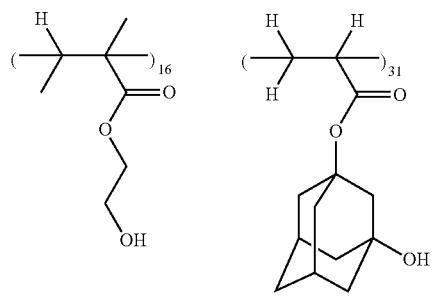
Comparative Example 5: Comparative Polymer 5
Mw=8,400
Mw/Mn=1.66
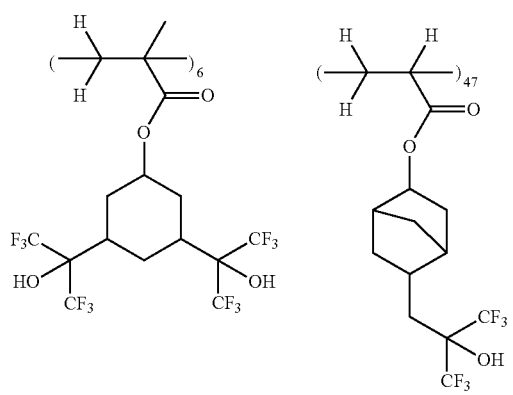
Comparative Example 6: Comparative Polymer 6
Mw=8,600
Mw/Mn=1.63
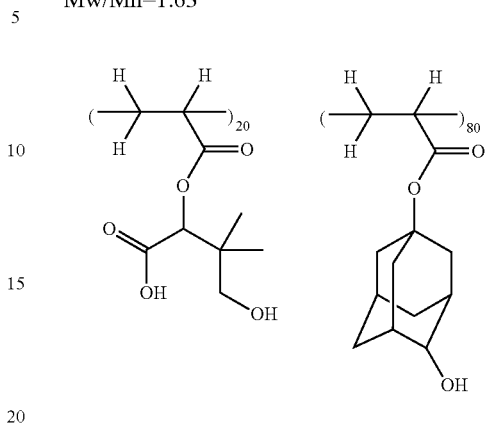
Comparative Example 7: Comparative Polymer 7
Mw=8,500
Mw/Mn=1.61
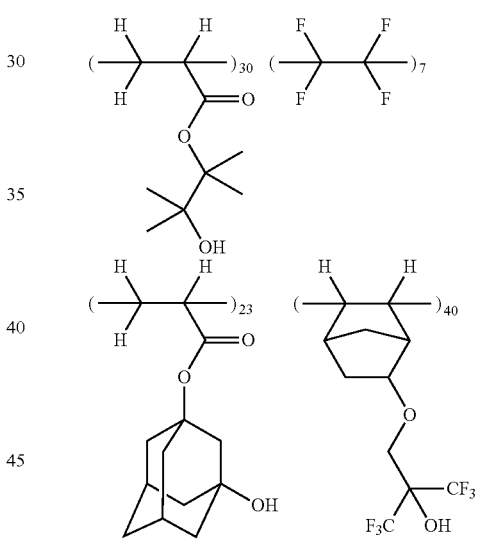
Comparative Example 8: Comparative Polymer 8
Mw=8,400
Mw/Mn=1.65
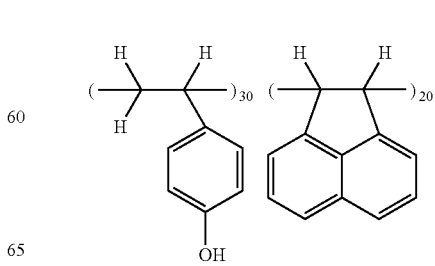

Comparative Example 9: Comparative Polymer 9

Mw=8,400
Mw/Mn=1.65

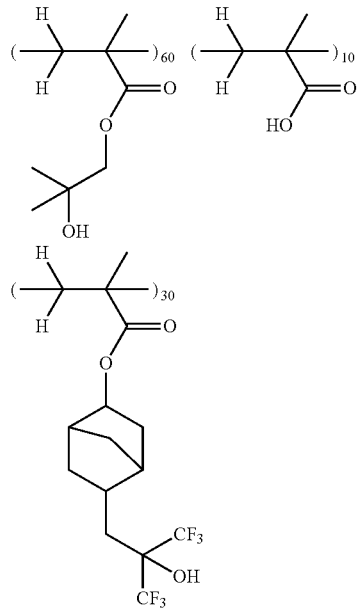

Comparative Example 10: Comparative Polymer 10

Mw=9,000
Mw/Mn=1.67

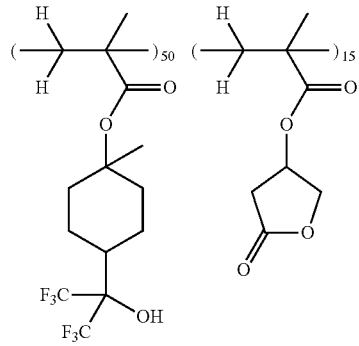

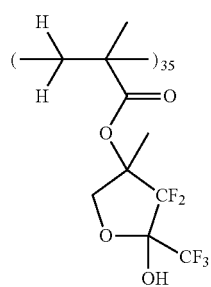

[3] Preparation of Resist Compositions

Examples 32 to 54 & Comparative Examples 11 to 20

Resist compositions R-01 to R-33 were prepared by using inventive Polymers 1 to 23 or Comparative Polymers 1 to 10 as the base resin, dissolving the polymer and other components in a solvent in accordance with the recipe shown in Tables 1 to 3, and filtering through a Teflon® filter having a pore size of 0.2 μm.

In Tables 1 to 3, acid generator (PAG-1 to 4), water-repellent polymer (SF-1), sensitivity regulator (Q-1 to 4), crosslinker (XL-1), and solvent are as identified below.

Photoacid Generator: PAG-1 to PAG-4

PAG-1

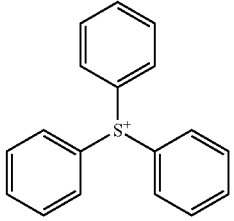

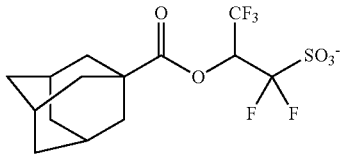

PAG-2

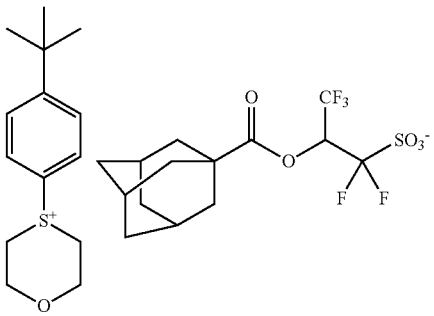

PAG-3

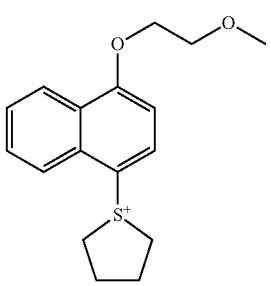

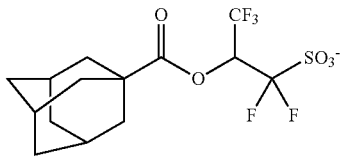

PAG-4
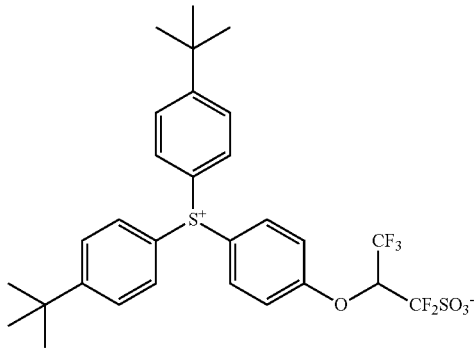
Sensitivity Regulator: Q-1 to Q-4
Q-3
Q-4
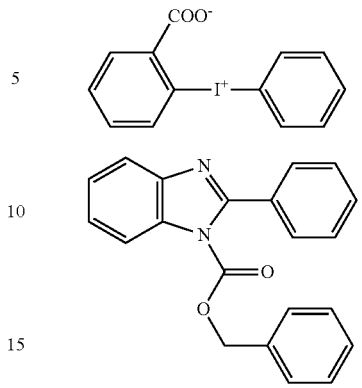
Water-Repellent Polymer: SF-1
Mw=8,700
Mw/Mn=1.85
SF-1
Q-1
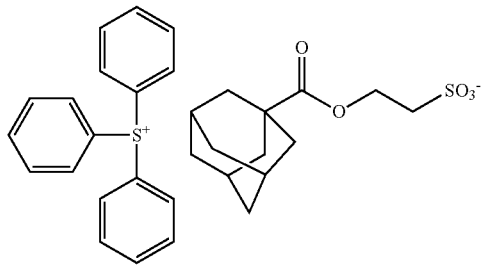
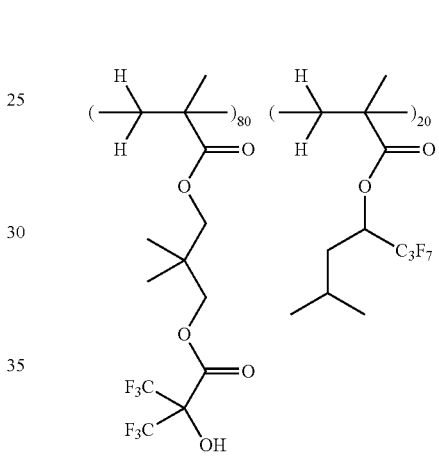
Crosslinker: XL-1
XL-1
Q-2
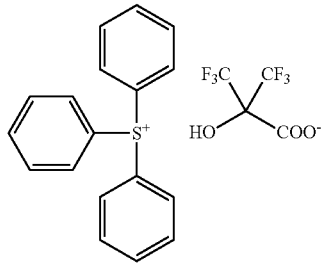
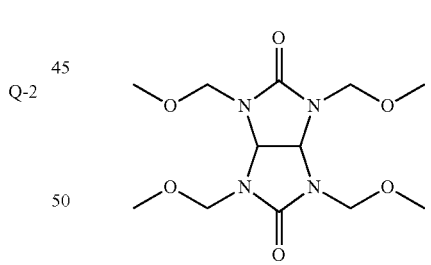
Solvent
PGEE: propylene glycol monoethyl ether
DAA: diacetone alcohol
GBL: γ-butyrolactone
TABLE 1
|  |  | Resist Composition | Resin (pbw) | PAG (pbw) | Sensitivity regulator (pbw) | Water-repellent polymer (pbw) | Crosslinker (pbw) | Solvent (pbw) |
| --- | --- | --- | --- | --- | --- | --- | --- | --- |
| Example | 32 | R-01 | Polymer 1 (100) | PAG-1 (6.0) | Q-1 (8.0) | SF-1 (5.0) | — | PGEE(2000) DAA(400) GBL(100) |

TABLE 1-continued

|  | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|
| 33 | R-02 | Polymer 2 (100) | PAG-1 (6.0) | Q-1 (8.0) | SF-1 (5.0) | — | PGEE(2000) DAA(400) GBL(100) |
| 34 | R-03 | Polymer 3 (100) | PAG-1 (6.0) | Q-2 (8.0) | SF-1 (5.0) | — | PGEE(2000) DAA(400) GBL(100) |
| 35 | R-04 | Polymer 4 (100) | PAG-2 (6.0) | Q-4 (8.0) | SF-1 (5.0) | — | PGEE(2000) DAA(400) GBL(100) |
| 36 | R-05 | Polymer 5 (100) | PAG-3 (6.0) | Q-4 (8.0) | SF-1 (5.0) | — | PGEE(2000) DAA(400) GBL(100) |
| 37 | R-06 | Polymer 6 (100) | PAG-4 (6.0) | Q-3 (3.0) | SF-1 (5.0) | — | PGEE(2000) DAA(400) GBL(100) |
| 38 | R-07 | Polymer 7 (100) | PAG-1 (6.0) | Q-2 (3.5) | SF-1 (5.0) | — | PGEE(2000) DAA(400) GBL(100) |
| 39 | R-08 | Polymer 8 (100) | PAG-1 (6.0) | Q-2 (3.0) | SF-1 (5.0) | — | PGEE(2000) DAA(400) GBL(100) |
| 40 | R-09 | Polymer 9 (100) | PAG-4 (6.0) | Q-3 (8.0) | SF-1 (5.0) | — | PGEE(2000) DAA(400) GBL(100) |
| 41 | R-10 | Polymer 10 (100) | PAG-4 (6.0) | Q-3 (8.0) | SF-1 (5.0) | — | PGEE(2000) DAA(400) GBL(100) |
| 42 | R-11 | Polymer 11 (100) | — | Q-2 (8.0) | SF-1 (5.0) | — | PGEE(2000) DAA(400) GBL(100)) |
| 43 | R-12 | Polymer 12 (100) | — | Q-3 (8.0) | SF-1 (5.0) | XL-1 (5.0) | PGEE(2000) DAA(400) GBL(100) |

TABLE 2

|  |  | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|---|
| Example | 44 | R-13 | Polymer 13 (100) | — | Q-1 (3.5) | SF-1 (5.0) | — | PGEE(2000) DAA(400) GBL(100) |
|  | 45 | R-14 | Polymer 14 (100) | — | Q-3 (8.0) | SF-1 (5.0) | — | PGEE(2000) DAA(400) GBL(100) |
|  | 46 | R-15 | Polymer 15 (100) | — | Q-3 (8.0) | SF-1 (5.0) | — | PGEE(2000) DAA(400) GBL(100) |
|  | 47 | R-16 | Polymer 16 (100) | — | Q-4 (8.0) | SF-1 (5.0) | — | PGEE(2000) DAA(400) GBL(100) |
|  | 48 | R-17 | Polymer 17 (100) | — | Q-3 (3.5) | SF-1 (5.0) | — | PGEE(2000) DAA(400) GBL(100) |
|  | 49 | R-18 | Polymer 18 (100) | — | Q-3 (8.0) | SF-1 (5.0) | — | PGEE(2000) DAA(400) GBL(100) |
|  | 50 | R-19 | Polymer 19 (100) | PAG-4 (6.0) | Q-2 (8.0) | SF-1 (5.0) | XL-1 (5.0) | PGEE(2000) DAA(400) GBL(100) |
|  | 51 | R-20 | Polymer 20 (100) | PAG-4 (6.0) | Q-2 (8.0) | SF-1 (5.0) | — | PGEE(2000) DAA(400) GBL(100) |
|  | 52 | R-21 | Polymer 21 (100) | PAG-4 (6.0) | Q-2 (8.0) | SF-1 (5.0) | — | PGEE(2000) DAA(400) GBL(100) |
|  | 53 | R-22 | Polymer 22 (100) | PAG-1 (6.0) | Q-1 (8.0) | SF-1 (5.0) | — | PGEE(2000) DAA(400) GBL(100) |

TABLE 2-continued

| | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|
| 54 | R-23 | Polymer 23 (100) | PAG-1 (6.0) | Q-1 (8.0) | SF-1 (5.0) | — | PGEE(2000) DAA(400) GBL(100) |

TABLE 3

| | | Resist Composition | Resin (pbw) | PAG (pbw) | Sensitivity regulator (pbw) | Water-repellent polymer (pbw) | Crosslinker (pbw) | Solvent (pbw) |
|---|---|---|---|---|---|---|---|---|
| Comparative Example | 11 | R-24 | Comparative Polymer 1 (100) | PAG-2 (12.5) | Q-4 (1.5) | SF-1 (5.0) | — | PGEE(2000) DAA(400) GBL(100) |
| | 12 | R-25 | Comparative Polymer 2 (100) | PAG-4 (10.0) | Q-3 (8.0) | SF-1 (5.0) | XL-1 (5.0) | PGEE(2000) DAA(400) GBL(100) |
| | 13 | R-26 | Comparative Polymer 3 (100) | PAG-3 (12.5) | Q-4 (1.5) | SF-1 (5.0) | XL-1 (5.0) | PGEE(2000) DAA(400) GBL(100) |
| | 14 | R-27 | Comparative Polymer 4 (100) | PAG-1 (10.0) | Q-1 (1.5) | SF-1 (5.0) | XL-1 (5.0) | PGEE(2000) DAA(400) GBL(100) |
| | 15 | R-28 | Comparative Polymer 5 (100) | — | Q-1 (1.5) | SF-1 (5.0) | XL-1 (5.0) | PGEE(2000) DAA(400) GBL(100) |
| | 16 | R-29 | Comparative Polymer 6 (100) | PAG-1 (10.0) | Q-1 (1.5) | SF-1 (5.0) | — | PGEE(2000) DAA(400) GBL(100) |
| | 17 | R-30 | Comparative Polymer 7 (100) | PAG-1 (10.0) | Q-3 (1.5) | SF-1 (5.0) | XL-1 (5.0) | PGEE(2000) DAA(400) GBL(100) |
| | 18 | R-31 | Comparative Polymer 8 (100) | PAG-1 (10.0) | Q-3 (1.5) | SF-1 (5.0) | XL-1 (5.0) | PGEE(2000) DAA(400) GBL(100) |
| | 19 | R-32 | Comparative Polymer 9 (100) | PAG-1 (10.0) | Q-3 (1.5) | SF-1 (5.0) | — | PGEE(2000) DAA(400) GBL(100) |
| | 20 | R-33 | Comparative Polymer 10 (100) | PAG-1 (10.0) | Q-3 (1.5) | SF-1 (5.0) | — | PGEE(2000) DAA(400) GBL(100) |

[4] Evaluation of Swell Quantity of Resist During Development, by the QCM (Quartz Crystal Microbalance) Technique Examples 55 to 58 & Comparative Example 21

The above-prepared resist solution (in Tables 1 to 3) was spin coated on a QCM substrate and baked on a hot plate at 100° C. for 60 seconds to form a resist film of 100 nm thick. The resist film was exposed by means of an ArF open-frame exposure system in a dose varying stepwise from 1 mJ/cm$^2$ to 13 mJ/cm$^2$ by an increment of 1 mJ/cm$^2$ and baked (PEB) on a hot plate at the temperature shown in Table 4 for 60 seconds. The resist film/QCM substrate was set on a quartz oscillator microbalance instrument RDA-Qz3 for resist development analysis (Litho Tech Japan Co., Ltd.). Development in a 2.38 wt % TMAH aqueous solution was carried out, during which a variation of thickness of resist film was observed as a function of development time. From graphs in which a film thickness variation was plotted relative to development time for each dose, the exposure dose corresponding to the maximum swell quantity and the maximum swell ratio (maximum swell quantity standardized per initial film thickness) are determined, with the results shown in Table 4. A smaller value of maximum swell ratio indicates that the swell of resist film is suppressed.

TABLE 4

| | | Resist | PEB temp. (° C.) | Dose (mJ/cm$^2$) | Maximum swell ratio (%) |
|---|---|---|---|---|---|
| Example | 55 | R-01 | 100 | 7 | 105 |
| | 56 | R-02 | 105 | 8 | 110 |
| | 57 | R-03 | 100 | 6.5 | 105 |
| | 58 | R-04 | 105 | 8 | 115 |
| Comparative Example | 21 | R-25 | 100 | 7 | 191 |

As is evident from Table 4, the resist compositions within the scope of the invention show lower maximum swell ratios than the comparative resist composition.

[5] Evaluation of Etch Resistance

Examples 59 to 61 & Comparative Examples 22 to 25

On a silicon wafer which had been surface treated in hexamethyldisilazane (HMDS) gas phase at 90° C. for 60 seconds, the resist solution (R-06, R-07, R-09, R-29, R-30, R-32 or R-33) in Tables 1 to 3 was spin-coated and baked (PAB) on a hot plate at 100° C. for 60 seconds, forming a resist film of 100 nm thick. Using an ArF excimer laser scanner (NSR-307E by Nikon Corp., NA 0.85), the entire surface of the wafer was subjected to open-frame exposure. The exposure was in a dose of 50 mJ/cm² so that the PAG might generate sufficient acid to induce deprotection reaction. This was followed by bake (PEB) at the temperature shown in Table 5 for 60 seconds for promoting dehydration or crosslinking reaction in the base resin of which the resist film was formed. The portion where the base resin has undergone dehydration reaction corresponds to the insoluble region in development. A reduction of resist film thickness by exposure and PEB was determined and divided by the initial film thickness, with the result being reported as PEB shrinkage (%).

Further, the resist film was developed in a 2.38 wt % TMAH aqueous solution for 30 seconds. The thickness of the resist film after development was measured. A minimum dissolution rate (nm/sec) was computed from a difference between the film thickness after PEB and the film thickness after development. A lower PEB shrinkage or lower minimum dissolution rate is preferable in that a film thickness necessary for dry etching is retained, or the initial film thickness can be reduced, which is advantageous in terms of resolution. The results are shown in Table 5.

TABLE 5

|  |  | Resist | PEB temp. (° C.) | PEB shrinkage (%) | Minimum dissolution rate (nm/sec) |
| --- | --- | --- | --- | --- | --- |
| Example | 59 | R-06 | 100 | 93 | 0.02 |
|  | 60 | R-07 | 100 | 94 | 0.01 |
|  | 61 | R-09 | 100 | 92 | 0.02 |
| Comparative | 22 | R-29 | 100 | 90 | 0.1 |
| Example | 23 | R-30 | 100 | 92 | 0.1 |
|  | 24 | R-32 | 100 | 93 | 0.15 |
|  | 25 | R-33 | 100 | 7.6 | 106 |

It is evident from Table 5 that the resist compositions within the scope of the invention show a low PEB shrinkage, like the resist compositions of Comparative Examples. The minimum dissolution rate is slow as compared with the negative resist compositions of Comparative Examples. It is demonstrated that a resist film of sufficient thickness is retained after development, and etch resistance after patterning is improved.

[6] ArF Lithography Patterning Test 1

Examples 62 to 81 & Comparative Examples 26 to 33

On a silicon wafer which had been coated with antireflective coating ARC29A (Nissan Chemical Industries, Ltd.) to a thickness of 78 nm, the resist composition (in Tables 1 to 3) was spin coated, then baked on a hot plate at 100° C. for 60 seconds to form a resist film of 100 nm thick. Using an ArF excimer laser scanner NSR-S307E (Nikon Corp., NA 0.85, σ 0.93/0.74, annular illumination), exposure was performed through a 6% halftone phase shift mask bearing a line-and-space pattern with a space width of 90 nm and a pitch of 180 nm, a space width of 80 nm and a pitch of 160 nm or a space width of 70 nm and a pitch of 140 nm (on-wafer size) or a trench pattern with a space width of 90 nm and a pitch of 1,650 nm (on-wafer size) while varying the dose and focus (dose pitch: 1 mJ/cm², focus pitch: 0.025 μm). After the exposure, the wafer was baked (PEB) at the temperature shown in Table 6 for 60 seconds and puddle developed in 2.38 wt % TMAH aqueous solution for 30 seconds. The wafer was rinsed with deionized water and spin dried, forming a negative pattern. The L/S patterns and trench pattern after development were observed under TD-SEM S-9380 (Hitachi Hitechnologies, Ltd.).

Evaluation of Sensitivity

As an index of sensitivity, the optimum dose (Eop, mJ/cm²) which provided an L/S pattern with a space width of 90 nm and a pitch of 180 nm was determined. A smaller dose value indicates a higher sensitivity.

Evaluation of Exposure Latitude (EL)

The exposure dose which provided an L/S pattern with a space width of 90 nm±10% (i.e., 81 nm to 99 nm) was determined. EL (%) is calculated from the exposure doses according to the following equation:

$$EL\ (\%) = (|E1-E2|/Eop) \times 100$$

wherein E1 is an exposure dose which provides an L/S pattern with a space width of 81 nm and a pitch of 180 nm, E2 is an exposure dose which provides an L/S pattern with a space width of 99 nm and a pitch of 180 nm, and Eop is the optimum exposure dose which provides an L/S pattern with a space width of 90 nm and a pitch of 180 nm.

Evaluation of Line Width Roughness (LWR)

The L/S pattern formed by exposure in the optimum dose (determined in the sensitivity evaluation) was observed under TD-SEM. The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

Evaluation of Depth of Focus (DOF)

As an index of DOF, a range of focus which provided a trench pattern with a space width of 90 nm±10% (i.e., 81 to 99 nm) was determined. A greater value indicates a wider DOF.

Evaluation of Resolution

Resolution is the minimum size that can be resolved among the L/S patterns with a size from 70 nm to 90 nm (pitch 140 to 180 nm). A smaller value indicates better resolution.

The results are shown in Table 6.

TABLE 6

|  |  | Resist | PEB temp. (° C.) | Eop (mJ/ cm²) | EL (%) | LWR (nm) | DOF (μm) | Resolution (nm) |
| --- | --- | --- | --- | --- | --- | --- | --- | --- |
| Example | 62 | R-01 | 100 | 34.5 | 16.3 | 6.0 | 0.20 | 65 |
|  | 63 | R-02 | 100 | 33.0 | 16.1 | 6.1 | 0.19 | 65 |
|  | 64 | R-03 | 100 | 37.5 | 17.6 | 6.0 | 0.19 | 65 |
|  | 65 | R-04 | 100 | 31.3 | 17.4 | 6.1 | 0.18 | 65 |
|  | 66 | R-05 | 100 | 38.4 | 15.4 | 6.1 | 0.18 | 65 |
|  | 67 | R-06 | 100 | 40.1 | 17.7 | 5.8 | 0.19 | 65 |
|  | 68 | R-07 | 105 | 40.0 | 17.1 | 6.0 | 0.18 | 65 |
|  | 69 | R-08 | 105 | 39.4 | 16.9 | 5.9 | 0.17 | 65 |
|  | 70 | R-09 | 95 | 39.2 | 17.4 | 6.1 | 0.19 | 65 |
|  | 71 | R-10 | 95 | 33.6 | 15.8 | 5.7 | 0.20 | 65 |
|  | 72 | R-12 | 95 | 30.2 | 17.4 | 5.5 | 0.19 | 65 |
|  | 73 | R-13 | 100 | 33.5 | 15.7 | 5.3 | 0.19 | 65 |
|  | 74 | R-14 | 100 | 35.5 | 15.4 | 5.3 | 0.20 | 65 |
|  | 75 | R-15 | 100 | 32.0 | 14.7 | 5.6 | 0.19 | 65 |
|  | 76 | R-16 | 100 | 38.5 | 17.6 | 5.7 | 0.19 | 65 |
|  | 77 | R-17 | 100 | 31.5 | 13.6 | 5.8 | 0.19 | 65 |
|  | 78 | R-18 | 100 | 43.4 | 14.4 | 6.0 | 0.18 | 65 |
|  | 79 | R-19 | 100 | 41.3 | 13.7 | 6.3 | 0.17 | 65 |
|  | 80 | R-20 | 95 | 35.3 | 15.5 | 6.4 | 0.17 | 65 |
|  | 81 | R-21 | 95 | 36.4 | 15.7 | 6.2 | 0.17 | 65 |

TABLE 6-continued

|  |  | Resist | PEB temp. (° C.) | Eop (mJ/cm$^2$) | EL (%) | LWR (nm) | DOF (μm) | Resolution (nm) |
|---|---|---|---|---|---|---|---|---|
| Compar- | 26 | R-24 | 100 | 36.3 | 9.5 | 10.3 | 0.10 | 90 |
| ative | 27 | R-25 | 95 | 25.3 | 10.5 | 9.8 | 0.08 | 90 |
| Example | 28 | R-26 | 110 | 28.3 | 8.3 | 11.5 | 0.10 | 90 |
|  | 29 | R-27 | 100 | 38.5 | 5.6 | 15.2 | 0.12 | 90 |
|  | 30 | R-28 | 100 | 35.6 | 7.5 | 9.5 | 0.08 | 90 |
|  | 31 | R-29 | 110 | 30.5 | 6 | 16.3 | 0.10 | 90 |
|  | 32 | R-30 | 100 | 33.3 | 6.6 | 10.7 | 0.08 | 90 |
|  | 33 | R-32 | 100 | 39.6 | 10.2 | 10.7 | 0.07 | 90 |

As is evident from Table 6, the resist compositions within the scope of the invention have practically acceptable sensitivity. Both EL and DOF have a wide margin. LWR is low as compared with the resists of Comparative Examples. Resolution is also excellent.

[7] ArF Lithography Patterning Test 2

Examples 82 to 85 & Comparative Example 34

On a substrate, a spin-on carbon film ODL-180 (Shin-Etsu Chemical Co., Ltd.) having a carbon content of 80 wt % was deposited to a thickness of 180 nm and a silicon-containing spin-on hard mask SHB-A940 having a silicon content of 43 wt % was deposited thereon to a thickness of 35 nm. On this substrate for trilayer process, the resist composition (in Tables 1 to 3) was spin coated, then baked on a hot plate at 100° C. for 60 seconds to form a resist film of 60 nm thick.

Using an ArF excimer laser immersion lithography scanner NSR-S610C (Nikon Corp., NA 1.30, σ 0.90/0.72, cross-pole opening 35 deg., cross-pole illumination, azimuthally polarized illumination), exposure was performed through a 6% halftone phase shift mask bearing a contact hole (CH) pattern with a hole size of 55 nm and a pitch of 110 nm (on-wafer size) while varying the dose and focus (dose pitch: 1 mJ/cm$^2$, focus pitch: 0.025 μm). After the exposure, the wafer was baked (PEB) at the temperature shown in Table 7 for 60 seconds and puddle developed in 2.38 wt % TMAH aqueous solution for 30 seconds. The wafer was rinsed with deionized water and spin dried, obtaining a negative pattern. The CH pattern after development was observed under TD-SEM CG4000 (Hitachi Hitechnologies, Ltd.).

Evaluation of Sensitivity

As an index of sensitivity, the optimum dose (Eop, mJ/cm$^2$) which provided a CH pattern with a hole size of 55 nm and a pitch of 110 nm was determined. A smaller dose value indicates a higher sensitivity.

Evaluation of Exposure Latitude (EL)

The exposure dose which provided a CH pattern with a hole size of 55 nm±10% (i.e., 49.5 nm to 60.5 nm) was determined. EL (%) is calculated from the exposure doses according to the following equation:

EL (%)=(|E1−E2|/Eop)×100 wherein E1 is an exposure dose which provides a CH pattern with a hole size of 49.5 nm and a pitch of 110 nm, E2 is an exposure dose which provides a CH pattern with a hole size of 60.5 nm and a pitch of 110 nm, and Eop is the optimum exposure dose which provides a CH pattern with a hole size of 55 nm and a pitch of 110 nm.

Evaluation of Critical Dimension Uniformity (CDU)

For the CH pattern formed by exposure in the optimum dose (determined in the sensitivity evaluation), the hole size was measured at 10 areas subject to an identical dose of shot (9 contact holes per area), from which a 3-fold value (3σ) of standard deviation (σ) was determined and reported as CDU. A smaller value of 3σ indicates a CH pattern having improved CDU.

The results are shown in Table 7.

TABLE 7

|  |  | Resist | PEB temp. (° C.) | Eop (mJ/cm$^2$) | EL (%) | CDU 3σ (nm) |
|---|---|---|---|---|---|---|
| Example | 82 | R-02 | 100 | 24.3 | 9.8 | 7.0 |
|  | 83 | R-08 | 95 | 32.3 | 12.3 | 6.6 |
|  | 84 | R-09 | 100 | 37.5 | 12.4 | 6.3 |
|  | 85 | R-10 | 90 | 33.4 | 10.3 | 6.9 |
| Comparative Example | 34 | R-24 | 100 | 22.3 | 7.2 | 10.1 |

As is evident from Table 7, the resist compositions within the scope of the invention show practically acceptable sensitivity, a wide margin of EL, and excellent CDU.

[8] EB Writing Test

Examples 86 to 87 & Comparative Examples 35 to 36

On a silicon wafer which had been surface treated in HMDS gas phase at 90° C. for 60 seconds, each of the inventive resist compositions or comparative resist compositions in Tables 2 and 3 was spin coated and prebaked on a hot plate at 100° C. for 60 seconds to form a resist film of 60 nm thick. Using an EB lithography system JBX-9000 (JEOL, Ltd.) at an accelerating voltage of 50 kV, a L/S pattern having a space width of 100 nm and a pitch of 200 nm (on-wafer size) was written while varying the dose (dose variation pitch 2 μC/cm$^2$). After the imagewise exposure, the resist film was baked (PEB) at the temperature shown in Table 8 for 60 seconds, puddle developed in 2.38 wt % TMAH aqueous solution for 30 seconds, rinsed with deionized water, and spin dried, obtaining a negative pattern. The L/S pattern after development was observed under TD-SEM S-9380 (Hitachi Hitechnologies, Ltd.).

Evaluation of Sensitivity

As an index of sensitivity, the optimum dose (Eop, μC/cm$^2$) which provided an L/S pattern with a space width of 100 nm and a pitch of 200 nm was determined. A smaller dose value indicates a higher sensitivity.

Evaluation of Exposure Latitude (EL)

The exposure dose which provided an L/S pattern with a space width of 100 nm±10% (i.e., 90 nm to 110 nm) was determined. EL (%) is calculated from the exposure doses according to the following equation:

EL (%)=(|E1−E2|/Eop)×100 wherein E1 is an exposure dose which provides an L/S pattern with a space width of 90 nm and a pitch of 200 nm, E2 is an exposure dose which provides an L/S pattern with a space width of 110 nm and a pitch of 200 nm, and Eop is the optimum exposure dose which provides an L/S pattern with a space width of 100 nm and a pitch of 200 nm.

Evaluation of Line Width Roughness (LWR)

The L/S pattern formed by exposure in the optimum dose (determined in the sensitivity evaluation) was observed under TD-SEM. The space width was measured at longitudinally spaced apart 10 points, from which a 3-fold value (3σ) of standard deviation (σ) was determined and reported as LWR. A smaller value of 3σ indicates a pattern having a lower roughness and more uniform space width.

The results are shown in Table 8.

TABLE 8

|  |  | Resist | PEB temp. (° C.) | Eop (µC/cm²) | EL (%) | LWR (nm) |
|---|---|---|---|---|---|---|
| Example | 86 | R-22 | 100 | 39.4 | 14.1 | 4.7 |
|  | 87 | R-23 | 100 | 38.7 | 18.9 | 4.2 |
| Comparative Example | 35 | R-24 | 100 | 42.2 | 8.6 | 8.9 |
|  | 36 | R-31 | 105 | 53.5 | 7.2 | 9.5 |

As is evident from Table 8, the resist compositions within the scope of the invention show practically acceptable sensitivity, a wide margin of EL, and low LWR.

Japanese Patent Application No. 2016-023878 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A monomer having the formula (1a) or (1b):

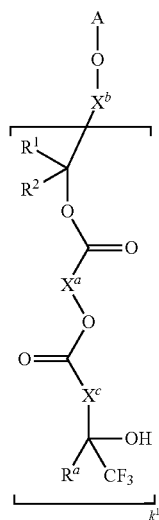
(1a)

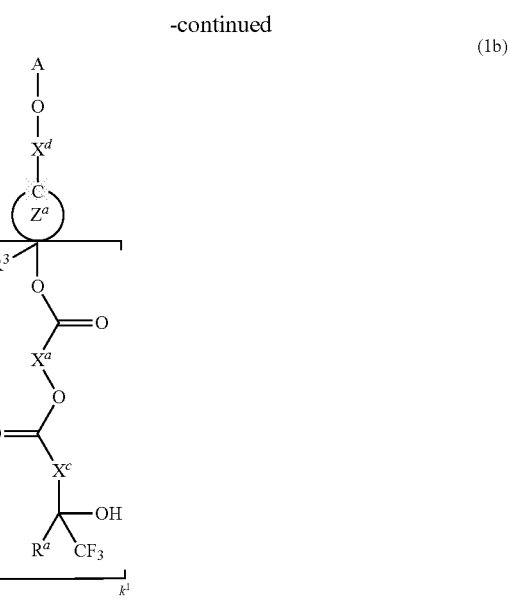
(1b)

wherein $R^1$ to $R^3$ are each independently a $C_1$-$C_6$ straight, branched or cyclic monovalent hydrocarbon group, $R^1$ and $R^2$ may bond together to form an alicyclic group with the carbon atom to which they are attached, $R^a$ is hydrogen, methyl or trifluoromethyl, $X^a$ is a $C_1$-$C_{10}$ alkylene group, $X^b$ is a $C_1$-$C_{10}$ straight, branched or cyclic ($k^1$+1)-valent hydrocarbon group in which any constituent —$CH_2$— moiety may be replaced by —O— or —C(=O)—, with the proviso that $X^b$ is exclusive of a group that forms the O—$X^b$ bond in the formula which is dissociable under the action of acid, $X^c$ is a single bond, methylene or ethylidene, $X^d$ is a single bond, methylene or ethylidene, $Z^a$ is an atomic group necessary to form a $C_3$-$C_{10}$ alicyclic group with the carbon atom to which it is attached, A is a polymerizable functional group, and $k^1$ is 1 or 2.

2. The monomer of claim 1 wherein A is acryloyl or methacryloyl.

3. A polymer comprising recurring units containing as pendant a group having the formula (2a) and/or a group having the formula (2b):

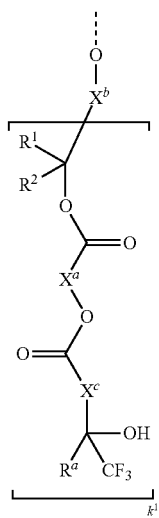
(2a)

-continued (2b)

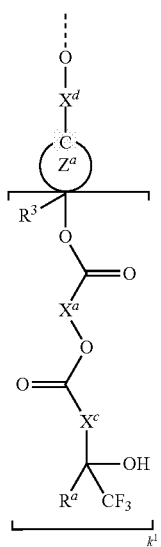

wherein $R^1$ to $R^3$ are each independently a $C_1$-$C_6$ straight, branched or cyclic monovalent hydrocarbon group, $R^1$ and $R^2$ may bond together to form an alicyclic group with the carbon atom to which they are attached, $R^4$ is hydrogen, methyl or trifluoromethyl, $X^a$ is a $C_1$-$C_{10}$ alkylene group, $X^b$ is a $C_1$-$C_{10}$ straight, branched or cyclic ($k^1$+1)-valent hydrocarbon group in which any constituent —$CH_2$— moiety may be replaced by —O— or —C(=O)—, with the proviso that $X^b$ is exclusive of a group that forms the O—$X^b$ bond in the formula which is dissociable under the action of acid, $X^c$ is a single bond, methylene or ethylidene, $X^d$ is a single bond, methylene or ethylidene, $Z^a$ is an atomic group necessary to form a $C_3$-$C_{10}$ alicyclic group with the carbon atom to which it is attached, and $k^1$ is 1 or 2.

4. The polymer of claim 3 wherein the recurring units have the formulae (2aa) or (2bb):

(2aa)

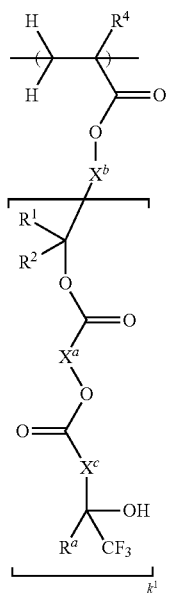

-continued (2bb)

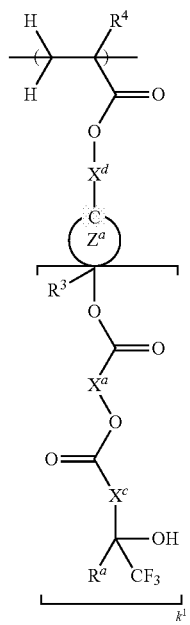

wherein $R^1$ to $R^3$, $R^a$, $X^a$ to $X^d$, $Z^a$ and $k^1$ are as defined above, $R^4$ is hydrogen or methyl.

5. The polymer of claim 3, further comprising recurring units of at least one type selected from recurring units having the formulae (3) to (5):

(3)

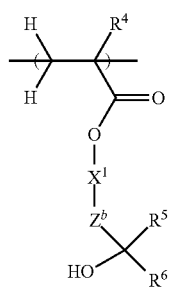

(4)

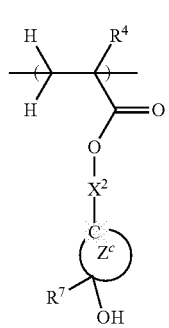

(5)

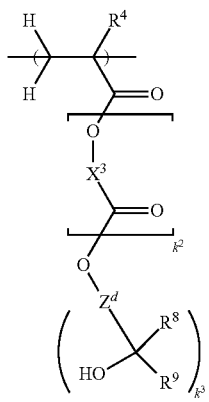

wherein R⁴ is hydrogen or methyl,
R⁵ and R⁶ are each independently a $C_1$-$C_6$ straight, branched or cyclic monovalent hydrocarbon group, R⁵ and R⁶ may bond together to form an alicyclic group with the carbon atom to which they are attached,
R⁷ is a $C_1$-$C_6$ straight, branched or cyclic monovalent hydrocarbon group,
R⁸ and R⁹ are each independently a $C_1$-$C_6$ straight, branched or cyclic monovalent hydrocarbon group, R⁸ and R⁹ may bond together to form an alicyclic group with the carbon atom to which they are attached,
$X^1$ and $X^2$ are each independently a single bond, methylene or ethylidene,
$X^3$ is a $C_1$-$C_{20}$ straight, branched or cyclic divalent hydrocarbon group in which any constituent —CH₂— moiety may be replaced by —O— or —C(=O)—,
$Z^b$ is a $C_1$-$C_9$ straight, branched or cyclic aliphatic hydrocarbon group,
$Z^c$ is an atomic group necessary to form a $C_2$-$C_{10}$ alicyclic group with the carbon atom to which it is attached,
$Z^d$ is a $C_1$-$C_{20}$ straight, branched or cyclic aliphatic hydrocarbon group in which any constituent —CH₂— moiety may be replaced by —O— or —C(=O)—,
with the proviso that $Z^b$ is exclusive of a group that forms the O—$Z^b$ bond in formula (3) which is dissociable under the action of acid, when $X^1$ is a single bond, and $Z^d$ is exclusive of a group that forms the O—$Z^d$ bond in formula (5) which is dissociable under the action of acid,
the total number of carbon atoms in $X^1$, $Z^b$, $R^5$ and $R^6$ is 5 to 12, the total number of carbon atoms in $X^2$, $Z^c$ and $R^7$ is 5 to 12, $k^2$ is 0 or 1, $k^3$ is an integer of 2 to 4.

6. The polymer of claim 3, further comprising recurring units of at least one type selected from recurring units having the formulae (A) to (D):

(A)

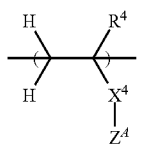

(B)

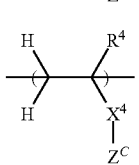

(C)

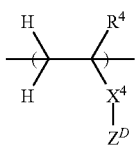

(D)

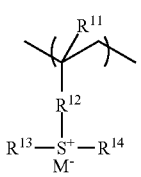

wherein R⁴ is hydrogen or methyl, $Z^A$ is a $C_1$-$C_{20}$ fluoroalcohol-containing group, exclusive of a structure undergoing a polarity switch under the action of acid, $Z^B$ is a $C_1$-$C_{20}$ phenolic hydroxyl-containing group, $Z^C$ is a $C_1$-$C_{20}$ carboxyl-containing group, $Z^D$ is a substituent group having a lactone structure, sultone structure, carbonate structure, cyclic ether structure, acid anhydride structure, alcoholic hydroxyl, alkoxycarbonyl, sulfonamide or carbamoyl moiety, $X^4$ is a single bond, methylene, ethylene, phenylene, fluorinated phenylene, naphthylene, —O—$R^{01}$—, or —C(=O)—$Z^X$—$R^{01}$—, $Z^X$ is —O— or —NH—, and $R^{01}$ is a $C_1$-$C_6$ straight, branched or cyclic alkylene, $C_2$-$C_6$ straight, branched or cyclic alkenylene, phenylene or naphthylene group, which may contain a carbonyl, ester, ether or hydroxyl moiety.

7. The polymer of claim 3, further comprising recurring units of at least one type selected from recurring units having the formulae (f1) to (f5):

(f1)

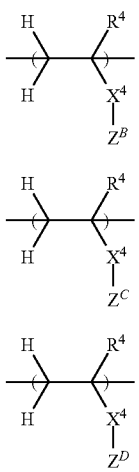

(f2)

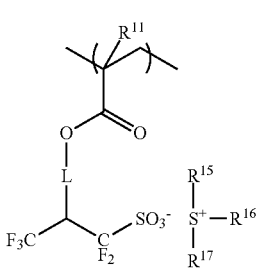

(f3)

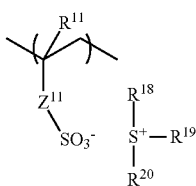

-continued (f4)
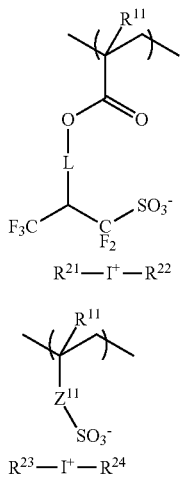

(f5)
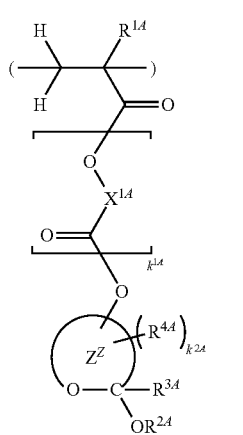

wherein $R^{11}$ is each independently hydrogen or methyl, $R^{12}$ is a single bond, phenylene, —O—$R^{25}$—, or —C(=O)—$Z^{22}$—$R^{25}$—, $Z^{22}$ is —O— or —NH—, $R^{25}$ is a $C_1$-$C_6$ straight, branched or cyclic alkylene group, $C_2$-$C_6$ straight, branched or cyclic alkenylene group or phenylene group, which may contain a carbonyl (—CO—), ester (—COO—), ether (—O—) or hydroxyl moiety, L is a single bond or —$Z^{33}$—C(=O)—O—, $Z^{33}$ is a $C_1$-$C_{20}$ straight, branched or cyclic divalent hydrocarbon group which may contain a heteroatom, $Z^{11}$ is a single bond, methylene, ethylene, phenylene, fluorinated phenylene, —O—$R^{26}$—, or —C(=O)—$Z^{44}$—$R^{25}$—, $Z^{44}$ is oxygen or NH, $R^{26}$ is a $C_1$-$C_6$ straight, branched or cyclic alkylene group, $C_2$-$C_6$ straight, branched or cyclic alkenylene group or phenylene group, which may contain a carbonyl, ester, ether or hydroxyl moiety, $M^-$ is a non-nucleophilic counter ion, $R^{13}$ to $R^{24}$ are each independently a $C_1$-$C_{20}$ straight, branched or cyclic monovalent hydrocarbon group which may contain a heteroatom, $R^{13}$ and $R^{14}$ may bond together to form a ring with the sulfur atom to which they are attached, any two or more of $R^{15}$, $R^{16}$ and $R^{17}$ or any two or more of $R^{18}$, $R^{19}$ and $R^{20}$ may bond together to form a ring with the sulfur atom to which they are attached.

8. The polymer of claim 3, further comprising recurring units of at least one type selected from recurring units having the formulae (X-1) to (X-4):

(X-1)
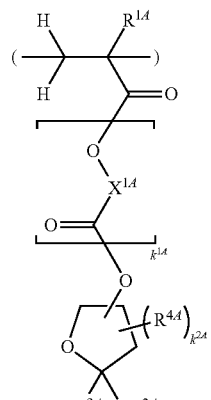

(X-2)
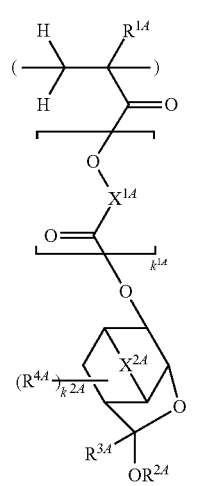

(X-3)

(X-4)
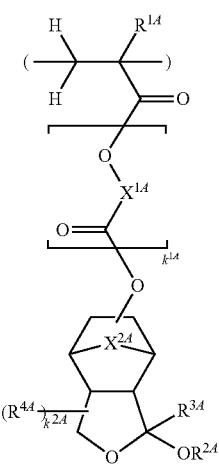

wherein $R^{1A}$ is hydrogen, methyl or trifluoromethyl, $R^{2A}$ to $R^{4A}$ are each independently hydrogen or a $C_1$-$C_{15}$ straight, branched or cyclic monovalent hydrocarbon group in which any constituent —$CH_2$— moiety may be replaced by —O— or —C(=O)—, $X^{1A}$ is a $C_1$-$C_{15}$ straight, branched or cyclic divalent hydrocarbon group in which any constituent —$CH_2$— moiety may be replaced by —O— or —C(=O)—, $X^{2A}$ is —$CH_2$— or —O—, $Z^Z$ represents a $C_4$-$C_{20}$ non-aromatic mono- or polycyclic ring having a hemiacetal structure, $k^{1A}$ is 0 or 1, and $k^{2A}$ is an integer of 0 to 3.

9. A resist composition comprising a base resin, an acid generator, and an organic solvent, the base resin comprising the polymer of claim 3.

10. A pattern forming process comprising the steps of applying the resist composition of claim 9 onto a substrate, baking to form a resist film, exposing the resist film to high-energy radiation to define exposed and unexposed regions, baking, and developing the exposed resist film in a developer to form a pattern.

11. The pattern forming process of claim 10 wherein the developing step uses an alkaline developer in which the unexposed region of resist film is dissolved and the exposed region of resist film is not dissolved, for forming a negative tone pattern.

* * * * *